US007255987B1

(12) United States Patent
Andersson et al.

(10) Patent No.: US 7,255,987 B1
(45) Date of Patent: Aug. 14, 2007

(54) SELECTING ANIMALS FOR PARENTALLY IMPRINTED TRAITS

(75) Inventors: Leif Andersson, Uppsala (SE); Michel Georges, Villers-aux-Tours (BE); Geert Spincemaille, Zwevegem (BE); Carina Danielle A. Nezer, Neupre (BE)

(73) Assignees: Melica HB, Uppsala (SE); University of Liege, Liege (BE); Seghersgentec N.V., Buggenhout (BE)

( * ) Notice: Subject to any disclaimer, the term of this patent is extended or adjusted under 35 U.S.C. 154(b) by 0 days.

(21) Appl. No.: 09/868,732

(22) PCT Filed: Dec. 16, 1999

(86) PCT No.: PCT/EP99/10209

§ 371 (c)(1),
(2), (4) Date: Nov. 1, 2001

(87) PCT Pub. No.: WO00/36143

PCT Pub. Date: Jun. 22, 2000

(30) Foreign Application Priority Data

Dec. 16, 1998 (EP) .................................. 98204291

(51) Int. Cl.
*C12Q 1/68* (2006.01)
(52) U.S. Cl. .................... 435/6; 435/325; 536/23.1; 536/23.5; 536/24.31
(58) Field of Classification Search ............. 435/6, 435/69.1, 320.1, 325, 350; 530/350; 536/23.5
See application file for complete search history.

(56) References Cited

FOREIGN PATENT DOCUMENTS

| AU | 779393 | 12/1998 |
|----|--------|---------|
| EP | 98204291.3 | 12/1998 |
| WO | WO98/03682 | 1/1998 |
| WO | WO 00/36143 | 6/2000 |

OTHER PUBLICATIONS

Pandya et al. (American Journal of Human Genetics 1994; 55(3) Suppl:A161).*
Witkowski et al. (Biochem. 1999, 38:11643-11650).*
Andersson-Eklund et al., "Mapping Quantitative Loci for Carcass and Meat Quality Traits in a Wild Boar x Large White Intercross," *J. Anim. Sci.*, vol. 76, 1998, pp. 694-700.
Kovács and Klöting, "Mapping of Quantitative Trait Loci for Body Weight on Chromosomes 1 and 4 in the Rat," vol. 44, No. 2, Feb. 1998, pp. 399-405.
Johansson et al., "Comparative Mapping Reveals Extensive Linkage Conservation—but with Gene Order Rearrangements—between the Pig and the Human Genomes," *Genomics*, vol. 25, 1995, pp. 682-690.
Reik et al., "Imprinting in Clusters: Lessons from Beckwith-Weidemann Syndrome," *Trends in Genetics*, vol. 13, No. 8, 1997, pp. 330-334.
Catchpole and Engström, "Nucleotide Sequence of a Porcine Insuline-like Growth Factor II cDNA," *Nucleic Acids Research*, vol. 18, No. 21, 1990, p. 6430.

Andersson et al., "Genetic Mapping of Quantitative Trait Loci for Growth and Fatness in Pigs," *Science*, vol. 263, Mar. 25, 1994, pp. 1771-1774.
Knott et al., "Multiple Marker Mapping of Quantitative Trait Loci in a Cross Between Outbred Wild Boar and Large White Pigs," *Genetics*, vol. 149, Jun. 1998, pp. 1069-1080.
Jeon et al., "A Paternally Expressed QTL Affecting Skeletal and Cardiac Muscle Mass in Pigs Maps to the IGF2 Locus," *Nat. Genet.*, vol. 21, Feb. 1999, pp. 157-158.
Nezer et al., "An Imprinted QTL with Major Effect on Muscle Mass and Fat Deposition Maps to the IGF2 Locus in Pigs" *Nat. Genet.*, vol. 21, Feb. 1999 pp. 155-156.
Van Laere, et al., "A regulatory mutation in 1GF2 causes a major QTL effect on muscle growth in the pig," Nature, Oct. 23, 2003, pp. 832-836, vol. 425.
De Vries, et al., "Gamatic imprinting effects on rate and composition of pig growth," Theoretical and Applied Genetics, 1994, pp. 1037-1042, vol. 88.
Evidence in Support of the Opposition by Monsanto Technology LLC to Australian Patent Application Acceptance No. 779393 (Appln No. 27952/00) in the name of University of Liege, Melica HB and Seghersgentec N.V., dated Oct. 10, 2005 with Application for Extension of Time.
Statutory Delcaration of Bruce Stephan Wellington dated Oct. 7, 2005.
Knott et al., Multiple marker mapping of quantitative trait loci in a cross between outbred Wild Boar and Large White Pigs, Genetics, 1998, pp. 1069-1080, vol. 149 (previously listed and submitted for this application with IDS of Jul. 31, 2001).
Andersson et al., Genetic mapping of quantitative trait loci for growth and fatness in pigs, Science, 1994, pp. 1771-1774, vol. 263 (previously listed and submitted for this application with IDS of Jul. 31, 2001).
De Vries et al., Gametic imprinting effects on rate and composition of pig growth, Theoretical and Applied Genetics, 1994, pp. 1037-1042, vol. 88 (previously listed and submitted for this application with IDS of Dec. 27, 2005).
Dechiara et al., Parential imprinting of the mouse insulin-like growth factor II gene, Cell, 1991, pp. 849-859.
Statement of Grounds and Particulars in Support of Opposition, dated Jul. 15, 2005.
Notice of Opposition, dated Apr. 19, 2005.
Notice of Acceptance for Patent Application No. 27952/00 dated Jun. 12, 2004.
Moore et al., Multiple imprinted sense and antisense transcripts, differential methylation and tandem repeats in a putative imprinting control region upstream of mouse Igf2, Proc. Natl. Acad. Sci., Nov. 1997, pp. 12509-12514, vol. 94.

\* cited by examiner

*Primary Examiner*—Jon E. Angell
(74) *Attorney, Agent, or Firm*—TraskBritt

(57) ABSTRACT

The invention relates to methods to select breeding animals or animals destined for slaughter for having desired genotypic or potential phenotypic properties, in particular related to muscle mass and/or fat deposition. The invention provides a method for selecting a pig for having desired genotypic or potential phenotypic properties comprising testing a sample from said pig for the presence of a quantitative trait locus (QTL) located at a Sus scrofa chromosome 2 mapping at position 2p1.7.

1 Claim, 48 Drawing Sheets

FIGURE 6

Contig 1 (500 bp)
GGGTGGGCAGCTTCCTCCCAGACCGCAGGAGGCCCAAGTTCCCTGGCCCTGCCCACCCAGGGCCAGCTGAAGC
AGGTCAGAGACACCCGCTCCTGTCCCTCCTGTCACCTAACCCAACAGGCCGGGGCCCAGGGACACAGGCCACA
TGGCATCTCCCCCCATGCCCCTGCCCCAAGGCGCCCAGCAGGTGAGGCTGGAGCAGAGTCTGGGTCCTGCGGG
CCAGACCGAGGGCAGGACAGCTGGGCATCTGTCCTCACAGTCCCCGCGCTTTGTCGGGAGGCGGCAGAGCCTC
ATCCAAGACGCCCGCAAGGAACGGGAGAAGGCGGAGGCCGCGGCTGCCGCGTCCGAGCCCGGGGAGGCCCTGG
AAGTGGGGGCCCTTGCCGAGCGGGACGGGAAGGCCCTGCTGAACCTGCTCTTCACCCTGAGGGCCACCAAGCC
CCCCTCGCTGTTCCGGTCCCTGAAAAAATTCTAGGTGAGGGGGCGGGCCAGGGCTCCCCGGG
Contig 2 (943 bp)
TGCTCCTCACACCCCGGGCGGGGCTGCTCTTGGGGCCATCCTCCCCATGGGCCCAGCACCCACTCTGGCCTTC
ACACCTGCCGTCTTCTGGGAAGTCCTCTGGTTCCCAAGGAAAGTTTCTGAGCTGGACAAGTGCCACCACCTGG
TCACCAAGTTCGATCCTGAGCTGGACCTGGACCACCCGGTGAGCCGGTGCCTCCCCTCCCCGGCCGCCATGTC
TCCCATCCCCAGGGGTGTCCCCACACTCAGGGCCGGGACTGGGCGTGAACCCCGGGTTGGGACGGATGTTGGC
CTGCTGTGTGGCTCCTGGCGGAACAGAGAGGCCTGGCTGGGTGCCACCCCCAGGGCCCCCGCCGATGACACGG
GCCGCGTCTGGGCTGGGCGGGCAGGGCGGCCAGGC
AGGGCAGCCTCCGATGGCGTCCCCGGCTGTCACCAGGGCTTCTCGGACCAGTTGTACCGCCAGCGCAGGAAGC
TGATTGCCCAGATCGCCTTCCAGTACAGGCAGTAAGTCCCTCCAGGGCCTCAGCCTGGGGGCCCAGACCTCAG
CCTGGGCCTCACGCCAGACCTGGGGGTGGAGGGAAGGGAGGTTGTCTTTGTCACCAACGCCACCACCTTCACT
GTCACCATGGTCACCGACTCTGGGTCCCAAATCACAGCTGAGGAAACTGGGGCACAGAGTGGTTAAGCATCT
TGCTGAAGCCACACAGCTGGCGGAGCATTTGGCCCCGGCCCCTCCTGCGGCTCCCACACGTGCTCCCTGAGGG
GCCCGGGACTGACAGCTGTCCCCTCCTCAGAGGTG
ACCCTATTCCCCGCGTGGAGTACACAGCCGAGGAGATTGCCACCTGGTGAGGCCCTGTGACAGCGGCTGGGAG
GGGCGGGAGTGGGGGAAGGGACAGGAAGACCTCAGAATTCCCGCGTGGAACGTGGTGGCCTCTATCATGA
Contig 3 (1500 bp)
GGGGAGGGGATGCTCAGACCCGCTCTGGGAAGAAGAGAGCCTCAGAAGAAATCCCTTCCCAAGGGTCACGCGG
TGGAGCCCAGGGGCCCGCTAGGGGCCGATTCCCACAGCTCGTGCTGCCACCTGCTGGCGCTCCCAGGAACTGC
GGAGGCGGTGGGGGCCCTGGATGGGTCCGGCAGTGGGCTCGCAGGAGACCCCTGGAGGGGCTGCGGACACCCC
AGCTGCCACTCACAAGGTGCCCAAGCGGCGGTGGCAATGGGCTGAGCCTCTCCCCCCCTCCTCCTCCGCAGGA
CATTGGCCTCGCATCCCTGGGGGTCTCGGACGAGGAAATTGAGAAGCTGTCCACGGTGGGTTTCTCCCCCTGC
AGGGCCCTGGGTTCCAGCCAGGCCCTCCTGTCCAA
GGGGTGTCGTCCTCACGCTGTGACCGCCCGGGAGCCTGGATCGGTTCTGCCTGGGTGGGCGGTGCCCGGGCCA
CGGGCAGCAGGGGCAGCGGTGCGGGCCCCAGCCGTGTCTGAGCCCCCTTGCCGCCTGTCCCCACCAGCTGTAC
TGGTTCACGGTGGAGTTTGGGCTCTGCAAACAGAACGGCGAGGTGAAGGCCTACGGGGCTGGGCTGCTGTCCT
CCTACGGGGAGCTCCTGGTGAGGCCTCCCCACGCGCTGGGGCCTGGGTCCCCGGGGAGGTGACCCCTGCGG
TGCCTTGTGGATTCCAGCTCTCGGGAGGCTGGAGCGAGGGCTGCCCTCCTGGGGGCACCAAGAAAGCTGGTC
TGCCGCCCCTCTCCACACACCTGTGCCTGGGCCCTG
GGGGGACCCCTGCTGGGGGATGTGGGTGCACAGCCAGGGCCACCAGGGAGTCAGGACACGGGGCTCCCTTCCC
TCGGGTCCCTGAGACCCCTGGCCTCCCGCCAGCACTCCCTGTCCGAGGAGCCCGAGATCCGGGCCTTCGACCC
CGACGCGGCGGCCGTGCAGCCCTACCAGGACCAGACCTACCAGCCCGTCTACTTCGTGTCTGAGAGTTTCAGT
GACGCCAAGGACAAGCTCAGGTGGGCCGGGGCCCGGGGCCCCCAAACTGGAGGATCCAGCCTGCAGCCCCGCC
TATGAGCCCATTTCCCAGCAGAGGGAGCTGCTGCGGACCCCACCGTCACAACCCCCCTCCCACAGCTGGAACC
CCAGAAAGCCTGCGGAGGGGGGACCTGCAGGGCTG
TGGCCAGGTCAAGGCCAGGTCGAGGCCAGGCTTTTAGGGGTGAAGTCTGACTTTGTAAGAGGGGTGCAGGGT
CCTTCCCAGCCTCCTCCCCTCCGAGCAGCTGGGGGCGGGGCGGGGGTGCGATGAAGGCAGAGATGACGCAGCC
ACCCGTTCACCCTCAGGAGGCGCCTCCTGTCCAGCCAGGCTCCTGTTGTCACAGGGGAAACTGAGGCCCCAGG
TGTGTGTGTGGGGGGGTGATTCTCACACACAAGCTTAGGGACAGGGACATAACGGCCTCTCCAGGGCACACAG
TCTGGAGG
Contig 4 (3024 bp)
TTAANTCCANGTTGGCCCCGACAAGTTTTCCCCATTTGAAAAGGGGCCAGTTAAGCCCCAACNCAATTAATTGG
AAGTTAGCTCCCCTCATTAGGCTCCCCAGNCTTTACNCTTTATGTTCCGGTTCGTATTTTTGTGGGAATTGTA
GCGGATACAATTTCTCTCAAGNAACCAGCTATGCCCATGATTACGCGGTACAGTAGTTCATCAGTCCCCCCCG
CCCATGGGACAGCGAAGGGAACCAGTATGTCGTGGGGCGGGTCTAAAGGGGTCACCACCAGGGAGGGGCAGG
GGCTCCAGGAGGCAGGGCCACTGAGCGGTACCTGGTGGGGGGAGGTGGTGGGGCCACACCCAGGAGTCCTGTG
CCCCCCCCACTCCCGCCGTTGGACATGAGAAGCAGGGGCCAGCCTGCGGGTCCCTGAGTTCAGCGCCCCCCC
CCCCACCGCCGCAGCAGCCCGGGGTCTCAGCAGGCTGCTGTGCTGGGGCGGGGCGCTTATGGRCCGGGAG
CAGCCCCCCCCACGGCTTCAGAGCATCTCTGGGGCCTCAGGGATGGACCGGGGTCTGCRGGCAGGTGTCCTC
TCGCGCCCCACTCCCTGGGCTATAACGTGGAAGATGCGGCCAAGCCCGGKCGGTTTGGCCTTTGTCCCCAG
CCAGTGGGACAGCCTGGCCCTCAGGCCGCTCGTTAAGACTCTAATGACCTCAAGGCCCCCAGAGGCGCTGAT
GACCCACGGAGATGATCCCGCAGGCCTGGCAGCAGGGAAATGATCCAGAAAGTGCCACCTCAGCCCCCAGCCA

FIGURE 6, CONTD.

```
TCTGCCACCCACCTGGAGGCCCTCAGGGGCCGGGCGCCGGGGGGCAGGCGCTATAAAGCCGGCCGGGCCCAGC
CGCCCCCAGCCCTCTGGGACCAGCTGTGTTCCCAGGCCACCGGCAAGCAGGTCTGTCCCCCTGGGCTCCCGTC
AGCTGGGTCTGGGCTGTCCTGCTGGGGCCAGGGCATCTCGGCAGGAGGACGTGGGCTCCTCTCTCGGAGCCCT
TGGGGGGTGAGGCTGGTGGGGGCTGCAGGTGCCCCTGGCTGGCCTCAACGCCGCCCGTCCCCCAGGTCCTCAC
CCCCCGCCATGGCCCTGTGGACGCGCCTCCTGCCCCTGCTGGCCCTGCTGGCSCTCTGGGCGCCCGCCCCGGC
CCAGGCCTTCGTGAACCAGCACCTGTGCGGCTCCCACCTGGTGGAGGCGCTGTACCTGGTGTGCGGGGAGCGC
GGCTTCTTCTACACGCCCAAGGCCCGTCGGGAGGCGGAGAACCCTCAGGGTGAGCCGAGGGGGYGTCCCGGGA
GCGGTYGGGGGAGTTTTTAAGGAGGAAATTGGTAAAAGTGACCAACTCCCTGGGAGCTGAGCCCAGAGACACC
CCTCCCACGCCCYGGTCCCGCTCGAGAAGCCCCCCTTCCCTCCCCTCCTCCCG
AGGCGGCTCCAGGGAGGAATCTTACGGAGTCAAGGCCCGGTGCCGCTGGTCTCCGAGTGACATGGCCGTGGT
GTCCCRTCTGCCGGCCCACATGCCCGTGAGAGAWGCCCCATCCCCCTGGGAGGGGGCCCCGTGCCGGGCAGGC
GGCGGGAGGCCCAGGACCGGTGGCTGCTGCGGCTTCCACTCCAGGGTGGGCGGGGTGGGGGGTGGCTGTCTCT
GTGTGACCGGCTCTCCCCGCAGCAGGTGCCGTGGAGCTGGGCGGAGGCCTGGGCGGCCTGCAGGCCCTGGCGC
TGGAGGGGCCCCCGCAGAAGCGTGGCATCGTGGAGCAGTGCTGCACCAGCATCTGTTCCCTCTACCAGCTGGA
GAACTACTGCAACTAGGCCGCCCCTGAGGGCGCCTGCTGCTCCCCGCACCCCAAAACCCAATAAAGTCCTGAA
TGAGCCCGGCCGAGTCCTGTGGTCTGTGTGGCCTGGGGCGGGGCCCTGGTGGGGAGGGGCCAGAAGGCTGT
GGGGGGCCTGCCTGCGACCCCTCTCTGCTCTCGCCACATCGGCTGCTCTAAGCTTCCTCCACATGCATCGGGT
GCCCACAGGCACATGGGCACCGGGGACCAGGGCCCAGGGCAGGGCCCTTCAATGTGGCGAGCTCTGGTTTTC
AGGGCTCCAGACACCCCCTCCTGGGTGCCCACTGCTGCACAGGGTCACTCTGAGGGTCACAGGGCACCCACCC
AGACTGCTCTTGGGCACACAAAATAGCCCAGGGGCTTCTTGGGCTGGCTGCRGTCTGGGAGGTCAGAGAGTGA
CCCCGCGGGACCAAGACCTGGCCAGCCTGCCAGTCGCCCAGGCCAAACCAATCTGCACCTTTGCTGAAGGTTC
CACCCGGGCCAGCACTGGGGGCGGCCGGGCCTAGAGCTGGGCGCCCGGGCCCCAGGGACTGCACACCCGCCAG
AGGTGGGCCTGAGGGGTGGCAGCAGGCTCTCCGCCTGGGACCCAGCCAGCTGGGCAGCTCACCTCTCAACACG
AGGCTCTCACCTGTGTCGTCCCCTCCCCACGGCCACACAGACACCCCTGGGGAGAAGTCACAGGCCCCCAGCA
GGCCCCGCCCCTGGACAGGACAGGCCAGGGCTGGGCAGGCGGGTGGCCGGCCGGACACTGGACCCGGAAGGGGGG
TAGGCGGCTGGGATGAGTGGCGAGCTGTCCATGGGAGCACCCAGCGGCCCCATTGGCACCAGTACAGGCAGGG
GCACCTGCAGCAGCTGAGGTACGTGGGGTCCCCGGACTGGTTGGTGTCCGGCTGCCCTCTGGGAGGCAGCGGG
CTGAGCTTGTGGTCCTGCCAACCAGGGAGACCCGTGACCACCCTGCTGCTTCCCCTCCCCCCAGGGCCAGCA
GACTCCTTTGGGACTCGGGGCCCCTGAGCCGCCCCCACTCGCAGGACTCACGGGGTGTGCGGTCCTGGGTGAG
TGGGGGCTTGGGAGAGGGTCACTCTTGTCCGTCGGGTGGGGAAGGCTGAGAGTCATGGTGTGACAGCGCCCTC
GGCCTGCCGGGTGGGGGGTCTCCCTTCTCCCGAGCCCAGATCCCCGGGTAC
```
Contig 5 (1730 bp)
```
CGTCACCCGCAGAAGCCAGGCCCACAGGCCTTGGCTCAGCCCCTCCACCCAGGCCCACGTTCCGCCCCTTCTG
GGAACTGGAGGACAGCCCGCCCTCGCCCTCGGACCTGGCTTCGTTTGCCCTGGCATCTGGCAGTGGCCGGCAG
CTGCGTTCAGCCCTGGATGACACCCTGGCGTGAGCGGTGGGTCCCCGTGCTGAGGGCAGCCCCACACACGTC
CTGCTCACTTGCCTTGTGTCTGCTCCGCATCCCGTCATCACACATGCCATGCTGGGGCACCGTAGCGCCTTGC
CCTGTGTGGCACTGTGGCACTGTGTTCCTGATGGGAAGACTGAGGCTGGGGTCAGGCCCGCTGCTGCCCACCC
TCTAAGGACATTCTGCCGGTGCAGCTGCCTCCAGG
CTGGCCCCCCGGATTGCATCTGCTTCTGGCACGGATGAACTGGCACCTCTGCCTGACCATTAGGGCTGTATTT
GCCTTCTCCTGTTGGCAGTAAATATTTACTGTCCCTCCCTGTTCCTCCAGGCCCGANCCAGTTCCTGAGGGGC
ATGGGAGGTGGACACAAAGGTGCCCAAGCAGCCCCCTGCTCTTGAGGGCCCAGTGTCTGGTGGGGGCCAGCCT
GGGAAGGAGGAGCGAGACTAGGAACCAGAGGCCTGTGTTCCTGGAAAAGGCCCCCTGGCAGAGTTCCGGCTGG
TGTGTGTCCAGCTAGGCTGTGAGTCTTCAAACTGGGGAGCCCGGCCCCTGGACCCAGGCAGGGCTGCACCCCT
GGTGCCAGTGCTTCACTGGGTGGGCACCTGTCCCC
ACCAGGCAAGGTGGTCCGAGCGGTCATTCACAGACAGAACCAGCAGAGGGCGCCAAAGCCCCACTTTTGACAA
ACTCCCCTTCGCCCTGAGCCGAAAGTCCAGGCGGCAGGTGGACCTCTCTGCAGGGCTCTGCCACCCCTGCTGC
CGCTTGCCAGCACTCACAGGGGCTGCGGGGGGTGCCCAACAGGCCGGCTACCCTGAGCTCTGGAGGCGATGCA
GTTTAGGAGGGAACGAGGGGACTCCTGGGGGTGACTTTCTTCAGCGCCCACATTGCGGCCCAGCAAACCGAGG
CTGGAGGAGGCCGGGCACCTGTGCCCAGCTGGAGCCTTTGCTGAGGGTCTCCAAGGCCTGGGGAAATTGAGGC
TGGGGGCTGGGGGGTGTCACTGTCGGGCCAGGAGG
CCCCTCGCTCTGATTGGAGCCGCCTCGGCCACTTGAGCCAGGAGGCTCACATGAGGCGGGGCTGCAGGGACA
GGACCCTCGGGGCCCGGGAGGCCCTTGGAGGGGGTCCAGCTGGGCCAGGGTTCGTTCTTTCCCGGGTCCATGTC
CACCGCCCTCCCGCTGCTGGGAGGAGAGGAGGTCCAGGGCAGAAAGAATGCGTGGGGATGGGGGGGTGGTCAG
GGGTCTGGGAGCTGTGGAAACAACAAACAGACAGCGAGGTCCTGGGGCGCCCGGCCCCCGCCCCCTCCGGCA
CTGTTGTTTCTGGCCGGGGTGCAGGGACAGCGAGGCAGATTCCTTCGAAAGTGGAGACTGGCGGGGGCCCCT
CGGGTCCTCAGCTCACCCCTGAGCTAGCCCGCCC
ACTCGGCTCCAACCTCCCGCAGGCCCCTGGCACGGTCTCCAGGAGTCCACTGAGGGGTCCCCAAAGCTGCCAC
CAGGAGCTGGGCCTGGGTCTGTCACCACCCCACCCCACCCTCCAAGTCTGAGATATG
```
Contig 6 (4833 bp)
```
ATGTGAGCTGCACAGCATGAGCCCTCGGCCCCACTGCTGTGGCCTTGCGGACATTGAGGTGTGTGCCGCCCAG
GGCGACCACACCCTGGCCTCTCAGGGTGCCCGTACAGAGGCGGCTGGGTCGTANGAGGTGCGGGGCTCTGGGG
ACCGCTGGTGAGTTCAGGACGGGGGTCATGCCACCTCCTCTCTGAAGGTTTGGTGAGGTGGCCCTTCTCTTAT
CGTGATGACAATACTGATTTCTGGAAGAGCCAGGTGTTTTCTGAGGCTGTGGTTGCACTTCTCCACGTGGCCA
CAAGGTGCCGGGCTCGGGTCAGATTTGAGAAGCCCTGCGGGAGCGGGTGTCATGCGCCAGATTCAGCTTGCCT
```

FIGURE 6, CONTD.

```
CCTGCGGGTCTGGGGTCAGGACGTGGTCCCCAGCAGTCTGCTCCAGAGCCTGTCAGTGATGTGTGGGATTTTA
CCGCTAGAACACAGTTTCCTCTGATTCTCAGAAACCAGCAGATGCTTTAGGAGGGGCGTGCAGGTTTCACCTG
TGCTGCANNGCCCCCTGCCACCTGGTCGGAGCCNCAAGACGGCATCTAAAGATCAGTTCCTCATCATCAGTTC
CGCAGTGCTGGGGTGGGGGCAGATGAGAACCTCAGGGCTGGGCGCAGAGGTGGGGAGCCCGCCTGGACCCCGA
CACTGCAGGGGGGCCTCCCCCTTGTAGGAAGAACAATGTCGCTTTGCCACCCAGCCCTCTCCCCAGGGTGCCC
CGAACTGTTGCTCCTAAGACCTCTGGGCTGTGTGCTGTAATTCTATAAGTGGCCACCAGGTGTCAGCAGGAGG
CCACTTAAGCATCCATGTGGCGGAAACCTGGAGCTGGGGGTTCCTAAGGGTCCCTCGAGTGTCTCCTGAATAA
ATAGGCGCTGACCTGATCCCCAGGAAGGGATAACCCTCTCCCAGGCCTAAGAGGCAGTGGGGCAATGAGGTTT
ATGTGTCCACTGTACCCCCAAATTGTCTCTTCCTTCCCTCTACCCTGTGTCCCCACCGTGGACGATACACGGA
GTGCGAGGCTGCGGGTCACAGCCCTCACAGCCCCAAAGCTGCAGGTCCTGCCTCAGGGGCACCGCAGCTTGGC
TGGTCCCCCTTGGGTCCTCCCCACCCTGACCCGTCCTCTGCTCCCCTCCCTTTGCTTAAATGCTCTGCGTTTC
AAGGTTCTGATGGAATAAAATAGCCCTGCACTGGTGTGTTCCTCTTTGGGGCTGTGCCAGAAGTGGGAATTCA
GACCAGGGCAGAGCTCAGATTCCACATACTGTGTTAGGGATGGCAGGTGCCACATTTCCAGGAGTTTCATTGG
TGGTTTGTAAATGCTACTTCCGTTTCAGCCCCTCAGCTGCCCACCTCCTCAATTTAGGGACCCCCCCCTTTGG
CGGGTTGCCCATGGAACCACATCATCTGGCGTGGGGTGAGCCCTTTATCCTCCCTGGCCCCACTGGGAGGGTT
TGGGGAAGTCCCAGCTAAATTTCTCCGTAGGGACCTGGAAGCACCCCTTGTGACATCTGGGCACAGATAAGAG
GTAGGGGGCACAGGCCGTGAACACTTGAAGCTGCAGAGCCCAGAGCAGAGCCAGCAGGAGCAAGTGACTGCTC
CCCACCCCAAGAACTGTGGGCTGCGTCACACACTCCCCACTGTGTGCCCTGGACCTGACAGGGCCTTTAGCCT
CCCTGCATCCCTCCCCACCCAAGAACCCAGTGAGGCACCCCACTTGCCCCTCCTTAGTGTTGTTATGGCTCTG
GGGCATCTGCATTTTGTTTAGGACACCCCCAGCTAGATTTAAGTCCCCCCAAGTGTGACTCTTTCCTCCACTG
AAAACCCTGTCCTCCCACCAAAGGGCCCTATCCCTTTAGCTGAGCCAAGGAAATTCAGGAGGGGCCTTGAATG
ACAAAGGAAGAGGGGAGAGTTAAACCCCAACACTGGCTGGCAAGCTGGGTGGGGTGGACACCCCAGGGTGCA
GGGGTGCAGTGAAGGTAGCGGCTGGTGGCCTTCTGGAAACTACATGTGACTTTGCCATTAGGTGAGTCTTTGC
TTTGCCCCTGCTCTATCTGCAGGCTTATGGAAGAAGTTTAAATTCCCAGGGACACTTGGTCTAACCAGGCAGC
GCTTGTATCTGGGCCCTTCCCCAGCTGCTGACCACTCTGAGTCTGCGCCTTAGTTGGAGTTTTGGCCAAGCTC
AAGAGGCTGTGGACCCCAGTCATCCCACCCAGGGGTGCCTGTGGGCAGGACGCTGCTGCCTGCCATTTGCTGC
AGTATTGTCACTGTCCGGCACCACACACATGGTGCAGGGGGTGGTATCAGGTGCCACTGGGGAAGGGAGAAAA
CTCCCAGGTGAGTCCCCTGCCTCTGGAAGCAAGATGGACATGACCGCACTGTGTTGCAGCTGCATTGGGAGGC
CCCGAAGAAAGATTTTTCTGATCTTTCTCGAACCCTGCTTTTCCCCATCATGCCCCGCCCCATTTTACCCGT
GCCACGCCCACTGGTGTGCCGGGGTGTCAAGTGACTGACAAGTGTCAATCTACTGAGGCCCTGCCCACTCTCC
ACCCCCCCACATAGTCCCACCTCCCAGCTGGCAGGGAGAACTTCCAGCTAATGCCCATGCCCACAAATGTCTT
TCTGTCAGCCTAGAGCTGGACCAAATCTCCACCCTGTAACATGCTGTGCCCTGGCGTGGGAAGGTGCCAGAGC
CAGTTGCCCCAGCAGCCCCAGAACCACTAAGTTGGCACAAAGCTACCCAAATTTGGAGGGGCTTGGGGAAGGG
CATGGAGGGGATGAGGAGGTGAGGGGCAAAACTAATTTCAGTTAGCATTTGAGCAGGTGCCACGCTCAGCGTG
GAGAGGCTCTCTTGCTTCTAGGGACCCATTATGATGCACACGCTAAAAGCGCCCTTCACCATCTCTCCAGCCT
CAGCTTTGTCCCCCTCCTCCTCCTCAGCGGCAACCCGGCTGGAGGGTCTGGCCACTACAGCCAGAGCGCCCCC
TACTTTGGTGGCGACTGCTACTATTGGCCCAACCAGCGGATCACCGGCCAGGCAGTTTCGGCAGAGAGTCTGG
GGCACCAGTGACTCCCCCGTCCTCTTTATCCACCACCCAGGAGCTTCAGGGACTACACAGCGACTAGAGGGCA
GGTAACTGGTCTGCCCTCCCTAGGGCTGCCCCCTCAGAGTGTGTGAGAAAAGCTGCATTGAGTGTTTGGGTGC
AGGTGGGCTGGGGGCTTGGGGCAGCCAACAGGAACGGCGGGACCTCTGCTTCCAGAGGACCCCAGATCCTGGC
AAGCTTCGACTTTGGAGGGGACAGGAAAGACAGGTGGAGAGGGACACTTCCCTCTTCTGTACAGACGCCCAC
CCGGAGCCACAGAGGCTTTTGCAAGGAAAATAGGTTTTCCCTCACTAATGCAGCAGGCAAAATGGGAGGGGCA
GGGGTGGAGGGTAGTGCCCCCGCCCCAGCAGGAGGGCACAGCTGTTTCTGCAAATGTAAAAAAGCAGGGTTT
TTCTGTGTGAGAAGTTCCCTCTTGCTGCATGTCCCCACCCCCGCCACCAAAGACAAACAGGACACTGTGCAGA
GGGGCCAGAGCCCCGAGATTTTGGAGTTGTTTTTATATGCATATATACCATTTGAAAGCAAAGCTTCCCTCT
CCCCTACTCCCTACATGTCCCCCTTCACCAAAAAATCCCACCACGTAACTGGAAAGGGGAGTGAGAAGGACGA
CGAAGGCGGCACTGTCCCCTCCCGTCCCACAGCGGGACTTAAAACGTACAGCTTTTCGCCTCCGGACAGTGTCC
CGCCCCCTGGCCCCCGTCACGCTCCCCTGCCCGGGGGGCTGAGTGTGGGGCCAGGGCCTGTCTCCAGGCATGC
ATTATTTTGTGCATGAAGGTTTTGTCCCGCCCACCCAGGCTGGTGGTTGGGGGGAAGGGGTTCATTGCTCCAAA
GAAGCCCATCTCCCCCCTCAGCCACCTTCAGCCGCCTTCGCAAGGCAGAGCTGTGTCCTCTGCTGTGTGCCTG
GCCCCCTCCTTGCTTCTATTCAAGGTGGAAGTGTTGGGGGGAGGAGAAGAGTTTTTATATTGTGTCTGTGATC
CCCCGAGGCAGGGCATTTGTGTGCGGCCCCCAGCCCCAGGCCCAGCCAGATGGGCCAGCCTGCCCGACAGA
AGGGTCTCCTGCTGCTTGGCTGCAGGGAAACCCAGCTCTGGGTGAACCGTGGGCACCTTCCTTCCTCCATGCC
CTGTATTTAAAGAAGGAGAGCTGGGGGGCCAGAGGCACAGGGAGGGGAGCCACGGCCCCAGGTCTGACAAGAT
GACCTGCGGGCCTCTCCACCCAAGAGTCGGGGTGGGGGGCGGATTTGGTTTGAAAAGAGAACAAATAGGAAC
ACACTCTTTATTTTCCCCAGGGGCCGAAGAGTCACCCCTGAACTTGAGGACGAGCAGCCGGATTCCAGCCCCC
AGCCCCAGGGCCCCACATCTCCTCGGGCTCAGCCGCGCGCCCCAGCTGCCCCCCAGCCTGAGCTGCAGCAGGC
CAGGGCTGCCCGAGACCCCAGCCCCCAGGTGAGCTGCCAGCCTGTGCCCAGGAGATCTCCGCCGGCTCAG
AACTGAGGCGGGCAGCCCACCCAGCCCACAGCGGTGAGTGTCTCCAGACCCCAGGGCAGGGCCGGTGTCCCC
CGGCACAGAGAGCTGTGCTGCAGGCCCAGACCTCCCAGGCCGTTTTAGTTCCCATCTCCCCTTGGGGAGGGG
TGGGGCTCAGAGGGGCTGGGGTGCATCCGCAGAGCTGGGGTGCAGGGCTCCAGGTGCCTCTCTCCCAGGCGGC
TGGCCCGGAGGGGGG
Contig 7 (2014 bp)
```

FIGURE 6, CONTD.

CTGGTTTCGCACTCCTCCGGGGACTGTTGAAGTACCCGAGAGCGCNCGCGGAGCGCCGGGGCGAGCGGGGGTG
GCCGCCGGGGGTGCTCCCGGGCCCCCGGACCGAGCCAGGGACGAGCCTGCCCGCGGCGGCAGCCGGGCCGCGG
CTTCGCCTAGGCTCACAGCGCGGGAGCGCGTGGGGCGCGGCCGCTGCCGGGAGTCCGCCTGCCTCCTCGGAGG
CGGCCGACCGGGGAGCCTGGGGGACCCCGAGCGCCCGGGGAGCAGCGCCCCGACACGCCCCGGGCCGCTCTCG
GCTTCCTCCCTTCCAGCCGGCGCCCGCGCGGCCGGGCTTCGGCACCGGGGCGCTCTCAGTGGCAGGAGAAGCG
TGCGCTCCCGCGGGGTGGGGGACCCGCAGGAAACC
CGCACCGCCTGGAGCCGCCGCCGCGCGGCCAGCGCTCGCGTCCCCCGGGGAGGGCGCCACTGCTCCGCGCGCG
CGTCCCCCGACGCCCCGCGCGCTTCCCCGGCCGGCCCGGGATCCTAACCTCTCTCTCGGTCGCAGCCCCGCAT
CCCCAGGGCTCCAGGCCCCCGGCGACTTGCCCGCTCCTCCCAATTGCAGACACGACTTTTTCTGGGACCTCCC
AAAGGACAGCCTGGCTCCAGGGTCCCCCAGATACATTCACCATTTCTCCAGATCACAAGTGGGTTTTTCGGGC
ACTAACTTCCAGAGACCTCAAAGCACATGAGCCCCTACTGGCTTTCCCAGGTTTCCACTAGTGGCCTCGGTCC
CCACCTCACTGGGGATTGTCTCCCAGGCTCTTCGC
GGTGTGATCCCACCCATTCGCGCCCAGGTCCCGCAGTGCCAATCCCTCCTCTAGAAAACTTAAACACTGACTC
CTGGTCTCGGGGTGAGGCTGCCCAATGTGCCTGACTCCCCAGAAGGTATACCAGTGTTTTTCTGGCATTTGGG
CACCGTTCCCCCAAAACACGTGAAGCTCTTTTCCCGCGTCCCCATAATTTTGGACGCCAGGGGCACCCAAGCT
TAGCGCCCCTGTTTGGCTCCCCCACACCGCGAAGCCCTGCTCCCTGGGGTTCACGACAGTTTGGGACTTTATC
TGCCAAGTTCCACAAACTGATTGGCCCCAAGCTGGGGTCCCTAAATTGTACACAAAGAACCCCAGCCCCCCCC
CCCAACTCCAGTACAGGAAGCGATGGCCCCAGGGA
CCCTCGGAGTTGGAACGTGGCTTCCTAAGCCTTCACCAAATTGAGGCTTTCCGCGCATGGCGCGCTGATGCC
CTTGCTGAATCAGAAGCACTCTGCCCTCTGATTCCTGCTTTCCACAACCCTGAGAGCATGATTTCTGGTCCCC
CAAACTCACTGAGCAAAAATCTTTTTGTGGGGGCTGCAAAGATAGGAGGCATTTCTCTCCGGAGCTCTCCAAA
CTCCCTTGCCTATAATCAAGTTCCCTAAAACTTAGACAGAGAGCTTCCCAGGCCCCAGAGGCACACAGAGCCATT
ATTGGAGCTGCGTTTAATGATGACAGGGACCATGGGTCATGCAGCTCCCCCAAGTCACAAATGCCCCAGGTAT
CCTTGGCTCCAGCCAAGCCCAAAGCAAACTCTTGC
ACAGATCCCATATCTTGTTATGTCAAGCGCTTTGCGTGTCCCAGTAAACAAATAGTCTGAGTGTTTTCTCCAC
CTCATAACATTCGGAATATTAAAAAATTCCCTGGGCCCCCGGAGCTGACAGACAAGAATCCGGGCTTCCTAAA
ATTCAGAACTGATTCCCAAATCCCAGGCCAACGCCAGACCCTCTCCCAATCTGGAGCCCCTCCGACTGGACAC
ACTGGACTCCTAAGTATTACGCGCTGTCCTCCAGGCACCCCAAATGCATTCAAAGTGACGCTTTGGTCACAGA
AAGGCACTGATTTCTTGGGCTCCAAAGCAGCCCATGCACCCCCGAGTCACCCCAAACTTAGTCAGCATTTCCC
GGGTCTCCCTCCGCACTGCAAACTCCCAACTGCGG
ACACCGGTTCTTCAGGACCCACCGCCTAGACGGTCTTAATCCCTTTTCCCCCAGACCTAGATTC
Contig 8 (371 bp)
AGATTCAAAAACTATTTTTCTGGGGCCTCCAAATTGAGGTGCTGCCTGCCAGTCCTCCAAAATAAACTGAGGG
GTTTTTTGTTTGTTTGTTTTTTTGTTTGTTTGTTTTTTTTTACCTTCCACGAAACAATCCAACTTTTTTGGA
CCATTGATTTATGGGTCCCCTGACTTTATGACCCTTGCCCCAAGTCCCCCTAAATGTAGGCCATTTTCCACGG
GCCTCCCAAAATGAAATTGCCCAGATCCCGCCGAAAAAAATATCCCCGGGTCCTGGAAATCCCAGGTATTACA
GGCCTGCGGCTGACACCCCTCCTTGCTACTAACCAGGTTCCCTGAAGTTTAGAGATCACTACCTAATGAACAA
ATCCAC
Contig 9 (2415 bp)
CCAAAACTGGGGCCCTATCTTACTAGGGTTCCCTAAATGCAGACAGCGCCCGGGAAAATAGGGGCGTTTTTTT
TCCTGTTTGCCAAAAATAAACTAATTGAAACCAATTTTTAGAATTAAAATCTAAAATGACCTTGATTTTCTGC
GTTCTCCAAATGTACTTTTCACAGCCCAGGTTGCCCCAGTTTAGACGGTGTTGCTTGAATCTCTAAAGCACC
CTGAGGATTTTTCCCGAGGAAGCCACCACAACTACGGAATTTACTGTCCTTCGGGGCCACAAGCCTCCAGGCC
ACCAACTTGGATTTCTAAACCGTGGAAATCAGCCTCCACTTCCCTCCGCCACCCCGAGGGTCTGCTCAGACCC
CCCAAACGTGCCCGCTGTTCTTCTCCCCCCAAATT
TTATTTAGAGAATATGCCTCTCTCGGGTTCTGCCAAGTTTCCCGCTGAGACTTCCTCGGTCATCCCCAAATCC
TCTTCCCCACAGTCCGGGAGCCCCCACAAGCTTACCGACCCACATGCTGGGGTCCCCCAACTTAAACGCGATC
CCCTGTCCCCCAGATTCACCGAGTGATTTCCCTGGTCCTCAGACTGGGACTCTTTTACTGGAGTCTCGAATTT
AGCCATTAATCACAGTTCTCCACTCCGACGCAGGCTCCCTTGGGTCCCACGTCGGGGACATGGGTTCTCTTG
CCTGCAAATCAGGCTGCTCTGACTTGCATTCAGGCCTTTGGGCATTGTTCCCCGCCCGCCGCGGTCTCGGTTC
TCCCCCCATCCCGCGCACGACGGGCACTGGGTCTG
GGCCTCTTGGTGTCTCCTACAAGTCCCCGGAGCTCCTCGGACTTGGGAACTGTCTCTTGCGTTCCCCAAATAC
ACTCGGCCCGGCAGTGTGTCCGCCAGGACGTAGGCAGAGCTTCTCCCGCGTCCAGGAAAACGACTGGGCATTG
CCCCCAGTTTCCCCCAAATTTGGGCATTGTCCCTGGGTCTTCCAACGGACTGGGCGTTGCCCCCGGACACTGC
GGACTGCCCCCGGGGTCTCGCTCACCTTCAGCGCGTCCACCGCCCGCTGCAGAGCGCTCGCTCTCCGTCTCTC
GGCTCCCAGCGCGCTTGGGGACGCGCAGCCTCCGGGCCTCCAGCCTTGCGGTGAGCTCCCCGTCGCCTCGCGTGT
CCCGGCCCGGCTCCCAAACCCACTCGCCGCCGTCC
CGCTGGGGCTGGCACTGGCCTCCGGCGACTGCCGGGGACACGGGAGCGGAGCGCGGGAGCCTGCTGCAGGCCA
GCCCGTCGGCCGGGCCGCGCGCCCTGAAACGCGCGCGGCTTTCGTTTGCTCTTTGCAAAGGTCACAACCGTGG
GGAAAACGCCTCGGCGGCCCCCAAGCGGGGCAGGCAGGGCGTTGGGAAGGAGGGACACGCGGGAGAGGAGCAC
CCCGCTGGGGCGGCGCAGCGCGGCGCCTCCAGCCGCCGGGCGGAGGATCCCGGGAGGCGCGCGCGGAGCGCGG
GCGAAGTGATTGATGGCGGAGCGAGGGGGCCAGCGGATCGCGGGCTTCCGCCGGCGGCGGCCCCTTCCCCTCG
GAGGGACTCGGGCGGCCCGGGTTTCTGGGGGCGGG

FIGURE 6, CONTD.

```
CGGGGCGCGGGGGCTTGTGCGTGGTCTCCACTTGGTAAAAATCACAACGACTTTTTACGTCGCCCCGACTCTC
CAGGAGATGGTTTCCCCAGACCCCCAAATTATCGTGGTGGCCCCCGGGGCTGAACCCGCGTCTACGCAAGGCC
AACGCGCTGAGGACGGGGGAACCATTATCCGGATATTTTGGGTGGGCCCCAAAGCGAGCTGCTTAGACGCGC
CCCGGTGAGCTCGGTCCTGCAGGTAGGCTTGGAGCGAGGTTCCCCGCCCTGCTCCTCTCTCTTCGGGCAGGCG
CGGCCAGGCCGGCCGGCCCTCCCCACGTACGGCACCTGGCGGCCGCCGAGACGACTCCCCGGTTCCCGCGCGG
CACCGGGGGGCGCTCGGGCTCTGGCTGCGGCTCGA
GGCGCTGCGCCTGCTCGGGCAGGTGGAGGCTTCACGCCGGGCCCGCGCCCAGGGACGACCCCTTACCCCGCAG
GTCCCAGCGGGACTCGGGGCCCCGGATCCAGCGTCTAGCCACCTGTGCCCGCACCGCCGCGAGGGCTTGTGA
CACCTACCACCCTGGCCGCCCCGCGTCCCCCGCGCACGAATGTAGGGATCCTGACACCCCGGAACCTAAGAC
GGGGCCCCCATACACTTTCGTACAGCGATTCGGGATTTCTCTCGAACTCTGCAGATCTGTATGGCAAAGTTGA
TGGCCTGCATTATTTTTCTGATAATTCAGCGAAAGATGGCGACCAGAGCTATGCGCGTCTGGGTTTTAAAGGC
GAAACCCAAATTAACGATCTGGTCAACGAACAGAT
ACAGCATACGTTTTT
```

Contig 10 (3753 bp)
```
AGATTCCAATGGGGATCCCGATGAGGAAGCCGCTGCTCGTGCTGCTCGTCTTCTTGGCCTTGGCCTCGTGCTG
CTATGCTGCTTACCGCCCAGTGAGACTCTGTGCGGCGGGGAGCTGGTGGACACCCTCCAGTTTGTCTGCGGG
GACCGCGGCTTCTACTTCAGTAAGTAGCTCAGCGGGGCACGGGGCGGGGCGGACACAGCAGGTGCTCCATCG
GTGCTGCCCCGGTACCTGTGCGGGTCCTTCGGATGGATGGTGTGGGGGACGGGGGGCGGGGGCGGCCAAGG
GAGGACCTCTCCTCCGAGGGTCTGAGACTTCAGAGCGGGGGCGCCCTGGCCCTGCGCAGTGATTGGCACCTGC
CATGTGCCTGGCTGGGGCTCACACCCCTGACGTTCCTGCAGCGTGACTCGAAACGGGAAACCGAAGGGACGG
GTGGCACGGGGTGGGGAGGCAGACCGTGAGTGGCAGGCGTGCGAGGGGTTCTTTCGGGCGGGGTGGCCCAGGC
AGGCCCCACAGGATGACAGCCTGTCCCCTCCTGCTCCTCCTTGACCTGCCCACAGCCAGGGCTGCAGGCACTG
ACATTCACCCATGGTATTGTGGTGCCTGACGTCTTGGCAGTGGGCATGGGTTCATGGACTGTTGGATTGAAAG
TGGAATAAGATGGGTTGAAAACCAATAAGAATAAAGGCGCGTGTGGCTGGCGGCATCTGCGAGAGGTGACCGC
TGCCCTCCCTGGGGTTGGGCTTTGGGTGGGTTCCCATGGGTGGGGCGGGCCGCCATGCAGGGTGCCCGCCTGC
TGGCCTCAGAGTGCTTTGCCGTCCTCATCTTTCTCTCTGGCCCCCGTCCCGCTCCTGAGGCTGGCTGGCTGGG
CCCGCGGAGACCTCCGCTCCCGCCTCGTCTGTGCCCAGGGAGCAGGGTGGACCCTCCCTTGGGCTCTTGCCTG
CACCTCCCAGCAGGCTGGGCCTCAGTGTCCTTACCTGTAGGATGGGTCAGGGGCGTCCTGGAGAGAGTCCTCG
GGACAATGGGGAGGCTGGGGCAGGCCCAGCCTGACCCTGAAGGTGGGAGTGTGTGCTCCCCCTGGGCTCAGC
CAGCCGCGCTTGGGGCCGGGAGGGGCTGGGGGACGTGGCTGGGGCAAGTTGTCAAGGGCCGCGAGGCTCACCC
CCGCCCATCGCTCCCCATGTGGCAGCCTCTTCTGCAGCCTCTACTTACCCACCCTCTGAAATGGGCTGAAAAC
ACCCATCTTGGCATGCCAAAGCTTCTCTGTAAAAAGCGTTGCTGCTTCTTGATGCTTTCTGAGGCCCCTGCCTG
CCCTGGCCTCTGAGCCCTCTCTCTCCTGCCTCGTTTGGGGGCAGGGAGTGGCACCATAGAATCTGGCGCTGGG
CCTGGGGAGCGGCCCCCTCGTGCCAGGCTTCCCCGAAAGGAGGGCTGGGCTGAGCTCCCGACCCTCTGGACCC
CTTACCAGGACCCCTTACCAGGGGCTTCCCCCCCCCCCCCCCCGGTGGCGGCGGGCTGGGCTGGGGCCTTTT
CCTTGCAGCCGAGTCGGAGCTGTCGGAGCCGAGGGCGAGGACGGGAAGAGAGGAGGGCGTGGTTTCTGCTGGT
CCTCACTCCTCTCCTCCCGTCTTCCTCCTCCTCCTCCCATTCCCACCTGTGTCTCCGGGTCCCGGGGCCGCAG
GCTGCCCAGGCGCCTGCTGATCCATTGGGGACCGCACTCGGGTCCCCGCTGGCCTTCGGGTCAGGGCCACGGC
CCACCTATTTTCCAAACAGCCTTGGGTCGAGGCCCAAGAGGCTGGGCCCGGTTTAAGGACGGGGAGGGAGGCG
CCAAGAGGCCAGGGGCTGGTCCCGAGCACGCCCGCACCCGCTCACCCCCGCTGTCCCCTCTCCTTCCCCGGGG
GGCCCCTGTGCACCCCACTCTCACTTCTTCTGCTCGAGGCCACGAGGCTGGCTGTCCCCGCAAGGTGACCGGG
CGTCCTGTCTGGAGGGCGGGGGCCGGGGCGGCTGGGGGCACCGTCCGTGCCCGGGGCCCCTGTGCTGACGTGC
CCTCCCCTTGGTCCTGTGGGACTTCCAGGCAGGCCGGCCAAGCCGGCGTGAACCGCCGCAGCCGTGGCATCGTGG
AAGAGTGCTGCTTCCGTAGCTGCGACCTGGCCCTGCTGGAGACCTACTGCGCGCACCCCGCCAAGTCCGAGAG
GGACGTGTCGACCCCTCCGACCGTGCTTCCGGTAAGGCAGCCCCTCTCTCGGCAGCGCCCCCCCCCGGGGGGG
GGCTGTCTCCTCTGAGCCGGGGGACCGGGGCGCAGCCGGCTCTTGGGCTTCAAGTGCTGCCAGAGGGGCCTTC
CCCGCTGGGGACCCTGGCCAGAAGCCAGGGCAGTCTTCGCTCTGTCGCAGGGCAGGCAGGCAGGAGGACCCCG
CAGAGGTTGTTGTTCTGGGACAGGGGCTGGGGGGCCAGGCCCCCCCTGACGGGCCCTTCCCCTCTCAGGACA
ACTTCCCCAGATACCCGTGGGCAAGTTCTTCCGCTATGACACCTGGAAGCAGTCCGCCCAACGCCTGCGCAG
GGGCCTGCCGGCCCTCCTGCGCGCCCGCCGGGGTCGCACGCTCGCCAAGGAGCTGGAGGCGGTCAGAGAGGCC
AAGCGTCACCGACCCCTGACCGCCCGTCCCACCCGAGACCCCGCCGCCCACGGGGCGCCTCTCCCGAGGCGT
CCGGCCATCGGAAGTGAGCCAAATTGTCGTAATTCTGCGGTGCCACCATCCACCTCGTGACCTCCTCTCGACC
GGGACCGCTTCCATCAGGTCCCCCTTCTGAGATCTCTGTACCCTTCTGTCTGCGGGCATCTCCGCCCCGGGCC
CCGTGCCCCAACCTCCCCATGTCAGGCTAGTCTCTCCTCGGCCCCTTCCATCGGGCCGAGGGCATCCAAACCA
CAAACCCAATTGGCTTGGTCTGTATCTCCCCCAAATTATGCCCCCAATTATCCCCAAGTTACATACCAAAAA
TTGAACCCCTCAACCACACCCACATACAATCAGCCCCCGTAAAACGAATTGGCATCTTTAAAACACCAGAAAA
GCGAATTAGCTTTAAAAAAAAATAAACCCAAAATATTAGCTGAAAAAAAAA:TACTAAAAATAAATTG
GCTTAAAAACAATTGGCAAAATAAAAGAATTTGGCCCCCCCCTTCCTTCTCTTTCTTTTCGGACCTTGAGTTA
AATTGGCTGTGACCCATCATCCAAGAGAAAGGAAGGGACCAAAATTTGCAGGTAGGCTTGTCGCCGCTCACAG
CCATCTCCCTCCTCCTGCCACACCCTCGCCGGCCACTGGCGGTGTGGCACCAAGGACCCAGTCCCGTCCTCTC
TCTAGTCCCATGACCGAGACCGCGGTGGAGTTGGCTGGGAGACCCCGTGAGATCAGAGGAGGGGAGCACGGAA
CCAGAAACCCAAACCTGCACAGGTACAACATGACTGGCCCCCCGCACAGCCCAAGACCTCTCATCTCAGTCTC
CACTTAAAAAGCACCTGTACCCACACGCATCCCTGCAGAAACACACACACACACACACACACACACGCACGCA
CGCACACACGCGCGCACGCACGCGCACACACACACTCATGCGTATACACACACACACACGCACGCACGCGCAC
```

FIGURE 6, CONTD.

```
CCACACACACACATGCATTCACACACACACACACTCGTGCATACACACGTGCGCGCGCACACACACACACACA
CACACTCTCTCTCTGTGGGATCCCTGAG
Contig 19 (500 bp)
TGGCTCTGGCATAGGCTGGCAGCTGCAGCTCTGACTGGACCCCTTGCCTG
GGAACCTCCATATGCCGTGGAAGCGGCCCTAGAAAAGGCGAAAAAAAAAA
AAAAAAAAAAACAACCAAACAAACAACAAAAGCCAAAACACACAGAACTC
ACAGACACAAGAAGAGACTGGTGGTTGCCAAAGGTGGGGTCGAGGGTGGG
AAAAATGAGGAGAGGGGGCAAAACACACAAACGTGCAGCCATAAAATGGT
AAAGTCCCGGGGACCTCCGGTAGCGCGTGTGGGGACTCGGGTTGAGAACA
CACCGTGATGTGTATTCGCGAGTTGCTAAGAGTCCCTGTTGGAGAAACAA
ATGCGTATCGACGTGTGGAAATGAAAGTTAACCCGACCTGCTGTCGTGAT
CACTTTGCAACACATACAGACATAGAATCATTATGTTTTACCCCTGGAGC
TGACAGCGTTATACGTCCCCCAGCCTCAATTTAAAAACAGCGTTGCCGTG
Contig 20 (400 bp)
TTCATACTGTGCAATGCCAGCCTTAAATGCACAGAGGAGAGCATTAACTT
CTTTGCAGAATCACTGAAATGATACCACTCATGTTTTGCAACTTGCACTT
GGGCGTTATTTTATTGGTGCCGGAACAGCGGCGATGTGGCACCAAACTAG
CGCCGCTGTTTTTATTTCCCCTCGGTATCCGCGCTCTCGCTGTCTTCCCC
CCCTTCCGCTTGCAGCTGAGGAAAGGGCTGAGAGGAGGAAAGTCTGCATT
CACCCATCTCCCCCTGCCTCTGTTGTCATCCTTCACAGAAGTGGTGGCCT
GTGCGGGAAGTCACTAAACCTAGGCAGGTGTCCCGTGGGGTCATGCTTG
TTACACCTTTGTGCACCTGGCCCAAGTTCTGGGTGGAGCGAGAACGTGGC
Contig 21 (559 bp)
AGCTAGCCCCCCAGCCAGGGCCAGGCCTCTCCTGCCACCCGCCCAGCCA
GCATGTCTCAAGAGGAGGGGGCCTCTAAGGGATGAGGACCTGCTCCAGTC
GGAGACACGAAGCCCCGCCGGCTCCTCCCCGAAAGTCCAGCTGCGGCTTT
CGAGCACGGCTGCGCCCTTCGTCAATCATTTCAGCCACAGAAGTGAAAGG
CGCTTTCGTGGCCGAGGCAGGCGGGACACAGAATGGAATCCCACCCCAGA
GCGAAGAGCCGCCGTGGGTGAAGCGCGTCTCTGGTGGGGACCGGGCCGGG
AACTTCACATGGGGGTCGCTGTCCCCATCTCCCCATCGTCATTACTGCAG
GGGCTCGGCCACACCCGGAGCTGCGGGGGCCAGTGCTGGACACTGGACCT
GGCCTCCGTCCTATGATGTCATGGGGGCGGGGCCAGCACAGGGCAGTGGC
CACACCTCGGGCCTCCCAGCACCAGCCAGGATGGCAGAGGGCCCCACCCC
ACCACGGGGCATGTACATCCCAGAGGACCAGCTGAGCAAGGCTTGATANG
GGCTTCAAC
Contig 22 (450 bp)
CGTGCAGGGACCCGTGCGGGCCTTCCTGTGGCCACAGAGAACAAACACAC
CATTATCTTCAGCCCCACCGCGCGGCCTGTTAATGGGTAAACTGGGGCAA
GGGGGCCCCTGCCTGAGGCGGGGTGGGGAGCGCAAGGCATGGCCTGTGT
GCCCCAGCCCAGTCCTTCAGGGCGCTGCTGTCCTGCACCGGGGGCCCCAG
GAAGCAGAGCACCCAGCTTCTCCCCTATTCTAGAACCAGCCCCCAGAACC
CTGGACCCAGACCCAGGCCCAGGGGATACTGACAGAGCCACGGCAAGGCG
GCCACTCCACACCCCACAGAGGGGCCAGCAAACCCCAGTCACTGCGCAGC
CCATGCCCAGGGGGCAGATGGGACACGAGAGCAGCCCTCATCCACAGCAG
GCAGGGGAGTGAACTGGTGCAAAACGGGGCGGTTCCACGAAAGTTAAGCA
Contig 23 (535 bp)
TGCCAGAGACCTCAGAGCTGGGCTCTGCCTTCCCGGGCTGACACGGAGGG
CTGTGGCTTCCACCACCCCAGGCCACAGCCAGCCTGCCCAAGTCCCTGAA
GTGTCCCCAGAGGTGGCCCTGCCTCCACGCCCAACATCAGGCCTGCTGCA
GCCCTGGACGGCCCCCTGTCCCCCGGAAGCCCTCGGGGCTCTCTCGCGTC
GCCTCTGGGGAACCCTCGGTAATGTGGCCCAGCCGTGCAGTGGCCGGATC
ATTTGCTCAGGGGGCCCAAGGCAGGGGGGTGACACATCCGCAAGTACCG
CATATGCACAGGATATGGATTGGGTGTGGATTTAACCTTTTCGCAAATGT
CTCTGCCGGTACAAATATTGTTTCTAATCCTCTGCCTCCCTGAGCCGGTG
AGTCTGCCCGGGAGCTGCGGGGAGCTGGCTTGCTGAACCTGCCCTGGCCC
CCACCCCCAAGGGAGCCCCCGGCCAGTGCTGAGGGCAGGAAGCTTGGGCA
CAGGCTGCAGAGGCCAGCGCTGGCCTCAGTCACCT
Contig 24 (868 bp)
TATTGAAGACCCTATCATGAGTTCCCAGAGCGGAGGGGTGGAAGCAGGGG
CCTACAGCCCACTCCCCATCACTCCAGACCCGTCCGGGGCTGGTGTCCCC
TGCCCCCTACTCCTGTCTCTGGTGGGCGGACGCTCGAAGGAGGCACTCTG
GCCTGGAGCCTGGAGGGTCCCTGAACTCCCGCTGCCACCTGGGCCCTCGG
GCTCCTCCTGCGCTGGGACCCGCGGTGGTGGGAAGCAGCCCTGCTCAGTG
GGAGGAGGCAGGGCTGTGGCCGCCCCGCACGGCCCTGGGGGGGACGCACG
```

FIGURE 6, CONTD.

```
CAGGACGCANGTGGGCGTGTGTGAGTCCGTCTACACGTCCAGCCAAGGGC
GGCCGCGACCGGCCAGGGTGGGCAGCCCCAGCCTCAGCAGGGCGCTCTCT
GGGGCTCAGGCTGCGCCGACGGGAGATGAGGGGTGAGGCGCAGTCTGGGG
CTGCTGCCGCAGAACCTCGCCCAGCTGGCAGCTGGGCACAGGGAGACCTG
TACTCCCAGAACCTGAGGCTGGACGTCCGAGACCCGCGTGCCGGCCTCTT
GGGTGCCTGGTCAGGGTCCTCTTTCTGGTTTGTGGGCAGAACCTCCTCAG
CGCGTCCTTGCATGGGGTGCTAATCACGGAGTAAGGAGCCAGAGAATGAG
GCACGGAGTATCCAGTGTTAACCCTGGAGTATGGAGACGGGAGTACTAAT
TGTGGAGCATGGCTCTAAGGAATGGAGTATTCGTCACGGAGAACGCGGGG
CCGGGTGAAATACGGAGAGCGGCGTACGGACAACGGGGACGGGGTATCCG
AAGGGGAGGATGGAGTATCGGCCGGAGGGTGGAGAATGGACACTAGAGGA
TGTATANNGGGCGTCAAT
```
Contig 25 (500 bp)
```
ACCAGTTTCGATGAGCAATCCCAGCGGCGTAACATTATGGCTGCAGCCTG
GTCAATGCCGGTGGAGTTTGAACCTCCACGCGTGGCGATTGTGGTAGATA
AATCGACATGGACCAGGGAGTTGATTGAACATAACGGTAAATTTGGCATC
GTTATCCCGGGCGTTGCAGCAACTAACTGGACGTGGGCGGTGGGAAGTGT
GTCGGGGCGTGATGAAGATAAATTTAATTGCTATGGCATTCCGGTTGTGA
GAGGCCCGGTATTTGGTTTGCCTCTGGTCGAGGAAAAATGTCTGGCGTGG
ATGGAGTGTCGATTGCTACCTGCGACTTCTGCGCAAGAAGAATACGACAC
GCTGTTTGGCGAAGTAGTATCAGCAGCGGCAGACGCACGGGTATTTGTCG
AAGGCCGCTGGCAGTTTGATGATGATAAGCTCAATACGTTGCATCATTTA
GGTGCTGGGACGTTTGTTACCAGCGGCAAGCGTGTTACGGCGGGTTAAGC
```
Contig 26 (900 bp)
```
ATGTTTGATGTCCGCGCGTGCTGTAAAAATTTACGCTGCTCGCGTTCTTT
GGCTTCGTCCACCACCGGAAAAACGGACAAAAATTTCCGTCATACCTTTT
CTTTCAGGCGGAAGCCAATGTCGTAATCTTCAGTAAGACTCTGCACGTCG
AAAGCAATACCGTCACCGTCAGCTAACAGTGCGGTCACGGCGCGGCGGCT
GAAACAGGTGCCGACGCCTGCGCTGGGCACTTGTCCGGCGAGGGCTTCAC
GCACCGGAACATCTTTGCCATGCAGCTCTGAAAACTCATCAATGTAAGTC
ATGCTGGTGAAGTGCGTCCATTCGCGTTCGAACGGATACACCGGGATCTG
AATCAGATCTTTACGCTCGACCAGATAGTTGAACAGACGCAATTCCATCG
GTGAAATCACATCTTCGGCGTCATGCAGAATAAAACCAGCAAAAGCGAAA
TTGGCGCTACGCTCAAATTGGGTGATGGCGTCCAGCACGTTGTTCAGACA
GTCGGCTTTGCTGGTGGGGCCAGGACGCGCGCAGACTACCTTATGCACAT
TCGGGAAGCGAGCGCACACTTCGTCAACATCACGCTGAGTATCGGGGTCG
TTGGGGTAGGTGCCAACAAAGATATGATAGTTTTCGTAGTCGAGCGTGGT
CGCCGCCAGCTCGGCCATATTGCCGATGACGCCCGTTTCATTCCACGCCG
GAACCATAATCGCTAACGGTTTTTCATCTGGTTTATACAGTTCGCGGTAA
CTCATTCGCGGGTAGCGGCGATAAACACTCAACTTGCGTTTAATGCGGCG
TACCCAGTATACGACATCTATAAAAAAATCGTCCAGCCCGCTGATGAACA
TGATGACCGCTAACGTTATCGCGATTACTTTTAAGCCGTATAGCCAGGTA
```
Contig 27 (500 bp)
```
AGCTGGATGCCCCCAGCTGTGGTCCCTTCCCTTCCCTCAGGGCAGGTTCT
GTCCCTCTTGCAGCCACCGTCACTGCTGTGGACAGGTCTGCACACCCGCC
GTCCACCAAGAGCGTGGCAGGTCCCTGGGCACGGGCCGGCTCCTGACGCA
CCATGTGTTCAAGGCAAGAGCACTGGACAGAGGGTCCAGACGTCCCCTTG
TCCTGCTCAGGCCTGGGCGGGGGCAGCCCTGGCGGGAGAGGCCCTGGGCA
TCAGAGCCTCTGTGGCCTGGAGCTTGGCGCCCTGCCCTCCCCACCTCCGT
CCTGCTCCTCGCCGCGCTGCACGGACCTCTCCCGGCCCCCCAGGCTCATT
ACTCTTAAGGACCCTAGCCCCCTATGCTGAAATGCTGTACCTCGTGCTTG
TTTTCATCTGTTTATTACCTTATCTTCATTCCTGCTTGATGATATCTGGT
TATTCTTTATTGATTATATATATCTTGTTCGTGTTTTTATAGGACACTGT
```
Contig 28 (450 bp)
```
AGTGCGGTCGGGCCGTCCTGACGCTCAACACCGTATTTCCACGCGACCGC
GGATTCAACCTGGTCACACGGACGCCATGTAGACATGTTCGGGGTTACGC
GCAGAGAAGCGACCTGCTCAACCGGCTGGTGAGTCGGGCCGTCTTCGCCC
AGACCGATGGAGTCGTGGGTGTAAACCATCACCTGACGCTGTTTCATCAG
CGCAGCCATACGTACGGCGTTACGTGCGTATTCCACGAACATCAGGAAGG
TGGAGGTGTACGGCAGGAAGCCACCGTGCAGGGAGATACCGTTAGCAATC
GCGGTCATACCGAACTCGCGAACACCGTAGTGGATGTAGTTACCCGCAGC
ATCTTCGTTGATTGCTTTAGAACCAGACCACAGGGTCAGGTTAGACGGCG
CCGGGTCAGCAGAACCGCCGAGGAATTCCGGCAACAGCCGGACGAACGCT
```
Contig 29 (450 bp)

FIGURE 6, CONTD.

```
TCAGGCCAATCTGTCTGGTCTCCAATGGGGACAATTTGGTTCTTTAGGCT
TCTGTCCAATGGTCCGAATGGCCCACTCCCCGGGCGCCGGCCAAGGGTCC
TCTGTGCCTCGGGTGGGCTGGCACGGACCGCCCCCAGGGTCGTGCCAGCC
CCGTCACCGGGGCCCAGAAGCTTCGGGCCTCTAGCTGGCTAGTCGGGCTG
CTGTGCAGGGGGGCTGCGCTGGGGGCAGAGGCGGGGGTGAGGTAAACCTC
CCAGCCGCCGGGGTCCCTGCCGCAGCCCTAGGCGCCGAGACGGTGGCTG
GGTCGGTACCGCCAGACCCGAGGGCCTCGGGGCCCGGGTGACCCCAGCTG
TCGCACACGCTCGCAGCTCTCTTGCTCATCAGGGCTCATCCCTCTGGACC
TCTCCTACTGCCCCACCTCACCCCGCCTGGACCCCATGAAGCCCCGCGGA
```
Contig 30 (600 bp)
```
TAAAACTAGCTCTAGTAGAAACATTTTATTTAAAAATAAAAAACCTGACT
ACGTCGGGAGTTCCCGTTGTGGCTCAGTGGTTGACGAATCCGATGAGGAA
CCATGAGGTTGCGAGTTCGATCCCTGGCCTCGCTCCGTGGGTTGAGGATC
CGGCGTTGCCGTGCGCTGTGGTGTAGGTTGCAGATGAGGCTCGGATCCTG
CGTGGCTGTGGCTCGGGTGTAGGCCGGCGGCTACAGCTCTGATGAGACCC
CTAGCCTGGGAACCTCCACATGCCCTGGGAGTGGCCCTAGAAAAAGGGCA
AAAGACAAAAAAACAAAAGAAAAAGGAAAATAAAATAAAAAAGACTATGT
AAATGAAATTAACGACTGCCTAGGGTGGGATTTACAGCATGGGAAGTACA
GCATGGCCGTGACAGTGCAAGGGTGAGGCGGGAAAATGGAAATAGGTTAG
GTGAGTTTCTCCTGCTATTTGTGATGTGGTCTGCTATCGCTTGAAGACGG
ACTGCAGTGAGATAAATATGTACAGTAAGCATCCGAAAAACCGCCAGAAC
GGCAAAACGAATGACTCCAAGTAAGAACCCAAAAGAGAAAAGGAAATAAT
```
Contig 31 (450 bp)
```
GCGCGGGCGTTCCGGCTGGGGTATTTAACGTGGTCACCGGTTCGGCGGGC
GCGGTCGGTAACGAACTGACCAGTAACCCGCTGGTGCGCAAACTGTCGTT
TACCGGTTCGACCGAAATTGGCCGCCAGTTAATGGAACAGTGCGCGAAAG
ACATCAAGAAAGTGTCGCTGGAGCTGGGCGGTAACGCGCCGTTTATCGTC
TTTGACGATGCCGACCTCGACAAAGCCGTGGAAGGCGCGCTGGCCTCGAA
ATTCCGCAACGCCGGGCAAACCTGCGTCTGCGCCAACCGCCTGTATGTGC
AGGACGGCGTGTATGACCGTTTTGCCGAAAAATTGCAGCAGGCAATGAGC
AAACTGCACATCGGCGACGGGCTGGATAACGGCGTCACCATCGGGCCGCT
GATCGATGAAAAATCGGTATCAAAAGTGGAAGAGCATATTGCCGATGCGC
```
Contig 32 (450 bp)
```
GGTGGATGCTGGCGATAGCGTCATCCTCGCTTATGCCGTGCAGCGGGCAA
GGATAAAGCGCGCGATAAACATGACCCGGCATCAGCCCCATGCCCGCAGA
GTACGGATTCACCTTGCCGGTCAGCGCCAGCGTGTAATGCGTGCGCCCGT
GATACGCGCCGCTAAAAGCGATGGTGCCGCTACGTTGGTGGCGGCGCGG
GCGATTTTTACCGCGTTTTCCACCGCTTCGGAACCGGTCGTAACCAGCAG
CGTTTTCTTGGCGAAATCGCCCGGCACCTTCTGATTCATAATCTCGCACA
GCTCCAGATACGGCTCGTAAGCCAGCACCTGGAAGCAGGTGTGCGACAGT
TTTTTCAACTGCGCTTCCACCGCGGCCACCACCTTCGGATGCAAGTGCCC
GGTATTGAGCACCGTAATCCCGCCCGCGAAATCAAGATACTCACGGCCTT
```
Contig 33 (500 bp)
```
ACGTGAGGTTTGGGGGAGGAAAGCGGGGGACGAGCAGCCCGAGAGGAGTG
GGGGCTGGCCTGTGGCTGATGAAACTCTGAGAAGGTTAAGAGCCCCCATT
TTTGTCTTCCTCTTTTTTATTATGGAAAATTCCAAATGGATGCAAAAGTC
CCAAACCTAACTGGACATCTTCTTGGTACCAGGAACGGTCAGGCACTTAT
GATGCACCGAGCCCCGAGGGAAAAACCCTGCCGTCCTGGAGCCCACGGTC
CAGCAGGGCACACAGGCCCCAGCCCGCAAGCGGCACGGCTGAGTCAGTGA
ATGGCGTGCCCTCTGGTCAAGGACGGGCACTCTGGACCCCAGGGAAGCCT
CTGAGGAGCCCCCTTCACAGCGTCAAAAACTGTTAACAGGGCCATGTTCG
CACCCCCCACACACGTGGTTCAGAAGCAGACCCCAGGCATCGTAATATG
TCATCCGTGAGTTCCCTGTGTGCCACCAACAGAAAGCCCATCGTCACGTT
```
Contig 34 (400 bp)
```
CGGCATCGATGTACATGGTACGCAAGGCACTCGTAAGGCCCCGAGCCTCT
AGGCCTTGTCATTGTCACGTGCTGCTCGCGGGGATCAGCAGCCAGGCTTG
TGACCCCGGCACTTTGACAGATAAGGACACAGAGAGGCCACAGCACTGG
TGTGAGGCCCACAGCCAGCAGCCCAGGGCAGGGAGGACTGGGTCTCACC
TGCCTCAGCTGGGCCCAGCCTCCCTGGGAGTCCCGGAGTCTCCCCAGCTT
AGGAGTGTCCCTGGAACCCTCTTCTCTCCCCTTCCCGCCCTCACCCGGAC
CCCCTGCCTCCCCCCCACCAACCCCCTCCCCCTCCTTCTTTCACCTTGAG
CTCCCCTCTGAGGACCTCTACTGTTCCTGCTTATCCTCCCCTTTGAGCCA
```
Contig 35 (500 bp)
```
TGGCGGTGAACTATGTCGTGCGTGAAGAGCATTTGTGGTCGGTAGCGCGT
```

FIGURE 6, CONTD.

TATATGCGGGAAGTTTAGGCGAACTGGACAGCCTGGGTTTATCCGGTAGC
GAAATCCGCTTTCACGGTAAAACGCTGCTAGCGCTGGTGGAAAAAGCGCA
GACATTGCCGGAAGATGCCTTACCGCAGCCGATGCTTAACCTGATGGACA
TGCCGGGTTATCGTAAAGCGTTTAAAGCGATTAAGTCGCTGATTACTGAC
GTGAGCGAAACGCATAAGATCAGCGCCGAATTGCTGGCATCGCGTCGGCA
AATCAACCAACTGCTGAACTGGCACTGGAAACTGAAACCGCAGAACAATT
TGCCGGAGCTGATTTCCGAGCTGGCGTGGTGAGCTGATGGCGGAAGCATT
ACACAATTTATTGCAGGAATATCCGCAGTAAAATCTTCCGAAGCCGGACT
GGGCGCGCTCAGCGCCACATCCGGCTTCGGCAAACTACAAATCCAACACC
Contig 36 (500 bp)
GATTTCACAAGCCTGACCCACGCGGAAATGCGCTAACAGCGTAAAGTCGT
GCGGCCAGAATTTTTCGTCTCTTCGCTTTGCGTCAATTCAAAAGTCAGC
GCTACGCCATCAGCATCTTCATGATGTGATTTCAGCGTCCACGGCAGGTT
GCGGGCAAAACCGTGCGCAGGCAGACCTTGTTGTGCCGCCGGACCAAACC
ACGGCCAGCAAACCGGTACGCCACCGCGAATAGCGACGCCATTTTTGAAC
GGTGTGTTGTTGCTCAACCACAGAACTTCTTCTTCACCCGCAGGTTTCCA
CGAGAGAAGGTGTGCGCCCTGTAATGCAAAAGAGGCTTTTACCTGGGGAT
GATCGACCACAATGAGGTCCAGTTCATCCAGTTTACGACGGGAGAGGACA
GGGGAGATTTGTTCGATGACCGGAAGGGCAAAAATTTTCTTAATCATGAC
GCAGTCCTTTAACTTCATTTTATCAGGTAAAAAAAAGAGCGACCGAAGTC
Contig 37 (300 bp)
ACCTGATCAGGCTCTGCACTGTGTTCATCAGCGGAGCCGAGATATTTGAC
CGCCCCATGCATAACGGAAAGGCGTGGGTAAACCCCCGGGCGCGTTCCTT
TATCAAGATGACGTTCGAATATTCCGGCAGGTGCAGTTTGTTTATTCCAG
AAAGGCGTTGAGCGCGTATGAATATAATTCTGTGGGATTTGAAGCATCCT
TTTCCCTCCTTCGGTGAATGCGCTGAAAACGGCTTATTCCAGCCGGTTCA
GGGTACGCCTGATAATTTGCATTTTAAATACCATTTATTGGGTACTTTTT
Contig 38 (450 bp)
ATCCTTTTGGGGTCTGGCAATTACGCAATAAAGAAGGCCCCCATGCGATT
AAAGTCACCGGCCCACTGTCGTCTAATCATGGAGAAATTGTCCATCAGTG
GGGTCTCGATGGGCAGGGGATTGCTCTGCGTTCCTGGTGGGATGTTAGCG
AAAACATTGCCAGTGGTCATTTAGTGCAAGTGCTACCGGAATATTACCAG
CCAGCGAACGTCTGGTCCGTTTATGTTTCAAGGCTGGCGACGTCAGCGAA
AGTGCGGATAACGGTAGAGTTTTACGCCAGTATTTTGCCGAGCACTACC
GGAATGTTTCACTGTTGCATGCCTGATTTATGATTCAATTATCGGGTTGA
TATCAGTTTAAAACCTGATTTTCTCCTTTCTAAGCCGCTACAGATTTGGT
AGCATATTCACCTTTAATCGCGCATGATCTAAAGATAATTGAAGAGGTTA
Contig 39 (450 bp)
AATGTACTGGCAAAAAGCCAATGGCGAAGCGTGGGGAACGTTACATGCTC
TGCTGGCGGATATTAATAGTCAGGGTCAGGTGCAGATGGCGATGAACGGC
GGCATCTATGATGAAAGCTATGCGCCGCTCGGTTTGTACATCGAAAACGG
TCAGCAGAAGGTGGCGTTAAATCTCGCTTCAGGTGAAGGGAATTTCTTTA
TCCGTCCTGGCGGCGTGTTTTATGTCGCGGGAGATAAAGTCGGCATCGTT
CGTCTGGATGCCTTCAAAACCAGTAAAGAGATTCAGTTTGCGGTGCAGTC
AGGGCCAATGTTGATGGAAAACGGTGTAATTAATCCGCGTATTCATCCCA
ACGTCGCCTCAAGCAAAATTCGTAACGGTGGTTGGGATTAATAAACATGG
GAACGCCGTGTTTTTGTTGAGCCAGCAGGCAACAAATTTTTATGATTTTG
Contig 40 (400 bp)
GACATTAATCATTTCAAAATCAAAGCCCCGGTTTTCCATCGCCCGTTTGG
TGGCGTGGCACTGAACGCAATCGTTACGAGTGTAAATAGTAATGCGCATG
ATTCGTATTTCCGTTTAAAATGAAGATACGGCGCGATGATACGCGTCGGG
TTGTCTCTCTGTTGATACAGAGATACTAGATGTAGTTGAAAAAAGATTCA
ACCACACAATATATAGCCCAGTAGGGGTCGAAATTACCCTGGATATGAGC
GTGACGGGGTAGGGGATTTTTGTGATTCACCAGGCAAAAAGAAACCCCG
AAGACAGGCTTCGGGGTCAAAGACGCGTATTTATTATCATTTTTGCACTA
CGATTTGCGCATGCTTAACAGTGCGCCGATTAAAATATCTACCGCAGCTG
Contig 41 (500 bp)
GCAAAATCACGTCCGCGACCTGGCGTTGTCGCTGGGCCATATTGGCAAAG
GAGCTGGATTGCGGTGCCTGCAAAGTGCCCTGAATAATGCCATTGTCCTG
TACCGGGAAGAAACCTTTCGGAATGAACACCCACAGCAGCACGCTAAGCA
GCAGCGTGCTGAGTGCCACGCTTAAGGTCAGCCACGGATGATTCAGCACT
TTCGCCAGTCCACGACCATAGGCGGCGATTATCCTGTCGAACATTTTTTC
CGAGGCACGGGAGAAGCGGTTCTGTTTACGCAACGACTCCTGGCTGAGCA
TCCGCGCGCACATCATCGGTGTCAGGGTCAGCGACACCACCGCTGAGATC

FIGURE 6, CONTD.

AAAATCGCTACCGCCAGGGTAATAGCAAATTCGCGGAACAGTCGCCCGAC
GATATCGCCCATAAACAGCAGTGGGATCAACACCGCAATCAGTGAGAAGG
TCAGCGAGATAATGGTAAAGCCGATTTCACCTGCGCCCTTGAGCGCCGCC
Contig 42 (400 bp)
AGCTATCTACGGCAAAAGGCACGGTAGTCAATTTCGTTGTTAAATACATC
AAGCGTTTGGCGCCGAAATACCATCTGCCAGATGCCATTTCATTTCGTAG
CGCACTGCATAACGGCTACCGGATGCAGTACGTCAAACCCGAACTGGGGC
CGGAAGGATTTAGCTTTTCTGCAATACACCGGCGGCACCACTGGTGTGGC
GAAAGGCGCGATGCTGACTCACCGCAATATGCTGGCGAACCTGGAACAGG
TTAACGCGACCTATGGTCCGCTGTTGCATCCGGGCAAAGAGCTGGTGGTG
ACGGCGCTGCCGCTGTATCACATTTTTGCCCTGACCATTAACTGCCTGCT
GTTTATCGAACTGGGTGGGCAGAACCTGCTTATCACTAACCCGCGCGATA
Contig 43 (450 bp)
GATTAGCGCCAGATGCTCGCCATCGAAAAGTTGAATCAACCCCAGCTGCG
GGTAATAAGTGCGCGTACGAACAAATTCAGTATCCAGGGCTATCGCCGGA
AAGGCACGGACGGCTTCACACAAAGAAGCCAGCGCATCGTCCGTGGTAAT
CATTTGGTAATTCAAATTGTTTTCTCTTTAGTGGGCGTCAAAAAAAACGC
CGGATTAACCGGCGTCTGACGACTGACTTAACGCTCAGGCTTTATTGTCC
ACTTTGCCGCGCGCTTCGTCACGTAATTCTCGTCGCAAAATTTTTCCGAC
GTTAGATTTCGGTAACTCATCACGAAACTCCACCAGCTTCGGTACTTTGT
ATCCCGTGAGCTGACGGCGGCAAAAAGTCACCAGTGACTCTTCGGTAAGC
GATGGATCTTTTTTCACTACGAAGATTTTCACCGCTTCACCACTGGAGCC
Contig 44 (750 bp)
GAGCAGCCCGCGTGATGACAGGCATGCGCCCGCGTCGGCTCTCTCTCTCT
GGTGCACTGAGTCACAGGATGGCGGCGGTGGGCGCGGTGGTGGAAGCGGT
CCTGGAGGGCTCGGGAGGGAGGATGCGCTCAAGCTGGCTCCCCGTGGGGC
TGGCCCGGAGTAGCCTCCGTGAGGGCACCGTGTCTGCTCCCAGAGCCCGC
TCCCCGGCCTGCCCTGCCTCCCTTCCCTGCCCCAGTTCCCCCGGAGCCCC
TGGATCCCGATGGGAGGCGCCCCTGGGGAGAGGGGACCAGGGAGGGGCCC
AGAGCTCTGAGGCCACCAGACCTGGCCAGGACCCTTCGTGGGAAGAAGAG
GTGGGCCCCAAAGGCACCTAGAGAGAGGGAGGCTCTGCTGGCTGGGGGGC
CTTCCAGGCGGGGCTTCCAGGCAGGGCCAGTGTCCTGGGGGCTGGAGGGA
GTCCCTGGCTGCTGGGGGGCGGCAGGAGCACCTGGGGCGTCTGGGAAGAG
AGCGGGAGGAGACTGGAGCCAACTGGGGGGACAGAGGAGGGGTCCAACCC
CAGCGGTGGTGTTGGGGGTGCTGGTGGTGGAGGCCCTGAGAGGCTGTGCT
GGGGGGCAGAGCGGGTGCTGGGAGGGGAGAAGGGGTCCCCAGGGCTCATG
GGCCCTTCGCAGCAGTGGCAGTTGGGGTGGGTGGCTGTCTCTAGGGCTGT
ACCACGGTGGGTGCCTGGAGAAAGAGGTCCTACCCCTAGTCTTTGCTGCA
Contig 45 (300 bp)
TGGGGACCCCACTCCAGCCCCACTGAGTGACGCGCCCCCCTGTGGTCCCA
CCGCCAACCCTGCCTCACACCAGAGGGGCTGTGGCCACACCTTGTCCACA
GCCTGTCCCTGAGACCACGAGCCCCCGGGCTCAGCCCCCTCCTCACCCCT
GGACCGAGGAGAAGCCCCCACCTGGGCTCAGCTCTTGGAGCTAAACTTCC
AGGAAGGTTCTGGTGCCCTCGGGTCTTAGAGCATGGTGGGGAGGGGGATG
CTGGTGGGGGCGCAAGCCCTCCCCACATTTCGCACTCGACCCGGTGGGNG
Contig 46 (300 bp)
CCGGCTAGAAGCCACGAGAGCCCCCAGGCCCCGCCCGACGTCTCTCCTGC
AGGGATTCGGCAGCCCTGGGGCCACAGGGCCTGAGCAGACCTTGGGGTTC
CGGTGTGACTCCAGCCAGGGTCCCTACTGTGTAGGCACCAGGGCAGAGTC
AGCCCTGGGACCATGGCCACAGCTGCTCCCGCCTGAGCCGGGCCCCCCGC
CCAGGCTGGGCCCCCTCAGTGCACTGTCCCAAGCCAGCTGCTCTCCCCAC
CTCCACCTTCTCCATCCAGGTCCTGCCCCACGGCCTTTGCTCAGGCCCAG
Contig 47 (500 bp)
TTGACTGGCACTAGCACGAGCTCTGTACCCGGGGATCTGGGCTCGGGAGA
AGGGAGACCCCCCACCCGGCAGGCCGAGGGCGCTGTCACACCATGACTCT
CAGCCTTCCCCACCCGACGGACAAGAGTGACCCTCTCCCAAGCCCCCACT
CACCCAGGACCGCACACCCCGTGAGTCCTGCGAGTGGGGGCGGCTCAGGG
GCCCCGAGTCCCAAAGGAGTCTGCTGGCCCTGGGGGGGAGGGGAAGCAGC
AGGGTGGTCACGGGTCTCCCTGGTTGGCAGGACCACAAGCTCAGCCCGCT
GCCTCCCAGAGGGCAGCCGGACACCAACCAGTCCGGGACCCCACGTACC
TCAGCTGCTGCAGGTGCCCCTGCCTGTACTGGTGCCAATGGGGCCGCTGG
GTGCTCCCATGGACAGCTCGCCACTCATCCCAGCCGCCTACCCCCCTTCC
GGGTCCAGTGTCCGGCCGGCCACCCGCCTGCCCAGCCCTGGCCTCCTCTC
Contig 48 (500 bp)

FIGURE 6, CONTD.

```
GGGGTTGCCGCAGGCTGCTGTGTAGGTCGCAGACGCAGCTTGGATCTGGC
GTGGCTGTGGCTGTGGCTGTGGCTGTGGCATAGGTCAGCCACTGCGACTC
CGATTTGACCCCCAGCCCGGCAACTCCCACATGGCACAGGTGCAGCAGGG
AAAATAAATAAATGAAATAAAAATAGGTGAAGACAGTGGATTTCATCTCT
TGGGGTTGCGGTAAGCTCTACACAATAGGGAGTTTACCATTTTACCTGTT
TCAAGTGGCACTGAGTCAGCTCACAGTCCTGAGGGCCCACAGATGCCGTC
TGCCTGGGAGATTGTTCCTCTCACCACACTGCCCCTCTGTCCCCACTAAA
TACTCACTGCCCTCCCCGTCCCAAGGGCCCCTGCCCCACCCTCTGCTTCC
TGTCTCTGAACTTGCTGGCCACCAGCGACCGTCTGGTGACCTCACTCTTC
GGCCCCATTTGTCGCACACCCCACCTGGCCTCTCCCCGGCATGGGCAGAN
Contig 49 (600 bp)
GGGATATTTGGGGGCATATTTGGGGGGGAGATCCCCACAAGGCATTTGGG
GTTTGTGGTTTGGAATGCCCCCGGGCCCGATGGAGGGGGCCGGGGAAGAA
TCTAAGCCTTACTTGGGGAGGGTTGGGCCCCGGGGCCCCGGGCCGGAAAT
GCCCCCAAGACAGAAGGTGTACAAAATTTCTCAAAAGGGTGACCCTTAAT
GAAACGGGTCCCGGTTGGAAAGAGGTCACCAGGGTGGATTGGTGGCACCG
CAGAATTTACGACATTTTGGCTCTCTTCCAATGGCCGGACGCCTGGGGAT
AGGCGCCCCGTGGACGGCGGGGTCTCGGGTGGGACGGGCGGTCAGGGGT
CGGTGACGCTTGGCCTCTCTGACCGCCTCCAGCTCCTTGGCGAGCGTGCG
AGCGCGGCGGGCGCGCAGGAGGGCCGCGCAGGCCCCTGCGCAGGCGTTGG
GCGGACTGCTTCCAGGTGTCATAGCGGAAGAACTTGCCCACGGGGTATCT
GGGGAAGTTGTCCTGAGAGGGGAAGGGCCCGTCAGGGGGGGGCCTGGCCC
CCCAGCCCCTGTCCCAGAACAACAACCTTTGCGGGGTCCTCCTGCCTGCC
Contig 50 (179 bp)
ATCTTCATATTCATGCAGAAGACACTCTCCTGCCTTTCTATCTTGGGGAA
AAGGACGATGTCACTTATGCAATAAAGCCCACTTGCTGGCCGGGGCTTGA
CATTATTCCTTCCTGTCTGGCTCTGCACCGTATTGAAACTGAGTTAATGG
GCAAATTTGATGAAGGTAAACTGCCCACC
Contig 51 (500 bp)
CTCGGGCTGCTTCCAGGGGGCCTTGGGGAGCCATAGAATGCTATGGAGCA
AGAGAGTGCTATGGTCAGACGACTTTGGGGGAAGGTCTGGGAGAAGAGGG
GTGACTGGCCACTGTGATAAAGAGTGGGCGCTTCCTTGAGATAACACGGT
GGGCAGCCGAGGTGGACCTGTGCAGGTGGAGAAGGCCTCCTGCCGCGGCC
AGTACGTGGCTCTGGGCTGCCGGACACGAGAAAGCCCACCTCCACGGCTG
CCTCCAGGCGGCCCTTCCTCTCTTCACACCGCCGGGCCATGCCCAGGTGC
AGGTGCCATCAGAGGGTGCTCAAGAGAAGCTCTGGGCTGGGGTTGTCCCA
GGTCCCGGAAGCCCCGTGTCCCAGGGGCCACCTGAGGAAGCGTGGGCGCA
CAGAGACTGTCCCTCGGTGCTCAGAGAGGGTCCCGTCCCCACGGCAACGA
CGCCCAAGGCGGAGGTGGTCAGAGGTCTTGGGAGGGAGGATGGCCGCGCA
Contig 52 (900 bp)
TGTGTTGCACCTGTTGCTGCCTGTCGACTCTAGAGGATCAATACTCCTTA
CATAATTAAGGAGAACAAAATGGAACTTAAAAAATTGATGGGACATATTT
CTATTATCCCCGATTACAGACAAGCCTGGAAAATGGAACATAAGTTATCG
GATATTCTACTGTTGACTATTTGTGCCGTTATTTCTGGTGCAGAAGGCTG
GGAAGATATAGAGGATTTTGGGGAAACACATCCCGATTTTTTGAAGCAAT
ATGGTGATTTTGAAAATGGTATTCCTGTTCACGACACCATTGCCAGAGTT
GTATCCTGTATCAGTCCTGCAAAATTTCACGAGTGCTTTATTAACTGGAT
GCGTGACTGCCATTCTTCAGATGATAAAGACGTCATTGCAATTGATGGAA
AAACGCTCCGGCATTCTTATGATAAGAGTCGCCGCAGGGGAGCGATTCAT
GTCATTAGTGCGTTCTCAACAATGCACAGTCTGGTCATCGGACAGATCAA
GACGGATGAGAAATCTAATGAGATTACAGCTATCCCAGAACTTCTTAACA
TGCTGGATATTAAAGGAAAAATCATCACAACTGATGCGATGGGTTGCCAG
AAAGATATTGCAGAGAAGATACAAAAACAGGGAGGTGATTATTTATTCGC
TGTAAAAGGAAACCAGGGGCGGCTAAATAAAGCCTTTGAGGAAAAATTTC
CGCTGAAAGAATTAAATAATCCAGCGCATGACAGTTACGCAATGAGTGAA
AAGAGTCACGGCAGAGAAGAAATCCGTCTTCATATTGTTTGCGATGTCCC
TGATGAACTTATTGATTTCACGTTTGAATAGAAAGGGCTGAAGAAATTAT
GCGTGGCAGTCTCCTTTCGGTCCATAATAGCAGAACAAAAGAAAGAGCTC
Contig 53 (450 bp)
CCAGCCACCAGCTGGACCCTCCCGGAGAGGGGCTGCCTCCTCTTTCCCGC
CCAGACGCCCCCCAGCAATCTGTGGCCAAGAGGGAGTGATACCGAAGATG
GCCACATGGGGCGCCAGCCCACAGGGAACCCCAGGAAGGCGCTGGACCG
TCAGGAGTCAGGGCTGCTGTGCACCCATGTGGCCTGGGGACTTTCCACAG
CCTGGTGGAGATGGCCGGGCACACCGCTGCCTCGGGGGAACGTGCACACG
```

FIGURE 6, CONTD.

```
GGTGGTACATGTGGCCGGAGCCCAGGGCACAGGGTGAGGGGAGAAGGGAG
CATGCGGGTGCAGACTCGGAGCCCGCGCGTGAGGTGCTGGGTCCTCAGGA
CACGCTCTGGGAGTGGAGGACCCCCATCCACGCCCTCACCCAGTGTGTGC
CCGCCTGCTCCCCGGAAACCCTCACAGACACGAGGGCACACCCAGCCCC
Contig 54 (1133 bp)
ATGGCGCTCATTAGAATTCGACCTCGGTACCTTGGGATCTTTTGACCCCT
ACCTCACGCCATCTACAACATTTACCTCCGAATGAATGAGAGACACCAAA
AGCAAATTCATAGAAGAGAAAAAAAGGTAACCTGGACTTTAAAAATGTAA
ACTTCTGCTCTTTAAAAGGCAGTGCTAATGAAGTTCAAATACAAACCACA
GACCATAAGAAAATACTTGCAAATCTTGTTCTGACAAAGACTAGTGTTCA
GAACATACGACGATCAGGGAGAGGAAAACCAGCAATCCTATAAAACTGGA
CAAAGAATTGGGGGGAAAAAAAACCCACTTGGCCAAGAAGTTGGTAAATA
AGGCCATGAAAACATGCTCAACATCATGAGTCATTAGAAAAATGCAAATT
AAAATTATAATGAGATACTACTACACAGCTATTTGAATGGATAAAAAATG
TTTTAAAAACTGATTATACCCAGGTTTGGCAAGAACATGAGAAACGAGAT
TTTCACACACGATTGGTGGAAAACAGAAAATGGTCCACCCACTTTGGAAA
AGAGCTGGGCACTTCCCTCAAAAGTTAAACATACATCCAGGACCTCACAC
AGGCTTTCCACCACAGGTGTTTATTCCAGAGACATGAAAGCGCTCATCCA
CACAAAGACTCGTAAATGAAGGTTTATAGCACCGTTTGTGGCCCGAACTG
AGAAAACCCAAATGACCTTTAACCAGAGAATATCTAAACAAAATATCCAT
TCACATTAATCACCCATAAGAAGGAACGGGCTATGGGGACGGGAACCGTA
TTGAAGAGGGTCAAAATACATACGCAGCATCAAAGAAGCCTGCCCAAAGG
ACACACACTGCAGGGTTCCATGGACTGAAACTCGAGAAGGTGAAAACTCG
CCAGCAGTGACAGAGAGCAGGTCCGAGATCAACCTGATGTGGAGGAAAGT
GAACCCTCGTGCGTTGTTGGCAGGACTATAAACTGGAGCAGCCCCTACGG
ACAACAGTAGCCCGGGCTCCTCTCCTCCATCTCCCTGGGGAGCCTGAGCC
TTGAGACGCTGGGGCAAGTGCACGGCATGCTGCCTCACGTGGGGCCCCGG
TGAAAACACCTGGCAGCTGGGGAAAGAATCGTA
Contig 55 (735 bp)
TACTGCCTGTCTCTATGGACTTGACTCCTCTCGGGACTTCATGCGAGGGA
TCTTACAGAATTTGTCCTTTTGCATCTGGCTTGTTTCACTGAGCATCGTG
TCCCCAAGGTCCATCCATGTTGCAGCCTGTGTCAGGATTTCCTTCCTTTT
CAAGGCTGAATAGTACTCCACTCTGCGGATGGACCACGTTTTGATTATCC
ATACTAGTAAATCCATACTAATAACTTGTTCACTGAAGCCCACAGCTTAT
GCTACCTTCCGTGGGCTCCTCCCTGCCCTGTCTACGCCTTCTGCTATA
GCCCCATCCCCTCTCATCCAGGCCACGCCTCCTGTCCCTGGACACTGTC
CCAGAAGCCAACTGCCCTCTGACTGCTGCTCTCGCGTGACGGAGGACAAG
GCAGGCTCAGGGGTCCACGGGCTGGGGCCCCAGGGCTCCCCATGGCTGGT
GCCCCTTCCTGATTCCAGAAGTACAGTGGCAGCACCAGCTTTCCAGCTGC
CCCACCTTCTGTCCGCAGGTGCTCGGGTGGGGGCAGGTGGGCAGTGATG
TCACCTGCTGTAACCACCCTACCGTCGCTCATCCCTGTCCAGGAGGTCAC
GGTGACCTTGGCAAACATTCTGAACAACACACACCTCCCTCTGCTTAGAG
GCCGGGGGCCTCCCCGGGTGACTGGGGGCACAGGCTGACCCCAGCCTGTC
TCTGTTCTCTGAAGGACATGATAAGTACTGCAACA Contig 56 (500 bp)
AGGAAGAACAGGAAACAACGGGGTTGAGGAGAAGAAACGGGTGTCTGGCA
GGGGCACGTGCCAACGGTCCACCGGGTGCTGCCGCGCTGCGGCCTGGCGC
CAGAGGGGGCAGCTCCGCCCCTCGGCCGCGCCCTGCCGCTTGTGCTGGC
TCGCGGCTGGGCTCTGCTTGGCTGGGTTACAGCTGGGTGCAGCCGCAGGC
TGTGGTGGGTGCCGCCGGGTCAGCCAGCCCGGCCCCACCCGGCCCGTCTC
GCCGGCCTGGCCCGGGCAGCCCTCCTGCAGTCGAGGAGTCGCCCTGACGG
GCTGATTGGTCCACAGCCTCAGATGCAAACCAGCCCCACGTGCCTGGAGC
CAGCCAGCCCGGGACACCCTGGTGGAGGCAGGAAGGCAGCAGCCTGGAGA
GCCGCGCCGGATGATGCTGCGGGGAAACCGGGCTCCCGCCGGGGCGCCC
TGGCTCTGGCCAGGCTTGGCTTGAATGCTGACGTGAGCGGTGGCCCTATA
Contig 57(500 bp)
TGGCGTTGCAGTGGCTCTGGCGGAGGCCGGCGGCTACAGCTCCGATTGGA
CCCCTAGGCTGGGAACCTCCATAAGCTGTGGGTGCAGCCCTAAAAAGCAA
AAAACCCCAACATATATATATATATATATATATAATTATGGTAAAATACA
CATAAAATAGAATTTACCTTCTTAATAATTTTCAGTGCACAATTCAGTGG
CACTAAGCACATTCATGCGGCCGTGTCACCTGCTCCAGAACTTTCCATCT
ACCCAAACGGACTCTCCGCCCCATGGAACACGCCCCCTGCCCCTCCCCG
GCCCTGCCCCGCCAGCTCCTCCCTGTGTCTGTGGATCCGGCTCCTCCAGG
```

FIGURE 6, CONTD.

```
GACCCCGTGCGTGGGCTCACAGAGTGTGTGTCCCTCTGTGACCGATCGTC
GTGTCCCCGAGGCCCGTTCTGTGGCAGCTGCGTTATGACCGACTACCTTC
GAATGCTCAGTGACTGCCGTGCATTGGACACGCAGTCCGCTACCCTTTTC
Contig 58 (550 bp)
TGCTTTCTGTGCCCCCCTCCAGCTTGGGACCCCAGCAGGGCAAGGGGTGT
ATAGGGCTTAAGGAGGCAGGGGGCGTCTCCTCCCGCTGGCTGCCCAGAGC
ACCCCCAGCCCCGCCTGCCCCTCGTCCATCTCCAGCCTGTCCTTTCCTGT
GCCCTCCCTGTCCCGGGCGGGCCGCACACTGGCTTCCACCTCCCCACCCA
ACTGGCGGCCCGGTCCTTCCTGCTGAGGCACCCCGAGGTCCCCGCTGCTG
GGGACCAGCTGGCAGGTGGGTCCCACTGCTTTCTCAGCGTGGGCTTTGGA
GGGGGATCTGCACATACCATCCCTTCAGGCCCCGTGGGGAGCCTGGGGA
CCATCCGGGACCCCTGTGGGCAGGCCCAGAGGACTGCCAGGAAGAGACCC
AGGGGACCAGGCAGCTCCCAGGCCTCTCAGCTTCAGGCCAGGGGAGCCCA
CCCCCAGGTGGCAGGTGAAGCCAGGCCCCCAACCCACAAAACTGCCCGCA
GGGAAGTAGGAGGGACAGGAGGAGGGGAGGCCAGGCCCGGGCCGCCCTTG
Contig 59 (800 bp)
TGAGGAGCGCAGGCCCAGGCCTGAGTGTGCCCAGCTTACACCCCTGGCAG
CTTCGTCCCTCCTGGCCCTAACCCCCATCCTACCCCAGCAGCAGGGGCTC
CCCCGGTGGGGCCTGGTGAGCGTCTGACTGGGGTTTGGAGTCAGGTCTGC
TCCAGGCTCAGCCCCCATCCCCAAGGGTGCCCTGCAGCACTGCTGCCCAC
CCCCTAGCGCCCCCAGACCTTCGCCCCTCCAGCCTGGATGTACCCACGGA
CCCTGAAAAGTGGGGCTGAGCAGGTGCCCTGGCTGGAGTCCCCCTGACTT
GGGGCTGGCCAGGCTGCCCTGGAGGGGCTGTGGGGGCACAGCCTGCCCCA
GGGGCCCGCTGGGCACTGGCTCTGGAGCTGACGACAGGCAGGCCCTCTCT
TCCTGGCGGGGCCACACCCTGCCCTGGGGTTTGGGGCCAAGGCGGGCACG
CCCCATGTCAGGCGGGGGCGAACCAGGTAATTACAGCCTGGCAGCCCGCT
CCCCAGACCCCCAGCCCCGGAGGGCCCCCACCCAGGCTGTGCCACCAAGA
CCTGGCATCCAGGGCCCAAAGCAGGTCAAGGGCAGCTGCTACAGATTCTT
TTAAGTTGAGACAGAATCGACACATGACAAGTTCCTGGTTTTAGGTACTT
CGCTGCCGGGGCCGCCAGTCAGTTTAGTGACCCAGCACACCCCACACAGG
TACAATTGCTCTTCTCAAAAGAGGCCCCTGAGAGAGCGCCTGTCTTGGCT
CAGGGGTAATGAGCCCAATGGGTATCCATGAGGTTGCGGGTTCCATCCCC
GGCCTCGCCGCGTTGGTTA
Contig 60 (500 bp)
GGCTCAGGAAGCGCAGGGGCAGCGTGTGGGGCGACGGGAACCATGGGGGT
CTGTCTTCCCGCCTCTCCTCAAGCCCACCGCCCTGCTGCCCACCTCCGAC
TCTGCAGCCAGCATGCCGGCTAGAGCCCCTGTGCACCCAGCTGGTGGCCT
CTGGCTAAGGGCAGTGCTGGCTGTGGACGCGTGTCCCCTCCCCAGCAGCC
CAAGGGTCCCATCTGCCAGGCTGGTGGCTGAGGTCTGCCCTGTGTGGTCC
TTGCAAAAACCCCGCCCTCTCCTGCCCCTTGAGGCGTGAGGGAGACGCGG
GCTGGGCGGATGCCCTCGGGCACAGCCGCCCGCGGTGGCGCCCTGTCGAG
GAGGGGGCTCCGACGTGCCCTGACGGCCCTGGCCGGGCGGAGAGGGTGAG
GCCACCTCCTGGCCACGTCCACCCAGCTGCCACGCCGCCTAGCCAGTGGC
CCGGGGCCAAGTCAGCAGAGCCAGGCTTCCGACAAGCAGAGGCTGTAGGC
Contig 61 (700 bp)
GATGAGGAAGCCGCTGCTCGTGCTGCTCGTCTTCTTGGCCTTGGCCTCGT
GCTGCTATGCTGCTTACCGCCCCAGTGAGACTCTGTGCGGCGGGGAGCTG
GTGGACACCCTCCAGTTTGTCTGCGGGGACCGCGGCTTCTACTTCAGTAA
GTAGCTCAGCGGGGCACGGGGGCGGGGCGGACACAGCAGGTGCTCCATCG
GTGCTGCCCCGGTACCTGTGCGGGTCCTTCGGGATGGATGGTGTGGGGGA
CGGGGGGCGGGGGCGGCCAAGGGAGGACCTCTCCTCCGAGGGTCTGAGA
CTTCAGACCGGGGCGCCCTGGCCGTGCGCATTGATTGGCACCTGCCATG
TGCCTGGCTGGGGCTCACACCCCCTGACGTTCCTGCAGCGTGACTCGAAA
CGGGAAACCGAAGGGACGGGTGGCACGGGGTGGGGAGGCAGACCGTGAGT
GGCAGGCGTGCGAGGGGTTCTTTCGGGCGGGGTGGCCCAGGCAGGCCCCA
CAGGATGACAGCCTGTCCCCTCCTGCTCCTCCTTGACCTGCCCACAGCCA
GGGCTGCAGGCACTGACATTCACCCATGGTATTGTGGTGCCTTGACGTCT
TGGCAGTGGGCATTGGGTTCATGGACTGTTTGGATTGAAAAGTGGGAATA
AGATGGGGTTTGAAAAACCCAATTAAGAAATAAAAGGGCGCCCTGTGGGC
Contig 62 (300 bp)
TTTGAAAAATTTTGAGTCAGTGCAGAATTCGCATCTATTCCGCATTCAGG
CTCTCCTGTTCTCACCTTGCCTTAGTGCGGATCTTCTATAACCACCACAG
TGACGTTTTCAAGGTACTTTATTGAATAATAAGAAAAAAGTGCACACAAT
CATGTAGTTAACTTTCTGTGCTCTTTGCCAGTTTGAAGGGACCCTCTTTT
```

FIGURE 6, CONTD.

```
TTTCCTTTTTAGGGCTTCGCCGACGGAAGTTCCCGGGCTAGGGGTTGAGT
CAGAGCTGCAGCTGCTGGCCTACAGCACAGCTCTTGGCGGCGATGGATCC
Contig 63 (450 bp)
TCCTGGGCCACAGGCTGCAGCAGCTCACCTGGGGGCTGGGGTCTCGCTCT
GCGGATGGACCCATGAAGGCCGGAGCCAGGTGGGGGCCGAGACGGCAGGG
CAAAGGGTCTGCACACACAGCGTCCCCCCGACCCGGCTTCTCTGGGTTCT
TGGGGGGTTGGCGAGGCTTCTCTCAGTCTGGGTTTCCTGGGGAACTTTCA
AGAACTGGGAAGTCTTCCAGAAAGTTGGGGTGAGGGGAGGTACCCCCAAA
GTGCTGCTCCTGTCCCCATCCCCCACCCCGCTGTCCATCGGCGAGACCCC
GGACCGCCGTCTCCCTGCCGAGGTGTGGGGTCCCCCCCTCTGCCGGCCAG
GCTGGGCAGGGGTGAGCGCCCCTGCTCTGCACTCGGGACTCAGCCTGGG
GAAGGCGGGCCCCAGGAGGTCCTGGCCTGGACGGCAGTGACCTTCCACCG
Contig 64 (500 bp)
TGTGCATCCAACCCCAGTGGCCACGGGGGGTGACCCTCGGCCGGTCAGCC
GCCCGCGTCTCCCACGGAACCGGGCCTTGGCCTGAGGCAGAAGGACCCAG
GACTCCATCCCTGCCCCGGACTCTGCCGGAGGGTGCGGTCTGCACAGAGA
CCCTGTGGGGGTGAGGCCGGTCGGGGCTGGGGTTGAGATGGGATGGTCAG
GGCGGCCCCGCGGGCCTGCAGGAGGCTGGGTGAAGGAGGGGGCCCAGCT
CAGACGCCCCAAACCTAGCTTGGGAGAGCTGCAGCCCCGCCCCGTCAAT
CGCGACAGCCTGCCCACAGAAGGCATTCAAATGAGAGACAAATATTTGGG
CTTGAAGACTATACCCAGCCACGTCTCTTTGGGAGCCCAAGCTGCTCCCA
GGCCCTCATTTGGGTATTAATTGGTTTTCGTTTAGAGATTTGCATGCTTA
TCAATGGCCACTGGGCGGCTGGGCCTGGATGCGGTCCCAGGCTTTGTATG
Contig 65 (661 bp)
TCCCACGACCTGCCCCTCCAGGGCCACATCTGGCGACACCGTCGCAAGAG
TTGGACCGGCCTGGTGTGGCCACAGCCTCAGGCCTTGTCTGGCCGCCCAG
GCCGGCTCCAGGCTCCAAGGAGCTCCTGCCTGCCCTCCGGAACCCCAGCA
CCCCGGGCCCGCTTCCCCACCAGACCTGTTTTTCCAGGTCAAGGTCACAG
CTAATTTGGGCTTAAACTGGACAAGGAGGCCTTATCTGGAGCAGGCTCCC
GGCCCTTTGGCCTCTGCCCTGGTGGGGAGGCCTTCCCAGAGGCTGTGTGT
TGGCGCTGACCGTGCAGCCCTGAGCTTGAACCCGGATAAGGAGGGACCCC
ACCTGGGCTGGAGCCAGAGAGCCCTCGTTCCCCAGCTCCGCAGGGTTCTC
ACAGTCCCGCCCCTGCCCTGGGGACCCTGGACGTCCCCAGCAGGTGAAAG
GTCCAGATGCCCTCTGACTAGAGGCTCCTCCGCTGTCAGACATGCTCCCT
TCCCGCACCGAGGACGAGACCTCAGCAGCCCTGCGTGGCCTGGGGTGCGG
ACCCCAAGGCGTCTCTGAGTGTGTTCTAATGGGGAGCCGTGGGGCCTCAA
CAGTGGGGGTGGCACTTGGAGGGGAGCCTCCCCACAGCTGCCCCAAGATG
GGCCCTGGACT Contig 66 (500 bp)
TTTGTTGGATGAATGAAATCATGAGAAAGTGATTGGACCGCCCCGTTCGT
CCAGCTGCTTGCCAGCTGCTTTGTAAAGATGACCTCTCACCTTCTCAGAG
GCCTGGCCGGCCCGAGGTGGCAGTCAGCTGAGATGCCATGCTTGTTTGGC
ACGTGGGAGGCCCCTGTCCACGGCGTGGGTGCCTCTTGTGTCTAATCAGG
GTCAGGGGAGCAGCAGGTGCAGGGCACATGTGGGGCCGGGGCCGATGTC
TGGGGAGGGCGGGAGGAGGGGGTGTGCGGAGGCCGTTGTGGGGGTGCAGG
GGACAGACCCCAGCGAGACCCTCCCTGGCCAGGCACCAGGACAGGTGATG
GGGGGCCGCCTCCGGGGCGTGTGACAGAAGCCTCTCAGAGGAGGCCCTCC
CACGGTCTCTGGACCATCAAGGGACCGGGGCGCTGGGCCTGGGGGTCAC
ACCCAGCTGGCCGGCCAGCCCGGGTGGGGTCGGAGGCCCGGGCAGTTCAC
Contig 67 (550 bp)
GGGCAGGAGGGGCCCGGGGCTGGTGCGGAGGGTGGAGGTGGTGCAGGAGG
GTGTGAGGCAGGGCTCACTGAGCGTGCGCGGCTGGCTGTGCCCTAGAGTG
GTTAGCACGTGCCCCCACCCTCCAGTGTCGCTCTGTTCACCTGTGCCTGG
CTCACAGGTGTGGAAACTGAGACTCGGGTGTTGCATGAGCTTCCAGGATG
AGAATCAGCAGGCTTCCCAGGCAGGGCTGTGTCCGGGGCTCTGGGCTCTT
ACCAAGGAGGGGACACCCAGGGACAGCCCTGCTTGGGGGTGTCGGGCTGG
CCAGGCTGGGTGGTCCTTCCTGTGGCTGGCAGCCCTTGGCAGTCACCCCC
TTACCCTCAACTGCCCCTCAGCTGAGACACGACCTCCCTGCAGAGCCCTG
TCCACCCAGACACTCACTCGCCTCCTCCAGGAAGCCTTCCAGGGCTGCCT
CGCCCTGGTCTCAGCAGGAGACAGAGAGAGGGTGGGCCCAGGAGCAGA
GGCAGGCAGCCAGAGGGGAAGCCCAGGGGCCCTCACTCACCCCTGGGGCC
Contig 68 (500 bp)
TTTGCATTCAGCTCGTACCCGGGATCCTTCCCGGGGGCTCTGGGGGTGGG
```

FIGURE 6, CONTD.

```
GGAATGGGGGTCAGAGGCAGCTGTCATCTGCCTGTCCTACCTGCTCTCAC
AGGCTGGCCCTGGAGCCCTGGCCTCCTCCTAGGGGCACATCAGGTTTTGG
GGGAGGCCCAGCCCACCGTCCCACCTCCAAGACCACAGCTGGGAGCCTGC
CCCCCAAGCCTAGACCTAGTGGGGCTCCTGCCAGCCAGGCCCCCACCTTC
ATGCTGCCACCCACCAAGGTGGGACAGTGCAGCCAGGACATCCAGCTTCT
GGAGCTGCCCGAGGCTCAGCACAGGCTGGTACCCTAGGGAGCAGGTCACC
CAGGGCCGCCTGGCGAGGCCTGCGGGGACGGGGGGTAGGGTGGGCAGCAA
AAGAACCTCTGAGCTGGGCCGGGCGGGTCGGTGAGGGCCCGGGGCCGCG
GGCTGTGTGCGTGGCCCCTGAGCCCGTGCAGACGCAGACCCTGGGTGGGT
Contig 69 (550 bp)
TGTGCTGCTGTGGCTGTGGTGTAGGCCGCCAGCTGCAGCTCTGATTCGGA
CTCCTAGCCTGCGAACCTCCATATGCTGCTCTAAAAAGACAAACATAAAA
TAAAATGGGTGCGCTGTTAATTTGAACACTCTGCCTCCTCCAGAGACGAG
GCCGAAACAGGCCTCTCTGAAGGTCCCACCTGGCAGGGAGGAGGAGGCCA
GCCCCGTGGGGGGCAGAGAGAAGCCCGATGTCCCCAGACACACACGCACA
GGGACCGTGGCCCCGGCTGCCAGCCCCGCGGGGGGAGGGCAAGGCCAGAG
ACTCCCAGCAGCCCACAGGACCTTGGTGGCCACAGGACACAAACACAGGT
GACGGTGGGTGAGGCCTGGCCTTTCCCCCCTGGGCACGAGCACAGGACA
CACAAGAGCCCCAGCGTGCTGACCGCCACGCCAAGGAGCCTGGATGAAGC
TGGACACCGAGAGTCCACACTGTGTGATTAGGCTGACGTGAAGTTTAAGA
ACAAGCGGGTGGCTCAGCGCTTGAAGGCCAGAACAAGGCCGGGAGGGCAG
Contig 70 (1300 bp)
ATGTCAGGATAGTAACCTGGGGTGCTGCAGTGACAATGCCAGATCCTTAA
CCACTGTGCCACAAGGGAACTCCTTGACCTAGAATCCTATACCCACTGCA
AATATATTTCAAAAAAGGTAAAGTCCTGAGCAGAAAAGCAAAAATGGGAT
AATTCATTTCTGGAAGACCTTCCTTGTTAAAGGAAGTTTTTTGGACGTGA
TGAAGGTAGAAACTCGGAGGCACACAAAGAAAGAAAGAAAGAAAGAGCAC
TGGAAACGGAGCAAATAAAGGTAAAAATAAAGTTCATCTCTTTCTCATTT
TTTAATTGCTCCAAAAGATAGCTGACCTCTAAAGTAAAAAATAGTGGAAA
TGTAGCATATGTCTCTAGCGTAATTTAAAGTATAACTTATAGCAATGATA
GCCCAAATAAAGGAGGAATTGAGAATATACAGTTGCTGTGTTCCCATTGT
GGCTCAGCAGTAATGAACCTGGCTAATATCCATGAGGATGCAGGTTCAAT
CCCTGGCCTCACTCAGTGGGTTAAAGGATCCAGGGTTGCAGTGAGATGTG
ACGTATGTCACAGACGTGGCTCGGATCTGGCATTTCTGTGACTGTGGCTG
TGGTGTAGGCCAGCATCTGCACCTCCGATTTGACCCCTAGCCTGGGAACC
ACCATATGCTGCTGGTGTGGCCCTAACAGACACAAAATAAAATAAAAATA
AAAGAGAGAGAGAATATACCATTGTAAATTTCCTCACATGACACAAAGAG
CAATGTGATATTATTTGGTATATGGTGATTGATTCAAGATGTATATCATA
ATATTGATTCAAGATGTATATATTCCTTTTCTAAAAAAGAGATTTATACA
ATAAGGCAAGAGTGAAAATAAAGTGGAATGCTAAAGAATAGTTAATCCAA
AAGAAGGCAGAAAATGGGGAAAAGACATATAACAGATGGAACAAATAAAA
AAGAGCTAATGAGATTGTAAAATTTAATCCAAACATACAGATAATCCCAT
TAAATTTAAACACTCTCAACACATTGATTAAAAGAAATTGTCAAATTGAA
TAAACAAAGCAAGACCCAACTAGATGCAGACTATGAAAAACCCACTTCAT
ATAAAGACATGGGTAGGTTTAGAGCAGAATGATGGGGAAACCATGTCACG
CAAACATTTGTCAAAATAAAGCTGGTGTGGCTGTATTCATCTCAGACACA
GCAGACTTCAGAACAAGAAACACTGCAAAGGATGAAAGAGATACTGCATA
ATGATAAAGGGATCAATTTTCCAAGTGCAGGCTCCAAACAACAGAGGTTT
Contig 71 (500 bp)
ATGACCTCATACTGAATCGAGCTCGGTATCAGGGGATCTCTCAGCTGGGG
GGGAGGGCAATGGGGCATTTGTCTGAGGATGCCCCAGGGCAGGCCCATTG
GCTGGTTTGGTGCCCATGCCCCCCCCCACACCCCGGCAGTGCCCCCTGCTG
AGCCTGGGACCCCCTCTGGGAGTTAGGGATTGGGGGTGGGAACCAGGCTT
TGCAGTAATTCCAGCCCCCAGGGCCCTTCCCTCCCCGCCCTCAGGACCCC
CAGCCCCGCCCCACACAGTCTCCACTGTGACAGCCTCACCCCTTGGGTCA
AGTCCTGTCCTCTCCGGCCCCGCTGGGCAGTGGAGCCAGCTAGGTGAGA
GGCACAGGCCACTAGGGCGGTGGGCACTGCTGAGGACAGAGGGGCCTGGG
TGGCCTTGGACGAGGCCCAGCGACGCTGAGACAGTGAGCCAGGCTCCAGG
CTTTCCCAGGGAGGGTCCCTGAATGTCCACTTCTTGTGACATCGGGTGAC
Contig 72 (550 bp)
AAGTCCATTAGGGAAGGGATTTGTGCAAACACAGAGACAGGTGCAGGGCT
GGGCCAGCTGCTGGGCTGGGGGCTCCTCAAGGCGCCCGTAAACCCCTCCC
TGCCAGCCGCCTGCCGCCAAGGTCTGCTGTCCACCCCGGCCGGGCTGCTG
TGTTCCCGGCGTGTGTCCTGCGAACCCGACTCCCGTTCACCCCTGAGCAC
```

FIGURE 6, CONTD.

```
TGCCTGGAGGCCGGCTGCCCAGGCGGGACGGGCCCTCAGGGCTGGGCTGG
CTCTTGGCCTGTGTTTCATTTCTGAGCAGGTCCTTCTCAGTGGGGGGGGC
CTTGGGTGAAGCAGGCATGTGCACCACTGGGGCCCTGTCCCCAGTGGGCA
TCCTGGGCGCTTGTCTGGCCCCCAAACCCCCAGGCCGTGTGCATCATACC
TTCACCCTGAGCCCCAGCCGAACCCCGGACATGTGCTGGGGGACCCTGGG
CACAGGGGTGAGGGAGCAGTGGCCTTGGTGGAAGCCCAGCCTTGGCACCT
GGGGAGGGGGTGCATCTGGCATGCTCTGCTGTAACCAAGCCCAGGGCAGG
```
Contig 73 (950 bp)
```
GACGTGCAGTAGCCATGACCTCTACGGCCCCCACTGACCAGCCCGTGTCC
TTGTCCCGAGACCGACCCCTAAGCAATAGGATGCAGCAGAAGTGACAGAA
CGGCCTCCGCGATGAGGTCGCAGAGGGCTCTGGCTCTGACTCAGGCCCCT
CATCCCTCGCTCTCCTGGAGCAGGGCCAGGTAGGGGCCCCCAGAGACGC
CCTAGAGGAGGTGACGGGCAGCCAGCCCGCCCCAGGGAAGGCCTGGGGAC
ACCAGGGAACAGAACGGCACAGGCTCCTGGCACAGTCTCCCAGGAGCCCC
CTGGTGGCACAGAAATCCTGACCGGCCCAGTGGAGGGGGCTGGGGCGGGG
CTCGGGGAGGAGGGACTGGGTGAGGCCGTCTGACTCCTGGCTGAGCGCCG
CATACTTGCTGCCTGCCCACGATGCCGGGCCAGGCCTTCCGCACGGACCC
AGGCTCACATTCGCCCTACATGCCACTGTGTGGGAGTTTGGGATGGTGTG
CCCGCTGGGCCCGGGGTCAGGGCACGCTTCCCAGAGGAGCGGGTTCCAG
AAGGCCCAGGTGGAGAGGCGATAGGAGGGCTCCAGGGGGCTTCCCAGGCC
ACCTGCGAGGACCCTCCTGGGGGGAAGGGAGCGGAGGGAGACAGCCGGGT
CCCTTAGGCCAAGGCTGAGTTGTGACCGCAGGGAGAGGAGAGAAGGAGCA
CCCACAGCAGGGCAGGGGCTGCGGGAGGCTGTGCTGGGTGGCCGGGTGGT
GGGTCTGGGGGCCAGGACCGTGGGAGGCCTCGAGGGGGGAGCAGGCACGG
GAGGGGCCCCTGGACGGCAGAGTCCCTGCTCCAGCTGCCGCCCCGACCCC
AGGTCCACCTTCATTTCACAGCCTGGCCCCCGGCCGCTCTGACCGGCCCT
GCCCATGCAGGTGTAGCGGGGCAGTGAGGGCCAGGCTCCGGCCGTCCCAA
```
Contig 74 (450 bp)
```
GCAGGCCTGGCAGCAGGGAAATGATCCAGAAAGTGCCACCTCAGCCCCCA
GCCATCTGCCACCCACCTGGAGGCCCTCAGGGGCCGGGCGCCGGGGGGCA
GGCGCTATAAAGCCGGCCGGGCCCAGCCGCCCCCAGCCCTCTGGGACCAG
CTGCGTTCCCAGGCCGCCGGCAAGCAGGTCTGTCCCCCTGGGCTCCCGTC
AGCTGGGTCTGGGCTGTCCTGCTGGGGCCAGGGCATCTCGGCAGGAGGAC
GTGGGCTCCTCTCTCGGAGCCCTTGGGGGGTGAGGCTGGTGGGGGCTGCA
GGTGCCCCTGGGCTGGCCTCAACGCCGCCCGGTCCCGCAGGTCCTCACCC
CCCGCCATGGGCCCTGTGGACGCGCCTCCTGCCCCAGGCTGGGCCCTTGC
TGGCCCCTCTGGAGCACCCCGCCCCCGGGCCCAAAGCCTTTCATGAACA
```
Contig 75 (1363 bp)
```
CCTCCAGCTGGGCCCGGCAGGGCACCGTGCCCCTCAGGGGACACCACGGG
GGGCCACAGTGGCCTCTCCTGCTCCAGGCTCTGCTCCCGCCTGGGGCCCC
CTGGGCCGCCCGCCCATGGCCAGGGCAAACTCCCAGTGCGGCTGCCCGTC
TGGGCAAAGAGGCCGCCAGGCCCCGCGTGGTCTTAGCAGGCACTGGCGGA
TGCCGNTAACTAACCATTTCTTCCGCAGGAGTCCGAATCTGCTCTGACCA
CGGGCCCTAAAAATCGCTCCTGGCCCGCAGAGGATCCCCGAACAGCGGGG
CTGCCTCCTGCTCCTCCTGCCGGGCCGGCACTCGGCAGGCACGTGCCCTC
GTCGTCCCCAGTCTGTCAACCGTCCCGTCGTTACGATCCCCAGAGTCCCA
CGCGCGGGCAGCTCTTTCCACACCCCGCACGGCCCCGGAGCTGCCTGGGC
ACCCAGATCGCCCCTGACGCCTTTGCTCCTAATTCTGCTGAAATACACAT
AACGTCTCCTTGAACGTTTGTCCATTTTCACGGGGACAATTCTGTGGCCG
TAGGTACACTCCCCTTGGGGCGCAGCCATCGCACCATCCGCTTCCAGGAG
GTCCCGTCGTCCAGATGGACACTGTCCCCACTGATCCCTAATTCCCTGT
CCCCCCCAGCCCTGCCCTTCCTGTCTCTGTGGCCCTGGCGCCTCCAGGGA
GCCCCTGTGCGTGGGATCACAAAACGTGTGTCCCTTTGCGTCCGGTGTGT
GTCTCTGAGCATCCGGAGCTTGGGGTGCTTCCACGCTGCGCCTGTGTCAG
GACGTCCTTCCCTTTTGCGGCTGCGCGATGCTCCCCGTGGGGCTGCCCCA
CACTGCGCGTGTTCGCTCATCCATCCACTAAGGCTGAGTTACTTTTGGCG
GTTGTGAATACTGCTGTGTGAACACGGGCGTGCAAATACCTGCTGGAGGC
CATGCTCTTAGGCCTCTCGGGGGCACACCCAGAGCGGATATGCTCAATA
AGGTAATTCTGTGTTTAGCTTTTTGGGGAACCATCAGGCTGGTCTCCAGA
GTGACGGAGCATGCGTCGCATTCACAGGAATGGTGCTCGAGGCTTTGAGG
TCTCCACCACTCGCTTCCTATTTTCTGTGCGTCACAGCCGTCGGAACGGC
TGGGTGGTGCCTCTGTGTGGCTTCAATGTGCTTTTTCTTTTCCTGGCTAT
GAGGTTGAGCGTTTTTTATGTACTTGCTGGCCATTCGCAGGGTTTTTGGG
GTTTCTTTTCTTTTTTGCCTTTGGGGACGGCGCCCAGAGCGTATAGAAGT
```

FIGURE 6, CONTD.

TCCCTGGCTGGGGACTGAATCAGAGCTGCAGCTGCCAGCCTAGCCCACAG
CCGCAGCAACGCA
Contig 76 (500 bp)
TCATGCCATCGCCACCGCCCCCCACCCCGACGTTTCAAACACCAGAACCA
CCCCTCGGGCGGCAGAGAGAGGACCGGAAGGAGAGACAGCCTGGTCCCAA
GGCCTCGCCCGGTCCTGTGTCTCCGAGCGACATTTCTTTCTGTTTCCCTC
CTCCGCGGTCCAAGTTTCACCCATCAGAGGCGCATTGTTTTCATCATCTG
AAAAAAAAATCTCTGTCTCTTAATAAAACACAAGAAAAAGTAGCCTTCGA
AGAAAGCACATGAATGATATGTGCTGGCGACAGTGCTGGCGGCCTCTGA
GCCGTGGTGGGAGGTGGGAGCCAGCGGAGCCCCTGACCGATCACGTGACC
CACGTCTCTCCTGCACAGCTGGCTGCACCTGCACGCGGTGACACAGGGAC
CCAGCCTCCTGCCAGCAGGTCACCCCACCCCGTCCGTCTCCTGTGGAAGG
GGCAGCGTTGCCTTCTGAGGGTGGGCTGCTCTGAGGGGCGTCCTTTGGCC
Contig 77 (626 bp)
GCCATGGGCTGCGGCGGTTCACGCGGCTTGCCGGCCTGCCTGGAAGTCCC
ACAGGACCAAGGGGAGGGCACGTCAGCACAGGGGCCCCGGGCACGGACGG
TGCCCCCAGCCGCCCCGGCCCCCGCCCTCCAGACAGGACGCCCGGTCACC
TTGCGGGGACAGCCAGCCTCGTGGCCTCGAGCAGAAGAAGTGAGAGTGGG
GTGCACAGGGGCCCCCCGGGGAAGGAGAGGGGACAGCGGGGGTGAGCGGG
TGCGGGCGTGCTCGGGACCAGCCCCTGGCCTCTTGGCGCCTCCCTCCCCG
TCCTTAAACCGGGCCCAGCCTCTTGGGCCTCGACCCAAGGCTGTTTGGAA
AATAGGTGGACCGTGGCCCTGACCCGAAGGCCAGCGGGGACCCGAGTGCG
GTCCCCAATGGATCAGCAGGCGCCTGGGCAGCCTGCGGCCCCGGGACCCG
GAGACACAGGTGGGAATGGGAGGAGGAGGAGGAAGACGGGAGGAGAGGAG
TGAGGACCAGCAGAAACCACGCCCTCCTCTCTTCCCGTCCTCGCCCTCGC
CTCCGACAGCTCCGACTCGGCTGCAAGGAAAAGGCCCCAGCCCAGCCCGC
CGCCACCGGGGGGGGGGGGGGGGGG
Contig 78 (500 bp)
TACTCGGGTTTGTTACCACTGAGCCACAAAGGGAGCTCCTAAAAATAATA
ATTTTCTTAAAGCCAATGACATGGAGAGCAGTTAGGGTGGAGGCTGGTGG
GTGGTGGGGCCGCGGCAGGCGCCCTGAAGGTCCTGAGTGGCACCCTTGGC
CGGGGGAGGTGGGTGGGCGAGGGGTGTTGAGAAGGGGCAGGGCCTCGTGG
GGGCAGGAAGGAAGAGCCAGTGGCTCCCAGTCCCCTGACCTTGCTGCCTT
GAGCCTGGTTCTCCCCAAAATTCTGTCTGTGTCCCTTCACTTCACGGAAG
CTTGGGGCCCGTTGCCAGGGAGACAGATGGGCTGGTGACACCCAAAATGA
GCCACCAGGAGGGGGCACTGACTTTAGCCAGCCGGTCACATCAAGAAGC
AAACAGGCCCCCCGCTGCTGTAAAGGCAGCTTGGGGCTGGGGTCCGGGAG
CACCCCCTGGGCTGGGGAAAGGGGGTCCTCTCAGGCCCCCGGGGAGGATG
Contig 79 (427 bp)
TCTATTCGCCGTGGCCGGAAGAGGCTAACCGTACATTGACCGGGCATCTG
GCGATGTATCACTTCTCTCCAACCGAAACTTCCCGGCAAAACTTGCTGCG
TGAAAACGTTGCGGATAGCCGAATCTTCATTACCGGTAATACAGTCATTG
ATGCACTGTTATGGGTGCGTGACCAGGTGATGAGCAGCGACAAGCTGCGT
TCAGAACTGGCGGCAAATTACCCGTTTATCGACCCCGATAAAAAGATGAT
TCTGGTGACCGGTCACAGGCGTGAGAGTTTCGGTCGTGGCTTTGAAGAAA
TCTGCCACGCGCTGGCAGACATCGCCACCACGCACCAGGACATCCAGATT
GTCTATCCGGTGCATCTCAACCCGAACGTCAGAGAACCGGTCAATCGCAT
TCTGGGGCATGTGAAAAATGTCATTCT
Contig 80 (650 bp)
GGCGTTGCCGTGAGCTGTGGTGCGGGTCACAGATGGGGCTCAGATCCCGC
GTGGCTGTGGCTCTGGCCTAGGCCGGTGGCTGCAGCTCCGATTCGACCCC
TGGCCTGGGAGCCTCCATATGCTGCGGGAGCAGCCCTAAAAAAAAAAAAA
AAAAAAAGGAAGAAAGAGAAGAAAGAAAAGAAAAGACAAAAGTCAAAAG
GAGCTCCCCTGAGCGATGTCTGTCTACGAGCAGGTCCCTGGGAGCCTGAG
GCAGGGTGAGCCTGGACCCCTGAGGGCCACTCCAGACTCAGTGCTCTCAC
TGGCCAAGGTCTTTGGGGACCGGCTGGGGCGCGCGCAGGCTAAGGAGGA
GGTCAGAGGAGGGGCTTCAGGCTGCAGGGCCAGCGGCAGCTCTGGGCCCG
GGGCGGGGGGGAGATGGCCTGAGGGCCTTGCGGGGGCTGGAGGGTGGGGG
GCTTCCTGGAGTGGGAAGACGGGAAGCCAGGTCAGAGGAGAGGAGCGAGG
GCTGAAGCTCCTGGAAGGCGCTGGCTACCCCAGCTGGCCCGCCCCGCTG
CCACATTCAACAGCCACCCGGCCTGTGGTCCTGGCAGGGTCCTGGCAGAA
AAGCCCCAAGGGCCCCAGCCTGGCCCTCTGGGCCTAAAGAGCCAAGCCCC
Contig 81 (550 bp)
TTAACCCACGGAGCAAGGCTGGGGATCGAACCTGTAACCTCGTGGCTCCT

FIGURE 6, CONTD.

```
CGTCGGATTCGTTAACCACTGCGCCACGACGGGGACCCCCCAGGGCTGGC
GTTTCCCTCTGTGTGCACACAGTGGACCTGAGCCAACCAGCAGGGCCTTC
ACCACCACGGCGCAAGAGTCGGCAGCAAGAGAGCAGTGTCTCATGGCTCA
CTTTCTCCCCCTTCCCCGGAGTGGTGACAAAACCCCGCCGCCACCGGACT
CGGTTAGACAAGGCGGTGCCCAGTGCCCCCGTCTGTCACCCGCACGGCAC
GGCGCTCTCCTTTCTTTCTCGGGGCTCCACCACGTGTCCTCAGTTTCCGC
ATGAGAGTACCGCGGCTGGCGGGGTGGTGGCTCTGGGGTCGGGGGCCGTG
AGGGCAGGGCTGGGCTGGGGAGGCAGGTCTTGGCCCATTACGCGGGGGG
CAGACTCCACATCACACGCTCTCTGTGCCTCTTGGCTGCCTGACACCATG
GACTTCAAACAGGAACAGCCGTGGAGGCATTGCAGCCCAGGGCCCGGGTT
Contig 82 (550 bp)
TGACACCTCCAGGCAGGAGGGTGCAGGCTGGGGTCCCAGGTAATGGTGTG
CTGGCCTGTGGGGCGTGGGCTCAGCTCTTAGGATGGTGGGCTGGGCGCCG
ACCCAGCAAGGACAGGGTGATGGCAGGTCGTGGGCTCAGCAAATGAGTGC
CCAGGTTGTGGGGGTGGGCACTTGGGGCTCAGGGGAAGCTCATCAGCTTG
GAGAGGGACGGGGGAGGGAGGGGGCCTTGGCCAGCTGGCCCAGATGCCTG
GATGTGAGCACTCACGTGCCCCGGGGTCCACCTCCCCTCCAGTGCCATCT
GGGCAGGAGGCTCCGATGCCTGTCCCTGGGACCCGCTGTCCTGAAATGAG
GTTCACTTGGTGCCTTCCCCAGAGATGCTCGGTCCGGAAGCTGACGAGGC
AGGAGTGCACAAGGGTCTGGGGAAATGGAGCAGAGTGCGGCTGGGGCACA
GAGGCTGCCCCCAGCCTGGGAAGATGGGGAGCTTTGCAGGGGTACCCCGC
CAGCTTGTGGGGCCCTGGATACCCAAGGGTGTGAAGAGGCTGAAGAGCGA
Contig 83 (984 bp)
CTGAGCCCAGCTATGTAGATTAGACCCCGGTCCGTCCCAAATTCTTCTCA
AAGCTGTCCCGAGATGAGAGATGAGGTTTTCGTGTCCTGTGCTCTCCTCG
CTTCCCCTGGGATGTGCCCTAGGGTGGGAGAGGGTGTGTCCCAGGGCTCA
GCAGGCGGTCCCATCTTCCCGAGACGGGAGAGATCCCCTCCTTCTCGGCG
CCTGTCCCCACGGCCCCCACAGACACCCCCCCCCCCGGCATGGCACCCAT
GCACCTGCCATCGTGCCCAGTAGGGGATGGGTTTGGCGAGACTGGAGATG
GCTGTAGCCAGTGAGACATGCCCTGCCACGTAGCCTGACCCCCTGGGTGT
GCTCTGTGAGATCTGGGGACCCCCAGCACACCTAGGGATCATCTTTGCCA
GCCTCCTGGGGAGCCTCTCAGAAATGGGGGCCCCAGAAGGCTGGCAAAG
GTGATGGGGAGCGTGGGAAGTCTGGCGGTTGGCGGGGTGGGTGGGGGGCA
GTGCGGGCTGGGTGGGGGGTGCTCCGGGGTCGGAAGTGGTCCAGCAAGGT
TTTGGACACAAAGTCAGGAGGAAGGAGTGACGAGGAGACTTGCAGAATTA
CAGGTAGAATCAGGAACCCACATCGACGCCAATTGATCTATCCCCCCCTT
TGATTGTTTTCTCCTGGGGCTTTTTTCCNTTTTTTTTTTTTTTTTTTTTT
TTAATCCCTCCTTAGCTTTTTACGCGCTCAACACCAAATTAAACGTACTC
CCCACCCCACGTAACAGGGGGGCGGTGACCCGAAGGACGAGGAGCACACG
AAGCCACCATCCGTCACCTTGGCGGCACCAGCCGCTGTCCTGCCCTCCGC
CCATTTATCGCCCTTGAATTGATTTTTGTTTTGCTCTGTCCCTGTCGCTT
GGGTAGAGTGGAAAAGGGAACCTCTGTGGGGGTGCCAGCCACTGGGCCCC
CCAAAGATTTCAGGGGAATGAAACGGCTGCCGCC
Contig 84 (550 bp)
TGCCCCTGACAACCCTGCCCTGTTAGCCACACTCGCGACTAATAAGGCGA
GAGGTCAGCGGGCAGCCCCACGGGGAGAAAGTGCCTCCGTGCCCCCCACC
CCTGGCTCTGATGGCCCAGCCTGGCACCCCAAGGTGGCCTCGGCCTTCCT
ACCTCCAAGGTCCAGGCGCATGTCCAAGCACCAGCAGAAGCTTCTCCAGG
GTTGGTGCCTGCTCAGGGCAGAAAGCAGGGGTGAGGCTCCCCAAAGGGCC
ACTGGCACCAATGCCCCCAGGCAGCCCCAGCGAAGGGGACAGCCCACCCC
CAGCCCGGGGACGCAGGCCTGAGGGACATGGGGAACCCAGAGCAGGGCC
AAGGGGAGCAGAGCCCCTCCTCCGGGACTTGAAATCTTTCCCGGGGGGCC
CAGGGAGCTGGGTCTGCAGAGGGCACTTTCAAAATACGGCCCACCCCCA
AATTGCCACGTGGGCCACAGAGCAAGGAGTCGCTGCCAAAGTGGCCTGGC
TTCAGCGCAGGAAGTTCCCCTCCTGGGGCCTCCCCTCCTATAGGCACAGG
Contig 85 (500 bp)
TGAGCCAGGGCCTGGCCCAGCTAAGCCCCTGGAGCCCTCCCGGCCTGTTT
CCTGCCTCCCATGCTGGCGGAGCTCGGCTTACTGAGCGGGGCCAGGCCA
GTGTGCGTGTGGAGGTAGATTCCACTCAGCTGGAGGTTGAGGTGGGCAGG
GGGCCGCAGACCCTCAGGCCAGCTCTGGCCGGCCAGGTCCCTGAAGCTCC
CCCGGCTGGCCTCCCCGTCCCTGCCTCTGGCCTTGTCCTGGCCCTTGCCT
GACAAGCTTCTGTGGCTCTGCCTGCAGGAGAGACACTGGCTCCCCGCTC
TCGGATGAGGACGGGGCTTTTCTGCACAAGTCCTGCCCCAGAATGTTTGG
GGCGCCAGCAGCTGAGCCCAGCACGTCTCCCCCTGCCCCTGGCTGGACAC
```

FIGURE 6, CONTD.

GAATCCCGGCATCGAGGCGGGAAGGGGGATGGAGGGATGGGCCCTACCCA
CCCCTGCTCCCCACCCAGAATAGCTGGGCGGCCCCCATGGGAGGCCGCCC

Contig 86 (913 bp)
CTGTTTTCACGTCTTCTGAGGACACACCCAGAAGAGGGGCTGCAGGCGCC
CATGGTGACTCCATGTGTTCACTGCTGAGGCCTCTGCAGACCGTCTCCCG
CAGCAGCCGCACCCGTTTCCATGCCACCAACAGCGTGCGAGGCCGCACTG
TCCCCACGGCTGTGCAACTGTTTTGAATCTGAGTTATATAAGCAACAGAC
GCTCCTTCAAACACACTCACGTGCACACGTGCGCACAGGCGCACAGACAC
ACACACGGAGTAATAGGCCTCCCCCCCCTCCCTGAGCCCAGAGGGGGCCT
GGGGCCCTGGAGCCTGTGCTTTAGGGCCTTTTAGGAAAGCTGGTGCCTCC
CAGAGGGGCCGCCCCGAGCGTTGGCTTCCCAAGTCCCCACCAACCCTCGA
CAGACTCAAACGTTGGTTTCTTTCGTGCTTTTGCCCAAGGGATGGGCCCG
AGGTGGCCCTGCCTGAGGTTTCAGCCCAGCGCCCCAGGCACCCTTTCTCT
CCCGGTCCCCGGCCACTTCATGGGACAGCGGGCCTTCCCCCACGTTGTCC
CCTGGGTTGTCGTGCTTTTCGTAATGAGACGGAGGCAGGTGCACCTGTCC
TGGGGTGAATTCTCTTCTGCAGGAACTCGCTTCCCCGGCGCCTGGTCTGT
CTGTTCCTCGGTTGTTGGAACCTCTCGTCACCAGAAAGGGTGGCTCTGAC
GTCGCCCTTTCCCTCCGTGGCTTTTGCAGTCTGGGTCTTGTCGGGGAACC
TGCCCCAAAGAGGGGAGTGACCCCCACGAGGGAGACGTAGCTCCTGTGG
CGACAGCACCGGGGCCCCCAGATTCATGGGGTTCACGCTCACAGTCGCA
TGACGCTGCCTTTGGACGAGGGCAGCTCAAGGGAAGCTTGTTTCCTGCCA
CGAGCCACAGGCA Contig 87 (650 bp)
TCCACACCTGTGGAGCCGCTGCCTCGCTGATGCCCTCTGCCCAGCTGATG
GTCAGGTGCCCAGACTTGGGGCTCAGTCCAAACAGGGGCCCACAGGTGCT
GCACCTGGGCAAGGGAGCCTGTGCGCAGGGCCTCAGGTGTCCCAGGCTCG
CTGGGACCGAAGCGCACTGGGTCCTGGACTCCGGGCTTCCCCAGGGGCTG
CTCGGGGCCACCTGGAAATGAAGCCCCACCTGGCTCATAGGGTCCACGTG
AGGGCCCTGAGGCCACCAAGCCACCAAACAACTCAGTTAAGGGAGGGGAG
CTTGGGGCTGCTAAGCTCCAAGCGGGAAGCGGCCGCACTCAGCACTGCCT
CTCTGCCAGCCAGCCGCCCAGCTTGCTGACGTCCCAACCAGGCCAGGGAC
CCTGTCCCACAGATGCTGGGCCCTTCCAGTCTCTGCTCCCTGGAGGCGCT
GGGCACTGTGTGGGCACACAGCCCGCACCCGCCTGTAAGGAAGGGAAAGG
CCCCATCCTCAAAAAAGCCGTGGGCAGGTGGGCCATGATGGTCCTCCGAG
GCAGGTCCTCCTGGGACCCCTTGCTCCCTCGGGCTCGCCCAGGAGCCGCC
AGGTCTGCCCTGGATTAACTCTGCCCCGCATGTCATTTTCAAACTGGCTT Contig 88 (700 bp)
TGGGGCCCTTTGGGGCCGGAGCGGCCAGTCTGCTGGGCCCGGGAGCAGGG
GGTCTCTGTCCGCAGGGAGGGGGCCTGGTCTCAGGGGAGGAGAGGAGGCA
GGTCTCACCTGAAAGGATCTGCCTTCTCCTCAGGCCTCTGGGATGCCTGG
GCAGAGAAACCAGAAGGAAAGGCCCAACTTGCTGGCTGGTGGGGATGGGG
CCGGGGGTCGCTCCCGGCACACCCCCCCAAACCCCACCTTAGTGGCCAA
AGTGGGTGTCATGATGGCCACTGACCTCACGGGGCGCAGGAGACAACAA
AATTTCAGCCACTCTTGGGGAAGGACACTTGTGGCCTGAGTCTTAGGGG
CTGAGTTTCGGGGGGGACCCCCAGCTCTCCCCCCAGTATGAGACACCCTG
CCCACTCCTCCCAGCTGCTCCCCAAACCCAGTGCTTCTGGACGGGCATCT
CCCCGCTGCCCCTGCAGCCGCTGTCCTCTGACCATGTCCCCTCCCCACCT
CCCCTCTGCAGGGCCAGGCCTCCAGGGAGCAGAGCCGAGGCCCCACCCTA
GACTGAGCTGGGGACCGAGACCCCAAGTCGCCACCCGGTCTCTGCGTTAG
AGAGGGGGTTCCGGGGGGCACCCTGGGGCGGCACTGGGGGGCGGGAAGGA
GAGCCCTGGGCCGTTCTGGGAAAGGTCTGGGAGGGAGGGAGGGGTTTTGC Contig 89 (1400 bp)
GCACACCCGGAGAACAGAGGGAGGGGTCCTTACCAGTCTCAGGGTTTTTT
TGGGGATTTCTTTGAACTTGCCCTATTGGTTTCGAGGCTTCTGTTCTCTC
CAATCCCCCTTCTGAACCCCCCAAAAATGGGTTCAGCCCCCACCCCAG
CCAGAGGAAACCAATTGGGGGATTGGGGGGAGGCGGGGCCAGCAAAAGCC
TTGGGCCCCCAGCCCCCCTGGCTTTGGCCTCTGGCCTGCCAGGTAGGGGG
AGGGACGCGGTGACCTCCGGGGCCTGGCCACGGACTCTGCCCCCACCCC
CAGGGCAGACGTGCACAGGAGGGGAGAGGCTCCGAGGAATGAGGCCATCA
AAGGGACAGGTGAGGCCAAGCCGTGGGACCTGGAAGTGTTTAGGGCCT
GGGGGACGAGGCTGCGGCCTGCGGGCTCCGTGGTCAGGAGGCCCTCTGCC
CACTGAGCAGCTCCCACCACTGGCACACGAGCCTCTCTGGGGTCCGGCTG

FIGURE 6, CONTD.

```
GTCTCCGGCAGGGGTGGGCTCTGAACGTCCAGCTCCGCAGACAAATCAGA
TTCCCCCGAGCCCTGAGAAAGCCCCCTCCCCCAGCCCGTCTCCCCACCTG
TCGGTGGACAGAGTGACCCCTGCTGACCCCCTGCCCGGGCTCCGCAGGA
GATGTGAGAGAGTAAGAGGCGGTACAGGACGGCCGGGGCGGCCCGGGCGA
GGTGCAGGTGTGTGGGTGTGAGGCTGGGCACAGGCTGGCACAGCCTCCCT
GGCCCAGTCCCTTGGGCACCTCTGGGCACCTCGGTGTGCCTGCCTCCTGA
AGGGATCCACCCTCCAGCCACCTCCTCTCGGGCCAGCCCCCACCCCACCC
CCGAGCTACAGATGCCTGCGCATTCGCCCCAAGTGTCCTGGACCCTGGAG
CCAGGCAGCCCACCCGCTCAGCCTGGCCAGACCCAGCGTTGCCCTTCACG
CCCTCCTCCCTCCCGCCGGGTCCTCGCGCTCGTCTCCTCAGGTTGGAAGC
CCCTTCCCACCTGCCATCTTGCCTGCGCCCAGGATACACGGCTCAACTCA
AGGCCTCACTCCTCGCCCTCTCCAAGGCTCTGTCCAGGCCCCTCTCTGAC
CTGGCACCACCTGCCGCCTCCTGGCAGCCCCAGCAAACCCCCTGCCACAG
TCCACGACAGTCCTCTTCTGGCTCTGCCCCCAGGATGCTTCTAGAACTGG
GGGGGGGTCCTTCCAGCCCACGCAGCATCCACTGGGCCCTGGGCTCCCT
CCCCAGGTGCCCCTCAGAGCTTGCAGCTGGTGCAGACGGCTCTGCTCCGA
ACCCATGCTCCCTGCGCCCTTGGACCTGGTGAGATGTTGCAGGTCATTTG
GCTGCACCCAAAAGAGTGGCCCCTCAGGGTCCCCCCTGCGCCCCTCCATC
```

Contig 90 (350 bp)
```
GTACTGTAGGGCCTCATTCGAATAGCCTACTAGGTCACAGCTGATCCACA
CCTTAGGCCATCACAACTTCCCAGAGGTAGTGCCGCTCCTGTCGTTGAAC
AAGACGGTAGTGACTGCTGTGAGAGCTCAGATCTGGTGGGTCACTGACCG
AGTGTGGAACCCTGGGGGAAGGCTGTGGGGTGTCCCCGGCTGGGTGGCCA
TGTCATGTGCCCCTTTCTATCCCTTGGACGAGGCTGGTTCACTCGGCTCT
AGAGCCCCAAGCCCCAGCTGCTCTGCCAACCCCCCAAGCCTGAGCCTCAT
CAGACCCACCACCCCATCGCCATGGCTACGCAGGACACACCGCTCTCCAC
CCCCACCAGCCGCCCCACCTCCCCGAGGTTCCAAAGCTTGA
```
Contig 91 (1464 bp)
```
TCCAGGACCTGATGCAGCAGCCACGTCGCGAGGCCCCTCCCACGAGGCCC
CTTGTTGACCAGCGCTAGGGAAGGGGACCAGGGAGATGCTGAGAACGGGG
CCTTCCGAGGGGGCAGGTGGGACTGACTGTGACCCAACACTCCCCACCCC
CCTCTCCCGCTCCAGAGGGTGCCAGCCTGGAAGCTGGCAAAGTCCAATCC
ACAGGTGGGCTCACGTGGGGAGGCTGGTGGCCCCCACCTGGTGGGGCCCC
AAGCTGCCTCTGGGCGGGGTGGGGGCTGCTCCCAGCAGGGTCCCATCCAG
CTTCTCCCTGGGGAGACTCACAGTTCTGGGAGAAGGGTCCTGACTGCACC
GCAGCGCCCGCCCCCTCCCCAGACTCACCCAAGTTCTCTCTCTGCATCGG
TGACTGGTCTCCGCATTTGCCCAGGCTGGGCATCTGCCCAGAGGATACGT
CCAAAGGCAGGGCAAAGCCGGGCCCGTCCCCGGAGCTCCCCACAGGCGC
TGAGGGCTGGGCTGGATCTCGGGGGGGTGGAGGGGAGGACTCAGAAGGTG
CAGCGGGGTGGAGCGAGGCTGAGCCAAGGTGCACGCGAGGGCCAGAGAAG
GCCGAGGCGGGCAGGAGGAGAGAGCGCCAGCCTGGAGGGGGGTGGGTGCC
CTGGGCAGGTCTGGGGCTCAAGAAGAAGAGAGTGTGTGTGCAGGGGGCTG
TCCAAGCTGCCCGGGAGGCTGCCTGCCCACCTCCAGGGAGCAAAGCAGGG
AGGCTGCAGCTGGCCCGGCCGGCCGCTCTCCAGGACCACGCGTGGCCCAG
GCCTCAACGCTCCTCCCACAGCCCAGGAGACCCAGGGCACCGGGTCCATT
TACCGCGGGCTCCGGGTCCGTTTGCCTGCGCCCTGGGATGGACTGTGGGG
GCGGGGCGCTGTCTGGGGAGGAGGGAGGTGTCTGAGGCTGGACACCTTGA
AGGCAGGTGAGAGTGACAGGTCCGTGCGCAGGAGCCTTCGGCTCTGGATT
CTGGCCCTGAGCGAGGGGCTGGCTGGAAACTGGGCCGGGCTGCCGCAGG
AGAGTGTGCAGGGAGAGGAGACGGGGTTTGGCCCCGGAGGTGCCGGGGTG
GTGCCCTGGAGTGCGGCTGAGCGGGAAGTGGGTGTTGGCGTCTGGAGACG
GGGGGTCGTGGGCTTGGGATGGTGACAAGACCCCCAGGTGGAGGCGGCC
GCAGAGGAGGCAGAGAAGCCAGGCCCCAGCCCCACGGCGGGAGGCCTGGG
AGTCAGGAGGGACCAGCAGAGCCCTGGGCTCAGTGTCACCGGTCCTGGCA
CCTCGCCGACGGATGTCCTGGCCGTGCAGTGGTTGTCCCCTCACCCTGAG
CCCTGAGAACCATGCAGGATGCTGGTGTCACAGCAGGAGGGGCCAGGGC
CTGGGGAGGAGTCTTACTGGAAGGCCTTCTCCTTCCGTTTGCAGCAGGCG
GGAATGACTGGGGG
```
Contig 92 (694 bp)
```
TGGAGCCAGGGCACGGCAGAGCGGTCCCGAGGCCGTGCGTGCTGACCCGG
GGGATGGGCGGACCTGGGGGTGGGCTGTGAGCCCAGGCATAGGGACCCCG
```

FIGURE 6, CONTD.

```
ACTTGGGCACGGCCAGGTGGGGCCGGGCAAGGGGGAACAAGGACGCTGGC
CTCCAAGGGCCCCACGTGGGCACAGAGGAAGAGCCGACCCAGGTTGTGGG
CGCATGGAACCCCCCACTCTGGGGGCCAGGAGGCCGAACGTCCCAAGGGC
TGAGGCTGGGAGGGAAGAGTCCCTTTGGGGGTCAGTCAGTGTCCCTTGTG
GGTGCCCCCCTGCCACTGGCGGCACCTCTGACCCCAACTCCTTGCGGGTG
GACGGTGGATGGATTTCCTGCAGCCTTTCTTCTGGAATAGTCTCTGCCAT
CCTCGGGGAAGCAGTGATTGCTCTGCCCAAGTCCAGGCCCCGCCCTGCAA
GGTGCCTCCCACCCCAATGAGCCCCCGGACAGTTCGAGGGCTTCTCACGC
TACTGAGGGGTATGAACAGCTGTCCCCCTCGGAAAGTGGGGGACAGGCCC
CTGCCACTCCATCCTCGGGACGCCCGGTCTAGTCAGCACTTGTCTCCCTG
CCTTGTGCCCCCCTGACCTTTTTTGAGGACCATCAAAACCTCAGCCTCTG
CCCCAGGAGGTCAAGCCCCCCGTCCCCAGCCCCCAGACCAGCA
Contig 93 (900 bp)
CCAGCCCCATCCCCCGGCTGGTCCCCCACCACACAGAGCCCCCGTTTCCC
AGGGGACAGCACAGCCTGCCCCCAGGTCTTACATAAAGTCACCTTCTCAG
AGCTCCTGTCGCGGCTCAGGGGAATGAATCTGACCAGCATCCATGAGGAC
ACAGGTTTGATCCCAGGCCCCGCTCAGCAGGTTAAGGATCTGGCGTTGCC
GTGAGCTGTGGTGGAGGTCGCAAGACGTGGCTCAGATCTGGTGTGGCTGT
GACTGAGGTGGCGGCCAGCAGCTGCAGCTCTGATTGGACCCCTAGCCTGG
GAACCTCCATATGCCGCGGGTGCAGCCCTGAAAGGACAAAAATAAATAAA
TAAATAAAAGAAGTAAACACACCTTCTCTAGCCATAACCACCTGCCTAGG
GGCGGAGGGCCAGGAAGCGGCACCCCCGCCCCAGGCTGCCCGTGCGCCC
CGGGCAGGCGGCTCAGCCTGCTTTTTGTCTGTGATGTGAGCCGCCCCAGC
CCCACATGGAGGGGCTGGGCTGCGCAGTAACTGCTTTAACTGACGGGAGC
TTCGACCAGCAATTCACCAGCGGGCATGCAGCCGGGAAGGGAAGTTATTC
GTGTGTAGCTATTAGGCGCCGGAGTGAGGGTGTGCCTCGCCCTGGGCCCA
CCCCTGGGGGGAGGCATCACAGGGGTTTTGAACACCTGCCCATGAACACG
GGGCAAAAGCCAGCCAAGGGGCAGGTGCCTGAGGCTGGGAACCAACCCG
TGTCTCTGAAATCCGGGGAATGCCCACTGCAGGCATGTTCAAAGGGTCAA
GACCGGGGCTCTGCCTGAGAAGGACTGGCGAAGGCCAACTACAAAAGCGC
ACCCCTCTGTGCAAACCCCCAACCAATGGAACAAAACTCCAGAGGGGCCA
Contig 94 (550 bp)
AGTCTGGGCTGTGTCCATGGGGTTGCCAAGGTGCCAGGCAGAGACCTTGG
GGACAAAGGTCCTGTGAGCAGAAGGACATGGCCACGTCCCCTGCTCAGCA
GGTGCCCAGGCTGGGGTCTGATGCCCTCGCTGGGGTGGGGCGGGTTGAG
GGGCCAGGCCCAGACACCCTTCGTCCCTGCCGGAGTTGTTTGCCCTTCTG
TTCCTGGAAGGCCCCCCTGCAGGTACAGGAGGCCCCTGGGGCTGACGCTG
CACCTTCTGACACCTGTGGTCTTGGGGATGGGACAGGACAGGGAGACCCC
GGGGCTGGACGGAGCGGGTAAGACAGAGAGTTGACTCTGTCCTCGAGTCT
GTGCAGGGCTGTCCCCGGCTTGGGCTTCGTCTGCAGGGCCTTTCGGGTCA
GGGTGGCCTCAAGGTGACGAAGACCTGGTCCTCGGGAGTCTGCAGGCGCA
AAAGTTGGAGCCCACCCCCCGGGGAGGGGCGCCAAGGACAGGAGGGCC
CAGGGAAGTCTGGGGCCTGCAAGGCCGTCCGGGCTGGGGAAGGCCAAGGT
Contig 95 (1200 bp)
GTTTGCTCTCAGCAGGCAAGGGCCTCCGAGGCCTTAATAGCCCATAATGA
CAGCGCCCGCTCCTGGCATGGGCCCCGCCTGGCATGGGGCAGGGCAGGG
CAGAGCAAGCAGCATGCAGCTTCTACCTTCTTCCTGACCTCGTGGCCCCT
TCCGAGGCCTCAGGGGGTCCCCGAGTGGGACCCCAGCCCTGGCTCTCCT
CTCCAGAGCCAGGCCCAAGGCTGGGAGTGGCCCAGAGATGAGGGTGCCCG
AGCAGGGCACTGCCTTGGCGTCCCCATCCCTGGCGCCTCAGGGCCGTACT
GTCCAAAACCAAAAGAAAGCAGTCAGCAAAACTTCTCCCAGCAAGCTGGG
GTCAAAGGTCGCTTCCGAGGCGTGATCAGGGTGGCCTTTGCTACTGTCAC
CGTGTGCCCTGGGAGAGGCACAGGGACACAGACACACACCTCCGAGAACC
TGGGGCTTCCAGGGCGTCAGGCTGCCTGGGCCATCCCGGGCCCCTGTGGT
CCCAGGATCTGCCGGGACCGTGAGGCCTGCGTCCCACCCTCTGCCTGGGA
CAGGCCCCACAGAGCTCACAGCCAGGGGACCGGGGACAGGGCCCCGCCTG
GGCCACCTGCCTCCAGCCTCACCCAGCCTGGGCCCCAGGCCTGTGCCTGC
GACACCCTGAGTCTCAGGACGGGCGCGGGACAAAGCCGCCCGGCCCCTCC
CCCGGCTGGGAGGAGACCCGCGTGGCCCTGACGTGTGGGCCTGTCAGAGC
TGAAATGTCACAGCAATTAGCCCTAACGAGGCCGAGGGAGGGAGCGGCGG
GGAGGCCGGCGGAGGGGATCCACGAGCCGAGGGCCCGGAGCTGGCCACCC
CACCGGTCGATTCCAGGCACTCAGGGATAATTGGGTGTTTAGAAGTCAGG
CGGCAGCAGAGAGCGGGCCAGGCGGGCTGTGCCCCCCCTCCCACCGCCCC
TTAACAGGTGCCCGAACACGCAGGTCTGGGGAGATGCTGAGGTCGCCAAG
```

FIGURE 6, CONTD.

```
GGCACCCCTGGCCGTGCCGCGGGTGCTATGCTGGTTCGGCACCATGGGAG
CTGCACCTGCAGCTGTATTGGTCTGTGTGTGTGTGTGTGCACGCGTGT
GCGTGTGTACGTGTGTGTGTGTGTGTGTGTGTGTGTGTGTACGTGG
GGGGGGGGGGCAAGCCCGTGCGTGTGGTGCACAGTAGACATTTAGAAGGT
```
Contig 96 (600 bp)
```
GGGGACCAGGGCCCAGCCCTCCAGCTCCCACGCATACCTGCTAGGAGCTT
GCAACCTGCGAGAGCTTTGTGGACCCCCTGCCGGGTGACCCCTGAAGCTG
GCAGCTCTCCTTGGCTCTGCAGCGGCTCTCTACACTACCCCCTCTCCAGC
GGCCTCGGGCCCAGACATCACCCACCCGCAAGGGAAGCAGCAAGCATCCA
CCAGCTGGGCCCTTTTCCCCCAGCCTGTGACCGGCCCGCGCCCCCTCAC
ACCTCTGCGGTCCAAGACCCCTCTCTGGCTGGGCCCTGGTGCTGCCCTTG
CCGTGCACATCTGGGGTCCATACCCCACCAACAGGCCCCACTTTTCTGTC
TCCCAGTGTCCCCCTCAGCTGCCCTGATGGGCCCACACCTGGCTTCTCTG
CTGCCCCCCTTGACCGCAAAAAGACTGGGGTCCAGGACCCCCTGCCCCAT
GACTGCCCTGGAAGACCTCAAGCCTCTCCTCTCAATCCTGACCCTTTAAG
GCTCTTGCCACGGAGAAAGCGGCTGGGGTTGGGGGAGGGTGTGGGTCCCA
AAGCAGCTTGCATACTTCTCCTGACTGGGAGCTCATTCCTCCACAGCGTG
```
Contig 97 (1350 bp)
```
CCCGCCTTATTTTTAAATTTCCGAAAACAAAAACCACACCTCTCCCGTCC
CCGAAATTATTTTGGTATAGTCTTATTCAAAGAAGTCCTGCCACTGAAGC
CCACTTGTCCTGTCCCGGGCTGCTTTGGCCAAGGGCCCTGACGGGCCCAG
GGTGGCTCATTCCCGCATCCCCGCAGAGGCCGCCTTCACATCCCATGCGG
GAGCCTGGCTTCCGGCACCCGGCTGTGCCCTCGCTGTGGCCATGGACTGC
TTTCGCAGAAGCATAGGGGCCACAACATGGGACAGCCTCGCTCTGCTCGC
TGTGGTTCCGCTGAACCTCTCAGCTGGACATCTGGGCAGCAAGCACCCCA
GCTTTGCTTCAGGCTCTGGTTCCAGGCTGGGCCCTCCTCGGCCCTGCCCG
CTGGGTGCCAAGCAGGGCTGGTCCGGCTGTGCCCCCGGGTCTATAGAAGC
CTCTGCAGGGCTTCCTACAGCCAGGCTGGGATTCGGCGGCTGCCCGGGAC
TGAGGCCCCCTCTGAGTCTGACCCCCCCATCCTTCCCTCCCACACAGCCC
CCCGCCCCGCTTCTGCTTCAGTGAGGCCCCACCCTGCCTCACTCGCTGA
CATTTCCAGAACAGGGGGTTCCAGGAAGCCCTGAGCCTGCAGGGGACTCA
GTGACCAGCCGCATCTGAATTTTCCCTCCTTCTGATCTCTGGAGACACGT
CTGGCTCAGCCTGGCTCGAGTGCCCTGAGCTGGGGACCAGGACAGACCTG
CAGATGGAGGTCTGAGCCTGGGCAGGGCAGGGCCCAAGGCTCAGGGAGAA
ATTGCAGGTGTGAGATCAATGACCGGAGCCTGGATGGGGCCGCCCTGGCC
AGGGCAGCTTTCTCCCTGCAGCTCCCTGCCACTGTCCCCCCCAACTCTGG
GCTCCTGCTCTGGACCCAGTTGTGTGTTCCCCTCCTCCCAGCCGAGCCAC
CCTCCCCCATTCTGCCCCCCCCCAATCCAACACCCTATCGTGGGAACCAGT
GGAGCTGAAAGAAGGACCCCCCAAGGGCCCCCCAGCCGCTGTAATCCTTG
GGGGCCTCTGCCCAGGTGCCAGGTCTCGGGCAGGAGGGGCCGCGGGCACA
GCCGTGGCAGATGCGCCCCCCAAGCCTGGGCTCGGAGGAGCCCCGCCCCC
ACTGACATTTCCAGGCCGCCCGCTGCAGACCCGGCTGGCCGTGATATTTA
GACAGGGCTTATTTGCCGTGACTGGTTTTTGATGACTTTGGGGCCCAGGA
TGAGCTCAGCCGAGCCCGCGTTGGCCCACCTTGGTCTCAGCTTGGGTTTG
ATAATATAACGCGTTCAACTGAACCGCTGACGCCTGCGTGGGCCGAGGCC
```
Contig 98 (1354 bp)
```
GCTTGCAGTAGTTCATCAGATTGGACGACTCATAAATGTCAAGACATCTA
AAGATTGGTGCATCCAATCATTTCCCACCAGGTTGTTTTTTGTAGATGT
CAAGAAGCTGACCCAAAAACTCACGTGGAAATGCACGTCAACTGGGAGAG
TTGAAACAATTTCTAAAAAGAAGAAGGACGTCGTGGGAGGACTCTTCGCG
CTCTTTGGTTTCGCTTCACTTTATATTATTAGTTACTGATTTTCCTAAAA
GCTGCAGTAGTCCAGACAGTGGGCCTCTATGAAGGGAGGGGCTCAGAGAT
GGTTGGGACAGAATAGAAAGCCCAGAAACGGACCCCCGCAAATGTGGTCA
ATTGAGTTTGGGCAAGGATGTGAAAGCGGTTCAGTGGAGAAGAGTCTTTT
CAAGAAATCTCTGGTCCTGGATCCACTGCTCATCCAGGCCCAAGAGTGAA
CTTGGCGCACATTTCTCACAGTGTATACAAAAACTGACTCAAAATAATTC
ACATACCGTCGTGTAGCGTATGAAGCCATGAAACATCCAGAAGAAAATCT
CGGTAACCTCAGGGCATCTGGGGCCTCCACCCTCAGCACCACTGGCCTTG
GGGCCAGATACTTACGTGTTCTCCTGTGCACTGTGGGACGTGCAGCCAAA
CCCCAACAAGGTGACCATCAGAAATGTCTCCAGACGTCGCCAAATAACTG
CCAGAGAGCACAGGAGCCCCTCACTGAGAACCACAGGGTGGGGCAGAGAG
ATCTCAGACATGACACGATTAGGGGAAAACAATCTGACACACTGGCTTTG
TTAAATTTAAAACTTTTCCCCTGTAAAAGGCAATGGTAAGACATTAAGAG
GCGAAGTGGCAGACTGGGAGAAAATATTTGCAAATCATGTATCAGATACG
```

FIGURE 6, CONTD.

AAGAAGATGCAGGAAATCCTCAAAGTTCAGTCACAAGAAAACCCAATTCA
AAAACCAGCAGAGCAGACATACGATGGCAAATAACCACGAGAAAGTCAGC
ACCCGCTGTCCCTGGGGGGACGCGAGTCAAAGCCAGGAGGACACCAGGAT
ATGCCCACTGCCAAGGCTACGGATAACGGGAAGCAAGAGACACAGACAGA
AAGGATGCTTCGGTGCTGGGGAGGGTGGGCTGGGCGGGGGTCCCCCCC
TGGAGCAGGATGTGAAGGCACTTGGGGGGGGCTCTGCACTCCTGGGGGCC
TTTCGCACAGGCGGAGGGCCCGGGAAGGCTCTAGGGGCACGGAGAGGGGT
GCCAGGCTTCCTTACCCAGCCCAGGCAGACCAGGCCCTGTCATGAAGCCT
GACGTGCAGCAGCAAGAGCAACATGCTACAGACATGTGTCTGTGTGTG
TGTG

Contig 99 (1000 bp)
GGTTCTCAGGCGCACGGGGCAGAGGCTGAGGGTCCGAGGGGCTTTGGGTG
CTGGAAAGCCTGAGTTTGAATCCCAGCTCGGTTTCTTAAAGCTGTGTCTC
CACGGCCAAGGAATGGGGCCTCTCTGGGAAAGGTCTGGGGTGAGGCTGGC
GGGACCTGCCAGCCCCGGAGGGCATCTGACCAGACAGCTTCTCAAGCTCA
CAGGGCTTCATGGCAGGATGGGGAAGGCTGTGGTGGGGAGTGGGGAGCAC
TCGACACCCTGTCCAGGCCTCTTGAGTCACGGTGGCCTCTGAAAAGGGGT
TCTCTGTGTCCAATGAGCAAGTCTTTGTCCGGGGCAGGATTACTAAGTCC
AAGGGTGTCTGCCCCTCCGTGGGGCACAGAGCAGGGGCCCCAGATCACGT
GGCTGTAACTGCCAGGTTGCAAAGCCTGCCACCATGTCCCACTGGGTTCT
CCAGTTACCTTGGGAGGTGCAGGGTGGGGTGATGGGGAAACTGAGGCAGA
GAGCTGGCAAAAGAGTGCCGGCAGGGACTGCGGGCGCCAGACCCAGCTAA
CCGACCCTCACACGGAGCTGCTTCTACTTTGCAGCCTGGACGTGGGAAAA
GGTTACCCCACAGCAGCGTGTGCAGGCACGCTGGTATGTCTGTGTACTTA
TGCATATGTTCTACGTGCATGCACGTGAGTGTGCTGTGTGCATTGTGCCT
GTGTGTGTGTGCATGTGTGTGCACTCATGTGTCTATACGTGTGTGTAG
TGAATGCTTGTGCATGTGTATTTGCATGTGTATGTTTGTACGTGTGCAGT
GAATGCATGTGTGTGCAGTGGCGGCATGTGCGTGTGTGCGCATGTGTCTG
TTTATACCTGTGTGTAGTGAATGCATGTGCATGTGTGTGTTTACATGTGCC
ACGTGAGAATGTGCACTCGTGCATGTTTGCATGTGAGTTTCATGTACACA
TGCTTTTAACGTGTGCACGTGTGCACATGTGTTTCTGTGTCCCTTGCACG
Contig 100 (1500 bp)
CGTATAAATATATTAATATAGAATAAAATAGATTGATAATATAGATAAAC
TAAACCCATTATCAATACCGGGTGGCCCCAGCAAAGGATACTAGCCAGTT
TATCAAGGTGCTAAGTCAGCACATAGAATGGCCACAAACGAAAACCTGTA
CTGCCTATGTCCACTCTAATGGAGTATGCCACTGACATCAGTGGTAGGTG
AGCTGAGTCCATCTGGGCTCCCAGTTCGGGCCCGGCTTGTCCCCCAACGG
AGGTTCCTTCCAGGGTTCCCCAAACCCAACCGGGCCCCAGGTCTCCCTG
TCTTGACTCGTTTCTGGAGTCTTCTGGGGCTCTGCAGTCCTCCCTTGTTG
GGGCTTCTGTCCCCCTGCCCCTGGCCTTGCGGGCTCGGCCCTGCCCTGGG
TCCCGGGCCTGCGGGCTCACCCTCCTTCTTTCCCTGGAAGAGAGGGGAGCC
AGGCTGGGCCGGGCCAGGAGGGAATGCGCCTGACTCTGCTCCAGATGGAC
AGGTCGGGACATGCAGTGGCCTCGCCTTGGGCTGCTGAGCCAAGAGCAGG
ACGGGTTCTTTCTGGAATGTGGGCCAGCCAGGTTCAGCGTGTGGGTGGG
CAGCCGCCAGCATCTGTCAGGGCCGCTGCAGGCGCGGGGAATGACCTCGA
CTTCTGCTTGGCACCCAGCTCTGGAACAGCCCCTGCGGAGCCTCCGCCC
AGAGCTGGGCCAGAGGGTCCCTGTGCCGGGGACCCCAGCAGGGCCCCTC
CCTGACTCTCCAACCCACCTGCCTGGGAGGAGTGGCCCCCTGGCCTCCGT
GGATCTCTGGGTCGGGGCTCAGCCGGCTTGACAGCCTGGGAACAGCCAAT
GCACATCCCCAGGCCTGGCCACACCCTTCCACCGGGAGCGGGCGGATCTG
CATTTCGCCAGGCTCTGCGGGCAGCTCTGAGAGCCCCGGGTCTCGGAGCC
CAGCCGTGGCCGTTGTACGCCCTGGGGGCTGTGGACAGCGTGTCCTCATT
GCCCCTCCGAGGTCCGGCCCAGGTCCCCTCCCACCTGCTCGCCCAGAGCC
CTCTCCCCACCAACCACACTTCCTGCTGTTCTGCAAGCGGGACACACACT
CCGGTTTCAGGACCTTTGCACGTGCCGCTTCCTCTGCAGAGAAATGCCTG
GAGCAGATGTTTGTCCGCACGGCTGCTCCGCGAGGCCTACCGAGAGCCCC
TCACCTAAACGGCCGGGCCTCAGCAGCCCGGGGCCCTGTCCCCACCGCCC
AGGTGGTGGGTTCTCCTGTGCCAGTGTGGGCATCTCTGTAAGATACCTGT
TTATCTGCTCATCGTCTGGTCTCCCCCAGAAGGTAGAGCAGGGCCCGGCA
CAGCCGTCCTCGGGGTGGCCACTCGCCCTTGGGGCTCAGCCTCCATGCAG
GGAGGGACGCCTGGTGACACGAGAGCCCCGTGTGAGTGTGCCGGGCCGCC
AGCCTGCCTTAGGTCACAGCCAAAGCCGGCATTAACCACCAGGCCCTCGA

FIGURE 6, CONTD.

Contig 101 (600 bp)
TCTAGAATACCTGGCCCTCCAGGGACGTGTCCTGTAGCTGCGGCTTTCAG
GGCAAAGTGTAATTAAACATCCCCAGGCTTCCCTTCCAGTTGGCACAGGG
CACCCACATGAGGAGCAGCCTCTGGGTGCCAAAGGGCCCACTGGTGCCAG
GCGCTGGGCTGAGTGCACCCCGCATGCTTCCCGCCCACTCACCTGCTGG
CCCCACCCCTGACCACAGCACCTGTGGGAACACTAGGCCTGGCAGCCACA
CGCTGCTCTCACTGGAGGCCAGTGCCAGGCAGCCTGCTTGGCTACGCTAG
CAGATGCCCGCTCGCCTCTGCCCCTGCCCCTAGCCCATGCAGGAGCCCAG
GGTGGGGCACAGGAAGGACGATTGGGGCCCCAGGTCAGGCACATCCAGGC
CACAGCCGTGGCCACACGAAGGCGGCCCTGAGGGGGCGTTGGGGGGCAGA
CCCTGCCCCCCGCTGCCGCCCCAGCTCCAGGCATTAATTCCCAGGGACC
TGTTGCACTGGGTGGCCGCCAGCCTGCCCCCTTGCCTTCCAAGGCCTCTA
AAATGCCCCTCTTTTCGTAAACTAGGACTTACCAAGCTCAGCGAGCCCTC
Contig 102 (1867 bp)
AGTATATCGGGTGAGACTGGGGACCGGTCTGCCGGGAAGCCCCACCATAA
AGGCCACGTTGGGCCACAGTCCGGGCCACGTGAGTGTGGGCGGGTCCGCG
GGTCTGCTCTTGGAACACCAGGATCTCTAAGAGGTACCAGCCGAGGCCAA
GTTCACGTGAGCAAGTGAGCAAATGACTGAATGAGAGCGTGAGCGAATGA
GTGAGGGGTGAGTCCGTCCACCACGCAGCCTAGGCTCAGCCAACCGCTGT
CCCCGCGTCTCCACTGGTGACCAGAACGGAAAGAGTGGGGAAAGAGTGGT
TGTCTCCCACAACCCAGTCCCCAACCCCCTGGACGCCCCACCCCTCCAG
GGGTGCCGGGCCTGGCCTGTGGGCCCCAGTCTGGAGGCTCTGGCACCTTC
CTCATCCGTTCTCCCAGCACCCCAGGTTCGTGCTGAGCCCTCCTGGCCCA
CAGGCCTCGGGGACAAAGAGGGCCACCTGGAGGCTCAGGGAGCCTCACCT
GCCTCGTGGTCCTGGCGGAGGCGGGTCTGGACATGTGATAGACCGGCCTG
GGCTCAGCAGCTCCTGCTGGAAGATGTCAGGGACAGCCTGGGCCACTCTC
CCACCAGGAGAACTTATTCCTCGGTGGGGTCCCCCCGGGGAAGGGATGGG
ATCCCAGCGGGGACCCCAGAGCGTCCAGCACACGGACCTGTCCCTCCAGC
CCCTGCCCCACACGGATGCTCACAGCTCAGCCTCGAACACGCACCTGTTG
GACTTTGCCTCCTGAGGCTGTCTTCTCAGCCGACGCGGGCCTCCGCTGCA
TGGTCTGGAAGCCCAGTGGGACTCGGTGGTGACAGGGAACAGGGCTCTT
GGAGTGGGGTGCCGGGGGAGCCCCGAGGGAGCTGCTTGGGCCTTTGATGG
CTGAGTGGGCTGAAGTCAGGCAGGCTCCCCAGGGCTCCCTGACCCCCCC
CACCTCAAAAAATCCAGAGCATCCTTTGCTTTGGGTCTGGTGAGGCTCTC
TGAGGTCAGACCCTGCGTGGCTGGGCCAGTGGGGCTGGAGCAGGAAGAAA
GCAGGACAGCCCCCGCCCCTGGCCCAGACTCCCCAAACCCAGCAGGAGAC
ACCTGAAACGGGATGGAACCATCCTGAAAAGAGCCACCTCCTCCTCCTTA
TGCATCAGCTGCCGGGGTCTGGGGGCCCGCCCCAGGCCCCAGATGTCCGG
GCTGCTCCCGTCTCACATCCAGGGGTTTCTGGGCCCAGGACTCTGTCCCC
CCAAGCATGCAGAGGGTCCAGGCTGGGTCTTCATGCCTGCCCGTGTGCA
TGGTGGGGAAGGAAGGGGACAGTCTGGAGACCCCCGCCCTCCCCATGCG
TGGCGCCGGGGGACAAAGCCGGCTGGGGTCTCAGGTTTGGGTTCAGAGCA
AACGTTGATCTGACCTGGTTCTGAGATGCTCGGCCCGATGCTGCGTTGTC
CGCTCGCATTTTCCTGTTTTCTCTGGGAGGCGCTGCGTGCGCTGTGGCTT
CCGGCCAGCCCCACGGAGGGACGCAGGGTGGCTGGCGGGGTCTGGGGGCC
CCTGCCCGCACCAGAACGTCTGGCTCAGGTTTTTGTCCTCGTGACCCATC
ACTAAGGGCCACCCTCTGACCCGGAGCCCTGTCTCCGAGGTGGGAATTGG
GGGCTGTCCCTGGCGTCATAGGACCTGGTTGGGGGCATCCAGGGCTGTGT
CATGCCCCTCCCCAGAAGACTCTGGGGCTGCGGGAGGGTTTCCCCAGCT
TCGGGCCAGCCTGGGGAGGGCGGAAGGCGCTGGAGGCCTTGCCTGTCCCA
GGGAGCATGGCTTCGCTGCAGACTGGGGCCCCGCACACCCAGCCACCACT
GGCCGTCTGGAAGCACT
Contig 103 (650 bp)
GTTGAGGATTCCTCGGCAATTTCCTCGTCACTGGCGCTCCAATCGCCTCG
ATGGGCTTCTCCTCCAGATACAGCTGCAGATCCTGGGCGGGCACACCGTT
GAGCGTCACCTCGTAGTGCAGATTGCACTCGTTGTCAATGGACATCCAGG
CCATGCCGACGGCATGTGGATTCTGTGCATCCGTGTGCTCCTGTCGCTTC
AGCAGAATGGGTTCCGCCGAGTCCCGAGCATCGGCCACTGGACGGGGCAC
TAGGCGGCCACGGATCAGGCTCGTCTCATGCTCGGTGGCCACATTAACGC
CCAGTTCGCCGGCATACAGCGACTCGAGGACCTTGGGACCCAACTTCTCC
ACACTACCAATGGCCTGGTTGAAGTTGAAGCTCGGCGTCAGATCCTCCAG
CTTGGCCTTCCGCTTGCCCTGCTCCTCAATCAAACTGATGTTGGGCCTAT
CCCGGGTGTTCACGTGCTCCGTTTCGATGTTGTAGGCCAGAGATCCATCG
GTGTTCAAGTAGACCCACGCCAAACCGCTGCTCTTGGTCGAGGATTCGGC

FIGURE 6, CONTD.

ACTGTGCGGCGCCAGCAGGGTCTGGAAGATTTCGCAGCTGGCTCGGGTCA
CGATGTGTCCCTGGATGCGCAGATGTGGGTACTTCTTGGACTCCACGGTC
Contig 104 (1630 bp)
GGTGTTGTCACTGCTGTGGCTCAGACCCCTGCTGTGGCACAGGGTCCATC
CTTAGCCCAGAAACTTGCACATGCCACAGGTGCAGCCAAAAGAAAATTCT
TACTAATAAGTTGTTCATTTGCCTTTACGTAGAGTGGCATCAAACAGCAA
ATTTAAAACACCATCTATCAATACATAGACCGCGGTCAAAGGGAAAGAAC
TTTCTATTTCAGCACCTTTAACATGGCTTTGCCCGAATTTGGGACCAGGG
TGCTGTGTTTTCATCTCTCCCTGCAGGTGGTCCCCAGATGACCAGGCCGG
TCCTGGGCGGGAGGAGCCGGACTGTGGATCCAGTTGCTTCCCAAGACAGG
CTGACAGGAGAGCAGCAAGGGCCACCCCCAACCGAAACCAAAGCCAGAAC
GAGCAGAAAGATGCCGTCTTCCAAGTGGGGGCTGGGAGCTTCCTCCCATC
CTCCGGAGCCGTGAGGCTGCCCTGGAGCTGGCAGGAGCCACAGAGGACCC
GGCTTTGACCGCCCCTCTGGGACCCACAATCAGGACCCTGACTCAGATGC
TGAGGGGCCTGGACAACACCCCAGGACCCTGCTGCTTCCCCAGAACCGCT
GTGTCCATCAAGGTCCAGATGGCACCCGTGTCCCCACTGGAGCACGCACT
CCGTGGGGCAGGCTTTCCCTTGGGCACCGATGCACCTTGAGGGCAGAGAC
GGGGCCCAATAAACGTTTCCAAACCAGTGGGTGAGGGACCCGACCGGCCC
GACACGGCAGCCCGGATGCAGGGACTCCGTGCTTGGCCCAGCCTCCCTTG
GGGTGGTCCTGTGTCCTCAGGGGTGGATAGGCCATCATGTGGGTGGCCTC
TGGGGACATCCGTTCTCTGATTGGGTGAGTTTCAGCCACAGAGATATTCC
CAGGACTACAAAGCTGGGTCCCTTGGGGCACCTGCTGTCACAAAAAGACA
AGGCCCTGACCCCCAGTAGCCAAGTTCCCCCAGGGGCTCCCCAGGGTCTG
GTCATCCAGACTGTGCCAGCCGTGCTGCCCGCCCAGTCCTGCCTGACCC
GAGTCTCTGTAAACATCCCCCGGCCCCACCCAGCTTTACCCCAAGGCCGA
AAGCACCAGCCCCCCTGCACCACAGATGAGGCCCCCATGGCTCCCCGACC
TAACTTCTGTCTGCAGTTGGCTTTCAGCCTCGGGTGGGGCAAGGCCTGC
ATCTCAGGCTCCCGGGAGAAGTTGCTGCCTCCACAGCAGAGCCAGGGGCC
TGCTGACCACCTGGGCCGGGTCGGATCTGGTCTAGAATGCTGCTAAGGTG
TCCTTGCAGGCAGCCCCGGGCGGCCCCGCCCTCCAGGAAGGAAGGGGACA
TTGCCAGGACTCAGGAATGAAGCCATCCCAGGTTTTGAATCCCCGGTCCC
ACCACCTTCCACCTCTGACCTCAGGCACCTCGGCTTTCAGAGCTGCCCTT
TCTGACTCTGGGACACGGGGCTGTGAGGCGCTCTCGGTGTGTGACAGCTG
GGGGGGGGCACTCTCTAACGAGGGTGGGCGTGCCCAGGTGACTGACCACA
GCCCTTTCCTCTCTCAAAAACGCCCGCCCGAGTGACCTCACGGGAGGCAG
GGCCAGGAACCCCAAACCAAACCAGAATCA
Contig 105 (1820 bp)
AGTGAGCCCTGCAGGACAGTCTGCTGAGGGGTGTCTGGGCTCCTCAGAGG
CTCATGGCCACGGGCACTGGGAGGATAGCAGGTGGACCCCTGCATCCAGG
TCCCAGGTCCCAGGTCCCAGACCCCCGGACAGGCTTTCTATCTGCAGGAG
GGGGGCTCCTGGGGCAGCAGGGATGTGGCTGTGAGGCCTCGTCAGTCTCC
CTGTTTCTATCTCTCTCTGTATCACACACACACACACACACACACACACA
CACACACACACGCACGCACGCACACACACAGAGGCGTGACCAGGGCTGCA
GACAGGGCCATGGGAGGACTGCCCGGCAGTGCACCCAGATGGCCACACGG
TGGGGCCCTCGTCCCACTTTTGCTGCTGATGCTTCCGCCCAGGCTGCTGG
GAGCAAGCACTAGCTTCCCAGGGCTCTGACCAGAGAGGGATGGGAGGGGT
CATGGGTCAACAGGCGCCAGGGAATGGGGAATAGGATCTGAGGGGCGGGG
GCAAGGGGCCCAGGCGAGGCTGCAGTGCCCAGAGCTCCCTGCACCTGCAG
GACCAGCCACAGGCCAACAGCTGCAGGCAGAGCAGGGCTGCTCCTGTCCC
CAGAAGCTGGCACAGCACATGGGGTCTGACAGCCCCACCCCGGGCCTCCC
ACAGAGGGCGGGTCCCCCAAACTCCTCCCCCGTCCCACCTCACAGCTCA
GCATCTCCACTGCCTGAGGACGAGCCCAACACACGGGCACACACACACAT
GCACGCACACACATGAATGCACCTGCAAGCACACACTCACACGTAAGCAG
GTACACACATGCATGCACACAATGAACACACATGCACGCACACACGCATG
CACACACGCACACACACTCAAACACGTACATGCAAGCACATGCTGGTCCT
TTGTCCCCGTGGAGGGAGGATGGAGGCCCAGCCCGTGGGGAGGGCATGT
GGAGTGTTGGGGGGCTGGCTCCAACGCCCTCGCTCAACAGGCACCAACGC
TGGACTGAGATAAGCCGGGGCGCTGGCTCCCTTGGGGCCGCTCAGCAGGT
TTGACGCCCACCACAGGTGGCACTGCCTCTTTCAGAAGACGGATGTGGCC
ATGCCACCCTCACAGCCTCACCAGTCCCCCCTCAGCTTTAGTGGTGTCCC
TGTCACTGTACCCGGGGCCTTCCTTCTTCCAGGGCCAAAAGCGAGTTCAG
GGGACAGTGGCGCCCCATAATTACTCACCCAGGGTGCTGTCCTCTGTGG
TGGCCTTGAGGCCAAGGTGCTCCCATGGGGGCCCACAGGGCTGGCAGGGT
CACTTCCTGAGAGCACCCAGGGCCAGGGGGGTGGCCCAGGCCTGGCCGGT

FIGURE 6, CONTD.

```
CCCCATCTGGAATGAGGGCCTTGCGCAGAGGCGGTGCACCCCTCTTTACA
GCAGCCCCGGGGGAGAGTGACTCCTGCGTCATGGACCTGGGGGCTGACCT
GTCACGTGTCTCGCCCAGTTGCACCCCATCCATTTCCGGGTGGAAGGGAC
AAAGCCATCCTGGTCGTCTCAGAGGACCTCTGGAGCCTCTTGGCCCCAGC
AGCCCAGCCCCTCCCGGGCCCGCATCCTCTGCCCACCCAAAATCACCTGT
GCCCACAGGGTCCCCTTCTGGGTGTCCAGGGCGACCCAGAACTGCCCCTG
CAGACACACCCAGCCCAGGACATGGCCGCCTTGCCGGGCCTGTCTGCCTG
GGGCAGCCTGACTGCCACAGACAGGCCGCTTGGAGGACCATCTGCCTGAG
CCCCCAAGGCACATCCCACGGGGCCCACACAGCCAGCGCCTGTAGACGAT
GCCACTTGGGGTGGGGGGAG
```

Contig 106 (1500 bp)
```
TGCCGAATAGAGGTGGAAACCAAGACCCGAAAAAATGTCCACATTTTTCA
ATTATTAGAAATTTAGAAAAATATTTTACAGGAGTTAAAAGGTATTCCAT
TCTGGGGGCGGGTGGGCATGCCCACGGCATGCAGGCATTCCCCGACCAGC
GACTGAACTCGAGCCACGGCAGTCACCATGCTGGATCCTTAACCTGCTGA
GCCCCTGGGCAACTCCAGACACTCCATATTCATGTAAACTATTTTTTAAC
CAAAAAAATGACAAAGCTTTTCAAAACAAAACACATTTCATGGGAAGAGT
GGCATTGCTTCACGCCTGGATGGTCGCTGCGGCTTGCGGGACGACGAGGG
CCCCCGCGGGAGCGCCTCCGCACGGCGCATCAGGACGTGGTGTCCAGGGA
AGCGGGGTCACTTCACGGCCTCTCGGGTGCGCGTGGGTTTCCTTTTCGGC
ACCACACCCGGACTCAGCACTTGGGGGTTCTTAAACGTGAGAGGCACTGC
GGGGCTCGAAGCCACATCACTGACCTCCTCAGACTCTGTTATGTGAAAAC
CCATCCGTCCACGAGACCAAAGAGACAGACGAACAAACGCAAGGTGGCGC
CTAGGTTGGGCACAGCATGAGGGCAGAGCGGAAACCTTGGCGAAATCCCG
GCGAAGCCTGGACGTCGCCAGCTCTTACTTGACGCAAACATAGGGGGATT
CAGGAACTCTCTTTACCGCATTTGCAATTAATTTGCTGCAAATCTAAAAT
CGTTCCAAGCACAATGCTCACTGCATGGAAAAACCCAGGGGTAGGTCTCG
CCCGATCAGGATGTTTTCCCGTGCCCTCTGTGCGGGTGCTGCCCCCTGCG
CTGGTCAGTGAGAAGTGTCCCTCCACCGACGACATGAAACTTCCCAGGTC
CACGCTCTCTGCTGTCCTGGACGAAAACTCATCTCTGTGAATCTCCCGCC
AGCTCCGCGGGAGCCTTCCAGGGCTGGAAGGACGGCCGTCCCGTTCCAGG
GGGCAGGTGCACGCTTCCCAAAGCTCCGCGTCCTGCTAGGACGCTCAGAC
GGCATCACCCACAAACCCCACGAACTGTTTCCCTCGAGGCGACAGGCTCG
CCCTTCTCCGAGAAAGCAGCCCGCACACGTCAGCAAGGGGCCAGCTGCGT
TTGTAACTCAAATGGCCACACATAGAGTTTGTCCTGGAGGCACGGGGTCTGT
CTGGGCCGCACCACTGCACACGCAGAATATGCTGGGACACGCTCCGGGGT
CCAGCTTCATGGAATTAATAAAGTTTACTGCTTCACCAAGTACATTCTTA
AGTGTAGCTGGCCGCCAGCCTGGGCGTCCGCTCCGAGGCTGCCTCTCTGC
CTGGAACCCTTGTGCTGGGGGACCCTCTCTCCAGCCCCACCCCAGCCCCG
AGCCCAGGCAACATCCTTCTTGTAAGACACCCGCTACCCTGCCCTCCCGC
TTCTCCTTCTCTGGATCCAATCTCCTCCGCTTCTAAGCTCTCTTGAGGCT
```

Contig 107 (550 bp)
```
ATGGCACTCGCGGTTGTGACTGAGCTACCGGACGGCGCGAGCAGGGCCAC
GAGGGCGACAAGCGCGGGGCTGAGAACCTGTGCGAGGGCAGGTCCCTGCG
GCTGCAGACAAGCCTCTATCGCAGGCCCACAGACAGGAGCCCCCGTGTGA
CCCTCAGGCTGCGAGACCAAAGTCACGGCTCTGCTGGGAAAACCTCGAAC
CTGATGACTGGGTGGGTGACCCCAGGACCTTGAATTCCGGCCTCTGCAGA
ACGCTCTGAGCCTACGGGAGTGGCCACCCTCTCGGTTAGGGCCTGTGTCC
TTCCCTGGCTTCCAGCCTAGAGCAAAAGCATTAAATCACAGTGTGGCCCA
GCCCGGACCGTGCAGGACCTTAGACAAAAGAGGAGGGAGAGAGAGATGAG
GCAGAGAGGCAGAGAGACAGAGGTGGAGAGACAGATAGACAGAGACAGAG
GCAGAGAGAGAGACAGACAGACAGAGACAGAGGCGGAGAGACAGACAGAG
ACAGAGGTGGAGAGACAGGCAGACAGAGACAGAGGCCGAGAGAGAGACAG
```

Contig 108 (900 bp)
```
TTTCTAAACTCTCTTACTAGTTCTAGTTTTCTATTGTTTTCTGGGGGGGT
TCTATATAAACATTCGTGTCGTGATTGGAGATGGTTTTGTTTTTTCCTCT
CCAAACTGTATGCCATGTGTTTCTTTTTCTTGTCTTATCACACTGGCTAG
GACTTCCAGTAAAACACTAGATATGAACAATGAGAGGAGAGCCAGGCCTT
CTTCTCAGTCTTGGAGGAAACAGTCAGTCTTTCCTCATTTAGAATGAGAG
CTTTTCTTTTCTTTTCTTTCTTTCTTTCTTTTTTTTTTTTAATAGGTT
AAGGAACTTCTCTTGTATTCTTATTTTTTTAGAGTTGTTATTTTTTTTTT
CTCTCTTTTTAGGGCTGCACCCGAGGCATATGGAGGTTCTAAGGCTGGGG
TCGAATTGGAGCTACAGTCGATGGCCTACGCCACAGCAATGTGAGATCTG
AGCCACATCTGCGACCTATACCACAGCTCACAGCAATGTCAGATGGTTAA
```

FIGURE 6, CONTD.

CCCACTGAACAAGGCCAGGGATTGAGCCCGCATCCTCATGGATGCCAGTC
AGTTTCGTGACCGCTGAGCCATGAAGGGAACTTCCAATAATGCACCAATT
TTAAATGAAAAAGACAAAGCATCCAGCCCACAGCCTGAGTAAGGAGTTTG
GAGGCCTGACCCCTGCGTGGTCCTGGGCCTGGGCCTGGGCTGGTCGGGGT
GGGGGGGGGTGGGGGGGACCCTGTGGACCCTCCCTCCTCAGCCAGGCCTG
CCCCTCCATCCCTAGCTGTCGGGGGCTCGGAGGAAGGCGGGTGGATGACG
GTCCCTGGGACCCCTCCTCATATGTATCTGGGTCCCTGGTCCCTCTGAGG
CCCAGGTCAGGTCATGGGAGTCAAAGGTCAGCCAAGGGGGTAGCCCAGAG
Contig 109 (950 bp).
TAACCCACTGACCGAGGCCAGGGATCAAACCTGCAACCTCATGCTTCCTA
GTCGGTTCGGTAACCACTGCGCCACAACGGGAACTCCTTTGCTTTTGTTT
TTAGGATTTCACATACACGTGATAACGTGCCGTATTTATCTTTCTCATCT
GAATTATTTCACTTAGCCTAAGCCCTTCAGGGTCCATCCATGGTGCTGGG
AGTGGCAGGATTTGCTTCTTTTTTTTTTTTTTTGTGGCTGAAAATCAG
TCCAGGATTATCTTCTTTTTCTGTTCATCTGTGGAGGACACAGGCTGCGT
CCGTGTGACGCTCTGCCGGGAATACGGGGGCCGATCGCTTTCTGAGCCAG
TGTTCTCATTTTCTTGGGAGAAGTACCCGGAGTGGAACGGCTGGGTCGTC
CTGCAGTTCTGTGCTGCATTTTTTGAAGACGCTCGGAGCGCTTTCCACAG
TGGCTGCACCGACTGACATTCCCACCGAAGTGCACGGATTTCCCCATCCT
TTTTCCACGTTTTCCCCGCACTTGCTATTTTTGCCCTGTGGATGTCGGCC
TCTCCGTCAGGTGTGAGGGGAGTCTCCGTGCGGCCCAGGCGAGGAGCGAC
CGTGAGCGTCGTTTCACGTTCCTGTTGGGCCACCTGCGTGGCTTCTCCGG
AAAAAGGGCTGTTCAGGCTTCTTGCCCATTTCTCAGTCTGATTGTTTGGG
GGGTTTGCTGTTGAGTTGTGTGAGTTCCGCACGTATGGGGGGCATCAACC
CTTTATCAGCTATGCGATTGGCAAGTCCGTTCTCCCATGTTCCGCCGGCC
GCCTTGGCACGTGTGGGCGGTCTCCTTGGCTCTTCCTTGGTGCAGAAGGC
TTCGGTCTGATGTGGGCCCATTTGTTTATCTTCTTTTCTTTCCTCACCGT
TGTTTTGATGTCAGATGCAAAAATCCATTGCCAGGGTCTGTGCCGAGAAC
Contig 110 (306 bp)
CGCCACCTCAATCGCCGGTTTGTTCTGCAACACGGTCCAGATAACCAGCG
CACCTAACAGGTCGAACACTGCCAGAACTGCGAACAGCGGGCTGAAGCCG
ATGGTGTCAGCCAGTGCACCGACAACCAGCGCAAACAGCGTACTTGCCAG
CCATGCGGACATCCCGGTTAAACCGTTTGCCGTTGCCACTTCGTTACGAC
CAAACACATCGGAAGAGAGCGTAATCAGCGCGCCAGACAGTGCCTGGTGG
GCAAAACCACCGATACACAGCAGCATAATTGCGACATACGGGTTGGTGAA
CAGGCC
Contig 111 (800 bp)
GTTTTCCATGATGCACCAGGGGGCCGGGACCGCAGCAGGGAAGGCTCCA
TCCTGGCTCTGTAAGACCTTGAAAACACCTCATTCCTCTGGTCTTGCCCT
GCTCTTCGGTACGCCAAGTTGCTGAGACTGATGTGGGGATCAGTGGGGAG
CAGGAATCTTTCTGATTCAGCCGTTTCAAAGTGTCCCAAGCAGAAGCTGT
GATGGCAATGCCAAGGCTATCCATGGAGGTGGCTGTGCCAGGGGCCCCAT
TTCCTGGGAGCCCATTCCAGGAAAGGAATCTTGTAGCCCCAGGCTCCAGC
AGCCAGTGCACGGCCCCTGGGACTATCCGGGTAGATCAGAGGGAGGAACA
GAGCTGTGGATGGTAAGCAGGTGGCCCAAGTCCAATTTATGTCTGTGGTC
CCAGCAGGGTGCCCAGGAGGCCCCTCGTAACTCTTAAGAATCTTGGTCTG
GTCAGCTAAATTGTATGACCATTGTACTGAGCACACATCCCGTTTAAGTA
GAATTTTCAAGGATGACTAGGAGTTTGCCACCTGAAGGCAGGAAGGGCAT
TCCAGGCAGAGGGTACAGAGGTGAGAGGGAGGCTCTGACACTTTGGGCGT
GCAGGGGGTTTGATGTGACTGCAGCTGGCACACAGTGTATGCCCAGGCCT
GGCACGGCTGTGTTGGTGTTTGGAGAGGAAGGGAGAGGTGAGTTGAGCCC
AAGGTCTTCCAGGCCAAAAGACTGAAGGTGACCGCGGCTGTCCGGGGCTG
GCCCGCAGACCAGGAGGGAGCAGGTGGGAGCTGGCTCTTGTTCCGGGGAC
Contig 112 (3062 bp)
CACACCCCAGGAGAGGAAAGACCCACACAGTCCTGATGACAGCTTGGCTC
GGGGCTGGAGCCCCGAGTTATAAATGTCCATCACGAGCTGTGTTCTGTCA
GAGCCATCAGTGGGAAGGCCAGGCCAGCTCAGCAGCCCAAAAATGAAGAG
CTAGGTCTGGGATTGGGCCCAAGCAGAGGGCACAGGAAAGCCACATAAAC
AAGGCACCCAACCCCCTGTCATCCACCAATGTCACATTCAGGTCACACC
CCTGGTCTTCGGGGGAGGTCCCCTAAGATCCGGTGGCAGGGGGAGGAAAA
GTCTGACTGGATTCCTTGACAGGTGTATCAGCGGAAGGCCAGGAGGAGTG
CTCGGGCACTGCCACCTCCCAGGGGCATGATGGTCATGGACCAGATGGCA
GTTATGGGAGGAACCTCCCCCGTGGTCAGAGCTCTGGGTGCTGTACCTGG
TCATGCATTTCGAGTGGAAGGAAAAGAAAACATACAACTCCACCCCCAGC

FIGURE 6, CONTD.

```
AGCTTTAGGCTGTTGGTCTAAAGGTCCTGCCTCCTGGAAGAGACACGCCT
CTGTCAGCGGACACTGCTAAACCTAAAGGAAGAACTGCCACCTGGTCACG
GGACTTCCTAGGCCAACCAACCTACAGGTGACGGCCCGGAGCATCACGAG
GAGGTAGGGGACGGGAAGGGATGCATTTGCTGCTCAGCGGATCCACTGGG
GCGTTTCTGGAGCCCCACGCCCACACTTTACTGCAAATGCACAAGCCCC
AGGCAGCAGGACAAGTCACAGTAGCTCTGGGTTATCCAAGGAGTCAGGGA
CCTACCTGGAAGAGTCTAGAACAGGTGACAGAGGAGGGAGAGGATGGTAC
CAGCAGTATAGGGAGAATCAGAAATCTGACCCACCCTGGGGCCTGACTG
ACTCCCAGACCAAATGCCACACTCAGGTTCCCCGTCTGCCTGCACTTCCA
GGGCTGGGCCACGGGAGTTATGGGCCCCAGGTAGCATCAGAGGCTCCCAG
GTACAGGCACAAGCAGCAACCACAGGAGGGATCCAGGCCAGGGAGCATCC
AAGAAGCAGCAGAAGCTCCACCTTAGGTACAGTTCTGGCACCTCCAAGTT
GAGAACATGTCCTAGACAGTGCCTGACCCCAACCCAATGGAGTGTCTGGG
ACTAGACTAGGCACGCCATTTTGGTCCCAGGTTGCCCCATCTGTACAAAG
GGTGTGCGGCCCCAGGGGACACAATGAGCTCCCATGGGAAGGGTCTTG
CGAATCTCCTTAGAAGCAGATGTAAGAGGTGACGTCCAGCTTGTGCCTGG
GATGTAGAAGTGGAAAAAGCACCCCTCCCCCGACAAGGATGAAAGCAAGA
GGCACAAAACAACCTGAAATTCCCAACGCCCTGGAGATCCTTGGAGAAC
TGGGATTCTCCACCTGTAGGGGCACCTGTGAGGAGAGGCTGTGTGAGCAC
CTGCTGACCTGGCACAGAGGATGCCCAATACTAAGAAGCATCAGCTAAAA
GTCTCCAGGAATTCCTGGAAGCTGAGGAAGGGCTCAGGAGAGGGTACAGA
AGCCCTGGGGCTATAGATATAAGGGACGTGCACACCCACTTGCAGGTCCC
CATGGACCCCAGGGACATTCACAGTGATGGGCAAGATTCCCAAAATGCAC
CCCTTGTGTGTGGGCCTGGTTCGGTGGGTCAGCAGACACCACACCAAAGG
CACAAAGCACACACCCTCAGGCTACTCTCCTCCCTCTCCCTTGTGGAACA
TGAGCCTTGAGATGCTGGGGCACGTGAAAAACACTGTCACACTTAGGTCC
TGGTGAAAACTGACTGCGGCCAGCGGAAAGAATCATAAAGACCCTACACC
CACACACAGCCTTAATTACAGCTGTGAGTGGGGCTGGAGCCCCAAGAATG
TCTACACCCATAAGACATAGCGTTAATCAGAAAAACAAGAACAGCCCCAA
CCCCACCACCAGGCTGACAACTAACAGGTCATGTTGGAATATCACTGGGA
ATGTTCTAGGAGTGTAGAAAGACACACCAACTAGGGCATGATGCAAAGAT
AATACTTCAGCCTGGGAGTGGATGTGACACAGGGAAAAGCATAAAGTGAT
GGCAGAGGACTTTGATGTCAGTGATGGAAGCCACAAAAACTTCTAGCTTA
GCTCCATTCCCAACAAGATTGACTGCAAACCCCATGCTAAAACAACAGCA
AAAAGAAAGAATCCTCATTTCCAGGCATAAAATTTTTCCCCCAGTCTCTG
CTGTCCTCCATAAGATGTCTGATTTCAACAGGAATTACGAGGCTATAAGA
AAGGCAAGAAAAAACTACACACTGTCAAGAGAAAGCCATCAGAATAACCA
GACTCGTAGCACAGACACTGGAATTGTCAGGATATTTTAAATAACCGTGA
CAAATACATTAAAGATTCTAATGAGAAGGGGTAGACATGTAAGATCACA
TAGATTTCAGCAAAGAGATGAAACTCGAAGGAAAATTAAATGGGAGCCCT
AGAGTGAAAAACACTGTAGCAGAGAAGATGGGTTCATCCGTAAACATGAC
ACAGCTTAGGAAAGAATCAGTGAACTTGAAGACAGGGCCACAGAAAAATAT
CCAAACTGAAATGCAAGGAGGAAAAATAATGAAAGGGGGAGAGAGAAAA
ATAAAAGAACAAAGCATCCAAGAGCTGGAGGGTGACACTGAAGAAGAGAG
CATAGGCATAGCTGGAATCTCAGAAAGAGAGAAAGAAATAACCCAAGATG
TAATGGATGAGAATTTCACAGAAGCGTTGTCAAGCAACAAACCATACATC
CAAGAAGCTCAGAGAACACCAAGCAAGGTAAGTACTGTAAAAAAATAGCC
CGAGGTATACCTCATTCAGGCTGCTGAAAATCCATGACAAAAGAAGTCTT
GAAAGTAGCCAGAAACAGAAGGCGTGTTCCATTCAGAGGGAAAAGACACC
ATTGTTGCCAGAAACCAAATAAACCAGGGCTGAAAGGGTAAAACTTTTTT
TTTTTTTTTTTTTTTTTTGGCCATGCCTGTGGCATGTGGAGGTTTCCCGA
TCAGGGATCAAC
Contig 113 (1300 bp)
AAACGGATAAATACAGGTGACCCACAGGCAGAAGCTGAAGTACAAACAGT
TCACAACGGCACCCAAAAAATACCGAAGGCTCAAGGGTAAATCTGACCCC
AGATGAAAGGCCTTCTCACGGAAAATGGCAAAGTGGCGCTGAGAGGCATG
AGAGGTTCGAATAGATGGAGGGCTCCGCCGTTTTCCCGGGTCCGAGGATT
CAGTGACGTCACGACGCCAATTCCTCTGAAACGCCTCTCTAGGTTCAGTG
CAGCCCAGACCCACTGGCAGCCGCCCTCGCTGCAGAGACAGCCCAGCTGG
GTCTTGAGGTTCCTACAGCGAAGCAAAGGGTCTAGAAAAAGCAGACGTCT
CTGGAAAGGGAGAAGCAGCCGATGGATTGGCATACGGCGACAGGAGATTC
CTCGGACAGTGGCACCAGGAGAGGGTGGACAGAGACTGGTGCAACCGAG
CGGGCCCAGGAATAAGTCCACACCCACACGTACCATCTCGTTGTTTATTT
ATTTTTTCCTTTTCAGGGCCACTCCTGGGGCATGTGGAGGCTCCCCAGCC
```

FIGURE 6, CONTD.

```
AGGAGTCGAATCGGAGCTGCAGCTACAAGCCTACCCCACAGCCACAGCGA
CACAGGATCTGAGCCATGTCTGCAGCCTACACCACAGCTCCCGGCAATAT
TGGATCCTTAACCCACTGAGCAAGGCCAGGGACTGAACCCACGTGCTCAT
GGATACTAGTTGGGTTTGTTACCACTGAGTCACAGTGGGAACTCCTTTAA
TTTTAATTTTTGAAGGTTCAGAACTCTTTAATTTTTTAGTGAGGTATAGA
TTATATTACGCACCATTTCTTTCTGACTTCGGTGCACGGCTTTTCAACAA
ATGGGTGCTGGACCTGCTGGGTGCCTTCTTCAAATGAACCACAAGCCCTC
CCTCGCGCCGTATGCAAAATTTAACTCGAGGGGCTCATAGACATAAACGT
AAACTCTAAAGCTATAAAATTTCCAGAAGAAAACGTAAGGAAAACCTTTG
GGGTCTTGGGCAAAGATTTCTTACCCATGACAGCAAAATTACAATCTACA
GAAGAACTGGTGGCCTTTATCGGCATTTAAAACACCTGCCCTTTGAATGA
TGCTGTCGCAAAACCGAACATGCAGCAAAACGGATGCAACTAGCAGGTCT
CACACTCAGTGACCCACGTCAGAAAGGGAAAGACACGCCACGTGACATCC
CTTAGATGCAGAATGTAAAACACGGCCCCCGTGAACCGACCTCAAGAGAG
AGACAGACCTACAGACGCAGCAAATTTGGGGTTGCCGAGGGGATGCCGG
Contig 114 (3000 bp)
TGTGAGACCCCTTGGCGGGCCAGGACCCCCCAAGGTGACCGAAGGCCTCA
GCGCCCCAGCCGCCCCATCCCCCTCTTTCCCGACACAGGATTTTTTTCC
CACCAAGCTCTGTTCCCTTGGTCACGCTCTCACTTGAGCAGCCTCAGGGT
CTCCCGGTGCCTGTATCCACGACAGCGTGACCTTCTTGGTGTGTCAACCC
AGGACCCCACGCTGGCCAGCCACGCCTTCCCAGAGCACCCCCGCCCATCC
TCAGAGTCCAGAGGAAAGGCCCCCATTGACCCCAGAAACCAAAACGCAGA
GACTCTGGGACGCCAGCAAGAACGTACACTGACTCCCACCTGCTTCAGGC
ACGGAGGCAGGGGTGGGTTATGAGCGACCCGTGGAAGGGCCTTCTTGTC
CATCGAGGGGCTTCCAGGGGCTCCTAGACGGGATGAGTGTGGCAACATG
TCGCCGCATTACAAAAGACCCTGCAGTGCTGCTGGGATGGGTCCCCCGGC
TAGAAAAGCAAAGGATTCCAGCCCAGTCGAGTAGGAGGCGGCCTCGGAGG
CTGCAGAGGCGCGGGGGGCGCTGACCACCACTCGGCAAGCCCCGTGTTGG
AGGGGACGCCCGGCCCGGCTGCAGCCGGTGCGCCTCCGGATAAGCTCCTA
AGAGGCCGCGTGCCCCATGCACGCGCGTGCACACACTCGCTGCCCGAGGG
TCCTTCAGCACAGACCTTGTGGGGACGGAGGACCTGGCAGGGGTGTGGCT
CTGGGGAAGGGGTCTGTCCCAGGAACCCTGTTCTGCATTTGGGGGTGGGC
GTGGATATCCCGTCCCAACCTACAGAAGGGAGGGGCTTAAAAAGAGCCCC
TTTGGTGTGAGGGGCCAGCAATCCTTTGGCTTTTTCTTGGCCCACTTGGA
GCTTGACGTCTGGTCAGTGACTGGGAGCCAGGGCCAGAGGGGGGCAGCCG
GGCTGAGGCAGGTTCAGGCCAACCATCTCTCGGCCACACTCCCGAGGTCG
GGCAGCTACGGGGCCCCAGAGACACAAGCCCCAGGGGTCCTTCCCCCCC
GCCCCCTGCCCCAGATCACCAGGAGACCCAAGCAGCTCTGCCTCCCCGTG
CCTGAGAAATGCCCCATCTGGGTACCCAAATCACCCTCCCAGAAGGTAGA
GTGGGGGGCCCAGGACAGGGGGACCCCAGTTACAGAGCCCCAGGCAGGCT
TCCCAGGGGCGAGGGGACTCCGTTTGGGGCACAGACGGAGGCAGAGCGGG
CTGATGGATTCTCCCCCGGTTCAGGGATGCTGGCTGCCTGGCCTCCAGGA
GCCGGCGGTGCCATCTGATCTGATTAAGGCCTGCAGTCCCAGCTGGGCGG
GCACAGCCTGGGGGCTCGGCGGGCAGGGAAGAAGGCGCTGTCGCCCCAGC
CGGTCAGGCTCGCTTTCTCTTCATTTCCTCTCCATTAAAAGTGTCAGAAC
CATTTATTGATTTTTTAAATCAGGACGTGCTGTCCGTGACACAGCAAAGT
GAACAAAATCAGAGCAAAGAGAGGCCAGGGCTGAAGCCCAGAGGGCGGC
GCCTCCAATCCGGGTTGTGCCCCGGGGCTCCAAGCCCCTTCTTCTTCTGG
GGTCCTGGGCGTAGTGGCCAGGGCAGAATGCACCTGCCGTCATCCTGGGA
GGCTTGGCCATCGCTGGCTTCTGTCTCATGACGCACCGTCGTTCCATATC
TACGGAAACAGCTTCGCATTAACAGGCAGGGGAGGCGGTTGTTTCTCCTT
TATCTGCCCACCATCGGCGCTGGGGCCACGTGGAGCCCAGCCGGCTGACT
TCCCGCTCGCACGCAGGGCACTGATTGCAGGAACGAGGACATCCAGCCCC
CGCCTCTCAATGCCCCGGGTGCTGAGAGCATTTCGCCCAAACGGCTTGGG
TGGGACAAGGGATGGAGCTGTGCGCCAGGGGCCTGGCTGGGGCAGAAGGG
GGCCTGCCCGTGTCTGCCCGTGCCTCCACCACCCTCGGCTGCCAGGCTG
CTCTGGAGAGGTGCCCGGGGCCGAGGGCCAGGGGCACCCTGTTCTGCCC
CACGTCTCTCTGTCCTGCTGAAAGTTCCACCAGACGCGTGCTATACCCTG
GGAGTCAGGAGGATGGGGATAGTTGGGGCTTGACGTCTGTTTCTGAAAA
AACACCGTTTTCCCTGAAATATATATGTATTAATTTTTCGTCAAGATAAA
ACTGTGTATAGTTTTTCGTGATGAGAAAACGCATCCATCTTCCTTAGAAA
GCCTGAAGAGGTACAGGAGCCTATAAAGGACAAGATGACAGATGCCTCTA
ACGCACACCAAATGTGCGGTGGCCCCAGGGGACCGCATAGACGGGGCGG
CTCCAGATGGCCACCGTGTGCGAGGGACACGGTTCAGGGTGGCAGAGTAT
```

FIGURE 6, CONTD.

TCCTGGGGGGGGGGGCTCAGCGGTTCCCATTTCCCCCTCCCTTCCTTCC
TTCATTTCTTTCCTTCTTTCTTTCTTTTTGTGGTTTTAGGGCCGCACCCG
CGGCGTGTGGAGGTTCCCAGCCTAGGGGTCTAATCAGAGCTACAGCTGCC
GGCCTCCACCACAGCTCACGGCAACGCCGGATCCTTAACCCACGGAGCGA
GACCAGGGATGGAACCTGGGACCTCATGGATCTTAGTTGGGTTTGTTCCC
GCTGAGCCACAACGGGAACTCCAGCCATTCCCATTTCTTGCTCCAGTTCC
AAGAATTCCAATTCTTATTCCTGTTCTTTAAGGCCAGAGGCGACAGCCAC
GCCGAGTCCCAGAAGCAGGGCTCAAGGATGCTGCTGTTGACTGTGTCCGT
GGGCGGGGGGAGTTGATAAGAACCCCCAACACAGGGTGGTGGCCAGCAAC
GGGGGAGGGAGGAGGGGGGCTGGTGGGGAAAAGTCCCCTGAACCCCATGG
GCTGCCCCCTCCAGGCTGGGGCACGACCCCGAGCCCCATGGCCCGAGGAG
AAACGGTCCCAGCCCCAGGCTGGGCTCCCGCACCCTGCCCTGACCCCGC
Contig 115 (1895 bp)
TCATGGAAGCCCTTATCACAACCTCGGATCCAAAACCCACTGCGCGAGTC
CAGGGATAGAACTCGCATCCCCACAGACCCTATGTTGGGTCTTAACCAG
CTGAGCCACATGGAAACTGGGTAATCTATTTTTAGATGTTCCTAGGGTTT
TTGGCCTTGCCTGTACGTGGGGACGCTGCTGGGCCAGGGATCAAACCCGC
GCCACAGCTGTGACCCAAGCAGAGCAGTGACAGCACCGGATCCTTAAGCA
CGAGGCCAGCAGGGAGCCCCTGTGTTTAGATTTTGGTGAGGATACTGCGT
GGGATTCAGGATATTCACTTTGGGGCTGTTGGAATTGCCCGTCGCTGTTT
AAGCAAAGAGAAATCCCTTCACTCTGTGTAACTGTGGGGAAATCCTTTAG
TCTCTTGAAACCATTGCGTGTGTTTAAGAGTGGTAACTCTGCCACCATAA
ATGCCCAGACCAGCGCCTTCCTGAGATCCGCTTTTGTTGCAAATATCTGG
TTTGAATGCTTTGATCGCCCGCACCAGACCAGGGTGGGCGGACGCCGCCG
GGGACCCGACGTGACCATCGTGCTTCTGTATCCGCCCTTTCTCCGGCACG
CGCCCCCTGGTTGCCTCTGGCTGCTTTTAGTGGAGGAACTGAAGCCTCGC
CACCCAGACCCCGAGACCGCAGGACCCACAATGCTTCAAACACCTGCCCT
CTGACTTTTACAGGTCAAGTTCGCCAACGCCGAATTTGCACCGATTGGCT
ACAGAGAGCACGGTGGCGCCAAGCCTCCACTTGGAGTTTTATAAGGTCTC
CCTCCAGCTCGCAATGAAAATGAGCTGTGATAAGGCAAAGACAAAATTAG
TATGAAATCCAGATGCTTCATCTACAATACAATGACCGCGGGATTTGGGT
CTGAGCGACTGAAATCAAGGTGGGCTTCCGGAGGGAGGCTGTTAGAGGAA
AGGCATTCACGGAGGCTCAGGTCCGAGAGGCTTCCACACCCCTAAGAGGG
CTGAGACGGCAAGTAGGGACCAAGCCCCGCAGTCGGGAGAGCTGGGCAGG
AAGGAAGTCTGAGGTCACCCCCACCTGGGGAGGAACTGCCTAGAGAAGCG
GGGGCGGGAAGCAGGGGATGCCCAGTCCCAAGACAGGGACAGGGCGGAAA
GGGCTCTCTGCAGGCCCTCAATGCTGCCACAGTGTCCTCGTAAGAGGGAG
GCAGAGAGAATTGACACCGGGGAGACCACGGGACCACGGAGGTGGAGACC
GGGCTGCCCGCGCGTGCCAGTTGCTCCCGAAGCCGGCCCCTCCCCAGAG
CCTTTGGGAAGAGGCGCCAACCTGCAGTTCTGCTACTCGGGGACAGGGAC
AGGGACAGCCCCCTGGAGCCGCCTCTTAGGGGCAGCATCCCCCAGAACCT
TCCTTAACAGACCATCTGGAGAGAGATGGGTCTGGGCTGCAGCTCCTGGA
ACTGTTTTGCCCACCCGGCGAGCACCAGTGGGTGCCAGCCTGGGCTGCCC
AGCCTCAGGGCCGGGAGGGCTGAGGGCACTGGGGCCCGGCTCTGGGACT
CCCCTGCCTCCTGCCCGTGCAGGACAGCCACCTCCCAGCATCTGCTTCCT
GCCACCCACATCCCCAGGACCGTCAGCCCAGGCATGCCCCTGGCGTCGGC
CACTCACACCACAGGCCAGGAACCCAAGGGGGCAACACAGAAGGGCAGTT
GCCATCTGCAGATGGAATGGACAAACTGGGGTCCGTGATGATGGCAGGCT
CTGGGCGCCCGGGCTGGCAGGGGAGCCAGGACTGTGCGGCCATCACAGGA
AGGGCATGACGGGGTGAAAGCAAGAGTGGAAACCTCTGCCACCCGCCTGG
GCGCACATACCGGCCACCCTGCAGCCCCACCCCCATTTGTTTGCT

FIGURE 8

Contig 1 (1040 bp)

```
GCGCGCCGGATCCTTAATTAAGTCTGAGAGATCTGCGGCCGCGGCCAGGGTCTGCTTCTG
GCCAAGTGTGGGGCTCTGCTCCATCCTGGCTCGGAGGTCCACCCATGGCAAAGCCTGGGG
TCCTCCCACTGAATATTTGGGGGTCCACTCGTGCCAAAGGCTGGGTGTCCAGTGTGCCAA
CGGTACATGGAAGCAATGTCTTCCCAAGGACCGTCCAAGGTGTGGTCAGGCCTGGACAGC
TGTGAGTCCCTTCGGGACTAGACTTGGTGGCCGAACCCTAGGGACCGTGCCCGAGGGCCC
CCACGAGGCCAGGTGTTTGCCCCAGGGACAGAACGGCCAAGGGTGGCCGAGGGTTCTTTT
TGTTTGTTTTTCTTCTTTCTCTTTTTCTTTGGCCGAGGGTTCTTAAAGCGCTCTCTCTG
CTCTTTGTCCCGATCCTGAGCGGGCAGTGTCCTGGTCGGTGGGGTGCTGGGCAGCCGCAG
CAGGGCTGAGAGAGCCCGGCTTGTCACTAGGGCGCGCCGGTGAGCCCAGCGGGCATGCCG
TGTCCAGACGTTGGATGGGGCAGCGAGGGGACTGGGGTGCCCCAGCCCCGTGGGAAGCC
CGCCCTGTGGAAGCCGCTGTGCTCGCCACAACAAGCACCGTCGACTAGCTGGTGAATCAG
CGCCCGTCGCCCGCGTAATCCCAGGCGCTTTCTGCCCAACCTGAGCCCTGACCCCACACC
CCTTGCGACCGCTCCGTGGACCCTGGGGCGATGAGGTGAACCGTGGGCTTGGCCATCGTG
GTGGCAGACGGTGGCACACCCGTGCGCCTGTCGGCCCCCCTCCATCCAGGAGCAGAGTGC
GCACCCAGTGGGGGCTGGGCAGGGAGCCGCCTCCACCTCCGCCCTGAGGGGACGGGACTC
TTTCGACCCGGAGTGGGAAGGGACATATGCGGACGATGCCAGACCCTGTCTGTGGGGGGA
GGGGGAGAAGGCCCTCTTTGGAGAATTCCAGGACGGGTGAGGAACGTGTGCTGGACCGGC
CGGGTCGGAGGTGGGCCTTG
```

Contig 2 (9234 bp)

```
GGCAACCAGGGGAAGATGGGGAAGCGGGGTGCAGGGGCGTTTGCGCGGGCCAAGGACCAC
CTTGGAAATCTGGAGCCTGGCAGGAGCGGCGCAGGGTTGAGGGGCTGGCTTGGGCAGGGC
TGGCTGGCACCTGGGAGCCTGGCGGGGTTGAGGTCCGGGCTCCCAGGTGCCCTATAGGCA
GGGCAACATCGGCATGGGGGGTGACAGGCCCGAGCTGGGGTGCGGAGGGAAGAGGGGGA
GCCAGGCATTCATCCCGGTCAATTTTGGTTTCAGGTCGTGGCGGCTGGTGGTCAGGGGA
GTTGGAGAGAGGTTCGCCCCGGGGCCTGGGGCAGCGGAGGTGTAGCTGGCAGCTGTGGGC
AGGTGAGGACAGCCGTCTGCCGGGCCAGGTGAGTCCCCTTCCCTCCCCAGGCCTTGTTTC
TCTGGCCTCCTGCATCCGGAGGTTCTGGGGAGCGAGGGCCGGCGAGGCGAAGCGGCTGAC
CCCCCGGCAGAGTGGCGGCGGACGACAGGCAAGGCGGGCAGAACAGGTGACACGTCTCAG
GGGGAGCTGGGACCGGGCGGGCTGGGGGCCGGGCCGTCCCAGGTGGAAAGAGCATCT
CAAGCGAGTCTGGTGGGAGACGAGGCAGGCTGCCAGCAGGGAGGAGACGCAACAGGCGG
GGGGCATTCCAGGCCCGGGTCGGACAGGACCCGTCGGGGGTGTCAGGACAGTGGGGTCCC
CAGCCGCCACTTCACCCACTGCAATTCATTTAGTAGCAGGTACAGGAGCGGCTCTGGCCG
GGCCTCTTGAGGCCTGAGCTGGAGCCTCGAGGGCCGGAGAATGGGAAAGAAGGTGCAGTG
TGCCAGACAGACGTCACCTGGAGGGAGCACGGCCGTGGGACGGGCCCAGAGAGATTTC
GGCAGCAGGGAGGCTGCGCGGGCCCAGCCTGCGGACGTGCGTTCCCACGCAGCACTGCGG
CCCAGGGGCTGGCGCGGCAGGCCCCGGTGTCCTTGGTGGCACTGTGCGCCCTCGCCGC
TCGCCCCTGGGACTGGCACGGCAGACAGGACAGCACCCAGGGGAGTCAAGGGCACTGACG
AGACCAGACTAGGCGAGGCGGGTGGGGTGGAATGGATGTGACCTCTGGGGGGAGGGAGGT
GGGGACGCAGGCAGGGGCGAGGCGCCGGAGCCTGGCGGCGAGCGAGGCCAAGGCGGGCCT
CTGCGGGTGACAACTGAGCACATATGGGTACCTTTGCGCTCGCACCGGAGACAGGTGAGT
GTCTGGCCCCGGCCTGCCGCCCTCCCGGCCCCGCCACTGCCTCTGCCCTCCCCCTCGACC
AGGGCCCTCTGCTTCCCCACAGCCTCGTCTCCAGTGGGGGTGGACACACTGCCAGCACCA
CAGGCCGGACGCCAGGATGTGCTTGGAGGGACATGACACAGTCCGGTGTGACGGAGAGGG
ACAGACGTGACGCCGTCCGGCCTTCCTGGTGAGCGCAGGTCCAGGCCTTGGCCCCAGGC
CAGCCGCCCCACCCCCACCCCTCATGGCCGTCTTCTGTCCCGCAGAACACTCTCGGCTG
GCCCCGCGGGGAGCTGCCACACCCAGCGTCTGTTCCTTTGCCTTCCTGAAGGAGCACGT
GCATGACTGCTGCTCTCTGGACCCCAGAACCCTCAAACGACAAGGTGAGGCAGGTCCCGC
CTCGCCCCACACGTGGAAGGGCGTGGGCGAGAGCCGGGCGCTCACGGTGCCCCCCTCCC
CCTGCAGAGATGGTGCTACCCAGCTCATGCCTGGGCCTTGGACCCGGACTTCTTCAAGTC
CTCCTAGCTCTGACTCAAGAATATGCTGCATTCTGGAGCCACTACACTACTTGACTCAGG
```

FIGURE 8, CONTD.

```
AATCAGCTCTGGAAGGTGGGCGCGCGCTCCTCCCGCTCCCGGAGCCCCGCCCGCTGCCCG
CTCCCCGCTCACGTCCTGTCTCTGTCCTCGTCCGCAGGTTGAGCCAAAGGAACAGACGTC
CCACACCACCGGACCAACGGCACCCGCGGGGTTCCCCACCCCCCGCCCGGCCACTCCACC
TCGGCGGCCACCCCCTGCTGCGCCCTGGAGACACCACCAGCCTCCCTCTCTCCCCTTCCT
CCTTTTTTTCCTCTGTCTTTTCTCTTCTCTTCTTTCCTCTCCTTTGCTCAGAAGACTCGG
GGCATCCAGGACTCTGTGTCCCCGTCCTTCCTGAATTAATTTGCACTAAGTCGTTTGCAC
TGGTTTGGAGTCCTGGAACCAGCCCCGGGTCTCGGAGCGGGTGTGTGAGCTGCCGAGTGG
CCTGGCCTCCTCGGCCCGCGCCCCCTCAGCACCTGCCATTGTCCATCTCTGTCTGGGGGT
GACTGGGTGGGGGCCTGAGTGTGTGGGGCCCCGCCCTCCCCTCTCCTAGTCTGGAAGCTC
CGACCACCGAGCAGACCTCAAACGCTGCACTGAGTGTCCATCTCGTCATGTGCCCCTCCT
CGCCAGGGCCACCCCAGAGCCCTGGACTCATCAATAAACTCAGTTACCGGAATCTGTCTC
AGGGGCTTTGCAATTGGGCTGGGGGTGCGCCGGGGAAGGGGGGGATGAGATGGGGAACAT
GCAAGGAAGGGCCTGTGGGCTGGGGGACACAGAATGGGTGGGGAGGGGGCTCACAGGACT
CGGGGGGTAATGAACGTGGGGCTGGGCGCAAAGGGGAGTGGGACGTGGGGATCAGGGCGG
GGGGCCTGGAGGATGCAGGGTCCCTGCAGGGAAAGGGGGCCGAGGGCGTGAGGCATGTCC
TCAGCCCTGAGAGGCCCTACCCCACAAAGCACAGCCTGCGCGCGACCTCCAGGCCCCCAA
ACCCCCGCCCCAGACCCTGAAGCCCTGGTCCAGGGCAGTGGGTCTGACTGGCGGAAGGAA
CATGCCACCCAGGCTGGCCACACCACTGGGACGCCCATGGGCGGCCACTTTCATCAAGAG
CCTGGCAGGCCCTGAGTGCTGGGCTGGAGGGCACAGAGGGTCCCCCTCCCCTCACGCTTT
GCGGTGCTGGGGCACCGCAGGAGTGCCCAACAGGAGACCCCAGGAAGTCTGCTGGGCTGC
AGCGAAGGGCAGGGTAGGGGGGCGGCCCACAGGGGCCCAGCTCAGTAGGCAGGTGGCAGT
GGGAGGCGGCAGAAAGTTGGAAAGGGTGGACTGGGCACGTCAGGATCTCGTGGCGGCAGC
CCCGGAGCCACGGCCTTGGGTGCACTGCAGCCCCCACGGTTGGTGTCCCGGTCCCAGGCA
GCAGCTGGGCTGGTGACGCCCCTCTGCCTCTGCCCACCCCCCCACCGCCCCCCGCCAG
CCTCCCAGCCCCTGGGCGCCTGGCGTGACGCTGGGAACGCGAGGGAGCAGGCCTCGGAAA
CAGGGCTGGGTCCTTGACCCCTTCCTCTGCTCAGGGCAGTCAGGAAATGCCTAGCGGGCC
GACTGACCGAGAGGAGATAGCGGAGGCCTGGGAGACCCCGCGCTCGTGCCGTTCCCAGCG
TCCGGCCGCGTGGCCCTTGGCTGGCCTGGTTTGGGCCCCATGAGCTCACCCCCCGCCCCC
CACAGCCTCCCCGCGTCTGGTCTCCTCTCTGGGCCCTGCTGTCCCTCCTGACGGGGGACA
GAGCCCTCCAGGGCCCCGGGGGGACGGTCCCGGGTCAGCAGGGCGGGTGGGCAGCACAGC
TGCGTTTGGTGAAGCCCCTGCCCAAAGCACCCTCAGCGTTTCCTCTGCGCGTCCGGCCGC
CCCCGGAGGCTTTCCCAAGTCCACGGGCAACTCGCAGGCGAGCCCACTCCACCTCCATCA
CGCGGGTTTGGCCAGCGGCAGAAGCACTCGCCCTTCAGGCGTCAGGAGTTAAGCCCCTCC
AAGGCCCGGTGCTAATCAGCTGCCTCTCCTGGAGCTTCGCAAAGCGGGCTCTCAGAGCCC
AGCTTCCCGGGGGCTCACCGTGGTGGCATGGGCACCACAGGTGGCCGGAGGGGCACCGAG
CACGACGGGGCTGTGGGGGGTGGAGGAGGGAGGTTGGTGACTCCGAACCTCTACTGAGGC
ACACAGAGGACACGGCCGCTTCCAGGGGAGTCAGCCTGCGAAGGGCAGAGGGGCTGTAGC
CTCCCGGTCACGCCCTCGCCTCTGCCCTGGATTCCTCCTGGGGGCCCGCGGCTCGTCGGG
GAGGTGAGTGCCCCTGGATGGGCGTAGGCTGGGGGGGCAGGGAGTGGGGGAGCCCCGAGG
CCCTGGGCCCACAGCCCTGTCTTGCCCCACACACAGGGCTGTCTACACTGGGTGCCCACT
TGCTCTGCTTCTAGGCTGTTCCCTGGGCAGCTGCCTGGAGGGCCGTGGGCACAGTGCGGG
CAGCCAGTGGGGAGGCCGGGGATGGGGCCGGGGATAGGGACCCCTGCCCCTGGGTGAGCC
CCACCTGGGCTGGGAAGACAGCAGCAGCGCCCCTTCAGGTCCATGGACCAGGGGACCCAG
GGTGGACTGTGTTTACCTTCAGCCCAGGCCAGTTTCCTGCTTGAGAAAGCCCGGGAGGGG
GTGCGGGACAGGCCCGGGCCCCCCACGCAAAGGCAGTTTCGCAATGTCCCTGCGCTGACT
GAAATGTCACCAGGCACACGGCTTGAATTTCTCCCCCAGACCTGGCAGGGGCGGGGGTGG
GGGCACCGGGCTGCTGGGATCTTGGCCCCTGAACCTCCCCCGGCCCTGCGGCCAGGGAGG
GTTAGGCTGAGTGACAGCCCACGGAAACCTGGACCCGACATGTCTGTGTGTCCATGTGT
GTCTGTGTGTGCGTCCACCTATGCGTCTGCGTGTGTGTCCATGTGTGTCCACATATCTGT
GTCCACGTGTCTGTGTCCACGTGTCTGTGTCCACGTGTGTCCACGTGTGTCCATGTGT
CTATGAGTCCTTGTGTGCATCTGTGTGCCCGTGTGTCTGTGTGTCTGTCCCCTGCAGTCC
CCGTGGACCTGTCTCTTATACACATCTCAACCTG
GCAGCGCCCCTTCAGGTCCATGGACCAGGGGACCCAGGGTGGACTGTGTTTACCTTCAGC
CCAGGCCAGTTTCCTGCTTGAGAAAGCCCGGGAGGGGGTGCGGGACAGGCCCGGGCCCCC
CACGCAAAGGCAGTTTCGCAATGTCCCTGCGCTGACTGAAATGTCACCAGGCACACGGCT
TGAATTTCTCCCCCAGACCTGGCAGGGGCGGGGGTGGGGGCACCGGGCTGCTGGGATCTT
GGCCCCTGAACCTCCCCCGGCCCTGCGGCCAGGGAGGGTTTAGGCTGAGTGACAGCCCAC
GGAAACCTGGACCCGACATGTCTGTGTGTCCATGTGTGTCTGTGTGTGCGTCCACCTATG
CGTCTGCGTGTGTGTCCATGTGTGTCCACATATCTGTGTCCACGTGTCTGTGTCCACGTG
TCTGTGTCCACGTGTGTGTCCACGTGTGTCCATGTGTCTATGAGTCCTTGTGTGCATCTG
TGTGCCCGTGTGTCTGTGTGTCTGTCCCCTGCAGTCCCCGTGGACCTGTGTGGTCTCTGG
TGTGCAGCCCTAGCCGCGGCCCGTCCCAGGCTGAGTGTCCCAGGGTGCAGCACAGCTGT
GACGAGGGTGTGGGTCCCGCTGGCCGTGTCGCTGGGCTGTGGGCCCTATCCTCTTTGTGG
CTGCTCTGCAAGGCCTGATGGCTTTTGTGTGGCCTGGCCGTTCGGGTCCATGCCCCTGG
```

FIGURE 8, CONTD.

AAGAGCAACGTCTGAGCTAGCTCCACGCGTGGGTCCATCTCGGCCCAGGTTTAATGAGCC
ACTTTCAGGCAGGGATTGCACAGGAGGCAGGGTGGGAAGTGGCTCTGCTCAGACCCCTGA
ACAGGGTCTGGAGATTCTCCAAGGGCACAAAAGAACGGACGATGCCCCTGGGGTCAGCGA
CAATGCTCCCTGAGAAATCTTGGCACACAGGGCTGGGCCTGCGAGGTGGCCCCTCGCCCC
ACCCCAGCCTCCTGGAGGACAACCGTCGCCCTGCTCCCAGAGCTGGGGGGCGCCACACGT
GGGGCACAGGGAGCATGGGCCCGATTCCAGGCCTGGGCTCCCTCTCGTGTCCAGGATCTC
CCCGTGTCTTGTCTCAACAAGCCCCTGACTTGGAGGCCCCAGGGTGACCCCTTAAAGGGG
GAACAGAAGGTTCTAGAAGGAGCGTGGCCAGCTTTGGCTTCCCTAGGGCTGTGGTGACCA
CACTGGGCCACGGCCCAGGCCACCCCACCCGCCTCCTTCCCCCTGGCCCCCTCCCTTCCC
CGCACCTCTCCCTGGCCTGCACCTGGTGACACGGCTGGCTCCCAGCCAGGGCTGAGGGGG
ACCAGCGGGGCCCCTTCCTGGAAGCCCACCTGCAGGCCGGCTTGCTGGGAAGGGGCCTGC
TCCTCGCCGGCCCCACCCGCCCGGGGCCGTTTCCTGGAAGCGGTCACTGGATATTTTGTT
CCTTGTCAGCGCCGAGCTTGCATAAAGCAGACACTGAGCTCCTTGTCCTCCGGGAGCACG
CGCTCCATCACCGAACACCTGGCCGGACACAGGCGGGCAGCCGGGCCTGGGGAGCAGCG
CGGGCCTGGGGCCGGACCAGCAAACGATCACGGCGCCGAGCGCAGGGCCCGCGCCGCTTC
TGCAGGCCGCCCCCACGTGCCCAGGCCCAGCGGTGCCCATCCTGCAGGCTGGGAGGAGGC
TGTGGGCGCAGAGCTGAGAAGGGGGCAGAGGCACTGGGGGGGACAGCCGTGTTCCCACA
CTTTGCAGAAACCTTGGCCGGCCTGGATGTCTTGCTGGGAGAGCTGGGGGAGGGGACAGG
GCAGGAAGCCGGTCCCCCCGAGCGGGGTAGGAAGAGGCCTCGGCCCTGGGAGGAGGAGGA
GGGGAGGGCAGTGAGATGGAAAGAGCACCAGGGGCTCGAGGCTTCTTTCTGGAACAAGGA
CTAGAAGGAGGAGGCCGGGCAGCTGCTTGGGATGCTTGGAACAGGCCGGCCCCAGTGCTG
ACAGGGACGTGACCTGGGGCCGGTCCCGGGCCCAGGCGGGCTGGGAGGGCGCCTGGTGG
GTCAGCGCCACTCAGAGCCCTGGCAGCAGGGGGCCTGGGCACGGCTGCAGGACAGAGCTC
AGGACACAGATGGGGGCGAGGACTGAGTGGGGCACCACAGATGCTCCCAGGAGGTGGCCA
AGGAGTGGCCTTGGGATCCCAGGATGGCCCTGGTCCCAGAAGATGCGGCAGCCCAAGGGA
CCAGGCCAGGGCCGCAGGGGGCCACAATCTGAGCAGGGCTCAGGCCCAGGGCAGAGGCCC
CCTCCCACCCAGCCCTCCCTGGGCCCGCCTCTCC
GTGCAGGCAGTGGGCTCAGATGGGGCAGACATGAGACCAGGTCCAGGGAGAAGCGGGGCC
CCTTGGCTTCATTCAGGTGGCTTTCAGACCGCGCCCCGTGCGTGGCAAGGCCCACAGCGC
TCAGGAGCACACAGACCCCCACCACGGGCTCCCCAGGTTGGGCGGTGACATCAGCCCTG
TGTCAACAGCAGGAGCTGGCAGCTCCCCACCGGGGCTTAGGGAGCGGGGACCCTGAGCCA
CCCTGCCACCGCCCCACCCCACCGTGGCCCACACGAGGGCCCGCTGCTCTGGGTCTGGGG
CCAAGGCCCCCAGGCGCCTGGCACTGTCTGCCCCTCCCGCTGGCTCTCCGTCTCCAGTG
TCCCCGCCAGAGAGCATGGGGCCACAGGCCTGAATGCCACCCTCTTCCTCCCTCTGGAGG
GGGCCTGAGGTTTTGGGGGTTCACAGAGTGGCCTCCGGGGTGGGTCCAGGCCCAGCGAGG
CAAAGCGGACCCCAGGGAGTCCCGCGGAATGTGGGACAGCCCCCCGTAGATCTCGGGGG
GGCCAAGCTCTGGTTGACCTCCATCCTGGGGCTGTGGGCCTTTGGTCAGTGGGGAGGGTC
ATGACACCCAGCCCACCAGCTGGTGACAGCCCTGGACGTGCCGGCTCAGGGCTGGCCTGC
CCCTGCAGCCTTGAACCCCTGTTCTCTGGGAGTGGGGGCGCAGGGGGCGCCGGGGCAGGG
TGAGAGACGAGAGCCTCTCTTCCCAGAACTTCTGCCTGCGATGAGGACCCAGCAGGGGCC
TCTCCTCACCAGAGGGCCTCTGCCGGCTGCAGGGCCCCAGAGAGGCCCAGAGGCTGGAGG
CCGGGCCTTGGGAAGAGGCCGGACTTCCAGAAACCAGCTGCCCGCTCCGCAGCACCCAGC
GCCCACTTGGGAGGGGGCGCGCCCCCGTGCCCCGCCCGGGTCCACTGCTGGGGCCGCCA
CAATAAAGTTTGTCCCTGCTGGTTACTGTCCGTGTCTGAGAGGTTTCTGGAGCCTGGCCA
CAATGGGCGTCAGGATGCGGCTGGGAGGGAGCCTCGCGAGTCAGAGTGTGCTGGTCTCGG
ACAGGCCCCGGCGCCCCCAGCCCGTGCTCTGTGGACAGATGGGTGGGTGGGTGGGTGTCG
GAGGGGGTTGGAGAGGGTGGGCGGGACGAGGGGCTTCCTGCACTCTGTCCCAGGGAAGCG
GGGACCAAGGAGGGGACAGCCCCCGGTCACCAGGAGGGTCCTGTCCCTCTCACCCCCGG
GACAGGTGAGCTCCCCGGAGCCGCCCTTCTGGGACAGGACCCCACGGCCAGGCCACGGCC
CCCCCCACCCCGTGGTCCCTCCGTCCCACGGCCGGCCTGGGGGGCCACGGGCCCAGGGCC
CCCGCTCCCCGTTGGCCCTCCGAGGGTGAACGACCTCGCCTGGGACGTGGGGCAGAGGGC
AGGCGCCAAGAGTGACCCCTGGGACACGTGGCTGTTTGCAGTTCTGGAGGCAGCCGAGA
TAAAGCGGCTGTTTTCCCAGTGGGCTCAGGGCCAGAGGGGGCGAGGGGCAGCCCAGTC
AAGGCCGGGCCGCTGCCTCGGGCTCCCCTCTGTGCGGAGGGAGGGGGCCGGTTGCACAGC
AGCCCCTGCCCGCCGCCCGCCCGCCGGCGCAGGCACCGTGGGACCCGGCCTGGTGCCCCT
CCCCCGCCCCTGCTCAGGGGCCAGCCCTCTCTGGTTCCCAGGACGCCCCCGCCCCGCAGG
CGGCCAGAGAGTCCCAGAGTGTTAGCCTCCCACGTGTGGGATCCTGTCATATGCGACAGC
TTAACTCAGGCCGAATTTCATGGGTCCTGGATTTGGGTGGGCACGGCCCCTGCACAGCGG
GGCTGGAAGCCTAAGGCGGTGGGCGTGGGGGTGAGAGGCCCGCAGACAACAGGAGGGAGG
CTGGGACACTTCAAGGGTTGACATGCTATGCCTGTCACGGATAAATGC

Contig 3 (5347 bp)

AGATGTGTATAAGAGACAGGGGCTGGGTGGGAAGGACAGAGGGTGGGGCCGGAGGAAATG

FIGURE 8, CONTD.

```
GGATGCAGAGCCCACCGTGCACGCTCTGCTGGCCTTTGAGCCTCGCTGAGTCGCAAGAAG
CCCTCGGGCCTGGAAACAGACCCCGGCCCCCACCCCCACCCCGGCCCCCGGATTACCCC
GGCATGGCTGGAGGGCCCGAGAAGCCACCCAGGCTTCCCGTGCCGAGCTGGGTGCTGGGC
CCAGCCGAGCGGGCTTGACGCCACGCTTAGCCCTCCCCAGGGAGCCCAGGGTCGGAAGGA
AGAGGCCGGCCGGAGGGCCGTGGCCGCTCAGGCTGGAGGGGGCCCCCGGGTCAGGATGGG
CCCCAGACGTCCCCGCTCCCCGGCCCATCCGTCACGGAGCTGTCACCCAGGAACGTGCTCC
AGACGTGCTTTCCTGCCGCCGAGGCCCCGAGCAGGCTCCAGGCGCCCCCACCCCCGAACG
CCCACGCACACCCTCGGTCTGCGAACACCCTGCCGTCATCCGGTGGCCCCGGTTCCCGCC
GCCCGCGCCATCCGGGTGCCCCTTCCTCCCTGGGTCGGGGGCCATGCCCTCAGCGGGCAC
GCAGGCCTGTGCAGGTCTGTTCTGACTCTTCCCCAAAGACGCAGGCCGGCTGCGGGCGCC
CCGACCTCGTCTGAGGCCCGTTTGTGCTCACTGGCTGTCTCAGAAAGGGGTGCCCACGGG
AAGCGCGTGTTCCTTGGGCCGCAAGGCAAGGGAGCCCACCCCAAGGTGGCTGAGGGCAAA
TGGCCCAGGGCCTCTAAGGAGTCCCTGGGGGCCGGGCCGGCCTGCAGCTTGAGGAGGAGA
GCCCTGGCTCTGCTCCCCGGGCAGGTGAGCCCACGGCAGGGGCTCCCCAGCAGCCTTG
GCAGGAAGCAGTGAGGAAGGGGTGAGGATGAAGGCAAGGGGGCCTGCGGGGACTTGGGCA
AAGCCCCTGAAGAACTGAGTTCCTCGGAAAGGCCGGAGCCCTCAGCCGAGCCTCGGCCTC
CGAGCGATGGAGGCGGCCCACCTGCGGCCCCAGGGTGCAGCTGTGCATCCGTCCCCCTCG
GGCCTCCCCCTGCCCCCCCGGCCACCACACTCTCCCCCTTTTGCCTTTGATCACTTGAGT
GCGACAGCTTGTGCGGCCTGAGCCCCAGAGACCGCTGCCCCCCTGCCGCCAGCCCCACGG
GAGCGTCCACCTGGGCCTGGCCTGGGCACTCATCCCTCCCGGATGAGGCCTTTCTAGCCT
GGGCCGCCCCGGGAGCGGCAGACCCAGCCCCTCGCCCCCCTCCCCCAGTGAAGGTGCTGC
CTGGTGGTCTGGGGAAGCCCCTGGAACAGGGGGCGCAGGTCCCACACGGGTGCTCTGGCC
TCCAGCTGCCAGGGAGGGCCGCGCTCAGGCCAGGGTCCCCTCCACCAGAACCGCCAGGGC
CCTGGGGAAAACCTGTCTGTGCTAACAGGGCCGCTCCCCGGGACTCCACGGAGAGGTGCG
AGGGACCCCTGAGCACCCACCGCCACTAAGGGGCCCAGCCAGCTCGCGGGTGCAGGCAGC
CGGCTGGGCGCTCACATGCATACTGCTCTCTGGCTTTGTGTGTGCGCCTGGGTTGGGGTG
AGCGGAGGTGCCCGAAGGCGGAAGAGCCCACCCTCCACTCGGGGACCTATTTCAGCAAGA
AGACGGATGGGACTGCCGGGCATGGACAAAGGAACAGGATGAACCTTCTGGAACGCACAA
GGCTTCCACGGCTGACCGGTCATAGGAAGGCGCGTCTCTAGGCCAATCCACCGTCCACCG
TCCATTCCCCAGCCCTCGAGAGGGGCAGGATGGACCGCTGCAGCGTGAGAGAGCTCTGG
GGCGCTCCCACAGGGCAAAGTCCCAGGGCACTGACCTCAGAGCCCAACCAGGCCACCGGG
GCTGGGCCCACCAGGGAGCCGGGGCCAGGGTCAGGGTCAGGGCCCAGAGTGCGGGAAAGG
GTGGCGTGTTGCTTGGGGCGGCGGGCGCGCAGACGGCCCCTCGCACCCCCCGACAGCCCT
GGAGCTGAGTGAAGCCCGCGGGTCACCTTGGCTGGGGTTGGGGTCTCCTGCGACCGGCAC
CCCAGCTCAGGTCATCCTTGCTGTACCGCAGAGGGGCAGGGGTTCTGAGCAGGGACAGGG
TGGGCCGCGCAGGAAGCCCCCTTCTCTCTGAGGCTGCCCCGGCCCTGGAGCCTCTCTGGG
GCATGCCACCCCTCTCACAGACGCCTCCCAGGAGCCCCCACTTTCCTGCTGCGTGGTGAG
GGTGTCTCTCACCCGATTCCTGGCCCCTGCAGGTCGAGTGAGTCCCTGCTAAGACCTGGGG
TTGGAGCAGGTGCAGGGCATCACCACACAGCAGCAGAGGCTGTGGGGGCCCCTGAGAGGC
GCTCCCAGGTACCCTCCTCAGGGGGCTGAGCCCGGGGTTGACCCGGGACCTCGCCTGCCC
CAAAGCCGGCGCCCTCCTCCCGCCCGCCCGACCAGGGCCAGAGAAGCAGGTGTGGGGCGG
CACAAACCCAAGTCAGCTTCCAGATCCTGCTGGGGCCGCGTTGAAACTCGAAGCCCCCAG
GCTGGGAGGTCTAGACACCCCTGCCCAGACCGACAGCCTGGGCCTGGCTCACAGCTGCCT
GGGGGCCCAGGGGTGCACCTGCCCTGTGGGTGGGGGTCAGAGGGCAGGGAACCCTCGGGA
AGGTCCCCCAGGGTCAAGGTTGGGCCTAAGCTCCGGTGACCTCTGGGAAGTCTGGGGCTG
GGTTTTGTTCCCAGAGGAGAGAGGGCCAGTAGCCTCAGAGGGGCTGTGGCACGGTGGGAA
GGCCCCAGGTGACCCCAGAGCGTGCGAAGCAAGCCCCCTTGACTGCAAAGC
GCAAAGGGCAGAGGTGGGGTGGGAGCCTCGACCCCCCGAGCCCAGGTACACAGGGGGAAG
GGCGAGGGATCCGGCAGGGGCCACACCCGCCACCCCAGGCAGCCCACAAAGCCTTTGGGC
CCGGAGCCCCAGATGGGCCCAGCCCAGCTCTGGGAACAGTCTTCCCAGAATTCCCCAGCT
CTGGGTACCAACAGGGCTGCCCGGCCCCAGAGCCCTCGGGCGGGAGACCCTTCCCCAGG
GGGATCTCCTAAGTGGCAAGGCCTGTTGGGAGGGGCTGGTGAGAGGCCACTCTGGCGGGA
AGACCCCCAGCCACCTGGAGCCCCTAGCCACTGCCTGCTGCGGCTCCCTAGGGATCCAGG
GCCATCAGAGAAGCTCCAGCGACACTGTTTATTTTCAAATGACACTTTTTAAGAAAAACA
GCCTCACCCAAATGCTTGGCCCTGAGTCTGGAATGTGCAGACAGACAGCTGCCCCTCCCC
AGAGCCTGCACGGCCCTCCGGGTGGGGAGGAGCAGGGGCACCCCTGGGACCGGGCCGC
AGGCTGTCAGGGCACGGAACGTGTCTCTGGGCCCTGTCCTCAATTCCCGGTGCCCAGTGG
CCCCAACTTCCCAGCAGACCCAGCAGGGCCCCAGCTTGTCTTGGCCTGGCCGCTGGTCCT
GTCACCCCAGGCCTGGAGTTCTGGAAGATTCTGCTCCTGCTCCCGTGTGCACATACCACT
CCCCGGGGCAGCCCTGCACTTCTGTTCCTGCTGGGCTCCCTGCCTGCATCCGTGAGGCCT
GCAGCCCGCCTGATCTTCCAGGTCCTCCTCCGAGCCCCCGCCTCCAGGAAGCCCTCCAGG
AGAGCTCAGGAGGGTCGGCTCCCTGCGCGCAGCTGTCAGACCCCTGGGCCCACCCCGCCG
GCTGCTAGGGTCCAGGTTCCCCACAAGCCCTCGGGCAGAGGCTGGGCCGCTGGGTCCCTC
GGAGACAACTGGCTCCGAGGCCTTGCCCTAGACGGGTTTCCGGGAGCCCGTCCCCAGCGG
```

FIGURE 8, CONTD.

CACCCACTGAGTTTTGAACACTTGGCGCCACCCCCACACCCCAGGCGGTGGCCAGGAGGC
CTCCTGGGCAGCAGACAGTCCGTGAGGTGGCCCTGGGGTGGCTCCTGACCTGGGCGCTGG
CCCAGCCCTGGGCACAGCTTTCCAGATCTTGCCTGCCGCTTCCTCCAGGCTGCCTCGGCC
CCTCCCGCCTGGGGGTGCCCAGCTTTTCCTGGAGGATGCCCACCCTTGCCCATGGTCAGG
GAGGGGCTGAGAAACCCCACCTCGTGCCTCTGCCCGGCCTATGCCAGGGGAACCAGGTTC
CCTCCCGCAGGAGGGGACCGAGTCCCTGACAGCCCACTGCAGAGGGGAGGAGGTGCCTGG
CTCTGCCCCCAGCCCCACCAACCCCGTGGCTTCCTGTTTCGCAGCCCACAAAGCACTAAA
GGCCGCAGGTCCTGGAACATCAAAGACCCGGGAAGTCCATTGTATTGAATTGAGTGTAAA
TGAGCCTGAGGCCTGTGGCTTGCGTTTCCCACAATTACCGCTGCCCGGGAAGGGCTCCGG
AACCGACACAGCCCCCAGGGCCCCTTGCCCATGTGGGGAGCCCAGGCTGGCCTGAAGAAG
CCCCATAAGGTGGACCCCACTTTGAGCCCCCACGAGAGTGGGCCAAGGACCAGGTCAGGG
GCTGCCCAGGCTCTGGGCCTCCTCTGCCTGCCAGGTGGGCTCCCTCGGGGCCCAGCCTGG
CCTGCAGGACCTTCCCACGCTGAGTTCCCCAGCCTGGTATGAGCGTAGTGGACGGCAGCC
ATGCCCAGCACTCAGGGGCCTGAGGGACAGAGCGGGAACTCCAGCCCCGGGTCCTCGGC
CCCTAGGATCCTTCTAGGTGGGGAAGCCCAAGGGAGCAGAGGGGTGAACGCAGCTGTGTG
GGGCCCCAGGCTGCCGAGCAGACCCCTCCTGCTCCACTCCTCGGCCGAGTGGGCGCCGAG
ATGCCGGGGCAGTGCCATTTCCCAGGCGCCACCGGAGGCTCCCAGAGGGAGTGAGGCACG
AGCTGGGAGGGAGGGCGGGGGGGCTGGGGAGGCAGAGAGCGGAGGCCGGAGGCCGGTGAG
GAGGCCCGGAGGGGGCCTGGAGTCAATGACCCAGGGATTATCGTGCTGGGTCTTTGCAAA
GTTGGCTGAGCAAACGCCGGAGCCAAGGGTCAGGGAGACGGGACTGGCGGGCCCCGCGG
CCCCCTTTCCCCTTTCTGGAAAAAGCCTGTTTCCCAGGTCAAAATCCAGCTCATGATCCG
CCCCCTTTGGGACTGATGTTCAGAGGCCCAGTGGTCCCAGCACCTCTGTCCACCGCCCCC
CCCACGCTCCCGGGGCCGCCAACCCCTGTGGGCTGCGAGGTGCGGGCACCTCTCCCTTCG
AAGCAAAGCCCTGCCCTGCGTGGGCAGCGTGATTTCCTGCTTCTCTGGGGCTGCACTTTG
ACTGGGGTGGGGGGGTGG

Contig 4 (1592 bp)

AGCCCCTCAGCCCCTCCGAGCAGCTGCTGGGCTCAGCGGGCTCGCCCCCCGATGTGCGGC
CCTCCATAATCAATCATGGAGGGCCGGGCCCGGGGGGGCGGGCCGACCTGTCAGCCAGC
TCCAAGGGCAGGGACAGCTGCTGTTCCGGAGGGTTCCCAGGGGCCAGCCCCACCAGACAG
CGGCCTCGGCCCCCCTTCCCCGAGGGGCACCCCCACGGAGGGCCCAGACCGGAGGGACTC
GGGGCCCAGAGGCCAGGGCAAGAGTGAAGGCAGCGCCGGTGGGAGCGGCGGTCAGCGGGG
TCCAGGCTTCAGTTCCCAAGGAGCCCCATGCCCTGAGCCCGCACTGAGCCCTGTGCAGCC
TGTGGGTGCCGCCGAGGCCCGCCACCCCGCCCCCCACCAGCCTGGGGTCGAAGGAGGGAG
GGGGTGGCCTGACGGATGGTAACAGCTGCTCCCCCCACCTCGCCGGCGTGGACAGGGCTC
GCTTCTCCTGCCCGAGCCCCCGGCTGCCCCATCCGTCACGGCCCACCCAGGACTGTGCGT
CCAGCCTCCCTCCCTCCTAATCCCCCCGCATTTTCCGAATTCTCGGGCCACTGCTGCTTC
CTCCTCAAATTCCTGGCCCCCCTCGCCCCATCCCCGCCATGGGAAAGGGCCGCGATGCCA
GGACACTTGCTCGTCTCGGCCGGGCGGGGGAGGAGCAGCTGGCTGGGCCCGGCAGCTGT
GAGGTGCGGGGGTGCCAGGGAGAAGGGCCCAGATTAGGGGCGTCATGGGAAAGCTGGGA
GGGAACGCTACCCAGAGCCCCTCCTGCCGCAGCCTGTGCTGCTCCCTCTCCGCATTTCTG
GCCTCTGAGTGCTCCCTGGAGGGAAGGGACCACTGTGTCCTGCCGGCCTCTGGCTCTGCC
AGGAATGTCCATCTGTCCGGGCCGGGTTACCTGGCTCAGAGCGTGGGTACCAGCTCATCC
AGCCCTGACGCCTGCTCTCGGGAACAGTGGATGGGCCAGGCGCCCCGTCACACCCCGCA
GCTGGGCTCCACAGACGGGCCCGGGATGGCCACGGAGGTGGGGGCGGCCCCAGGGCGAG
GCTCCCTCCTGGAAGGGCTAGAGTGTGGGCTGCGCGGAGAGGGAGGCCGGACGGCCAGGC
CAGGTGCAGCCCGGGGCAGGTGCTGGTGGGGCTGTGACCCACGTGTGCAGCTCAAGGGT
CCAGGAGCCCCAGGGACAGAGCCTCAGGGACAGACCCTCAGAGCCACAGCAGGAAGCCTG
GTGGCAGTAGCTGGCGGGGCCGTGGGGTGCTCGGCCCTGCAGACAGAGGCAGAGGCAGGC
TCCCTGCTGATGACAGGGGCTTTCTCTGTCCCCTGGGGGCGGAGGGGGCCCGACCATGG
ACCCCGGGCCTCCTCTCGCACGATTCCCAGGCCAGCCTGGTCTCAGGCAGTCCAAGGTTG
CACAATGGTCTCCATCGTCCAGAGTTGCAGAGCCAGCACTCTCCCACTGGACGGCGGCCC
GGGGTGGGCTGCACCGCCGCTCAGGGCTCAGGGCCGCGGCCGGCCAGCCCNCCGCAGGCC
TTGACCCTGTCTCTTATACACATCTCAACCCTG

Contig 5 (831 bp)

TGAGATGTGTATAAGAGACAGGCCTTGACCCTGGGCCTGGCTCAGCTGCGCGCCCTCCTC
CTTGCAGCTCCGCCTCGACCCCATCCATCAGCCATTTTCCTACCCTTCCTGTAATAAAAA
ACCCGAAGCGGCGTGGCCCCGTGTCCGCTGGGGTGACTGCGGCCTGCCTGCTGGTGGCTC
CCACCTGGGCCCGGCCCCCTGAAAACACACACCCGGCGATGGCTTGCCCGGGGCCCTGGT
GGAGGGGCGGGGGGCCTCGCCTGCCTCTTGTCTGAAATTTTCGGTCCCACATGCCCCGAC
TCCTCTCCCGGCCCACCCTGCAGGCCCGGCCGGTGCCCCGGCCACTTTCCCGAAGGACGG

FIGURE 8, CONTD.

```
ACTCAGCATTTCCCAGGGCACCTGCTGATGGTGCCCAGACCCCGGGGGCCTTCCCGCCGG
GCGCGGCCCCACGTCGCCCCTCCAGTGGCCACAGCGGGCCTGGGCCAAGGCTGGGAGTTC
TGCACGGGCCTGGGGGAGGAAGGCGGGGGAGAGGGGACAGTCTCCTGGCGGGGACGAGGG
TGGGGGCAGCAGGTGGGGAGTTCCCACAGCCGGGGCAGCGGGACGCCGCTTGGCTGCCCT
GGGTCTCAGCCGGGGACAGTGCCCACCAGGAGAGAGACGGCAGACAGTACAGCCCACCCG
TTTTATATCCTCTCAGGCGGTCTGTGCTTTATTGGGGTAAATATGCAGGACATAGAAACT
CTGCCACTGGACCCCTTGGCCGGGGGACACAGCAGCGGCATTGCATGCTTTCTGGGTGCA
GCGCAGCCAGCACCACCGGCCAGAGCACCCCATCTTCCCGATCAACCGGAC
```

Contig 6 (4634 bp)

```
CTCTGGGCTAGCACCGTGGGGGCTTTGCCAGAGTGGAACTGAACTGGGTCCACCCCGGAG
CCCAGAGGGCGGTGAATGGGAGGCAGAGCCCATCCTGGGAATGGACCAGAAGAAAGGGAG
CGGGGGTGGGGGAAGGGGCATCAGATCCTGGTCCTTCCTTGTCGCCTGCGGTCCCTCTGC
CACCACTCCCCGAAGCTGATCTGGAGCACACGCGTCGTTAAAGCCGCCATCGAGGCCCCA
CTTCTGACAGACGGAAGGGGGCAGAGTGCCTTCCTCACCGGCCTCGCCCTGGGAAGGCCC
CTCCCTGCAGCCCAGGAAGCCAGCAGCAGGTGACAGAGCCAGGGGCCCAGGGCCCCAGGG
ACGGGCTCGCGCGCCCGAGCCGGGGGTCCCTTGGCGTCCCCATCCTCTCGTCCTGGAGCC
CTCCTGGGTGACCACAGGAATGTGCAAGGCGGCAGCCGGGTGGCGGCCGGGAGGCGGGTG
GGAGGCGGGCGGGGTGGCCTCTTCACGGGCGGGCCTGAGAGATGGGCGCCCGTCCGGCCC
TGGCGTCATCGTCTCCGCGTCTCTACCCACTGAGCAAAGACACACGAAATGAAGCTCGAA
CGAGCACAGCCAAAGAACGGCCGTTTCTGTCCTTTCTTCTTAATCCCTTTGGCTTAGGGT
TTCCCGGCCTGGACAGCCTGCCCAAGGGCACATGGGCATCCGTCCGGGGACATTCAGGCA
GTGACCAATCCCAGGCCACCCAGGCTGTGCCCTGCGTCGTGGGCCATTTCCCAGCCGGCC
AGAGATGGAGCAGCCACTGCGGGTCCCCGAGTCTCGGTGAGACAGTCAAGGATGGACCTT
GGATGGAGACCGGCGTGCGGCCATGTCCGTGGGTGAAGGAGGCGTGCAGGCCGTGCTGGG
GGACATGGTTGCTGTCCCCTCGGCCAAACCATGAAAAGCAGCCCTCTCCCCCAACCCCCA
GCACCAACCCGGAGACCACCCTCGGCCGGAGCCCAGCACGGCCACCGTCACGTCTCGGTC
GTCCAGCTTGGGACAGGTCAGTTCCCAGATGTCCAGGCTGGAGCTGGTCCTTGAAGATCC
TAGGGGTCCAGCCCAGCACAGGAGGGCCAGGTGAGAGCCCCTGTGGTTCTAAGGATGCA
ACCAGGGGCCGGCGGGGTGCCTGCCCTAGAGGGGTAACTCGGCCCCCTGGGGACCAGTC
ACCCCAGGAGGTCCCCAGAGCCCAGCTCGGAGGGCCACAGGTGCCCAGAGTCCCACCTGG
GGAAGGCTGCCCCTCCTGCCAGCCCCCGAGCCGGGCCCCTGGCGCCCGCGTCCAGCCGCG
ACCCCGGGGAGATATTCACCCCCTGCCCCCGTGAATCAGGAGGCCCCGAGCCCATGTTTT
CAGTCCTTTTCCTCCCATCCCAGCCCCCCAGGAGAAGAGGTGCTGAACTGGGTCCCCTGG
AGGCTCCTGAGCCCCAGAACAGTGCCCTCTGAGCAGACGGGCACTCTCAGACCAGCTCAC
GCTGGACAAGTCAGCTCCTGCCTGCCGCCTGATGGGCCCTTGGGAGAAGCAGACATGGTG
AGGAAAAGGCCCCTGTGCCCTTCACCCTAATTCCCCAGCCCCAAGTCCCACTGGGTTGCC
AGCTTCAACCTAAGCAAATAATTCGTGCCCTCTAAACAAACGCGCGGGAATCCCACCTGC
CCTTCCCCCGCCCGCCCCCCC
ACCCCTGGCCTTGACCTCCAAAAGCACTTGAGGGGGCTTTCTCCAGACACCCTCCAACCC
CGACCCCATGAAGAAGGGGTGATGGGGCTGTTACCCCAACAAGCAAGAGAACGAAGCCCA
GAGAGGAGTTGGCGTGGACAGCAGGGGTCAGGCCCCTTTGCCCCGAGGGCAGGGCTGGTG
CCACCTGGGTCAGGCGGCAGGCCCTGGAAAAGCACCGGAAATGAGCACACCTGGGTCTCT
AGAAGGTTCTTCCAGACCTCTGGGGGCTGAGTCATTTCAACACTCCTGGGCCGGGCAGGG
CTTCTTCTTGGCCCCGAGGGACAAGGTCCCCTTCGTCCGGGGGGTACGGCCCCTGGACCC
CTGTCCCCCGCACCCCACCCTCCGCCTGGTGAGGGCCGCGGCCAGCTCTGGACACAGATC
CCTCAGAGCCCCTTCTCCCTCCCTGCTCCCTCGTCTTCCCAAGATGCCCCGGCCTCCAGG
TGGGCCAGCCAGGCGGCAGAATGTGGTCCAGGCCTCTCGGCCCCACCCACACCCCCCTGC
TCTGCCCTGACAGCCTCCAAGACGCAGGCACGTCGCTGCGTTCTGCGTCCTGTCTCCTCA
TGGCACAAAACGGTGCCCGCCTAGCTTCCCCAGAGAAGGGAGATCGTGCTCCCCGGACG
GACCCTGCTCTGCCTGTCCTCCCGCCCGGCCTTCAGGGCCTCTCCCCAAGGGTGGCCGCG
AGGAGGCCCTCGCCTCCGGCCACGGGGGCTCCATCCTCCCGAGCCCGACAGGCCTCCGCC
TGGTGGTCCGACCTCTTCCCCAAGGCCCCGCCCATCCTCCTCGCGCTCCCCCAAACCCTG
CCTCTTTCCCCAGCGCCCTTGTCCCCACGGAAGACCTCCACCCGTGCCATTACACGCTC
TCGCCCCACCCTCCCAGCCACCCCCCCTTCCCCATCCTCCTGGAAGCTCCCACTTCCTTC
CCGTCTCCCACGGCAGCAGAGGGTCAGCAGCTCAGGGGTCCTGGGGCCGTGGAGATGGCC
TGCCCGGGGGTCTCGCTGACCGCCTCCTACGGAAGCTGTGCCGGGGGGTGGGGTGTCTC
TGCCCGAACGGCTGGAGGACGAGCCACATCCCAGGGCAGCCGGAACCTGCGTCCTGGTCT
GAGACGGAGAGGCTGGGTGCAGGTGGCTGAGGGGCCTGCACACAGCTTGGCCTGGGGTCC
CCTAGGTGACAACACTGGCTGAACACTCATTGCTGCTCCCCTTCCAGGGTGACCCTGGGG
TCCCCGTGTGGCCCTCAGGGCACACGGGGGCCCCACCAGGCCTCACAGAACCCCAGTGGG
ACTGCACCCAGGGCCCACAGAAGTGCGGGGGCACTGGGGGTCCAGAAACAACCCCACAAC
```

FIGURE 8, CONTD.

CAGGCCAAGGTGGCCAAGGCCTTACTCGAGCGGGGCTGCCCGTCCCAAGAGACTCTGGCC
AGTCGTCCGGATCCAGCTTCCCGGGGCCGGGCCGCCCGCTGGGCTCCAGGCGGTTCTGGG
GGGCCCTCCCCCGGGGGTTCGCCCTCCGCTCTCAGCAGCAGGAAGAGGAGCGCGGCCAGC
GGATGGGGAGAAGAGGGCGCCCTGGCCATCTTGCTCCCCCTGGGACTTGAGGAGGGTCTC
GGGCCGGGCAGGCGGGACCGGGAGCCACAGAGACCCTGGAGGAGGCAGCATGGCGGGGAG
GTGACCGGGGAAGAGGGCCGTGTCCCAGGCTCACAGCCCGGCCTGGCCGCCCGGCCCTCG
GGAGGCGTGCCGCTGACCGCCTGGCCGGGAGGTTTGCTGCGTGTGGGGTTTGCAGAAAGT
GCTGAGCTGCTGAGCCCACAGGCCAGGCTCAGAGGGGACAGGAAGGAGGTTGCTGCCCAG
CCTCGGGCACTGCTGACCCATCTCCCGTTTCCAGGGCACCAGAGCCACCTAATCTGCCGG
CTCTGTGCCCAGGGACAGGCTTGCCTGATCTCTCAAGGCCGGGCGCTCCGCCTTCCCTGG
GAGAGGGTTAAACATCCAGCCCCAGCCAGCATCTCGGGCAGGTTCCTGGCTCCCCCGCT
CGTGCCTCCTCTGAGACCCTGGTCGGCACACCTTTCCCTTGAGAGGAGGAGGAGGAGGAA
AGCGGATGGAACCAGTGACCCTGCAGCCCTGAGGGCACCTTCCCACGTGCCCCCGCCCG
CCCCGCGTCCTCCGCCCCCAGTTCTCACGGCCCCAGTCCTGATGGAGGGAGGGCGACCTC
CGGGCTCCCTGGCTCCCGCCGGCTCCGGAAGACAGGGCCGCTCGGCTGGGGCTGCAGGGA
GGGGCCCGAGACGCAGGAGAGCAGCCCGGAGGCAAACCCCGCGGGTCTTCCAGAAGGAGG
CCTGGCAGGGGAGGGGGGTGCCACCACTGCTGTCCCTCTCGTGCCACAGTGGAGGGTGT
GGGTGGGCAGTGCCGGGGTGGGAAGTGCAGAAAGACCCTGGACCGTGGGGCTGGGCCGCC
ACGGGGGAGCGGGGTCTGTCAGGGACCCTGGGGGAGGGAGGCGAAGGGCTGGGGCAGAGG
CCGGATCACTTCCAGATTTGCTGTGGGACCAAGGGCCGGACCTCGGGGTGACTTCTTTTG
TGTGCTGGCCACAGGGGGCCCCGGCGAGGTCACACGGAAGGGGCTTCGGACCTGGCCT
AACAAGCCCACTCCCGAGGAAGATGCAAGGGGAGGCAGACGGAAGGGCCGAAGGGGGCGA
TCGGGGGACACCGCGGCAGGGCCGGGGCAGAGAAGGGAGGCAGAGGGCAGAGAAGGGAGG
CAGAGGGCAGAGAAGGGAGGCAGAGGGGCCACATGCTTGGAGGGCCAGGGAGGAGCGGGA
ACGGCGTCCGGCGTCCAGCGCCGAATCAGGCCCGTCAGGCGGAGGGTGCGTGGACCTGCC
TGGCCTTCACGAGCACAGTCAGCAGGCTGTCTCTTATACACATCTCAACCATCAT

Contig 7 (482 bp)

AGCAATGGGGCCGTGACCTAAGGAGGCAGGCCCAGGTCAGTGGGGTGACCTCTCGTGGCC
CCGATGTTTGGAAATCCCCAAATCAAAATGACCCATCCGACAAGCTTGCATGCCTGCAGG
TCGACTCTAGAGGATCCCCGGGTACCGAGCTCGAATTCGCCCTATAGTGAGTCGTATTAC
AATTCACTGGCCGTCGTTTTACAACGTCGTGACTGGGAAAACCCTGGCGTTACCCAACTT
AATCGCCTTGCAGCACATCCCCCTTTCGCCAGCTGGCGTAATAGCGAAGAGGCCCGCACC
GATCGCCCTTCCCAACAGTTGCGCAGCCTGAATGGCGAATGGCGCCTGATGCGGTATTTT
CTCCTTACGCATCTGTGCGGTATTTCACACCGCATATGGTGCACTCTCAGTACAATCTGC
TCTGATGCCGCATAGTTAAGCCAGCCCCGACACCCGCCAACACCCGCTGACGCGAACCCC
TT

FIGURE 10

IDENTIFIED POLYMORPHISMS:

POLYMORPHISMS TYROSINE HYDROXYLASE GENE - CONTIG C3 (figure 6)

| | | | |
|---|---|---|---|
| 1 | GGATCCAGCC(A:T)GCAGCC | 1081 | bp |
| 2 | ACAACCCCC(-:C)TCCCACAG | 1149 | bp |
| 3 | TGCGGAGGGG(A:G)GACCTG | 1186 | bp |
| 4 | AGGT(CAAGGCCAGGT:-)CGAGG | 1210 | bp |

POLYMORPHISMS INSULIN-IGF2 - CONTIG C4 (figure 6)

| | | | |
|---|---|---|---|
| 5 | CCC(C:A)CCCC(A:C)CGCCGC | 438 | bp |
| 6 | CCC(C:A)CCCC(A:C)CGCCGC | 443 | bp |
| 7 | CGCCGCAGCA(G:A)GCCG | 455 | bp |
| 8 | GCTTATGG(G:A)GCCGGG | 503 | bp |
| 9 | CACGGC(T:C)TC(G:A)GAGCA | 525 | bp |
| 10 | CACGGC(T:C)TC(G:A)GAGCA | 528 | bp |
| 11 | GTCTGC(A:G)GGCAGGTG | 571 | bp |
| 12 | CAAGCCCGG(G:T)CGGTT | 636 | bp |
| 13 | ACCTC(A:G)AGGCCCCA | 710 | bp |
| 14 | GC(C:T)GGGCCCAGCCGC | 867 | bp |
| 15 | ACCAGCTG(C:T)GTTCCC | 903 | bp |
| 16 | GGC(C:G)CTCTGGGCGCC | 1148 | bp |
| 17 | GGGGG(C:T)GTCCCGGGA | 1305 | bp |

FIGURE 10, CONTD.

| | | |
|---|---|---|
| 18 | GCGGT(C:T)GGGGGAGTT | 1320 bp |
| 19 | CGCCC(C:T)GGTCCCGCT | 1400 bp |
| 20 | TCCC(G:A)TCTGCCGGCC | 1519 bp |
| 21 | GA(T:A)GCCCCATCCCCC | 1547 bp |
| 22 | GG(C:T)GGCTGCTGCGGC | 1607 bp |
| 23 | TGGCTGC(G:A)GTCTGGG | 2222 bp |

POLYMORPHISMES IN CODING REGION - CONTIG C10 (figure 6)

| | | |
|---|---|---|
| 24 | GCGCA(G:T)TGATTGGCA | 341 bp |
| 25 | CGCCCCCCCC(-:C)(G:C)GG | 2247 bp |
| 26 | CGCCCCCCCC(-:C)(G:C)GG | 2248 bp |
| 27 | GCAGCCGGCTC(C:T)TGG | 2257 bp |
| 28 | GTTGTTG(C:T)TCTGGGA | 2413 bp |

MICROSATELLITES

29 *PIGQTL1*: (AT)$^{11}$      112 to 133 bp Contig 57

30 *PIGQTL2*: (GT)$^{8}$GCACGCGTGTGCGTGTGTAC(GT)$^{17}$   1074 to 1144 bp Contig 95

31 *PIGQTL3*: (CA)$^{19}$      223 to 260 bp Contig 105

SEQUENCE LISTING

<160> NUMBER OF SEQ ID NOS: 123

<210> SEQ ID NO 1
<211> LENGTH: 21
<212> TYPE: DNA
<213> ORGANISM: Pig

<400> SEQUENCE: 1
ggcaagttct tccgctaatg a                                              21

<210> SEQ ID NO 2
<211> LENGTH: 20
<212> TYPE: DNA
<213> ORGANISM: Pig

<400> SEQUENCE: 2

-continued gcaccgcaga attacgacaa                                           20

<210> SEQ ID NO 3
<211> LENGTH: 26
<212> TYPE: DNA
<213> ORGANISM: Pig

<400> SEQUENCE: 3
gtttctcctg tacccacacg catccc                                    26

<210> SEQ ID NO 4
<211> LENGTH: 19
<212> TYPE: DNA
<213> ORGANISM: Pig

<400> SEQUENCE: 4
ctacaagctg ggctcaggg                                            19

<210> SEQ ID NO 5
<211> LENGTH: 25
<212> TYPE: DNA
<213> ORGANISM: Pig

<400> SEQUENCE: 5
cccctgaact tgaggacgag cagcc                                     25

<210> SEQ ID NO 6
<211> LENGTH: 25
<212> TYPE: DNA
<213> ORGANISM: Pig

<400> SEQUENCE: 6
atcgctgtgg gctgggtggg ctgcc                                     25

<210> SEQ ID NO 7
<211> LENGTH: 19
<212> TYPE: DNA
<213> ORGANISM: Pig

<400> SEQUENCE: 7
cgccccagct gcccccag                                             19

<210> SEQ ID NO 8
<211> LENGTH: 19
<212> TYPE: DNA
<213> ORGANISM: Pig

<400> SEQUENCE: 8
cgccccagct gcccccaa                                             19

<210> SEQ ID NO 9
<211> LENGTH: 20
<212> TYPE: DNA
<213> ORGANISM: Pig

<400> SEQUENCE: 9
cctgagctgc agcaggccag                                           20

<210> SEQ ID NO 10
<211> LENGTH: 500
<212> TYPE: DNA
<213> ORGANISM: Pig

<400> SEQUENCE: 10

-continued

```
gggtgggcag cttcctccca gaccgcagga ggcccaagtt ccctggccct gcccacccag    60
ggccagctga agcaggtcag agacacccgc tcctgtccct cctgtcacct aacccaacag   120
gccgggcccc agggacacag gccacatggc atctccccc  atgccctgc cccaaggcgc    180 ccagcaggtg aggctggagc agagtctggg tcctgcgggc cagaccgagg gcaggacagc   240
tgggcatctg tcctcacagt ccccgcgctt tgtcggagg  cggcagagcc tcatccaaga   300
cgcccgcaag gaacgggaga aggcggaggc cgcggctgcc gcgtccgagc ccggggaggc   360
cctggaagtg ggggcccttg ccgagcggga cggaaggcc  ctgctgaacc tgctcttcac   420
cctgagggcc accaagcccc cctcgctgtt ccggtccctg aaaaaattct aggtgagggg   480
gcgggccagg gctccccggg                                               500
```

<210> SEQ ID NO 11
<211> LENGTH: 943
<212> TYPE: DNA
<213> ORGANISM: Pig

<400> SEQUENCE: 11

```
tgctcctcac accccgggcg gggctgctct tggggccatc ctccccatgg gcccagcacc    60
cactctggcc ttcacacctg ccgtcttctg ggaagtcctc tggttcccaa ggaaagtttc   120
tgagctggac aagtgccacc acctggtcac caagttcgat cctgagctgg acctggacca   180
cccggtgagc cggtgcctcc cctccccggc cgccatgtct cccatcccca ggggtgtccc   240
cacactcagg gccgggactg ggcgtgaacc ccggggttggg acggatgttg gctgctgtg   300 tggctcctgg cggaacagag aggcctggct gggtgccacc ccagggcccc cgccgatga   360 cacggggccgc gtctgggctg gcgggcagg  gcggccaggc agggcagcct ccgatggcgt   420
ccccggctgt caccagggct tctcggacca gttgtaccgc cagcgcagga agctgattgc   480
ccagatcgcc ttcagtaca  ggcagtaagt ccctccaggg cctcagcctg ggggcccaga   540
cctcagcctg ggcctcacgc cagacctggg ggtggaggga agggaggttg tctttgtcac   600
caacgccacc accttcactg tcaccatggt caccgactct gggtccccaa atcacagctg   660
aggaaactgg ggcacagagt ggttaagcat cttgctgaag ccacacagct ggcggagcat   720
ttggccccgg cccctcctgc ggctcccaca cgtgctccct gagggccccg ggactgacag   780 ctgtccccctc ctcagaggtg accctattcc ccgcgtggag tacacagccg aggagattgc   840
cacctggtga ggccctgtga cagcggctgg gaggggcggg agtgggggaa gggacaggaa   900
gacctcagaa ttccgcgtg  gaacgtggtg gcctctatca tga                    943
```

<210> SEQ ID NO 12
<211> LENGTH: 1500
<212> TYPE: DNA
<213> ORGANISM: Pig
<220> FEATURE:
<221> NAME/KEY: variation
<222> LOCATION: (1081)..(1081)
<223> OTHER INFORMATION: Polymorphism A:T
<221> NAME/KEY: variation
<222> LOCATION: (1210)..(1210)
<223> OTHER INFORMATION: Polymorphism CAAGGCCAGGT:-
<221> NAME/KEY: variation
<222> LOCATION: (1186)..(1186)
<223> OTHER INFORMATION: Polymorphism A:G
<221> NAME/KEY: variation
<222> LOCATION: (1149)..(1149)
<223> OTHER INFORMATION: Polymorphism -:C

<400> SEQUENCE: 12

-continued

```
gggggagggga tgctcagacc cgctctggga agaagagagc ctcagaagaa atcccttccc        60
aagggtcacg cggtggagcc caggggcccg ctaggggccg attcccacag ctcgtgctgc       120
cacctgctgg cgctcccagg aactgcggag gcggtggggg ccctggatgg gtccggcagt       180
gggctcgcag gagacccctg gaggggctgc ggacacccca gctgccactc acaaggtgcc       240
caagcggcgt tggcaatggg ctgagcctct ccccccctcc tcctccgcag gacattggcc       300
tcgcatccct gggggtctcg gacgaggaaa ttgagaagct gtccacggtg ggtttctccc       360
cctgcagggc cctgggttcc agccaggccc tcctgtccaa gggtgtcgt cctcacgctg        420 tgaccgcccg ggagcctgga tcggttctgc ctgggtgggc ggtgcccggg ccacgggcag       480
caggggcagc ggtgcgggcc ccagccgtgt ctgagccccc ttgccgcctg tccccaccag       540
ctgtactggt tcacggtgga gtttgggctc tgcaaacaga acggcgaggt gaaggcctac       600
ggggctgggc tgctgtcctc ctacgggag ctcctggtga ggcctccccc acgcgctggg        660
gcctgggtcc ccggggagg tgacccctgc ggtgccttgt ggattccagc tctcgggagg       720
ctggagcgag gggctgccct cctgggggca ccaagaaagc tggtctgcgc ccctctccac       780
acacctgtgc ctgggccctg gggggacccc tgctggggga tgtgggtgca cagccagggc       840
caccagggag tcaggacacg gggctcccctt ccctcgggtc cctgagaccc ctggcctccc     900
gccagcactc cctgtccgag gagcccgaga tccgggcctt cgaccccgac gcggcggccg       960
tgcagcccta ccaggaccag acctaccagc ccgtctactt cgtgtctgag agtttcagtg      1020
acgccaagga caagctcagg tgggccgggg cccgggcccc ccaaactgga ggatccagcc      1080
tgcagccccg cctatgagcc catttcccag cagagggagc tgctgcggac cccaccgtca      1140
caacccccct cccacagctg gaaccccaga aagcctgcgg agggggacc tgcagggctg       1200 tggccaggtc aaggccaggt cgaggccagg ctttttagggg tgaagtctga ctttgtaaga   1260
gggggtgcag ggtccttccc agcctcctcc cctccgagca gctgggggcg gggcgggggt    1320
gcgatgaagg cagagatgac gcagccaccc gttcaccctc aggaggcgcc tcctgtccag    1380
ccaggctcct gttgtcacag gggaaactga ggccccaggt gtgtgtgtgg gggggtgatt    1440
ctcacacaca agcttaggga caggggacata acggcctctc cagggcacac agtctggagg  1500
```

```
<210> SEQ ID NO 13
<211> LENGTH: 3024
<212> TYPE: DNA
<213> ORGANISM: Pig
<220> FEATURE:
<221> NAME/KEY: misc_feature
<222> LOCATION: (5)..(5)
<223> OTHER INFORMATION: Nonspecific nucleotide
<221> NAME/KEY: misc_feature
<222> LOCATION: (10)..(10)
<223> OTHER INFORMATION: Nonspecific nucleotide
<221> NAME/KEY: misc_feature
<222> LOCATION: (62)..(62)
<223> OTHER INFORMATION: Nonspecific nucleotide
<221> NAME/KEY: misc_feature
<222> LOCATION: (103)..(103)
<223> OTHER INFORMATION: Nonspecific nucleotide
<221> NAME/KEY: misc_feature
<222> LOCATION: (110)..(110)
<223> OTHER INFORMATION: Nonspecific nucleotide
<221> NAME/KEY: misc_feature
<222> LOCATION: (168)..(168)
<223> OTHER INFORMATION: Nonspecific nucleotide
<221> NAME/KEY: variation
<222> LOCATION: (438)..(438)
<223> OTHER INFORMATION: polymorphism C:A
<221> NAME/KEY: variation
```

```
<222> LOCATION: (443)..(443)
<223> OTHER INFORMATION: polymorphism A:C
<221> NAME/KEY: variation
<222> LOCATION: (455)..(455)
<223> OTHER INFORMATION: polymorphism G:A
<221> NAME/KEY: variation
<222> LOCATION: (503)..(503)
<223> OTHER INFORMATION: polymorphism G:A
<221> NAME/KEY: variation
<222> LOCATION: (525)..(525)
<223> OTHER INFORMATION: polymorphism T:C
<221> NAME/KEY: variation
<222> LOCATION: (528)..(528)
<223> OTHER INFORMATION: polymorphism G:A
<221> NAME/KEY: variation
<222> LOCATION: (571)..(571)
<223> OTHER INFORMATION: polymorphism A:G
<221> NAME/KEY: variation
<222> LOCATION: (636)..(636)
<223> OTHER INFORMATION: polymorphism G:T
<221> NAME/KEY: variation
<222> LOCATION: (710)..(710)
<223> OTHER INFORMATION: polymorphism A:G
<221> NAME/KEY: variation
<222> LOCATION: (867)..(867)
<223> OTHER INFORMATION: polymorphism C:T
<221> NAME/KEY: variation
<222> LOCATION: (903)..(903)
<223> OTHER INFORMATION: polymorphism C:T
<221> NAME/KEY: variation
<222> LOCATION: (1148)..(1148)
<223> OTHER INFORMATION: polymorphism C:G
<221> NAME/KEY: variation
<222> LOCATION: (1305)..(1305)
<223> OTHER INFORMATION: polymorphism C:T
<221> NAME/KEY: variation
<222> LOCATION: (1320)..(1320)
<223> OTHER INFORMATION: polymorphism C:T
<221> NAME/KEY: variation
<222> LOCATION: (1400)..(1400)
<223> OTHER INFORMATION: polymorphism C:T
<221> NAME/KEY: variation
<222> LOCATION: (1519)..(1519)
<223> OTHER INFORMATION: polymorphism G:A
<221> NAME/KEY: variation
<222> LOCATION: (1547)..(1547)
<223> OTHER INFORMATION: polymorphism T:A
<221> NAME/KEY: variation
<222> LOCATION: (1607)..(1607)
<223> OTHER INFORMATION: polymorphism C:T
<221> NAME/KEY: variation
<222> LOCATION: (2222)..(2222)
<223> OTHER INFORMATION: polymorphism G:A

<400> SEQUENCE: 13
ttaantccan gttggcccga caagttttcc ccatttgaaa aggggccagt taagccccaa      60
cncaattaat tggaagttag ctcccctcat taggctcccc agnctttacn ctttatgttc     120
cggttcgtat ttttgtggga attgtagcgg atacaatttc tctcaagnaa ccagctatgc     180
ccatgattac gcggtacagt agttcatcag tccccccgc ccatgggaca gcgaagggaa      240
ccagtatgtc gtggggccgg gtctaaaggg gtcaccacca gggaggggca ggggctccag     300
gaggcagggc cactgagcgg tacctggtgg ggggaggtgg tggggccaca cccaggagtc     360
ctgtgccccc cccactcccg ccgttggaca tgagaagcag gggccagcct gcgggtccct     420
gagttcagcg cccccccccc ccaccgccgc agcagcccgg ggtctcagca ggctgctgtg     480 ctggggggcgg gggcgcttat ggrgccggga gcagcccccc cccacggctt cagagcatct   540
ctggggcctc aggatggac cggggtctgc rggcaggtgt cctctcgcgc ccccactccc     600
tgggctataa cgtggaagat gcggcccaag cccggkcggt ttggcctttg tcccagcca     660 gtggggacag cctggcctc aggccgctcg ttaagactct aatgacctca aggccccag     720
```

```
aggcgctgat gacccacgga gatgatcccg caggcctggc agcagggaaa tgatccagaa    780
agtgccacct cagcccccag ccatctgcca cccacctgga ggccctcagg ggccgggcgc    840
cggggggcag gcgctataaa gccggccggg cccagccgcc cccagccctc tgggaccagc    900
tgtgttccca ggccaccggc aagcaggtct gtcccctgg gctccgtca gctgggtctg    960
ggctgtcctg ctggggccag ggcatctcgg caggaggacg tgggctcctc tctcggagcc   1020
cttgggggt gaggctggtg ggggctgcag gtgcccctgg ctggcctcaa cgccgcccgt    1080
cccccaggtc ctcaccccc gccatggccc tgtggacgcg cctcctgccc ctgctggccc   1140
tgctggcsct ctgggcgccc gccccggccc aggccttcgt gaaccagcac ctgtgcggct   1200
cccacctggt ggaggcgctg tacctggtgt gcggggagcg cggcttcttc tacacgccca   1260
aggcccgtcg ggaggcggag aaccctcagg gtgagccgag ggggygtccc gggagcggty   1320
gggggagttt ttaaggagga aattggtaaa agtgaccaac tccctgggag ctgagcccag   1380
agacacccct cccacgcccy ggtcccgctc gagaagcccc cttccctcc cctcctcccg    1440
aggcggctcc agggaggaat cttacggagt caaggcccgg gtgccgctgg tctccgagtg   1500
acatggccgt ggtgtcccrt ctgccggccc acatgcccgt gagagawgcc ccatccccct   1560
ggaggggc ccgtgccgg gcaggcggcg ggaggcccag gaccggtggc tgctgcggct     1620
tccactccag ggtgggcggg gtgggggtg gctgtctctg tgtgaccggc tctccccgca    1680
gcaggtgccg tggagctggg cggaggcctg ggcggcctgc aggccctggc gctggagggg   1740
cccccgcaga agcgtggcat cgtggagcag tgctgcacca gcatctgttc cctctaccag   1800
ctggagaact actgcaacta ggccgcccct gagggcgcct gctgctcccc gcaccccaaa   1860
acccaataaa gtcctgaatg agcccggccg agtcctgtgg tctgtgtggc ctggggcggg   1920
ggccctggtg ggggaggggc cagaaggctg tgggggcct gcctgcgacc cctctctgct   1980
ctcgccacat cggctgctct aagcttcctc cacatgcatc gggtgcccac aggcacatgg   2040
gcaccggggg accagggccc aggcagggc ccttcaatgt ggcgagctct ggttttcagg    2100
gctccagaca cccctcctg ggtgcccact gctgcacagg gtcactctga gggtcacagg    2160
gcacccaccc agactgctct tgggcacaca aaatagccca ggggcttctt gggctggctg   2220
crgtctggga ggtcagagag tgaccccgcg ggaccaagac ctggccagcc tgccagtcgc   2280
ccaggccaaa ccaatctgca cctttgctga aggttccacc cggccagca ctggggggcgg   2340
ccgggcctag agctgggcgc ccgggcccca gggactgcac accgccaga ggtgggcctg   2400
aggggtggca gcaggctctc cgcctgggac ccagccagct gggcagctca cctctcaaca   2460
cgaggctctc acctgtgtcg tcccctcccc acggccacac agacaccct ggggagaagt    2520
cacaggcccc cagcaggccc cgcccctgga gaggaggcca gggctgggca ggcgggtggc   2580
cggccggaca ctggacccgg aagggggta ggcggctggg atgagtggcg agctgtccat    2640
gggagcaccc agcggcccca ttggcaccag tacaggcagg ggcacctgca gcagctgagg   2700
tacgtggggt cccggactg gttggtgtcc ggctgccctc tgggaggcag cgggctgagc    2760
ttgtggtcct gccaaccagg gagacccgtg accaccctgc tgcttcccct cccccccagg   2820
gccagcagac tcctttggga ctcggggccc ctgagccgcc cccactcgca ggactcacgg   2880
ggtgtgcggt cctgggtgag tggggcttg ggagagggtc actcttgtcc gtcgggtggg    2940
gaaggctgag agtcatggtg tgacagcgcc ctcggcctgc cgggtggggg gtctcccttc   3000
tcccgagccc agatccccgg gtac                                         3024
```

<210> SEQ ID NO 14
<211> LENGTH: 1730
<212> TYPE: DNA
<213> ORGANISM: Pig
<220> FEATURE:
<221> NAME/KEY: misc_feature
<222> LOCATION: (530)..(530)
<223> OTHER INFORMATION: Nonspecific nucleotide

<400> SEQUENCE: 14

```
cgtcacccgc agaagccagg cccacaggcc ttggctcagc ccctccaccc aggcccacgt      60
tccgccccct ctgggaactg gaggacagcc cgccctcgcc ctcggacctg gcttcgtttg     120
ccctggcatc tggcagtggc cggcagctgc gttcagccct ggatgacacc ctggcgtgag     180
cggtgggtcc ccgtgctgag ggcagccccc acacacgtcc tgctcacttg ccttgtgtct     240
gctccgcatc ccgtcatcac acatgccatg ctggggcacc gtagcgcctt gccctgtgtg     300
gcactgtggc actgtgttcc tgatgggaag actgaggctg gggtcaggcc cgctgctgcc     360
caccctctaa ggacattctg ccggtgcagc tgcctccagg ctggccccccc ggattgcatc     420
tgcttctggc acgatgaact ggcacctct gcctgaccat tagggctgta tttgccttct     480
cctgttggca gtaaatattt actgtccctc cctgttcctc caggcccgan ccagttcctg     540
aggggcatgg gagtggaca caaaggtgcc caagcagccc cctgctcttg agggcccagt     600
gtctggtggg ggccagcctg gaaggagga gcgagactag gaaccagagg cctgtgttcc     660
tggaaaaggc ccctggcag agttccggct ggtgtgtgtc cagctaggct gtgagtcttc     720
aaactgggga gcccggcccc tggacccagg cagggctgca ccctggtgc cagtgcttca     780
ctgggtgggc acctgtcccc accaggcaag gtggtccgag cggtcattca agacagaac     840
cagcagaggg cgccaaagcc ccacttttga caaactcccc ttcgccctga gccgaaagtc     900
caggcggcag gtggacctct ctgcagggct ctgccacccc tgctgccgct tgccagcact     960
cacagggct gcgggggggtg cccaacaggc cggctaccct gagctctgga ggcgatggag    1020
tttaggaggg aacagggga ctcctggggg tgactttctt cagcgcccac attgcggccc    1080
agcaaaccga ggctggagga ggccgggcac ctgtgcccag ctggagcctt tgctgagggt    1140
ctccaaggcc tggggaaatt gaggctgggg gctgggggt gtcactgtcg ggccaggagg    1200
cccctcgctc tgattggagc cgcctcggcc acttgagcca ggaggctcac atgaggcggg    1260
ggctgcaggg acaggaccct cggggcccgg gaggccttgg aggggtcca gctgggccag    1320
ggttcgttct ttcccgggtc catgtccacc gccctcccgc tgctgggagg agaggaggtc    1380
cagggcagaa agaatgcgtg gggatggggg ggtggtcagg ggtctgggag ctgtggaaac    1440
aacaaacaga cagcgaggtc ctgggggcgcc cggcccccccg ccccctccgg cactgttgtt    1500
tctggccggg gtgcagggac agcgaggcag attccttcga aagtggagac tggcgggggg    1560
cccctcgggt cctcagctca cccctgagc tagcccgccc actcggctcc aacctcccgc    1620
aggcccctgg cacggtctcc aggagtccac tgagggtcc ccaaagctgc caccaggagc    1680
tgggcctggg tctgtcacca ccccacccca ccctccaagt ctgagatatg               1730
```

<210> SEQ ID NO 15
<211> LENGTH: 4833
<212> TYPE: DNA
<213> ORGANISM: Pig
<220> FEATURE:
<221> NAME/KEY: misc_feature
<222> LOCATION: (127)..(127)
<223> OTHER INFORMATION: Nonspecific nucleotide
<221> NAME/KEY: misc_feature
<222> LOCATION: (519)..(520)
<223> OTHER INFORMATION: Nonspecific nucleotides
<221> NAME/KEY: misc_feature
<222> LOCATION: (545)..(545)
<223> OTHER INFORMATION: Nonspecific nucleotide

<400> SEQUENCE: 15

```
atgtgagctg cacagcatga gccctcggcc ccactgctgt ggccttgcgg acattgaggt      60
gtgtgccgcc cagggcgacc acaccctggc ctctcaggt gcccgtacag aggcggctgg     120
gtcgtangag gtgcgggct ctggggaccg ctggtgagtt caggacgggg gtcatgccac     180
ctcctctctg aaggtttggt gaggtggccc ttctcttatc gtgatgacaa tactgatttc     240
tggaagagcc agtgtttttc tgaggctgtg gttgcacttc tccacgtggc cacaaggtgc     300
cgggctcggg tcagatttga gaagccctgc gggagcgggt gtcatgcgcc agattcagct     360
tgcctcctgc gggtctgggg tcaggacgtg gtccccagca gtctgctcca gagcctgtca     420
gtgatgtgtg ggattttacc gctagaacac agtttcctct gattctcaga aaccagcaga     480
tgctttagga ggggcgtgca ggtttcacct gtgctgcann gccccctgcc acctggtcgg     540
agccncaaga cggcatctaa agatcagttc ctcatcatca gttccgcagt gctggggtgg     600
gggcagatga gaacctcagg gctgggcgca gaggtgggga gcccgcctgg accccgacac     660
tgcaggggg cctcccccctt gtaggaagaa caatgtcgct ttgccaccca gccctctccc     720
cagggtgccc cgaactgttg ctcctaagac ctctgggctg tgtgctgtaa ttctataagt     780
ggccaccagg tgtcagcagg aggccactta agcatccatg tggcggaaac ctggagctgg     840
gggttcctaa gggtccctcg agtgtctcct gaataaatag gcgctgacct gatccccagg     900
aagggataac cctctcccag gcctaagagg cagtggggca atgaggttta tgtgtccact     960
gtacccccaa attgtctctt ccttccctct accctgtgtc cccaccgtgg acgatacacg    1020
gagtgcgagg ctgcgggtca cagccctcac agccccaaag ctgcaggtcc tgcctcaggg    1080
gcaccgcagc ttggctggtc cccttgggt cctccccacc ctgacccgtc ctctgctccc    1140
ctcccttgc ttaaatgctc tgcgtttcaa ggttctgatg gaataaaata gccctgcact    1200
ggtgtgttcc tctttggggc tgtgccagaa gtgggaattc agaccagggc agagctcaga    1260
ttccacatac tgtgttaggg atggcaggtg ccacatttcc aggagtttca ttggtggttt    1320
gtaaatgcta cttccgtttc agcccctcag ctgcccacct cctcaattta gggaccccc    1380
cctttggcgg gttgcccatg gaaccacatc atctggcgtg gggtgagccc tttatcctcc    1440
ctggccccac tgggagggtt tggggaagtc ccagctaaat ttctccgtag ggacctggaa    1500
ggagcccttg tgacatctgg gcacagataa gaggtagggg gcacaggccg tgaacacttg    1560
aagctgcaga gcccagagca gagccagcag gagcaagtga ctgctcccca ccccaagaac    1620
tgtgggctgc gtcacacact ccccactgtg tgccctggac ctgacagggc ctttagcctc    1680
cctgcatccc tccccaccca agaacccagt gaggcaccc acttgcccct ccttagtgtt    1740
gttatggctc tggggcatct gcattttgtt taggacaccc ccagctagat ttaagtcccc    1800
ccaagtgtga ctctttcctc cactgaaaac cctgtcctcc caccaaaggg ccctatccct    1860
ttagctgagc caaggaaatt caggaggggc cttgaatgac aaaggaagag ggggagagtt    1920
aaaccccaac actggctggc aagctgggtg gggtggacac cccagggtgc aggggtgcag    1980
tgaaggtagc ggctggtggc cttctggaaa ctacatgtga ctttgccatt aggtgagtct    2040
ttgctttgcc cctgctctat ctgcaggctt atggaagaag tttaaattcc cagggacact    2100
```

-continued

```
tggtctaacc aggcagcgct tgtatctggg cccttcccca gctgctgacc actctgagtc    2160
tgcgccttag ttggagtttt ggccaagctc aagaggctgt ggaccccagt catcccaccc    2220
aggggtgcct gtgggcagga cgctgctgcc tgccatttgc tgcagtattg tcactgtccg    2280
gcaccacaca catggtgcag gggtggtat caggtgccac tggggaaggg agaaaactcc    2340
caggtgagtc ccctgcctct ggaagcaaga tggacatgac cgcactgtgt tgcagctgca    2400
ttgggaggcc ccgaagaaag attttctga tctttctcga accctgcttt tccccatcat    2460
gccccgcccc cattttaccc gtgccacgcc cactggtgtg ccggggtgtc aagtgactga    2520
caagtgtcaa tctactgagg ccctgcccac tctccacccc cccacatagt cccacctccc    2580
agctggcagg gagaacttcc agctaatgcc catgcccaca aatgtctttc tgtcagccta    2640
gagctggacc aaatctccac cctgtaacat gctgtgccct ggcgtgggaa ggtgccagag    2700
ccagttgccc cagcagcccc agaaccacta agttggcaca agctaccca aatttggagg     2760 ggcttgggga agggcatgga ggggatgagg aggtgagggg caaaactaat ttcagttagc    2820
atttgagcag gtgccacgct cagcgtggag aggctctctt gcttctaggg acccattatg    2880
atgcacacgc taaaagcgcc cttcaccatc tctccagcct cagctttgtc ccctcctcc     2940 tcctcagcgg caacccggct ggagggtctg gccactacag ccagagcgcc cctactttg     3000 gtggcgactg ctactattgg cccaaccagc ggatcaccgg ccaggcagtt tcggcagaga    3060
gtctggggca ccagtgactc ccccgtcctc tttatccacc acccaggagc ttcagggact    3120
acacagcgac tagagggcag gtaactggtc tgccctccct agggctgccc cctcagagtg    3180
tgtgagaaaa gctgcattga gtgtttgggt gcaggtgggc tggggcttg gggcagccaa     3240 caggaacggc gggacctctg cttccagagg accccagatc ctggcaagct tcgactttgg    3300
aggggacagg aaagacaggt ggagagggga cacttccctc ttctgtacag acgcccaccc    3360
ggagccacag aggcttttgc aaggaaaata ggttttccct cactaatgca gcaggcaaaa    3420 tgggagggc agggtggag ggtagtgccc ccgcccccag caggagggca cagctgtttc      3480
tgcaaatgta aaaagcagg gttttctgt gtgagaagtt ccctcttgct gcatgtcccc      3540 accccgcca ccaaagacaa acaggacact gtgcagaggg gccagagccc cgagattttg     3600
gagttgtttt tatatgcata tataccattt tgaaagcaaa gcttccctct cccctactcc    3660
ctacatgtcc cccttcacca aaaatccca ccacgtaact ggaaagggga gtgagaagga    3720
cgacgaaggg gcactgtccc ctcccgtccc acagcgggac ttaaaacgta cagcttttcg    3780
cctccggaca gtgtgccgcc ccctggcccc cgtcacgctc cctgcccgg gggctgagt    3840 gtggggccag gcctgtctc caggcatgca ttattttgtg catgaaggtt ttgtcccgcc    3900
cacccaggct ggtgttgggg ggaaggggtt cattgctcca aagaagccca tctcccccct   3960
cagccacctt cagccgcctt cgcaaggcag agctgtgtcc tctgctgtgt gcctggcccc   4020
ctccttgctt ctattcaagg tggaagtgtt gggggagga gaagagtttt tatattgtgt   4080
ctgtgatccc ccgaggcagg gcatttgtgt gcggccccc agccccagg cccaggcaga     4140 tgggccagcc tgcccgacag aagggtctcc tgctgcttgg ctgcagggaa acccagctct   4200
gggtgaaccg tgggcacctt ccttcctcca tgccctgtat ttaaagaagg agagctgggg   4260
ggccagaggc acaggagggg agccacggcc cccaggtctg acaagatgac ctgcgggcct   4320
ctccacccaa gagtcggggt ggggggcgg atttggtttg aaagagaac aaataggaac    4380 acactcttta ttttccccag gggccgaaga gtcacccctg aacttgagga cgagcagccg   4440
gattccagcc cccagcccca gggccccaca tctcctcggg ctcagccgcg cgccccagct   4500
```

-continued

```
gcccccagc ctgagctgca gcaggccagg gctgcccgag accccagccc ccaggtgagc    4560
tgctgcagcc tgtggcccag gagatctccg ccggctcaga actgaggcgg gcagcccacc    4620
cagcccacag cggtgagtgt ctccagaccc cagggcaggg cccggtgtcc cccggcacag    4680
agagctgtgc tgcaggccca gacctcccag gccgttttag ttcccatctc cccttggggg    4740
aggggtgggg ctcagagggg ctgggtgca tccgcagagc tggggtgcag ggctccaggt     4800
gcctctctcc caggcggctg gcccggaggg ggg                                 4833
```

<210> SEQ ID NO 16
<211> LENGTH: 2064
<212> TYPE: DNA
<213> ORGANISM: Pig
<220> FEATURE:
<221> NAME/KEY: misc_feature
<222> LOCATION: (46)..(46)
<223> OTHER INFORMATION: Nonspecific nucleotide

<400> SEQUENCE: 16

```
ctggtttcgc actcctccgg ggactgttga agtacccgag agcgcncgcg gagcgccggg    60
gcgagcgggg gtggccgccg ggggtgctcc cgggcccccg gaccgagcca gggacgagcc   120
tgcccgcggc ggcagccggg ccgcggcttc gcctaggctc acagcgcggg agcgcgtggg   180
gcgcggccgc tgccgggagt ccgcctgcct cctcggaggc ggccgaccgg ggagcctggg   240 ggacccgag cgcccgggga gcagcgcccc gacacgcccc gggccgctct cggcttcctc    300
ccttccagcc ggcgcccgcg cggccgggct tcggcaccgg ggcgctctca gtggcaggag   360
aagcgtgcgc tcccgcgggg tggggaccc gcaggaaacc cgcaccgcct ggagccgccg    420
ccgcgcggcc agcgctcgcg tccccgggg agggcgccac tgctccgcgc gcgcgtcccc    480
cgacgccccg cgcgcttccc cggccggccc gggatcctaa cctctctctc ggtcgcagcc   540
ccgcatcccc agggctccag gccccgcgcg acttgcccgc tcctcccaat tgcagacacg   600 acttttctg ggacctccca aaggacagcc tggctccagg gtcccccaga tacattcacc    660
atttctccag atcacaagtg ggttttcgg gcactaactt ccagagacct caaagcacat    720
gagcccctac tggctttccc aggtttccac tagtggcctc ggtccccacc tcactgggga   780
ttgtctccca ggctcttcgc ggtgtgatcc cacccattcg cgcccaggtc ccgcagtgcc   840
aatccctcct ctagaaaact taaacactga ctcctggtct cggggtgagg ctgcccaatg   900
tgcctgactc cccagaaggt ataccagtgt ttttctggca tttgggcacc gttcccccaa   960
aacacgtgaa gctcttttcc cgcgtcccca taattttgga cgccaggggc acccaagctt  1020
agcgcccctg tttggctccc ccacaccgcg aagccctgct ccctgggtt cacgacagtt   1080 tgggacttta tctgccaagt tccacaaact gattggcccc aagctgggt ccctaaattg    1140 tacacaaaga accccagccc cccccccaa ctccagtaca ggaagcgatg gccccaggga   1200
ccctcggagt tggaacgtgg cttcctaagc cttcaccaaa attgaggctt tccgcgcatg   1260
gcgcgctgat gcccttgctg aatcagaagc actctgccct ctgattcctg ctttccacaa   1320
ccctgagagc atgatttctg gtccccaaa ctcactgagc aaaaatcttt ttgtggggc     1380 tgcaaagata ggaggcattt ctctccggag ctctccaaac tcccttgcct ataatcaagt   1440
tccctaaaac ttagacagag cttcccaggc cccagaggca cacagagcca ttattggagc   1500
tgcgtttaat gatgacaggg accatgggtc atgcagctcc cccaagtcac aaatgcccca   1560
ggtatccttg gctccagcca agcccaaagc aaactcttgc acagatccca tatcttgtta   1620
```

```
tgtcaagcgc tttgcgtgtc ccagtaaaca aatagtctga gtgttttctc cacctcataa    1680
cattcggaat attaaaaaat tccctgggcc cccggagctg acagacaaga atccgggctt    1740
cctaaaattc agaactgatt cccaaatccc aggccaacgc cagaccctct cccaatctgg    1800
agcccctccg actggacaca ctggactcct aagtattacg cgctgtcctc caggcacccc    1860
aaatgcattc aaagtgacgc tttggtcaca gaaaggcact gatttcttgg gctccaaagc    1920
agcccatgca cccccgagtc accccaaact tagtcagcat ttcccgggtc tccctccgca    1980
ctgcaaactc ccaactgcgg acaccggttc ttcaggaccc accgcctaga cggtcttaat    2040
cccttttccc ccagacctag attc                                           2064

<210> SEQ ID NO 17
<211> LENGTH: 371
<212> TYPE: DNA
<213> ORGANISM: Pig

<400> SEQUENCE: 17
agattcaaaa actattttc tggggcctcc aaattgaggt gctgcctgcc agtcctccaa      60
aataaactga gggtttttt gtttgtttgt tttttgttt gtttgttttt ttttacctt      120 ccacgaaaca atccaacttt tttggaccat tgatttatgg gtccctgac tttatgaccc     180 ttgcccccaag tccccctaaa tgtaggccat tttccacggg cctcccaaaa tgaaattgcc    240
cagatcccgc cgaaaaaaat atccccgggt cctggaaatc ccaggtatta caggcctgcg    300
gctgacaccc ctccttgcta ctaaccaggt tccctgaagt ttagagatca ctacctaatg    360
aacaaatcca c                                                         371

<210> SEQ ID NO 18
<211> LENGTH: 2415
<212> TYPE: DNA
<213> ORGANISM: Pig

<400> SEQUENCE: 18
ccaaaactgg ggccctatct tactagggtt ccctaaatgc agacagcgcc cgggaaaata     60
ggggcgtttt ttttcctgtt tgccaaaaat aaactaattg aaaccaattt ttagaattaa    120
aatctaaaat gaccttgatt ttctgcgttc tccaaatgta cttttcacag cccaggttgc    180 ccccagtttta gacggtgttg cttgaatctc taaagcaccc tgaggatttt tcccgaggaa    240
gccaccacaa ctacggaatt tactgtcctt cggggccaca agcctccagg ccaccaactt    300
ggatttctaa accgtggaaa tcagcctcca cttccctccg ccaccccgag ggtctgctca    360 gacccccaa acgtgcccgc tgttcttctc cccccaaatt ttatttagag aatatgcctc    420 tctcggggttc tgccaagttt cccgctgaga cttcctcggt catccccaaa tcctcttccc    480
cacagtccgg gagccccac aagcttaccg acccacatgc tggggtcccc caacttaaac    540
gcgatcccct gtccccaga ttcaccgagt gatttccctg gtcctcagac tgggactctt    600
ttactggagt ctcgaattta gccattaatc acagttctcc actccgacgc aggctcccttt   660 gggtccccac gtcggggaca tgggttctct tgcctgcaaa tcaggctgct ctgacttgca    720
ttcaggcctt tgggcattgt tcccgcccg ccgcggtctc ggttctcccc ccatcccgcg    780
cacgacgggc actgggtctg ggcctcttgg tgtctcctac aagtcccggg agctcctcgg    840
acttgggaac tgtctcttgc gttccccaaa tacactcggc ccggcagtgt gtccgccagg    900
acgtaggcag agcttctccc gcgtccagga aaacgactgg gcattgcccc cagtttcccc    960
caaatttggg cattgtccct gggtcttcca acggactggg cgttgccccc ggacactgcg   1020
```

-continued

```
gactgccccc ggggtctcgc tcaccttcag cgcgtccacc gcccgctgca gagcgctcgc      1080
tctccgtctc tcggctccca gcgcgcttgg ggacgcagcc tccgggcctc cagccttgcg      1140
gtgagctccc cgtcgcctcg cgtgtcccgg cccggctccc aaacccactc gccgccgtcc      1200
cgctggggct ggcactggcc tccggcgact gccggggaca cgggagcgga gcgcgggagc      1260
ctgctgcagg ccagcccgtc ggccgggccg cgcgccctga acgcgcgcg ctttcgttt        1320 gctctttgca aaggtcacaa ccgtggggaa aacgcctcgg cggccccaa gcggggcagg       1380 cagggcgttg ggaaggaggg acacgcggga gaggagcacc ccgctggggc ggcgcagcgc      1440
ggcgcctcca gccgccgggc ggaggatccc gggaggcgcg cgcggagcgc gggcgaagtg      1500
attgatggcg gagcgagggg gccagcggat cgcgggcttc cgccggcggc ggcccctcc       1560 cctcggaggg actcggcgg ccccgggtttc tgggggcggg cggggcgcgg gggcttgtgc      1620
gtggtctcca cttggtaaaa atcacaacga cttttttacgt cgccccgact ctccaggaga     1680
tggtttcccc agacccccaa attatcgtgg tggcccccgg ggctgaaccc gcgtctacgc      1740
aaggccaacg cgctgaggac gggggaacca ttatccggat attttgggtg ggcccccaaa      1800
gcgagctgct tagacgcgcc ccggtgagct cggtcctgca ggtaggcttg gagcgaggtt      1860 ccccgcccctg ctcctctctc ttcgggcagg cgcggccagg ccggccggcc ctccccacgt     1920
acggcacctg gcggccgccg agacgactcc ccggttcccg cgcggcaccg gggggcgctc      1980
gggctctggc tgcggctcga ggcgctgcgc ctgctcgggc aggtggaggc ttcacgccgg      2040
gcccgcgccc aggacgacc ccttaccccg caggtcccag cgggactcgg ggcccccgga       2100
tccagcgtct agccacctgt gcccgcaccg ccgcgagggc ttgtgacacc taccaccctg      2160
gccgccccgc gtccccccgc gcacgaatgt agggatcctg acaccccgga acctaagacg      2220
gggcccccat acactttcgt acagcgattc gggatttctc tcgaactctg cagatctgta      2280
tggcaaagtt gatggcctgc attatttttc tgataattca gcgaaagatg gcgaccagag      2340
ctatgcgcgt ctgggttttta aaggcgaaac ccaaattaac gatctggtca cgaacagat      2400 acagcatacg ttttt                                                       2415
```

<210> SEQ ID NO 19
<211> LENGTH: 3752
<212> TYPE: DNA
<213> ORGANISM: Pig
<220> FEATURE:
<221> NAME/KEY: variation
<222> LOCATION: (341)..(341)
<223> OTHER INFORMATION: Polymorphism G:T
<221> NAME/KEY: variation
<222> LOCATION: (2247)..(2247)
<223> OTHER INFORMATION: Polymorphism -:C
<221> NAME/KEY: variation
<222> LOCATION: (2248)..(2248)
<223> OTHER INFORMATION: Polymorphism G:C
<221> NAME/KEY: variation
<222> LOCATION: (2257)..(2257)
<223> OTHER INFORMATION: Polymorphism C:T
<221> NAME/KEY: variation
<222> LOCATION: (2413)..(2413)
<223> OTHER INFORMATION: Polymorphism C:T

<400> SEQUENCE: 19

```
agattccaat ggggatcccg atgaggaagc cgctgctcgt gctgctcgtc ttcttggcct        60
tggcctcgtg ctgctatgct gcttaccgcc ccagtgagac tctgtgcggc ggggagctgg      120
tggacaccct ccagtttgtc tgcggggacc gcggcttcta cttcagtaag tagctcagcg      180
```

-continued

| | |
|---|---|
| gggcacgggg gcggggcgga cacagcaggt gctccatcgg tgctgcccg gtacctgtgc | 240 |
| gggtccttcg ggatggatgg tgtgggggac gggggcggg gggcggccaa gggaggacct | 300 |
| ctcctccgag ggtctgagac ttcagagcgg gggcgccctg ccctgcgca gtgattggca | 360 |
| cctgccatgt gcctggctgg ggctcacacc ccctgacgtt cctgcagcgt gactcgaaac | 420 |
| gggaaaccga agggacgggt ggcacggggt ggggaggcag accgtgagtg gcaggcgtgc | 480 |
| gaggggttct ttcgggcggg gtggcccagg caggccccac aggatgacag cctgtcccct | 540 |
| cctgctcctc cttgacctgc ccacagccag ggctgcaggc actgacattc acccatggta | 600 |
| ttgtggtgcc tgacgtcttg gcagtgggca tgggttcatg gactgttgga ttgaaagtgg | 660 |
| aataagatgg gttgaaaacc aataagaata aggcgcgtg tggctggcgg catctgcgag | 720 |
| aggtgaccgc tgccctccct gggttgggc tttgggtggg ttcccatggg tggggcgggc | 780 |
| cgccatgcag ggtgcccgcc tgctggcctc agagtgcttt gccgtcctca tctttctctc | 840 |
| tggcccccgt cccgctcctg aggctggctg gctgggcccg cggagacctc cgctcccgcc | 900 |
| tcgtctgtgc ccagggagca gggtggaccc tcccttgggc tcttgcctgc acctcccagc | 960 |
| aggctgggcc tcagtgtcct tacctgtagg atgggtcagg ggcgtcctgg agagagtcct | 1020 |
| cgggacaatg gggaggctgg gggcaggccc agcctgaccc tgaaggtggg agtgtgtgct | 1080 |
| cccctgggc tcagccagcc gcgcttgggc cgggagggg gtgggggacg tggctggggc | 1140 |
| aagttgtcaa gggccgcgag gctcaccccc gcccatcgct ccccatgtgg cagcctcttc | 1200 |
| tgcagcctct acttacccac cctctgaaat gggctgaaaa cacccatctt ggcatgccaa | 1260 |
| agcttctctg taaaaagcgt tgctgcttct tgatgcttct gaggcccctg cctgccctgg | 1320 |
| cctctgagcc ctctctctcc tgcctcgttt ggggcaggg agtggcacca tagaatctgg | 1380 |
| cgctgggcct ggggagcggc cccctcgtgc caggcttccc cgaaaggagg gctgggctga | 1440 |
| gctcccgacc ctctggaccc cttaccagga ccccttacca ggggcttccc cccccccc | 1500 |
| ccccggtggc ggcgggctgg gctggggcct tttccttgca gccgagtcgg agctgtcgga | 1560 |
| ggcgagggcg aggacgggaa gagaggaggg cgtggtttct gctggtcctc actcctctcc | 1620 |
| tcccgtcttc ctcctcctcc tcccattccc acctgtgtct ccgggtcccg gggccgcagg | 1680 |
| ctgcccaggc gcctgctgat ccattgggga ccgcactcgg gtccccgctg gccttcgggt | 1740 |
| cagggccacg gcccacctat tttccaaaca gccttgggtc gaggcccaag aggctgggcc | 1800 |
| cggtttaagg acggggaggg aggcgccaag aggccagggg ctggtcccga gcacgcccgc | 1860 |
| acccgctcac ccccgctgtc ccctctcctt ccccggggg ccctgtgca ccccactctc | 1920 |
| acttcttctg ctcgaggcca cgaggctggc tgtccccgca aggtgaccgg gcgtcctgtc | 1980 |
| tggagggcgg gggccggggc ggctggggc accgtccgtg cccggggccc ctgtgctgac | 2040 |
| gtgccctccc cttggtcctg tgggacttcc aggcaggccg gcaagccgcg tgaaccgccg | 2100 |
| cagccgtggc atcgtggaag agtgctgctt ccgtagctgc gacctggccc tgctggagac | 2160 |
| ctactgcgcc accccgcca agtccgagag ggacgtgtcg acccctccga ccgtgcttcc | 2220 |
| ggtaaggcag ccctctctc ggcagcgccc ccccggggg ggggctgtc tcctctgagc | 2280 |
| cggggaccg gggcgcagcc ggctcttggg cttcaagtgc tgccagaggg gccttccccg | 2340 |
| ctggggaccc tggccagaag ccagggcagt cttcgctctg tcgcagggca ggcaggcagg | 2400 |
| aggacccgc agaggttgtt gttctgggac aggggctggg gggccaggcc cccctgac | 2460 |
| gggcccttcc cctctcagga caacttcccc agatacccg tgggcaagtt cttccgctat | 2520 |
| gacacctgga agcagtccgc ccaacgcctg cgcagggggcc tgccggccct cctgcgcgcc | 2580 |

-continued

```
cgccggggtc gcacgctcgc caaggagctg gaggcggtca gagaggccaa gcgtcaccga    2640
cccctgaccg cccgtcccac ccgagacccc gccgcccacg ggggcgcctc tcccgaggcg    2700
tccggccatc ggaagtgagc caaattgtcg taattctgcg gtgccaccat ccacctcgtg    2760
acctcctctc gaccgggacc gcttccatca ggtccccctt ctgagatctc tgtacccttc    2820
tgtctgcggg catctccgcc ccgggccccg tgccccaacc tccccatgtc aggctagtct    2880
ctcctcggcc ccttccatcg ggccgagggc atccaaacca caaacccaat tggcttggtc    2940
tgtatctccc cccaaattat gcccccaatt atccccaagt tacataccaa aaattgaacc    3000
cctcaaccac acccacatac aatcagcccc cgtaaaacga attggcatct ttaaaacacc    3060
agaaaagcga attagcttta aaaaaaaaat aaacccaaaa tatcaattag ctgaaaaaaa    3120
aatactaaaa ataaattggc ttaaaaacaa ttggcaaaat aaaagaattt ggcccccccc    3180
ttccttctct ttcttttcgg accttgagtt aaattggctg tgaccatca tccaagagaa    3240 aggaagggac caaaatttgc aggtaggctt gtcgccgctc acagccatct ccctcctcct    3300
gccacaccct cgccggccac tggcggtgtg gcaccaagga cccagtcccg tcctctctct    3360
agtcccatga ccgagaccgc ggtggagttg gctgggagac cccgtgagat cagaggaggg    3420
gagcacggaa ccagaaaccc aaacctgcac aggtacaaca tgactggccc cccgcacagc    3480
ccaagacctc tcatctcagt ctccacttaa aaagcacctg tacccacacg catccctgca    3540
gaaacacaca cacacacaca cacacacacg cacgcacgca cacgcacgcg cacgcacgcg    3600
cacacacaca ctcatgcgta tacacacaca cacgcacg cacgcgcacc cacacacaca    3660
catgcattca cacacacaca cactcgtgca tacacacgtg cgcgcgcaca cacacacaca    3720
cacacactct ctctctctgt gggatccctg ag                                 3752
```

<210> SEQ ID NO 20
<211> LENGTH: 500
<212> TYPE: DNA
<213> ORGANISM: Pig

<400> SEQUENCE: 20

```
tggctctggc ataggctggc agctgcagct ctgactggac cccttgcctg ggaacctcca     60
tatgccgtgg aagcggccct agaaaaggcg aaaaaaaaaa aaaaaaaaa acaaccaaac    120 aaacaacaaa agccaaaaca cacagaactc acagacacaa gaagagactg gtggttgcca    180
aaggtggggt cgagggtggg aaaaatgagg agaggggca aaacacacaa acgtgcagcc    240
ataaaatggt aaagtcccgg ggacctccgg tagcgcgtgt ggggactcgg gttgagaaca    300
caccgtgatg tgtattcgcg agttgctaag agtccctgtt ggagaaacaa atgcgtatcg    360
acgtgtggaa atgaaagtta acccgacctg ctgtcgtgat cactttgcaa cacatacaga    420
catagaatca ttatgtttta cccctggagc tgacagcgtt atacgtcccc cagcctcaat    480
ttaaaaacag cgttgccgtg                                              500
```

<210> SEQ ID NO 21
<211> LENGTH: 400
<212> TYPE: DNA
<213> ORGANISM: Pig

<400> SEQUENCE: 21

```
ttcatactgt gcaatgccag ccttaaatgc acagaggaga gcattaactt ctttgcagaa     60
tcactgaaat gataccactc atgttttgca acttgcactt gggcgttatt ttattggtgc    120
```

```
cggaacagcg gcgatgtggc accaaactag cgccgctgtt tttatttccc ctcggtatcc    180
gcgctctcgc tgtcttcccc cccttccgct tgcagctgag gaaagggctg agaggaggaa    240
agtctgcatt cacccatctc ccctgcctc tgttgtcatc cttcacagaa gtggtggcct     300
gtgcggggaa gtcactaaac ctaggcaggt gtcccgtggg gtcatgcttg ttacaccttt    360
gtgcacctgg cccaagttct gggtggagcg agaacgtggc                          400
```

<210> SEQ ID NO 22
<211> LENGTH: 559
<212> TYPE: DNA
<213> ORGANISM: Pig
<220> FEATURE:
<221> NAME/KEY: misc_feature
<222> LOCATION: (549)..(549)
<223> OTHER INFORMATION: Nonspecific nucleotide

<400> SEQUENCE: 22

```
agctagcccc cccagccagg gccaggcctc tcctgccacc cgcccagcca gcatgtctca    60
agaggagggg gcctctaagg gatgaggacc tgctccagtc ggagacacga agccccgccg   120
gctcctcccc gaaagtccag ctgcggcttt cgagcacggc tgcgcccttc gtcaatcatt   180
tcagccacag aagtgaaagg cgctttcgtg gccgaggcag cgggacaca gaatggaatc    240 ccaccccaga gcaagagcc gccgtgggtg aagcgcgtct ctggtgggga ccgggccggg   300
aacttcacat gggggtcgct gtccccatct ccccatcgtc attactgcag gggctcggcc   360
acacccggag ctgcgggggc cagtgctgga cactggacct ggcctccgtc ctatgatgtc    420 atggggggcgg ggccagcaca gggcagtggc cacacctcgg gcctcccagc accagccagg   480
atggcagagg gccccacccc accacggggc atgtacatcc cagaggacca gctgagcaag   540
gcttgatang ggcttcaac                                                 559
```

<210> SEQ ID NO 23
<211> LENGTH: 450
<212> TYPE: DNA
<213> ORGANISM: Pig

<400> SEQUENCE: 23

```
cgtgcaggga cccgtgcggg ccttcctgtg gccacagaga acaaacacac cattatcttc    60
agccccaccg cgcggcctgt taatgggtaa actggggcaa gggggcccct gcctgaggcc   120
ggggtgggga gcgcaaggca tggcctgtgt gccccagccc agtccttcag ggcgctgctg   180
tcctgcaccg ggggccccag gaagcagagc acccagcttc tccctatc tagaaccagc     240 ccccagaacc ctggacccag acccaggccc agggatact gacagagcca cggcaaggcg    300
gccactccac acccccacaga ggggccagca aaccccagtc actgcgcagc ccatgcccag   360
ggggcagatg ggacacgaga gcagccctca tccacagcag gcaggggagt gaactggtgc    420 aaaacgggc ggttccacga aagttaagca                                     450
```

<210> SEQ ID NO 24
<211> LENGTH: 535
<212> TYPE: DNA
<213> ORGANISM: Pig

<400> SEQUENCE: 24

```
tgccagagac ctcagagctg ggctctgcct tcccgggctg acacggaggg ctgtggcttc    60 caccaccccca ggccacagcc agcctgccca agtccctgaa gtgtcccag aggtggccct    120 gcctccacgc ccaacatcag gcctgctgca gccctggacg gcccctgtc cccggaagc     180
```

```
cctcggggct ctctcgcgtc gcctctgggg aaccctcggt aatgtggccc agccgtgcag      240
tggccggatc atttgctcag gggggcccaa ggcaggggg tgacacatcc gcaagtaccg      300
catatgcaca ggatatggat tgggtgtgga tttaaccttt tcgcaaatgt ctctgccggt      360
acaaatattg tttctaatcc tctgcctccc tgagccggtg agtctgcccg ggagctgcgg      420
ggagctggct tgctgaacct gccctggccc caccccccaa gggagccccc ggccagtgct      480
gagggcagga agcttgggca caggctgcag aggccagcgc tggcctcagt cacct           535

<210> SEQ ID NO 25
<211> LENGTH: 868
<212> TYPE: DNA
<213> ORGANISM: Pig
<220> FEATURE:
<221> NAME/KEY: misc_feature
<222> LOCATION: (310)..(310)
<223> OTHER INFORMATION: Nonspecific nucleotide
<221> NAME/KEY: misc_feature
<222> LOCATION: (857)..(858)
<223> OTHER INFORMATION: Nonspecific nucleotide

<400> SEQUENCE: 25
tattgaagac cctatcatga gttcccagag cggaggggtg gaagcagggg cctacagccc       60
actccccatc actccagacc cgtccggggc tggtgtcccc tgcccccta  tcctgtctct      120 ggtgggcgga cgctcgaagg aggcactctg gcctggagcc tggagggtcc ctgaactccc      180
gctgccacct gggccctcgg gctcctcctg cgctgggacc cgcggtggtg ggaagcagcc      240
ctgctcagtg ggaggaggca gggctgtggc cgccccgcac ggccctgggg gggacgcacg      300
caggacgcan gtgggcgtgt gtgagtccgt ctacacgtcc agccaagggc ggccgcgacc      360
ggccagggtg ggcagcccca gcctcagcag ggcgctctct ggggctcagg ctgcgccgac      420
gggagatgag gggtgaggcg cagtctgggg ctgctgccgc agaacctcgc ccagctggca      480
gctgggcaca gggagacctg tactcccaga acctgaggct ggacgtccga gacccgcgtg      540
ccggcctctt gggtgcctgg tcagggtcct ctttctggtt tgtgggcaga acctcctcag      600
cgcgtccttg catgggtgc taatcacgga gtaaggagcc agagaatgag gcacggagta      660
tccagtgtta accctggagt atggagacga gagtactaat tgtggagcat ggctctaagg      720
aatggagtat tcgtcacgga gaacgcgggg ccgggtgaaa tacggagagc ggcgtacgga      780
caacggggac ggggtatccg aagggagga tggagtatcg gccggagggt ggagaatgga      840
cactagagga tgtatanngg gcgtcaat                                           868

<210> SEQ ID NO 26
<211> LENGTH: 500
<212> TYPE: DNA
<213> ORGANISM: Pig

<400> SEQUENCE: 26
accagtttcg atgagcaatc ccagcggcgt aacattatgg ctgcagcctg gtcaatgccg       60
gtggagtttg aacctccacg cgtggcgatt gtggtagata aatcgacatg gaccagggag      120
ttgattgaac ataacggtaa atttggcatc gttatcccgg gcgttgcagc aactaactgg      180
acgtgggcgg tgggaagtgt gtcggggcgt gatgaagata aatttaattg ctatggcatt      240
ccggttgtga gaggcccggt atttggtttg cctctggtcg aggaaaaatg tctggcgtgg      300
atggagtgtc gattgctacc tgcgacttct gcgcaagaag aatacgacac gctgtttggc      360
gaagtagtat cagcagcggc agacgcacgg gtatttgtcg aaggccgctg gcagtttgat      420
```

| | |
|---|---|
| gatgataagc tcaatacgtt gcatcattta ggtgctggga cgtttgttac cagcggcaag | 480 |
| cgtgttacgg cgggttaagc | 500 |

<210> SEQ ID NO 27
<211> LENGTH: 900
<212> TYPE: DNA
<213> ORGANISM: Pig

<400> SEQUENCE: 27

| | |
|---|---|
| atgtttgatg tccgcgcgtg ctgtaaaaat ttacgctgct cgcgttcttt ggcttcgtcc | 60 |
| accaccggaa aacggacaaa aatttccgtc ataccttttt ctttcaggcg gaagccaatg | 120 |
| tcgtaatctt cagtaagact ctgcacgtcg aaagcaatac cgtcaccgtc agctaacagt | 180 |
| gcggtcacgg cgcggcggct gaaacaggtg ccgacgcctg cgctgggcac ttgtccggcg | 240 |
| agggcttcac gcaccggaac atctttgcca tgcagctctg aaaactcatc aatgtaagtc | 300 |
| atgctggtga agtgcgtcca ttcgcgttcg aacggataca ccgggatctg aatcagatct | 360 |
| ttacgctcga ccagatagtt gaacagacgc aattccatcg gtgaaatcac atcttcggcg | 420 |
| tcatgcagaa taaaaccagc aaaagcgaaa ttggcgctac gctcaaattg ggtgatggcg | 480 |
| tccagcacgt tgttcagaca gtcggctttg ctggtggggc caggacgcgc gcagactacc | 540 |
| ttatgcacat tcgggaagcg agcgcacact tcgtcaacat cacgctgagt atcggggtcg | 600 |
| ttggggtagg tgccaacaaa gatatgatag ttttcgtagt cgagcgtggt cgccgccagc | 660 |
| tcggccatat tgccgatgac gcccgtttca ttccacgccg gaaccataat cgctaacggt | 720 |
| ttttcatctg gtttatacag ttcgcggtaa ctcattcgcg ggtagcggcg ataaacactc | 780 |
| aacttgcgtt taatgcggcg tacccagtat acgacatcta taaaaaatc gtccagcccg | 840 |
| ctgatgaaca tgatgaccgc taacgttatc gcgattactt ttaagccgta tagccaggta | 900 |

<210> SEQ ID NO 28
<211> LENGTH: 500
<212> TYPE: DNA
<213> ORGANISM: Pig

<400> SEQUENCE: 28

| | |
|---|---|
| agctggatgc cccagctgt ggtcccttcc cttccctcag ggcaggttct gtccctcttg | 60 |
| cagccaccgt cactgctgtg gacaggtctg cacacccgcc gtccaccaag agcgtggcag | 120 |
| gtccctgggc acgggccggc tcctgacgca ccatgtgttc aaggcaagag cactggacag | 180 |
| agggtccaga cgtcccctttg tcctgctcag gcctgggcgg gggcagccct ggcgggagag | 240 |
| gccctgggca tcagagcctc tgtggcctgg agcttggcgc cctgccctcc ccacctccgt | 300 |
| cctgctcctc gccgcgctgc acggacctct cccggccccc caggctcatt actcttaagg | 360 |
| acccctagccc cctatgctga aatgctgtac ctcgtgcttg ttttcatctg tttattacct | 420 |
| tatcttcatt cctgcttgat gatatctggt tattctttat tgattatata tatcttgttc | 480 |
| gtgtttttat aggacactgt | 500 |

<210> SEQ ID NO 29
<211> LENGTH: 450
<212> TYPE: DNA
<213> ORGANISM: Pig

<400> SEQUENCE: 29

| | |
|---|---|
| agtgcggtcg ggccgtcctg acgctcaaca ccgtatttcc acgcgaccgc ggattcaacc | 60 |

```
tggtcacacg gacgccatgt agacatgttc ggggttacgc gcagagaagc gacctgctca    120
accggctggt gagtcgggcc gtcttcgccc agaccgatgg agtcgtgggt gtaaaccatc    180
acctgacgct gtttcatcag cgcagccata cgtacggcgt tacgtgcgta ttccacgaac    240
atcaggaagg tggaggtgta cggcaggaag ccaccgtgca gggagatacc gttagcaatc    300
gcggtcatac cgaactcgcg aacaccgtag tggatgtagt tacccgcagc atcttcgttg    360
attgctttag aaccagacca cagggtcagg ttagacggcg ccgggtcagc agaaccgccg    420
aggaattccg gcaacagccg gacgaacgct                                     450

<210> SEQ ID NO 30
<211> LENGTH: 450
<212> TYPE: DNA
<213> ORGANISM: Pig

<400> SEQUENCE: 30
tcaggccaat ctgtctggtc tccaatgggg acaatttggt tctttaggct tctgtccaat     60
ggtccgaatg gcccactccc cgggcgccgg ccaagggtcc tctgtgcctc gggtgggctg    120
gcacggaccg cccccagggt cgtgccagcc ccgtcaccgg ggcccagaag cttcgggcct    180
ctagctggct agtcgggctg ctgtgcaggg gggctgcgct gggggcagag gcggggtga    240 ggtaaacctc ccagccgccc ggggtccctg ccgcagccct aggcgccgag acggtggctg    300
ggtcggtacc gccagacccg agggcctcgg ggcccgggtg accccagctg tcgcacacgc    360
tcgcagctct cttgctcatc agggctcatc cctctggacc tctcctactg ccccacctca    420
ccccgcctgg accccatgaa gccccgcgga                                     450

<210> SEQ ID NO 31
<211> LENGTH: 600
<212> TYPE: DNA
<213> ORGANISM: Pig

<400> SEQUENCE: 31
taaaactagc tctagtagaa acattttatt taaaaataaa aaacctgact acgtcgggag     60
ttcccgttgt ggctcagtgg ttgacgaatc cgatgaggaa ccatgaggtt gcgagttcga    120
tccctggcct cgctccgtgg gttgaggatc cggcgttgcc gtgcgctgtg gtgtaggttg    180
cagatgaggc tcggatcctg cgtggctgtg gctcgggtgt aggccggcgg ctacagctct    240
gatgagaccc ctagcctggg aacctccaca tgccctggga gtggccctag aaaaagggca    300
aaagacaaaa aaacaaaaga aaaggaaaa taaaataaaa aagactatgt aaatgaaatt    360
aacgactgcc tagggtggga tttacagcat gggaagtaca gcatggccgt gacagtgcaa    420
gggtgaggcg ggaaaatgga aataggttag gtgagtttct cctgctattt gtgatgtggt    480
ctgctatcgc ttgaagacgg actgcagtga gataaatatg tacagtaagc atccgaaaaa    540
ccgccagaac ggcaaaacga atgactccaa gtaagaaccc aaaagagaaa aggaaataat    600

<210> SEQ ID NO 32
<211> LENGTH: 450
<212> TYPE: DNA
<213> ORGANISM: Pig

<400> SEQUENCE: 32
gcgcgggcgt tccggctggg gtatttaacg tggtcaccgg ttcggcgggc gcggtcggta     60
acgaactgac cagtaacccg ctggtgcgca aactgtcgtt taccggttcg accgaaattg    120
gccgccagtt aatggaacag tgcgcgaaag acatcaagaa agtgtcgctg gagctgggcg    180
```

```
gtaacgcgcc gtttatcgtc tttgacgatg ccgacctcga caaagccgtg gaaggcgcgc    240
tggcctcgaa attccgcaac gccgggcaaa cctgcgtctg cgccaaccgc ctgtatgtgc    300
aggacggcgt gtatgaccgt tttgccgaaa aattgcagca ggcaatgagc aaactgcaca    360
tcggcgacgg gctggataac ggcgtcacca tcgggccgct gatcgatgaa aaatcggtat    420
caaaagtgga gagcatatt gccgatgcgc                                      450

<210> SEQ ID NO 33
<211> LENGTH: 450
<212> TYPE: DNA
<213> ORGANISM: Pig

<400> SEQUENCE: 33
ggtggatgct ggcgatagcg tcatcctcgc ttatgccgtg cagcgggcaa ggataaagcg     60
cgcgataaac atgacccggc atcagcccca tgcccgcaga gtacggattc accttgccgg    120
tcagcgccag cgtgtaatgc gtgcgcccgt gatacgcgcc gctaaaagcg atggtgccgc    180
tacgtttggt ggcggcgcgg gcgatttta ccgcgttttc caccgcttcg gaaccggtcg    240
taaccagcag cgttttcttg gcgaaatcgc ccggcaccct ctgattcata atctcgcaca    300
gctccagata cggctcgtaa gccagcacct ggaagcaggt gtgcgacagt ttttcaact     360 gcgcttccac cgcggccacc accttcggat gcaagtgccc ggtattgagc accgtaatcc    420
cgcccgcgaa atcaagatac tcacggcctt                                     450

<210> SEQ ID NO 34
<211> LENGTH: 500
<212> TYPE: DNA
<213> ORGANISM: Pig

<400> SEQUENCE: 34
acgtgaggtt tgggggagga aagcggggga cgagcagccc gagaggagtg ggggctggcc     60
tgtggctgat gaaactctga gaaggttaag agcccccatt tttgtcttcc tcttttttat    120
tatgaaaaat tccaaatgga tgcaaaagtc ccaaacctaa ctggacatct tcttggtacc    180
aggaacggtc aggcacttat gatgcaccga gccccgaggg aaaaaccctg ccgtcctgga    240
gcccacggtc cagcagggca cacaggcccc agcccgcaag cggcacggct gagtcagtga    300
atggcgtgcc ctctggtcaa ggacgggcac tctggacccc agggaagcct ctgaggagcc    360
cccttcacag cgtcaaaaac tgttaacagg gccatgttcg cacccccca cacacgtggt    420 tcagaagcag accccaggca tcgtaatatg tcatccgtga gttccctgtg tgccaccaac    480
agaaagccca tcgtcacgtt                                                500

<210> SEQ ID NO 35
<211> LENGTH: 400
<212> TYPE: DNA
<213> ORGANISM: Pig

<400> SEQUENCE: 35
cggcatcgat gtacatggta cgcaaggcac tcgtaaggcc ccgagcctct aggccttgtc     60
attgtcacgt gctgctcgcg gggatcagca gccaggcttg tgaccccggc cactttgaca    120
gataaggaca cagagaggcc acagcactgg tgtgaggcc cacagccagc agcccagggc    180
agggaggact gggtctcacc tgcctcagct gggcccagcc tccctgggag tcccggagtc    240
tccccagctt aggagtgtcc ctggaaccct cttctctccc cttcccgccc tcacccggac    300
```

```
cccctgcctc ccccccacca acccccctccc cctccttctt tcaccttgag ctcccctctg    360
aggacctcta ctgttcctgc ttatcctccc ctttgagcca                          400

<210> SEQ ID NO 36
<211> LENGTH: 500
<212> TYPE: DNA
<213> ORGANISM: Pig

<400> SEQUENCE: 36
tggcggtgaa ctatgtcgtg cgtgaagagc atttgtggtc ggtagcgcgt tatatgcggg    60
aagtttaggc gaactggaca gcctgggttt atccggtagc gaaatccgct ttcacggtaa   120
aacgctgcta gcgctggtgg aaaaagcgca gacattgccg aagatgccct taccgcagcc   180
gatgcttaac ctgatggaca tgccgggtta tcgtaaagcg tttaaagcga ttaagtcgct   240
gattactgac gtgagcgaaa cgcataagat cagcgccgaa ttgctggcat cgcgtcggca   300
aatcaaccaa ctgctgaact ggcactgaaa actgaaaccg cagaacaatt tgccggagct   360
gatttccgag ctggcgtggt gagctgatgg cggaagcatt acacaattta ttgcaggaat   420
atccgcagta aaatcttccg aagccggact gggcgcgctc agcgccacat ccggcttcgg   480
caaactacaa atccaacacc                                                500

<210> SEQ ID NO 37
<211> LENGTH: 500
<212> TYPE: DNA
<213> ORGANISM: Pig

<400> SEQUENCE: 37
gatttcacaa gcctgaccca cgcggaaatg cgctaacagc gtaaagtcgt gcggccagaa    60
ttttttcgtc tcttcgcttt gcgtcaattc aaaagtcagc gctacgccat cagcatcttc   120
atgatgtgat ttcagcgtcc acggcaggtt gcgggcaaaa ccgtgcgcag gcagaccttg   180
ttgtgccgcc ggaccaaacc acggccagca aaccggtacg ccaccgcgaa tagcgacgcc   240 attttttgaac ggtgtgttgt tgctcaacca cagaacttct tcttcacccg caggtttcca   300
cgagagaagg tgtgcgccct gtaatgcaaa agaggctttt acctggggat gatcgaccac   360
aatgaggtcc agttcatcca gtttacgacg ggagaggaca ggggagattt gttcgatgac   420
cggaagggca aaaattttct taatcatgac gcagtccttt aacttcattt tatcaggtaa   480
aaaaaagagc gaccgaagtc                                                500

<210> SEQ ID NO 38
<211> LENGTH: 300
<212> TYPE: DNA
<213> ORGANISM: Pig

<400> SEQUENCE: 38
acctgatcag gctctgcact gtgttcatca gcggagccga gatatttgac cgccccatgc    60
ataacggaaa ggcgtgggta accccgggg cgcgttcctt tatcaagatg acgttcgaat   120
attccggcag gtgcagtttg tttattccag aaaggcgttg agcgcgtatg aatataattc   180
tgtgggattt gaagcatcct ttccctcct tcggtgaatg cgctgaaaac ggcttattcc   240
agccggttca gggtacgcct gataatttgc attttaaata ccatttattg ggtacttttt   300

<210> SEQ ID NO 39
<211> LENGTH: 450
<212> TYPE: DNA
<213> ORGANISM: Pig
```

<400> SEQUENCE: 39

```
atcctttttgg ggtctggcaa ttacgcaata aagaaggccc ccatgcgatt aaagtcaccg      60
gcccactgtc gtctaatcat ggagaaattg tccatcagtg gggtctcgat gggcagggga     120
ttgctctgcg ttcctggtgg gatgttagcg aaaacattgc cagtggtcat ttagtgcaag     180
tgctaccgga atattaccag ccagcgaacg tctggtccgt ttatgtttca aggctggcga     240
cgtcagcgaa agtgcggata acggtagagt ttttacgcca gtattttgcc gagcactacc     300
ggaatgtttc actgttgcat gcctgattta tgattcaatt atcggggtga tatcagttta     360
aaacctgatt ttctcctttc taagccgcta cagatttggt agcatattca cctttaatcg     420
cgcatgatct aaagataatt gaagaggtta                                      450
```

<210> SEQ ID NO 40
<211> LENGTH: 450
<212> TYPE: DNA
<213> ORGANISM: Pig

<400> SEQUENCE: 40

```
aatgtactgg caaaaagcca atggcgaagc gtggggaacg ttacatgctc tgctggcgga      60
tattaatagt cagggtcagg tgcagatggc gatgaacggc ggcatctatg atgaaagcta     120
tgcgccgctc ggtttgtaca tcgaaaacg tcagcagaag gtggcgttaa atctcgcttc     180
aggtgaaggg aatttcttta tccgtcctgg cggcgtgttt tatgtcgcgg gagataaagt     240
cggcatcgtt cgtctggatg ccttcaaaac cagtaaagag attcagtttg cggtgcagtc     300
agggccaatg ttgatggaaa acggtgtaat taatccgcgt attcatccca acgtcgcctc     360
aagcaaaatt cgtaacggtg gttgggatta ataaacatgg gaacgccgtg tttttgttga     420
gccagcaggc aacaaatttt tatgattttg                                      450
```

<210> SEQ ID NO 41
<211> LENGTH: 400
<212> TYPE: DNA
<213> ORGANISM: Pig

<400> SEQUENCE: 41

```
gacattaatc atttcaaaat caaagccccg gttttccatc gcccgtttgg tggcgtggca      60
ctgaacgcaa tcgttacgag tgtaaatagt aatgcgcatg attcgtattt ccgtttaaaa     120
tgaagatacg gcgcgatgat acgcgtcggg ttgtctctct gttgatacag agatactaga     180
tgtagttgaa aaaagattca accacacaat atatagccca gtagggtcg aaattaccct      240
ggatatgagc gtgacgggt aggggatttt tgtgattca ccaggcaaaa agaaaccccg       300
aagacaggct tcgggtcaa agacgcgtat ttattatcat ttttgcacta cgatttgcgc     360
atgcttaaca gtgcgccgat taaaatatct accgcagctg                           400
```

<210> SEQ ID NO 42
<211> LENGTH: 500
<212> TYPE: DNA
<213> ORGANISM: Pig

<400> SEQUENCE: 42

```
gcaaaatcac gtccgcgacc tggcgttgtc gctgggccat attggcaaag gagctggatt      60
gcggtgcctg caaagtgccc tgaataatgc cattgtcctg taccgggaag aaaccttttcg    120
gaatgaacac ccacagcagc acgctaagca gcagcgtgct gagtgccacg cttaaggtca     180
```

```
gccacggatg attcagcact ttcgccagtc cacgaccata ggcggcgatt atcctgtcga      240 acatttttc  cgaggcacgg agaagcggt  tctgtttacg caacgactcc tggctgagca      300
tccgcgcgca catcatcggt gtcagggtca gcgacaccac cgctgagatc aaaatcgcta      360
ccgccagggt aatagcaaat tcgcggaaca gtcgcccgac gatatcgccc ataaacagca      420
gtgggatcaa caccgcaatc agtgagaagg tcagcgagat aatggtaaag ccgatttcac      480
ctgcgccctt gagcgccgcc                                                  500

<210> SEQ ID NO 43
<211> LENGTH: 400
<212> TYPE: DNA
<213> ORGANISM: Pig

<400> SEQUENCE: 43
agctatctac ggcaaaaggc acggtagtca atttcgttgt taaatacatc aagcgtttgg       60
cgccgaaata ccatctgcca gatgccattt catttcgtag cgcactgcat aacggctacc      120
ggatgcagta cgtcaaaccc gaactggggc cggaaggatt tagcttttct gcaatacacc      180
ggcggcacca ctggtgtggc gaaggcgcg  atgctgactc accgcaatat gctggcgaac      240
ctggaacagg ttaacgcgac ctatggtccg ctgttgcatc cgggcaaaga gctggtggtg      300
acggcgctgc cgctgtatca cattttttgcc ctgaccatta actgcctgct gtttatcgaa      360
ctgggtgggc agaacctgct tatcactaac ccgcgcgata                            400

<210> SEQ ID NO 44
<211> LENGTH: 450
<212> TYPE: DNA
<213> ORGANISM: Pig

<400> SEQUENCE: 44
gattagcgcc agatgctcgc catcgaaaag ttgaatcaac cccagctgcg ggtaataagt       60
gcgcgtacga acaaattcag tatccagggc tatcgccgga aggcacgga  cggcttcaca      120 caaagaagcc agcgcatcgt ccgtggtaat catttggtaa ttcaaattgt tttctcttta      180
gtgggcgtca aaaaaaacgc cggattaacc ggcgtctgac gactgactta acgctcaggc      240
tttattgtcc actttgccgc gcgcttcgtc acgtaattct cgtcgcaaaa ttttttccgac     300 gttagatttc ggtaactcat cacgaaactc caccagcttc ggtactttgt atcccgtgag      360
ctgacggcgg caaaaagtca ccagtgactc ttcggtaagc gatggatctt ttttcactac      420
gaagattttc accgcttcac cactggagcc                                       450

<210> SEQ ID NO 45
<211> LENGTH: 750
<212> TYPE: DNA
<213> ORGANISM: Pig

<400> SEQUENCE: 45
gagcagcccg cgtgatgaca ggcatgcgcc cgcgtcggct ctctctctct ggtgcactga       60
gtcacaggat ggcggcggtg ggcgcggtgg tggaagcggt cctggagggc tcggagggga      120
ggatgcgctc aagctggctc cccgtggggc tggcccggag tagcctccgt gagggcaccg      180
tgtctgctcc cagagcccgc tccccggcct gccctgcctc ccttccctgc ccagttccc       240 ccggagcccc tggatcccga tgggaggcgc ccctggggag aggggaccag ggaggggccc      300
agagctctga ggccaccaga cctgccagg  acccttcgtg ggaagaagag gtgggcccca      360
aaggcaccta gagagaggga ggctctgctg gctgggggc  cttccaggcg gggcttccag      420
```

```
gcagggccag tgtcctgggg gctggaggga gtccctggct gctgggggc ggcaggagca      480 cctgggcgt ctgggaagag agcgggagga gactggagcc aactgggggg acagaggagg      540
ggtccaaccc cagcggtggt gttgggggtg ctggtggtgg aggccctgag aggctgtgct    600
ggggggcaga gcgggtgctg ggaggggaga agggtcccc agggctcatg ggcccttcgc      660
agcagtggca gttggggtgg gtggctgtct ctagggctgt accacggtgg gtgcctggag    720
aaagaggtcc taccctagt ctttgctgca                                       750
```

```
<210> SEQ ID NO 46
<211> LENGTH: 300
<212> TYPE: DNA
<213> ORGANISM: Pig
<220> FEATURE:
<221> NAME/KEY: misc_feature
<222> LOCATION: (299)..(299)
<223> OTHER INFORMATION: Nonspecific nucleotide

<400> SEQUENCE: 46
tggggacccc actccagccc cactgagtga cgcgccccc tgtggtccca ccgccaaccc      60
tgcctcacac cagagggggct gtggccacac cttgtccaca gcctgtccct gagaccacga    120 gccccccgggc tcagccccct cctcacccct ggaccgagga gaagccccca cctgggctca   180
gctcttggag ctaaacttcc aggaaggttc tggtgccctc gggtcttaga gcatggtggg    240
gagggggatg ctggtggggg cgcaagccct ccccacattt cgcactcgac ccggtgggng    300
```

```
<210> SEQ ID NO 47
<211> LENGTH: 300
<212> TYPE: DNA
<213> ORGANISM: Pig

<400> SEQUENCE: 47
ccggctagaa gccacgagag cccccaggcc ccgcccgacg tctctcctgc agggattcgg    60
cagccctggg gccacagggc ctgagcagac cttggggttc cggtgtgact ccagccaggg   120
tccctactgt gtaggcacca gggcagagtc agccctggga ccatggccac agctgctccc   180
gcctgagccg ggccccccgc ccaggctggg ccccctcagt gcactgtccc aagccagctg    240
ctctccccac ctccaccttc tccatccagg tcctgcccca cggcctttgc tcaggcccag    300
```

```
<210> SEQ ID NO 48
<211> LENGTH: 500
<212> TYPE: DNA
<213> ORGANISM: Pig

<400> SEQUENCE: 48
ttgactggca ctagcacgag ctctgtaccc ggggatctgg gctcgggaga agggagaccc     60 cccaccggc aggccgaggg cgctgtcaca ccatgactct cagccttccc cacccgacgg     120
acaagagtga ccctctccca agcccccact cacccaggac cgcacacccc gtgagtcctg    180
cgagtggggg cggctcaggg gccccgagtc ccaaaggagt ctgctggccc tgggggggag    240
gggaagcagc agggtggtca cgggtctccc tggttggcag gaccacaagc tcagcccgct    300
gcctcccaga gggcagccgg acaccaacca gtccggggac cccacgtacc tcagctgctg    360
caggtgcccc tgcctgtact ggtgccaatg gggccgctgg gtgctcccat ggacagctcg    420
ccactcatcc cagccgccta ccccccttcc gggtccagtg tccggccggc cacccgcctg    480
cccagccctg gcctcctctc                                                 500
```

```
<210> SEQ ID NO 49
<211> LENGTH: 500
<212> TYPE: DNA
<213> ORGANISM: Pig
<220> FEATURE:
<221> NAME/KEY: misc_feature
<222> LOCATION: (500)..(500)
<223> OTHER INFORMATION: Nonspecific nucleotide

<400> SEQUENCE: 49 gggggttgccg caggctgctg tgtaggtcgc agacgcagct tggatctggc gtggctgtgg    60
ctgtggctgt ggctgtggca taggtcagcc actgcgactc cgatttgacc cccagcccgg   120
caactcccac atggcacagg tgcagcaggg aaaataaata aatgaaataa aataggtga    180
agacagtgga tttcatctct tggggttgcg gtaagctcta cacaataggg agtttaccat   240
tttacctgtt tcaagtggca ctgagtcagc tcacagtcct gagggcccac agatgccgtc   300
tgcctgggag attgttcctc tcaccacact gcccctctgt ccccactaaa tactcactgc   360
cctccccgtc ccaagggccc ctgccccacc ctctgcttcc tgtctctgaa cttgctggcc   420
accagcgacc gtctggtgac ctcactcttc ggcccatttt gtcgcacacc ccacctggcc   480
tctccccggc atgggcagan                                               500

<210> SEQ ID NO 50
<211> LENGTH: 600
<212> TYPE: DNA
<213> ORGANISM: Pig

<400> SEQUENCE: 50
gggatatttg gggcatatt tggggggggag atccccacaa ggcatttggg gtttgtggtt    60
tggaatgccc ccgggcccga tggaggggc cggggaagaa tctaagcctt acttggggag   120
ggttgggccc cggggccccg ggccggaaat gccccaaga cagaaggtgt acaaaatttc   180
tcaaaagggt gacccttaat gaaacgggtc ccggttggaa agaggtcacc agggtggatt   240
ggtggcaccg cagaatttac gacattttgg ctctcttcca atggccggac gcctggggat   300
aggcgccccc gtgacggcg gggtctcggg tgggacgggc ggtcaggggt cggtgacgct   360
tggcctctct gaccgcctcc agctccttgg cgagcgtgcg agcgcggcgg gcgcgcagga   420
gggccgcgca ggcccctgcg caggcgttgg gcggactgct tccaggtgtc atagcggaag   480
aacttgccca cggggtatct ggggaagttg tcctgagagg ggaagggccc gtcaggggg    540
ggcctggccc cccagcccct gtcccagaac aacaaccttt gcggggtcct cctgcctgcc   600

<210> SEQ ID NO 51
<211> LENGTH: 179
<212> TYPE: DNA
<213> ORGANISM: Pig

<400> SEQUENCE: 51
atcttcatat tcatgcagaa gacactctcc tgcctttcta tcttggggaa aaggacgatg    60
tcacttatgc aataaagccc acttgctggc cggggcttga cattattcct tcctgtctgg   120
ctctgcaccg tattgaaact gagttaatgg gcaaatttga tgaaggtaaa ctgcccacc     179

<210> SEQ ID NO 52
<211> LENGTH: 500
<212> TYPE: DNA
<213> ORGANISM: Pig

<400> SEQUENCE: 52
```

```
ctcgggctgc ttccaggggg ccttggggag ccatagaatg ctatggagca agagagtgct    60
atggtcagac gactttgggg gaaggtctgg gagaagaggg gtgactggcc actgtgataa   120
agagtgggcg cttccttgag ataacacggt gggcagccga ggtggacctg tgcaggtgga   180
gaaggcctcc tgccgcggcc agtacgtggc tctgggctgc cggacacgag aaagcccacc   240
tccacggctg cctccaggcg gcccttcctc tcttcacacc gccgggccat gcccaggtgc   300
aggtgccatc agagggtgct caagagaagc tctgggctgg ggttgtccca ggtcccggaa   360
gccccgtgtc ccaggggcca cctgaggaag cgtgggcgca cagagactgt ccctcggtgc   420
tcagagaggg tcccgtcccc acggcaacga cgcccaaggc ggaggtggtc agaggtcttg   480
ggagggagga tggccgcgca                                              500

<210> SEQ ID NO 53
<211> LENGTH: 900
<212> TYPE: DNA
<213> ORGANISM: Pig

<400> SEQUENCE: 53
tgtgttgcac ctgttgctgc ctgtcgactc tagaggatca atactcctta cataattaag    60
gagaacaaaa tggaacttaa aaaattgatg ggacatattt ctattatccc cgattacaga   120
caagcctgga aaatggaaca taagttatcg gatattctac tgttgactat ttgtgccgtt   180
atttctggtg cagaaggctg ggaagatata gaggattttg ggaaacaca tcccgatttt    240 ttgaagcaat atggtgattt tgaaaatggt attcctgttc acgacaccat tgccagagtt   300
gtatcctgta tcagtcctgc aaaatttcac gagtgcttta ttaactggat gcgtgactgc   360
cattcttcag atgataaaga cgtcattgca attgatggaa aaacgctccg gcattcttat   420
gataagagtc gccgcagggg agcgattcat gtcattagtg cgttctcaac aatgcacagt   480
ctggtcatcg gacagatcaa gacggatgag aaatctaatg agattacagc tatcccagaa   540
cttcttaaca tgctggatat taaaggaaaa atcatcacaa ctgatgcgat gggttgccag   600
aaagatattg cagagaagat acaaaaacag ggaggtgatt attttattcgc tgtaaaagga   660 aaccagggc ggctaaataa agcctttgag gaaaaatttc cgctgaaaga attaaataat    720
ccagcgcatg acagttacgc aatgagtgaa aagagtcacg gcagagaaga aatccgtctt   780
catattgttt gcgatgtccc tgatgaactt attgatttca cgtttgaata gaaagggctg   840
aagaaattat gcgtggcagt ctccttccgg tccataatag cagaacaaaa gaaagagctc   900

<210> SEQ ID NO 54
<211> LENGTH: 450
<212> TYPE: DNA
<213> ORGANISM: Pig

<400> SEQUENCE: 54
ccagccacca gctggaccct cccggagagg ggctgcctcc tctttcccgc ccagacgccc    60
cccagcaatc tgtggccaag agggagtgat accgaagatg ccacatgggg gcgccagcc    120 cacagggaac cccaggaagg cgctggaccg tcaggagtca gggctgctgt gcacccatgt   180
ggcctgggga cttccacag cctggtggag atggccgggc acaccgctgc ctcgggggaa    240
cgtgcacacg ggtggtacat gtggccggag cccagggcac agggtgaggg gagaagggag   300
catgcgggtg cagactcgga gcccgcgcgt gaggtgctgg gtcctcagga cacgctctgg   360
gagtggagga ccccccatcca cgccctcacc cagtgtgtgc ccgcctgctc ccccggaaac   420
```

```
cctcacagac acgagggcac acccagcccc                                      450

<210> SEQ ID NO 55
<211> LENGTH: 1133
<212> TYPE: DNA
<213> ORGANISM: Pig

<400> SEQUENCE: 55
atggcgctca ttagaattcg acctcggtac cttgggatct tttgacccct acctcacgcc      60
atctacaaca tttacctccg aatgaatgag agacaccaaa agcaaattca tagaagagaa     120
aaaaaggtaa cctggacttt aaaaatgtaa acttctgctc tttaaaaggc agtgctaatg     180
aagttcaaat acaaaccaca gaccataaga aaatacttgc aaatcttgtt ctgacaaaga     240
ctagtgttca gaacatacga cgatcaggga gaggaaaacc agcaatccta taaaactgga     300
caaagaattg gggggaaaaa aaacccactt ggccaagaag ttggtaaata aggccatgaa     360
aacatgctca acatcatgag tcattagaaa aatgcaaatt aaaattataa tgagatacta     420
ctacacagct atttgaatgg ataaaaaatg ttttaaaaac tgattatacc caggtttggc     480
aagaacatga gaacgagat tttcacacac gattggtgga aaacagaaaa tggtccaccc     540
actttggaaa agagctgggc acttccctca aaagttaaac atacatccag gacctcacac     600
aggctttcca ccacaggtgt ttattccaga gacatgaaag cgctcatcca cacaaagact     660
cgtaaatgaa ggtttatagc accgtttgtg gcccgaactg agaaaaccca atgacctttt    720
aaccagagaa tatctaaaca aaatatccat tcacattaat cacccataag aaggaacggg     780
ctatggggac gggaaccgta ttgaagaggg tcaaaataca tacgcagcat caaagaagcc     840
tgcccaaagg acacacactg cagggttcca tggactgaaa ctcgagaagg tgaaaactcg     900
ccagcagtga cagagagcag gtccgagatc aacctgatgt ggaggaaagt gaaccctcgt     960
gcgttgttgg caggactata aactggagca gccctacgg acaacagtag cccgggctcc    1020
tctcctccat ctccctgggg agcctgagcc ttgagacgct ggggcaagtg cacggcatgc    1080
tgcctcacgt ggggcccegg tgaaaacacg tggcagctgg ggaaagaatc gta          1133

<210> SEQ ID NO 56
<211> LENGTH: 735
<212> TYPE: DNA
<213> ORGANISM: Pig

<400> SEQUENCE: 56
tactgcctgt ctctatggac ttgactcctc tcgggacttc atgcgaggga tcttacagaa      60
tttgtccttt tgcatctggc ttgtttcact gagcatcgtg tccccaaggt ccatccatgt     120
tgcagcctgt gtcaggattt ccttccttt caaggctgaa tagtactcca ctctgcggat     180
ggaccacgtt ttgattatcc atactagtaa atccatacta ataacttgtt cactgaagcc     240
cacagcttat gctaccttcc gtgggctcct ccctgccctg tctctacgcc ttctgctata     300
gccccatccc ctctcatcca ggccacgcct cctgtcccct ggacactgtc ccagaagcca     360
actgccctct gactgctgct ctcgcgtgac ggaggacaag gcaggctcag ggtccacgg     420 gctgggccc cagggctccc catggctggt gcccttcct gattccagaa gtacagtggc     480
agcaccagct ttccagctgc cccaccttct gtccgcaggc tgctcgggtg ggggcaggtg     540
ggcagtgatg tcacctgctg taaccaccct accgtcgctc atccctgtcc aggaggtcac     600
ggtgaccttg gcaaacattc tgaacaacac acacctccct ctgcttagag gccggggggcc     660 tccccgggtg actgggggca caggctgacc ccagcctgtc tctgttctct gaaggacatg     720
```
ataagtactg caaca 735

<210> SEQ ID NO 57
<211> LENGTH: 500
<212> TYPE: DNA
<213> ORGANISM: Pig

<400> SEQUENCE: 57

| | | | | | |
|---|---|---|---|---|---|
| aggaagaaca | ggaaacaacg | gggttgagga | gaagaaacgg | gtgtctggca | ggggcacgtg | 60 |
| ccaacggtcc | accgggtgct | gccgcgctgc | ggcctggcgc | cagaggggc | agctccgccc | 120 |
| ctcgggccgc | gccctgccgc | ttgtgctggc | tcgcggctgg | gctctgcttg | gctgggttac | 180 |
| agctgggtgc | agccgcaggc | tgtggtgggt | gccgccgggt | cagccagccc | ggccccaccc | 240 |
| ggcccgtctc | gccggcctgg | cccgggcagc | cctcctgcag | tcgaggagtc | gccctgacgg | 300 |
| gctgattggt | ccacagcctc | agatgcaaac | cagccccacg | tgcctggagc | cagccagccc | 360 |
| gggacaccct | ggtggaggca | ggaaggcagc | agcctggaga | gccgcgccgg | atgatgctgc | 420 |
| ggggaaaccg | ggctcccgcc | gggggcgccc | tggctctggc | caggcttggc | ttgaatgctg | 480 |
| acgtgagcgg | tggccctata | | | | | 500 |

<210> SEQ ID NO 58
<211> LENGTH: 500
<212> TYPE: DNA
<213> ORGANISM: Pig
<220> FEATURE:
<221> NAME/KEY: misc_feature
<222> LOCATION: (112)..(133)
<223> OTHER INFORMATION: Microsatellite PIGQTL1: (AT)11

<400> SEQUENCE: 58

| | | | | | |
|---|---|---|---|---|---|
| tggcgttgca | gtggctctgg | cggaggccgg | cggctacagc | tccgattgga | ccctaggct | 60 |
| gggaacctcc | ataagctgtg | ggtgcagccc | taaaaagcaa | aaaacccaa | catatatata | 120 |
| tatatatata | tataattatg | gtaaaataca | cataaaatag | aatttacctt | cttaataatt | 180 |
| ttcagtgcac | aattcagtgg | cactaagcac | attcatgcgg | ccgtgtcacc | tgctccagaa | 240 |
| ctttccatct | acccaaacgg | actctccgcc | ccatggaaca | cgccccctgc | ccctcccccg | 300 |
| gccctgcccc | gccagctcct | ccctgtgtct | gtggatccgg | ctcctccagg | accccgtgc | 360 |
| gtgggctcac | agagtgtgtg | tccctctgtg | accgatcgtc | gtgtccccga | ggcccgttct | 420 |
| gtggcagctg | cgttatgacc | gactaccttc | gaatgctcag | tgactgccgt | gcattggaca | 480 |
| cgcagtccgc | tacccttttc | | | | | 500 |

<210> SEQ ID NO 59
<211> LENGTH: 550
<212> TYPE: DNA
<213> ORGANISM: Pig

<400> SEQUENCE: 59

| | | | | | |
|---|---|---|---|---|---|
| tgctttctgt | gccccctcc | agcttgggac | cccagcaggg | caaggggtgt | atagggctta | 60 |
| aggaggcagg | gggcgtctcc | tcccgctggc | tgcccagagc | accccagcc | ccgcctgccc | 120 |
| ctcgtccatc | tccagcctgt | cctttcctgt | gccctccctg | tccgggcgg | gccgcacact | 180 |
| ggcttccacc | tccccaccca | actggcggcc | cggtccttcc | tgctgaggca | cccgaggtc | 240 |
| cccgctgctg | gggaccagct | ggcagtgggg | tcccactgct | ttctcagcgt | gggctttgga | 300 |
| gggggatct | gcacatacca | tcccttcagg | ccccgtgggg | agcctgggga | ccatccggga | 360 |

| | | |
|---|---|---|
| ccctgtggg caggcccaga ggactgccag gaagagaccc aggggaccag gcagctccca | 420 | |
| ggcctctcag cttcaggcca ggggagccca ccccaggtg gcaggtgaag ccaggcccc | 480 | |
| aacccacaaa actgcccgca gggaagtagg agggacagga ggaggggagg ccaggcccgg | 540 | |
| gccgcccttg | 550 | |

<210> SEQ ID NO 60
<211> LENGTH: 819
<212> TYPE: DNA
<213> ORGANISM: Pig

<400> SEQUENCE: 60

| | |
|---|---|
| tgaggagcgc aggcccaggc ctgagtgtgc ccagcttaca ccctggcag cttcgtccct | 60 |
| cctggcccta accccatcc taccccagca gcagggctc cccggtggg gcctggtgag | 120 |
| cgtctgactg ggtttggag tcaggtctgc tccaggctca gccccatcc ccaagggtgc | 180 |
| cctgcagcac tgctgcccac ccctagcgc ccccagacct tcgcccctcc agcctggatg | 240 |
| tacccacgga ccctgaaaag tggggctgag caggtgccct ggctggagtc ccctgactt | 300 |
| ggggctggcc aggctgccct ggaggggctg tggggcaca gctgcccca ggggcccgct | 360 |
| gggcactggc tctggagctg acgacaggca ggccctctct tcctggcggg gccacaccct | 420 |
| gccctggggt ttggggccaa ggcgggcacg ccccatgtca gcggggggcg aaccaggtaa | 480 |
| ttacagcctg gcagcccgct ccccagaccc ccagcccgg agggccccca cccaggctgt | 540 |
| gccaccaaga cctggcatcc agggcccaaa gcaggtcaag ggcagctgct acagattctt | 600 |
| ttaagttgag acagaatcga cacatgacaa gttcctggtt ttaggtactt cgctgccggg | 660 |
| gccgccagtc agtttagtga cccagcacac cccacacagg tacaattgct cttctcaaaa | 720 |
| gaggcccctg agagagcgcc tgtcttggct caggggtaat gagcccaatg ggtatccatg | 780 |
| aggttgcggg ttccatcccc ggcctcgccg cgttggtta | 819 |

<210> SEQ ID NO 61
<211> LENGTH: 500
<212> TYPE: DNA
<213> ORGANISM: Pig

<400> SEQUENCE: 61

| | |
|---|---|
| ggctcaggaa gcgcaggggc agcgtgtggg gcgacgggaa ccatgggggt ctgtcttccc | 60 |
| gcctctcctc aagcccaccg ccctgctgcc cacctccgac tctgcagcca gcatgccggc | 120 |
| tagagcccct gtgcacccag ctggtggcct ctggctaagg gcagtgctgg ctgtggacgc | 180 |
| gtgtcccctc cccagcagcc caagggtccc atctgccagg ctggtggctg aggtctgccc | 240 |
| tgtgtggtcc ttgcaaaaac cccgcccctct cctgcccctt gaggcgtgag ggagacgcgg | 300 |
| gctgggcgga tgccctcggg cacagccgcc cgcggtggcg ccctgtcgag gaggggctc | 360 |
| cgacgtgccc tgacggccct ggccgggcgg agagggtgag gccacctcct ggccacgtcc | 420 |
| acccagctgc cacgccgcct agccagtggc ccggggccaa gtcagcagag ccaggcttcc | 480 |
| gacaagcaga ggctgtaggc | 500 |

<210> SEQ ID NO 62
<211> LENGTH: 700
<212> TYPE: DNA
<213> ORGANISM: Pig

<400> SEQUENCE: 62

| | |
|---|---|
| gatgaggaag ccgctgctcg tgctgctcgt cttcttggcc ttggcctcgt gctgctatgc | 60 |

```
tgcttaccgc cccagtgaga ctctgtgcgg cggggagctg gtggacaccc tccagtttgt    120
ctgcggggac cgcggcttct acttcagtaa gtagctcagc ggggcacggg ggcggggcgg    180
acacagcagg tgctccatcg gtgctgcccc ggtacctgtg cggtccttc  gggatggatg    240 gtgtggggga cgggggggcgg ggggcggcca agggaggacc tctcctccga gggtctgaga    300
cttcagaccg gggcgccct  ggccgtgcgc attgattggc acctgccatg tgcctggctg    360
gggctcacac cccctgacgt tcctgcagcg tgactcgaaa cgggaaaccg aagggacggg    420
tggcacgggg tggggaggca gaccgtgagt ggcaggcgtg cgaggggttc tttcgggcgg    480
ggtggcccag gcaggcccca caggatgaca gcctgtcccc tcctgctcct ccttgacctg    540
cccacagcca gggctgcagg cactgacatt cacccatggt attgtggtgc cttgacgtct    600
tggcagtggg cattgggttc atggactgtt tggattgaaa agtgggaata agatgggggtt    660 tgaaaaaccc aattaagaaa taaagggcg  ccctgtgggc                          700
```

<210> SEQ ID NO 63
<211> LENGTH: 300
<212> TYPE: DNA
<213> ORGANISM: Pig

<400> SEQUENCE: 63

```
tttgaaaaat tttgagtcag tgcagaattc gcatctattc cgcattcagg ctctcctgtt     60
ctcaccttgc cttagtgcgg atcttctata accaccacag tgacgttttc aaggtacttt    120
attgaataat aagaaaaaag tgcacacaat catgtagtta actttctgtg ctctttgcca    180
gtttgaaggg accctctttt tttccttttt agggcttcgc cgacggaagt tcccgggcta    240
ggggttgagt cagagctgca gctgctggcc tacagcacag ctcttggcgg cgatggatcc    300
```

<210> SEQ ID NO 64
<211> LENGTH: 450
<212> TYPE: DNA
<213> ORGANISM: Pig

<400> SEQUENCE: 64

```
tcctgggcca caggctgcag cagctcacct gggggctggg gtctcgctct gcggatggac     60
ccatgaaggc cggagccagg tgggggccga cacggcaggg caaagggtct gcacacacag    120 cgtcccccg  accggcttc  tctgggttct tgggggggttg gcgaggcttc tctcagtctg    180
ggtttcctgg ggaactttca agaactggga agtcttccag aaagttgggg tgaggggagg    240
tacccccaaa gtgctgctcc tgtccccatc ccccaccccg ctgtccatcg gcgagacccc    300
ggaccgccgt ctccctgccg aggtgtgggg tcccccctc tgccggccag ctgggcagg     360 ggtgagcgcc ccctgctctg cactcgggac tcagcctggg gaaggcgggc cccaggaggt    420
cctggcctgg acggcagtga ccttccaccg                                     450
```

<210> SEQ ID NO 65
<211> LENGTH: 500
<212> TYPE: DNA
<213> ORGANISM: Pig

<400> SEQUENCE: 65

```
tgtgcatcca accccagtgg ccacgggggg tgaccctcgg ccggtcagcc gcccgcgtct     60
cccacggaac cgggccttgg cctgaggcag aaggacccag gactccatcc ctgccccgga    120
ctctgccgga gggtgcggtc tgcacagaga ccctctgggg gtgaggccgg tcggggctgg    180
```

```
ggttgagatg ggatggtcag ggcggcccc gcgggcctgc aggaggctgg gtgaaggagg      240
gggcccagct cagacgcccc caaacctagc ttgggagagc tgcagcccg ccccgtcaat      300 cgcgacagcc tgcccacaga aggcattcaa atgagagaca aatatttggg cttgaagact      360
atacccagcc acgtctcttt gggagcccaa gctgctccca ggccctcatt tgggtattaa      420
ttggttttcg tttagagatt tgcatgctta tcaatggcca ctgggcggct gggcctggat      480
gcggtcccag gctttgtatg                                                 500
```

<210> SEQ ID NO 66
<211> LENGTH: 661
<212> TYPE: DNA
<213> ORGANISM: Pig

<400> SEQUENCE: 66

```
tcccacgacc tgcccctcca gggccacatc tggcgacacc gtcgcaagag ttggaccggc      60
ctggtgtggc cacagcctca ggccttgtct ggccgcccag gccggctcca ggctccaagg     120
agctcctgcc tgccctccgg aaccccagca ccccgggccc gcttccccac cagacctgtt    180
tttccaggtc aaggtcacag ctaatttggg cttaaactgg acaaggaggc cttatctgga    240
gcaggctccc ggccctttgg cctctgccct ggtggggagg ccttcccaga ggctgtgtgt    300
tggcgctgac cgtgcagccc tgagcttgaa cccggataag gagggacccc acctgggctg    360
gagccagaga gccctcgttc cccagctccg caggggttctc acagtcccgc cctgccctg    420 gggaccctgg acgtccccag caggtgaaag gtccagatgc cctctgacta gaggctcctc    480
cgctgtcaga catgctccct tcccgcaccg aggacgagac ctcagcagcc ctgcgtggcc    540
tggggtgcgg accccaaggc gtctctgagt gtgttctaat ggggagccgt ggggcctcaa    600
cagtgggggt ggcacttgga ggggagcctc cccacagctg ccccaagatg ggccctggac    660
t                                                                   661
```

<210> SEQ ID NO 67
<211> LENGTH: 500
<212> TYPE: DNA
<213> ORGANISM: Pig

<400> SEQUENCE: 67

```
tttgttggat gaatgaaatc atgagaaagt gattggaccg ccccgttcgt ccagctgctt      60
gccagctgct ttgtaaagat gacctctcac cttctcagag gcctggccgg cccgaggtgg    120
cagtcagctg agatgccatg cttgtttggc acgtgggagg cccctgtcca cggcgtgggt    180
gcctcttgtg tctaatcagg gtcaggggga gcagcaggtg cagggcacat gtggggccgg    240
ggccgatgtc tggggagggc gggaggaggg ggtgtgcgga ggccgttgtg ggggtgcagg    300
ggacagaccc cagcgagacc ctccctggcc aggcaccagg acaggtgatg gggggccgcc    360 tccgggggcgt gtgacagaag cctctcagag gaggccctcc cacggtctct ggaccatcaa    420
gggaccgggg gcgctgggcc tgggggtcac acccagctgg ccggccagcc cgggtgggt    480 cggaggcccg ggcagttcac                                                500
```

<210> SEQ ID NO 68
<211> LENGTH: 550
<212> TYPE: DNA
<213> ORGANISM: Pig

<400> SEQUENCE: 68

```
gggcaggagg ggcccggggc tggtgcggag ggtggaggtg gtgcaggagg gtgtgaggca      60
```

-continued

```
gggctcactg agcgtgcgcg gctggctgtg ccctagagtg gttagcacgt gcccccaccc      120
tccagtgtcg ctctgttcac ctgtgcctgg ctcacaggtg tggaaactga gactcgggtg      180
ttgcatgagc ttccaggatg agaatcagca ggcttcccag gcaggctgt gtccggggct       240 ctgggctctt accaaggagg ggacacccag ggacagccct gcttgggggt gtcgggctgg      300
ccaggctggg tggtccttcc tgtggctggc agcccttggc agtcaccccc ttaccctcaa      360
ctgcccctca gctgagacac gacctccctg cagagccctg tccacccaga cactcactcg      420
cctcctccag gaagccttcc agggctgcct cgccctggtc tcagcaggag acagagagag      480
agggtgggcc caggagcaga ggcaggcagc cagagggaa gcccaggggc cctcactcac       540
ccctggggcc                                                              550
```

<210> SEQ ID NO 69
<211> LENGTH: 500
<212> TYPE: DNA
<213> ORGANISM: Pig

<400> SEQUENCE: 69

```
tttgcattca gctcgtaccc gggatccttc ccgggggctc tgggggtggg ggaatggggg      60
tcagaggcag ctgtcatctg cctgtcctac ctgctctcac aggctggccc tggagccctg     120
gcctcctcct agggggcacat caggtttgg gggaggccca gccaccgtc ccacctccaa      180 gaccacagct gggagcctgc ccccaagcc tagacctagt ggggctcctg ccagccaggc      240
ccccaccttc atgctgccac ccaccaaggt gggacagtgc agccaggaca tccagcttct     300
ggagctgccc gaggctcagc acaggctggt accctaggga gcaggtcacc cagggccgcc     360
tggcgaggcc tgcggggacg ggggtaggg tgggcagcaa agaacctct gagctgggcc       420 gggcggggtc ggtgagggcc cggggccgcg ggctgtgtgc gtggcccctg agcccgtgca     480
gacgcagacc ctgggtgggt                                                   500
```

<210> SEQ ID NO 70
<211> LENGTH: 550
<212> TYPE: DNA
<213> ORGANISM: Pig

<400> SEQUENCE: 70

```
tgtgctgctg tggctgtggt gtaggccgcc agctgcagct ctgattcgga ctcctagcct      60
gcgaacctcc atatgctgct ctaaaaagac aaacataaaa taaatgggt gcgctgttaa      120 tttgaacact ctgcctcctc cagagacgag gccgaaacag gcctctctga aggtcccacc     180
tggcagggag gaggaggcca gccccgtggg gggcagagag aagcccgatg tcccagaca      240 cacacgcaca gggaccgtgg ccccggctgc cagccccgcg ggggagggc aaggccagag      300 actcccagca gcccacagga ccttggtggc cacaggacaa aaacacaggt gacggtgggt     360
gaggcctggc ctttccccccc ctgggcacga gcacaggaca cacaagagcc ccagcgtgct    420
gaccgccacg ccaaggagcc tggatgaagc tggacaccga gagtccacac tgtgtgatta    480
ggctgacgtg aagtttaaga acaagcgggt ggctcagcgc ttgaaggcca gaacaaggcc    540
gggagggcag                                                              550
```

<210> SEQ ID NO 71
<211> LENGTH: 1300
<212> TYPE: DNA
<213> ORGANISM: Pig

```
<400> SEQUENCE: 71
atgtcaggat agtaacctgg ggtgctgcag tgacaatgcc agatccttaa ccactgtgcc      60
acaagggaac tccttgacct agaatcctat acccactgca atatatttc aaaaaaggta     120
aagtcctgag cagaaaagca aaaatgggat aattcatttc tggaagacct tccttgttaa    180
aggaagtttt ttggacgtga tgaaggtaga aactcggagg cacacaaaga aagaaagaaa    240
gaaagagcac tggaaacgga gcaaataaag gtaaaaataa agttcatctc tttctcattt    300
tttaattgct ccaaaagata gctgacctct aaagtaaaaa atagtggaaa tgtagcatat    360
gtctctagcg taatttaaag tataacttat agcaatgata gcccaaataa aggaggaatt    420
gagaatatac agttgctgtg ttcccattgt ggctcagcag taatgaacct ggctaatatc    480
catgaggatg caggttcaat ccctggcctc actcagtggg ttaaaggatc cagggttgca    540
gtgagatgtg acgtatgtca cagacgtggc tcggatctgg catttctgtg actgtggctg    600
tggtgtaggc cagcatctgc acctccgatt gacccctag cctgggaacc accatatgct    660
gctggtgtgg ccctaacaga cacaaaataa aataaaaata aagagagag agaatatacc    720
attgtaaatt tcctcacatg acacaaagag caatgtgata ttatttggta tatggtgatt    780
gattcaagat gtatatcata atattgattc aagatgtata tattcctttt ctaaaaaga    840
gatttataca ataaggcaag agtgaaaata aagtggaatg ctaaagaata gttaatccaa    900
aagaaggcag aaaatgggga aaagacatat aacagatgga acaaataaaa aagagctaat    960
gagattgtaa aatttaatcc aaacatacag ataatcccat taaatttaaa cactctcaac   1020
acattgatta aaagaaattg tcaaattgaa taaacaaagc aagacccaac tagatgcaga   1080
ctatgaaaaa cccacttcat ataaagacat gggtaggttt agagcagaat gatggggaaa   1140
ccatgtcacg caaacatttg tcaaaataaa gctggtgtgg ctgtattcat ctcagacaca   1200
gcagacttca gaacaagaaa cactgcaaag gatgaaagag atactgcata atgataaagg   1260
gatcaatttt ccaagtgcag gctccaaaca acagaggttt                          1300

<210> SEQ ID NO 72
<211> LENGTH: 500
<212> TYPE: DNA
<213> ORGANISM: Pig

<400> SEQUENCE: 72
atgacctcat actgaatcga gctcggtatc aggggatctc tcagctgggg gggagggcaa     60
tggggcattt gtctgaggat gccccagggc aggcccattg gctggtttgg tgcccatgcc    120
cccccacac cccggcagtg cccctgctg agcctgggac cccctctggg agttagggat    180
tgggggtggg aaccaggctt tgcagtaatt ccagccccca gggcccttcc ctccccgccc   240
tcaggacccc cagccccgcc ccacacagtc tccactgtga cagcctcacc ccttgggtca   300
agtcctgtcc tctccggccc ccgctgggca gtggagccag ctaggtgaga ggcacaggcc   360
actagggcgg tgggcactgc tgaggacaga ggggcctggg tggccttgga cgaggcccag   420
cgacgctgag acagtgagcc aggctccagg ctttcccagg gagggtccct gaatgtccac   480
ttcttgtgac atcgggtgac                                               500

<210> SEQ ID NO 73
<211> LENGTH: 550
<212> TYPE: DNA
<213> ORGANISM: Pig

<400> SEQUENCE: 73
```

-continued

```
aagtccatta gggaagggat ttgtgcaaac acagagacag gtgcagggct gggccagctg      60
ctgggctggg ggctcctcaa ggcgcccgta aaccccctccc tgccagccgc ctgccgccaa    120
ggtctgctgt ccaccccggc cggggctgctg tgttcccggc gtgtgtcctg cgaacccgac    180
tcccgttcac ccctgagcac tgcctggagg ccggctgccc aggcgggacg ggccctcagg    240
gctgggctgg ctcttggcct gtgtttcatt tctgagcagg tccttctcag tgggggggc     300 cttgggtgaa gcaggcatgt gcaccactgg ggccctgtcc ccagtgggca tcctgggcgc    360
ttgtctggcc cccaaacccc caggccgtgt gcatcatacc ttcaccctga gccccagccg    420
aaccccggac atgtgctggg ggaccctggg cacagggtg agggagcagt ggccttggtg     480
gaagcccagc cttggcacct ggggagggg tgcatctggc atgctctgct gtaaccaagc    540
ccagggcagg                                                             550
```

<210> SEQ ID NO 74
<211> LENGTH: 950
<212> TYPE: DNA
<213> ORGANISM: Pig

<400> SEQUENCE: 74

```
gacgtgcagt agccatgacc tctacggccc ccactgacca gcccgtgtcc ttgtcccgag      60 accgaccccct aagcaatagg atgcagcaga agtgacagaa cggcctccgc gatgaggtcg   120
cagagggctc tggctctgac tcaggcccct catccctcgc tctcctggag cagggccagg   180
taggggcccc ccagagacgc cctagaggag gtgacgggca gccagcccgc cccagggaag   240
gcctggggac accagggaac agaacggcac aggctcctgg cacagtctcc caggagcccc   300
ctggtggcac agaaatcctg accggcccag tggagggggc tggggcgggg ctcggggagg   360
agggactggg tgaggccgtc tgactcctgg ctgagcgccg catacttgct gcctgcccac   420
gatgccgggc caggccttcc gcacggaccc aggctcacat tcgccctaca tgccactgtg   480
tgggagtttg ggatggtgtg cccgctgggc ccggggggtca gggcacgctt cccagaggag   540
cgggttccag aaggcccagg tggagaggcg ataggagggc tccaggggc ttcccaggcc    600 acctgcgagg accctcctgg ggggaaggga gcggagggag acagccgggt cccttaggcc   660
aaggctgagt tgtgaccgca gggagaggag agaaggagca cccacagcag ggcaggggct   720
gcgggaggct gtgctgggtg gccgggtggt gggtctgggg gccaggaccg tgggaggcct   780 cgaggggga gcaggcacgg gaggggcccc tggacggcag agtccctgct ccagctgccg    840
ccccgacccc aggtccacct tcatttcaca gcctggcccc cggccgctct gaccggccct   900
gcccatgcag gtgtagcggg gcagtgaggg ccaggctccg gccgtcccaa               950
```

<210> SEQ ID NO 75
<211> LENGTH: 450
<212> TYPE: DNA
<213> ORGANISM: Pig

<400> SEQUENCE: 75

```
gcaggcctgg cagcagggaa atgatccaga aagtgccacc tcagccccca gccatctgcc      60
acccacctgg aggccctcag gggccgggcg ccggggggca ggcgctataa agccggccgg   120
gcccagccgc ccccagccct ctgggaccag ctgcgttccc aggccgccgg caagcaggtc   180 tgtcccctg ggctcccgtc agctgggtct gggctgtcct gctggggcca ggcatctcg     240 gcaggaggac gtgggctcct ctctcggagc ccttgggggg tgaggctggt gggggctgca   300
```

```
ggtgccctg ggctggcctc aacgccgccc ggtcccgcag gtcctcaccc cccgccatgg    360
gccctgtgga cgcgcctcct gccccaggct gggcccttgc tggcccctct ggagcacccc    420
gccccccggg cccaaagcct ttcatgaaca                                     450
```

<210> SEQ ID NO 76
<211> LENGTH: 1363
<212> TYPE: DNA
<213> ORGANISM: Pig
<220> FEATURE:
<221> NAME/KEY: misc_feature
<222> LOCATION: (206)..(206)
<223> OTHER INFORMATION: Nonspecific nucleotide

<400> SEQUENCE: 76

```
cctccagctg ggcccggcag ggcaccgtgc cctcagggg  acaccacggg gggccacagt     60
ggcctctcct gctccaggct ctgctcccgc ctggggcccc ctgggccgcc cgcccatggc    120
cagggcaaac tcccagtgcg gctgcccgtc tgggcaaaga ggccgccagg cccgcgtgg    180 tcttagcagg cactggcgga tgccgntaac taaccatttc ttccgcagga gtccgaatct    240
gctctgacca cgggccctaa aaatcgctcc tggcccgcag aggatccccg aacagcgggg    300
ctgcctcctg ctcctcctgc cgggccggca ctcggcaggc acgtgccctc gtcgtcccca    360
gtctgtcaac cgtcccgtcg ttacgatccc cagagtccca cgcgcgggca gctctttcca    420
caccccgcac ggccccggag ctgcctgggc acccagatcg cccctgacgc ctttgctcct    480
aattctgcta aaatacacat aacgtctcct tgaacgtttg tccattttca cggggacaat    540
tctgtggccg taggtacact cccttgggg  cgcagccatc gcaccatccg cttccaggag    600
gtcccgtcgt cccagatgga cactgtcccc actgatccct aattccctgt ccccccagc    660 cctgcccttc ctgtctctgt ggccctggcg cctccaggga gccctgtgc  gtgggatcac    720 aaaacgtgtg tcccttttgcg tccggtgtgt gtctctgagc atccggagct tggggtgctt    780
ccacgctgcg cctgtgtcag gacgtccttc ccttttgcgg ctgcgcgatg ctccccgtgg    840
ggctgcccca cactgcgcgt gttcgctcat ccatccacta aggctgagtt acttttggcg    900
gttgtgaata ctgctgtgtg aacacgggcg tgcaaatacc tgctggaggc catgctctta    960
ggcctctcgg ggggcacacc cagagcggat atgctcaata aggtaattct gtgtttagct   1020
ttttggggaa ccatcaggct ggtctccaga gtgacggagc atgcgtcgca ttcacaggaa   1080
tggtgctcga ggctttgagg tctccaccac tcgcttccta ttttctgtgc gtcacagccg   1140
tcggaacggc tgggtggtgc ctctgtgtgg cttcaatgtg ctttttcttt tcctggctat   1200
gaggttgagc gttttttatg tacttgctgg ccattcgcag ggttttttggg gtttctttc    1260 tttttttgcct tgggggacgg cgcccagagc gtatagaagt tccctggctg gggactgaat   1320
cagagctgca gctgccagcc tagcccacag ccgcagcaac gca                      1363
```

<210> SEQ ID NO 77
<211> LENGTH: 500
<212> TYPE: DNA
<213> ORGANISM: Pig

<400> SEQUENCE: 77

```
tcatgccatc gccaccgccc cccacccga  cgtttcaaac accagaacca cccctcgggc     60
ggcagagaga ggaccggaag gagagacagc ctggtcccaa ggcctcgccc ggtcctgtgt    120
ctccgagcga catttctttc tgtttccctc ctccgcggtc caagtttcac ccatcagagg    180
cgcattgttt tcatcatctg aaaaaaaaat ctctgtctct taataaaaca caagaaaaag    240
```

-continued

```
tagccttcga aagaaagcac atgaatgata tgtgctggcg acagtgctgg cggcctctga      300
gccgtggtgg gaggtgggag ccagcggagc ccctgaccga tcacgtgacc cacgtctctc      360
ctgcacagct ggctgcacct gcacgcggtg acacagggac ccagcctcct gccagcaggt      420
caccccaccc cgtccgtctc ctgtggaagg ggcagcgttg ccttctgagg gtgggctgct      480 ctgagggcg tcctttggcc                                                    500
```

<210> SEQ ID NO 78
<211> LENGTH: 626
<212> TYPE: DNA
<213> ORGANISM: Pig

<400> SEQUENCE: 78

```
gccatgggct gcggcggttc acgcggcttg ccggcctgcc tggaagtccc acaggaccaa      60
ggggagggca cgtcagcaca ggggcccggg gcacggacgg tgccccagc cgccccggcc      120 cccgccctcc agacaggacg cccggtcacc ttgcgggac agccagcctc gtggcctcga       180
gcagaagaag tgagagtggg gtgcacaggg gccccccggg gaaggagagg ggacagcggg      240
ggtgagcggg tgcgggcgtg ctcgggacca gcccctggcc tcttggcgcc tccctccccg      300
tccttaaacc gggcccagcc tctttgggcct cgacccaagg ctgtttggaa aataggtgga    360
ccgtggccct gacccgaagg ccagcgggga cccgagtgcg tccccaatg gatcagcagg       420 cgcctgggca gctgcggcc ccgggacccg gagacacagg tgggaatggg aggaggagga       480
ggaagacggg aggagaggag tgaggaccag cagaaaccac gccctcctct cttcccgtcc      540
tcgccctcgc ctccgacagc tccgactcgg ctgcaaggaa aaggccccag cccagcccgc      600
cgccaccggg ggggggggg gggggg                                             626
```

<210> SEQ ID NO 79
<211> LENGTH: 500
<212> TYPE: DNA
<213> ORGANISM: Pig

<400> SEQUENCE: 79

```
tactcgggtt tgttaccact gagccacaaa gggagctcct aaaataata attttcttaa       60 agccaatgac atgagagca gttagggtgg aggctggtgg gtggtggggc cgcggcaggc      120
gccctgaagg tcctgagtgg caccccttggc cgggggaggt gggtgggcga gggtgttga      180 gaaggggcag ggcctcgtgg gggcaggaag gaagagccag tggctcccag tcccctgacc      240
ttgctgcctt gagcctggtt ctccccaaaa ttctgtctgt gtcccttcac ttcacggaag      300
cttggggccc gttgccaggg agacagatgg gctggtgaca cccaaaatga gccaccagga     360 gggggcact gactttagcc agccggtcac atcaagaagc aaacaggccc ccgctgctg       420 taaaggcagc ttggggctgg ggtccgggag caccccctgg gctggggaaa ggggtcctc     480 tcaggccccc ggggaggatg                                                  500
```

<210> SEQ ID NO 80
<211> LENGTH: 427
<212> TYPE: DNA
<213> ORGANISM: Pig

<400> SEQUENCE: 80

```
tctattcgcc gtggccggaa gaggctaacc gtacattgac cgggcatctg gcgatgtatc      60
acttctctcc aaccgaaact tcccggcaaa acttgctgcg tgaaaacgtt gcggatagcc     120
```

```
gaatcttcat taccggtaat acagtcattg atgcactgtt atgggtgcgt gaccaggtga      180
tgagcagcga caagctgcgt tcagaactgg cggcaaatta cccgtttatc gaccccgata      240
aaaagatgat tctggtgacc ggtcacaggc gtgagagttt cggtcgtggc tttgaagaaa      300
tctgccacgc gctggcagac atcgccacca cgcaccagga catccagatt gtctatccgg      360
tgcatctcaa cccgaacgtc agagaaccgg tcaatcgcat tctgggcat gtgaaaaatg      420 tcattct                                                                427

<210> SEQ ID NO 81
<211> LENGTH: 650
<212> TYPE: DNA
<213> ORGANISM: Pig

<400> SEQUENCE: 81
ggcgttgccg tgagctgtgg tgcgggtcac agatggggct cagatcccgc gtggctgtgg       60
ctctggccta ggccggtggc tgcagctccg attcgacccc tggcctggga gcctccatat      120
gctgcgggag cagccctaaa aaaaaaaaaa aaaaaagga agaaaagaga agaaagaaaa      180
gaaaagacaa aagtcaaaag gagctcccct gagcgatgtc tgtctacgag caggtccctg      240
ggagcctgag gcagggtgag cctggacccc tgagggccac tccagactca gtgctctcac      300
tggccaaggt ctttgggac cggctggggg cgcgcgcagg ctaaggagga ggtcagagga      360
ggggcttcag gctgcagggc cagcggcagc tctgggcccg gggcggggg gagatggcct      420 gagggccttg cggggctgg agggtgggg gcttcctgga gtgggaagac gggaagccag      480
gtcagaggag aggagcgagg gctgaagctc ctggaaggcg ctggctaccc ccagctggcc      540
cgccccgctg ccacattcaa cagccacccg gcctgtggtc ctggcagggt cctggcagaa      600
aagccccaag ggccccagcc tggccctctg ggcctaaaga gccaagcccc                650

<210> SEQ ID NO 82
<211> LENGTH: 550
<212> TYPE: DNA
<213> ORGANISM: Pig

<400> SEQUENCE: 82
ttaacccacg gagcaaggct ggggatcgaa cctgtaacct cgtggctcct cgtcggattc       60
gttaaccact gcgccacgac ggggaccccc cagggctggc gtttccctct gtgtgcacac      120
agtggacctg agccaaccag cagggccttc accaccacgg cgcaagagtc ggcagcaaga      180
gagcagtgtc tcatggctca ctttctcccc cttccccgga gtggtgacaa aacccgccg      240 ccaccggact cggttagaca aggcggtgcc cagtgccccc gtctgtcacc cgcacggcac      300
ggcgctctcc tttctttctc ggggctccac cacgtgtcct cagtttccgc atgagagtac      360
cgcggctggc ggggtggtgg ctctggggtc ggggccgtg agggcagggc tgggctgggg      420
gaggcaggtc ttggcccatt acgcgggggg cagactccac atcacacgct ctctgtgcct      480
cttggctgcc tgacaccatg gacttcaaac aggaacagcc gtggaggcat tgcagcccag      540
ggcccgggtt                                                             550

<210> SEQ ID NO 83
<211> LENGTH: 550
<212> TYPE: DNA
<213> ORGANISM: Pig

<400> SEQUENCE: 83
tgacacctcc aggcaggagg gtgcaggctg ggtcccagg taatggtgtg ctggcctgtg       60
```

```
gggcgtgggc tcagctctta ggatggtggg ctgggcgccg acccagcaag gacagggtga    120
tggcaggtcg tgggctcagc aaatgagtgc ccaggttgtg ggggtgggca cttgggctc     180 aggggaagct catcagcttg gagagggacg ggggagggag ggggccttgg ccagctggcc    240
cagatgcctg gatgtgagca ctcacgtgcc ccggggtcca cctcccctcc agtgccatct    300
gggcaggagg ctccgatgcc tgtccctggg acccgctgtc ctgaaatgag gttcacttgg    360
tgccttcccc agagatgctc ggtccggaag ctgacgaggc aggagtgcac aagggtctgg    420
ggaaatggag cagagtgcgg ctggggcaca gaggctgccc ccagcctggg aagatgggga    480
gctttgcagg ggtaccccgc cagcttgtgg ggccctggat acccaagggt gtgaagaggc    540
tgaagagcga                                                           550
```

```
<210> SEQ ID NO 84
<211> LENGTH: 984
<212> TYPE: DNA
<213> ORGANISM: Pig
<220> FEATURE:
<221> NAME/KEY: misc_feature
<222> LOCATION: (679)..(679)
<223> OTHER INFORMATION: Nonspecific nucleotide

<400> SEQUENCE: 84
ctgagcccag ctatgtagat tagaccccgg tccgtcccaa attcttctca aagctgtccc     60
gagatgagag atgaggtttt cgtgtcctgt gctctcctcg cttcccctgg gatgtgccct    120
agggtgggag agggtgtgtc ccagggctca gcaggcggtc ccatcttccc gagacgggag    180
agatcccctc cttctcggcg cctgtcccca cggcccccac agacaccccc cccccggca    240 tggcacccat gcacctgcca tcgtgcccag taggggatgg gtttggcgag actggagatg    300
gctgtagcca gtgagacatg ccctgccacg tagcctgacc ccctgggtgt gctctgtgag    360
atctggggac ccccagcaca cctagggatc atctttgcca gcctcctggg gagcctctca    420
gaaatggggg cccccagaag gctggcaaag gtgatgggga gcgtgggaag tctggcggtt    480
ggcggggtgg gtgggggggca gtgcgggctg ggtgggggggt gctccggggt cggaagtggt    540
ccagcaaggt tttggacaca aagtcaggag gaaggagtga cgaggagact tgcagaatta    600
caggtagaat caggaaccca catcgacgcc aattgatcta tcccccccctt tgattgtttt    660 ctcctggggc tttttttccnt tttttttttt tttttttttt ttaatccctc cttagctttt    720
tacgcgctca acaccaaatt aaacgtactc cccaccccac gtaacagggg ggcggtgacc    780
cgaaggacga ggagcacacg aagccaccat ccgtcacctt ggcggcacca gccgctgtcc    840
tgccctccgc ccattatcg cccttgaatt gattttttgtt ttgctctgtc cctgtcgctt    900
gggtagagtg gaaaagggaa cctctgtggg ggtgccagcc actgggcccc ccaaagattt    960
caggggaatg aaacggctgc cgcc                                           984
```

```
<210> SEQ ID NO 85
<211> LENGTH: 550
<212> TYPE: DNA
<213> ORGANISM: Pig

<400> SEQUENCE: 85
tgcccctgac aaccctgccc tgttagccac actcgcgact aataaggcga gaggtcagcg     60
ggcagcccca cggggagaaa gtgcctccgt gcccccacc cctggctctg atggcccagc    120
ctggcacccc aaggtggcct cggccttcct acctccaagg tccaggcgca tgtccaagca    180
```

```
ccagcagaag cttctccagg gttggtgcct gctcagggca gaaagcaggg gtgaggctcc      240
ccaaagggcc actggcacca atgccccag gcagccccag cgaaggggac agcccacccc       300
cagcccgggg acgcaggcct gaggggacat ggggaaccca gagcagggcc aaggggagca      360
gagcccctcc tccgggactt gaaatctttc cgggggggcc cagggagctg ggtctgcag       420 agggcacttt caaaatacgg cccacccca aattgccacg tgggccacag agcaaggagt      480
cgctgccaaa gtggcctggc ttcagcgcag gaagttcccc tcctggggcc tcccctccta      540
taggcacagg                                                            550

<210> SEQ ID NO 86
<211> LENGTH: 500
<212> TYPE: DNA
<213> ORGANISM: Pig

<400> SEQUENCE: 86
tgagccaggg cctggcccag ctaagcccct ggagccctcc cggcctgttt cctgcctccc      60
atgctggcgg agctcggctt actgagcggg ggccaggcca gtgtgcgtgt ggaggtagat     120
tccactcagc tggaggttga ggtgggcagg gggccgcaga ccctcaggcc agctctggcc     180
ggccaggtcc ctgaagctcc cccggctggc ctccccgtcc ctgcctctgg ccttgtcctg     240
gcccttgcct gacaagcttc tgtggctctg cctgcaggag agacactggc tccccgctc     300 tcggatgagg acggggcttt tctgcacaag tcctgcccca gaatgtttgg ggcgccagca     360
gctgagccca gcacgtctcc ccctgccct ggctggacac gaatcccggc atcgaggcgg     420 gaaggggat ggaggatgg ggcctaccca cccctgctcc caccagaa tagctgggcg       480 gcccccatgg gaggccgccc                                                 500

<210> SEQ ID NO 87
<211> LENGTH: 913
<212> TYPE: DNA
<213> ORGANISM: Pig

<400> SEQUENCE: 87
ctgttttcac gtcttctgag gacacaccca gaagaggggc tgcaggcgcc catggtgact      60
ccatgtgttc actgctgagg cctctgcaga ccgtctcccg cagcagccgc acccgttcc      120 atgccaccaa cagcgtgcga ggccgcactg tccccacggc tgtgcaactg ttttgaatct      180
gagttatata agcaacagac gctccttcaa acacactcac gtgcacacgt gcgcacaggc      240
gcacagacac acacacggag taataggcct cccccccctc cctgagccca gagggggcct     300
ggggccctgg agcctgtgct ttagggcctt ttaggaaagc tggtgcctcc cagagggggcc    360 gccccgagcg ttggcttccc aagtccccac caaccctcga cagactcaaa cgttggtttc     420
tttcgtgctt ttgcccaagg gatgggcccg aggtggccct gcctgaggtt tcagcccagc     480
gccccaggca ccctttctct cccggtcccc ggccacttca tgggacagcg ggccttcccc     540
cacgttgtcc cctgggttgt cgtgcttttc gtaatgagac ggaggcaggt gcacctgtcc     600
tggggtgaat tctcttctgc aggaactcgc ttccccggcg cctggtctgt ctgttcctcg     660
gttgttggaa cctctcgtca ccagaaaggg tggctctgac gtcgccctt ccctccgtgg     720 cttttgcagt ctggtcttg tcggggaacc tgccccaaag aggggagtga ccccccacga      780
gggagacgta gctcctgtgg cgacagcacc ggggcccc agattcatgg ggttcacgct      840
cacagtcgca tgacgctgcc tttggacgag ggcagctcaa gggaagcttg tttcctgcca     900
cgagccacag gca                                                        913
```

<210> SEQ ID NO 88
<211> LENGTH: 650
<212> TYPE: DNA
<213> ORGANISM: Pig

<400> SEQUENCE: 88

```
tccacacctg tggagccgct gcctcgctga tgccctctgc ccagctgatg gtcaggtgcc      60
cagacttggg gctcagtcca acaggggcc cacaggtgct gcacctgggc aagggagcct     120
gtgcgcaggg cctcaggtgt cccaggctcg ctgggaccga agcgcactgg gtcctggact    180
ccgggcttcc ccaggggctg ctcggggcca cctggaaatg aagcccacc tggctcatag     240
ggtccacgtg agggccctga ggccaccaag ccaccaaaca actcagttaa gggaggggag    300
cttggggctg ctaagctcca agcgggaagc ggccgcactc agcactgcct ctctgccagc    360
cagccgccca gcttgctgac gtcccaacca ggccagggac cctgtcccac agatgctggg    420
cccttccagt ctctgctccc tggaggcgct gggcactgtg tgggcacaca gcccgcaccc    480
gcctgtaagg aagggaaagg ccccatcctc aaaaaagccg tgggcaggtg ggccatgatg    540
gtcctccgag gcaggtcctc ctgggacccc ttgctccctc gggctcgccc aggagccgcc    600
aggtctgccc tggattaact ctgccccgca tgtcattttc aaactggctt                650
```

<210> SEQ ID NO 89
<211> LENGTH: 700
<212> TYPE: DNA
<213> ORGANISM: Pig

<400> SEQUENCE: 89

```
tggggcccctt tggggccgga gcggccagtc tgctgggccc gggagcaggg ggtctctgtc    60
cgcagggagg gggcctggtc tcaggggagg agaggaggca ggtctcacct gaaaggatct    120
gccttctcct caggcctctg ggatgcctgg gcagagaaac cagaaggaaa ggcccaactt    180
gctggctggt ggggatgggg ccgggggtcg ctcccggcac accccccca aaccccacct    240
tagtggccaa agtgggtgtc atgatggcca ctgacctcac gggggcgcag agacaacaa    300
aatttcagcc actcttgggg gaaggacact tgtggcctga gtcttagggg ctgagtttcg    360
ggggggaccc ccagctctcc ccccagtatg agacaccctg cccactcctc ccagctgctc    420
cccaaaccca gtgcttctgg acgggcatct ccccgctgcc cctgcagccg ctgtcctctg    480
accatgtccc ctccccacct cccctctgca gggccaggcc tccagggagc agagccgagg    540
ccccacccta gactgagctg ggaccgaga ccccaagtcg ccaccggtc tctgcgttag     600
agaggggtt ccgggggggca ccctgggggcg gcactggggg gcgggaagga gagccctggg   660
ccgttctggg aaaggtctgg gagggaggga ggggttttgc                           700
```

<210> SEQ ID NO 90
<211> LENGTH: 1400
<212> TYPE: DNA
<213> ORGANISM: Pig

<400> SEQUENCE: 90

```
gcacacccgg agaacagagg gagggtcct taccagtctc agggtttttt tggggatttc      60
tttgaacttg ccctattggt ttcgaggctt ctgttctctc caatccccc ttctgaaccc     120
ccccaaaaat gggttcagcc cccacccag ccagaggaaa ccaattgggg gattgggggg    180
aggcggggcc agcaaaagcc ttgggccccc agcccccctg gctttggcct ctggcctgcc   240
```

```
aggtaggggg agggacgcgg tgacctccgg gggcctggcc acggactctg ccccccacccc    300 cagggcagac gtgcacagga ggggagaggc tccgaggaat gaggccatca aagggacagg    360
tgaggccacg agccgtggga cctggaagtg tttagggcct gggggacgag gctgcggcct    420
gcgggctccg tggtcaggag gccctctgcc cactgagcag ctcccaccac tggcacacga    480
gcctctctgg gtccggctg gtctccggca gggtgggct ctgaacgtcc agctccgcag      540
acaaatcaga ttccccgag ccctgagaaa gccccctccc ccagcccgtc tccccacctg     600
tcggtggaca gagtgacccc tgctgacccc ctgcccgggc tcccgcagga gatgtgagag    660
agtaagaggc ggtacaggac ggccggggcg gcccgggcga ggtgcaggtg tgtgggtgtg    720
aggctgggca caggctggca cagcctccct ggcccagtcc cttgggcacc tctgggcacc    780
tcggtgtgcc tgcctcctga agggatccac cctccagcca cctcctctcg ggccagcccc    840
caccccaccc ccgagctaca gatgcctgcg cattcgcccc aagtgtcctg gaccctggag    900
ccaggcagcc cacccgctca gcctggccag acccagcgtt gcccttcacg ccctcctccc    960
tcccgccggg tcctcgcgct cgtctcctca ggttggaagc cccttcccac ctgccatctt   1020
gcctgcgccc aggatacacg gctcaactca aggcctcact cctcgccctc tccaaggctc   1080
tgtccaggcc cctctctgac ctggcaccac ctgccgcctc ctggcagccc cagcaaaccc   1140
cctgccacag tccacgacag tcctcttctg gctctgcccc caggatgctt ctagaactgg   1200
ggggggggtc cttccagccc acgcagcatc cactgggccc tgggctccct ccccaggtgc   1260
ccctcagagc ttgcagctgg tgcagacggc tctgctccga acccatgctc cctgcgccct   1320
tggacctggt gagatgttgc aggtcatttg gctgcaccca aaagagtggc ccctcagggt   1380
cccccctgcg cccctccatc                                              1400

<210> SEQ ID NO 91
<211> LENGTH: 391
<212> TYPE: DNA
<213> ORGANISM: Pig

<400> SEQUENCE: 91
gtactgtagg gcctcattcg aatagcctac taggtcacag ctgatccaca ccttaggcca     60
tcacaacttc ccagaggtag tgccgctcct gtcgttgaac aagacggtag tgactgctgt    120
gagagctcag atctggtggg tcactgaccg agtgtgaaac cctgggggaa ggctgtgggg    180
tgtccccggc tgggtggcca tgtcatgtgc cctttctat cccttggacg aggctggttc     240
actcggctct agagccccaa gccccagctg ctctgccaac cccccaagcc tgagcctcat    300
cagacccacc accccatcgc catggctacg caggacacac cgctctccac ccccaccagc    360
cgccccacct ccccgaggtt ccaaagcttg a                                   391

<210> SEQ ID NO 92
<211> LENGTH: 1464
<212> TYPE: DNA
<213> ORGANISM: Pig

<400> SEQUENCE: 92
tccaggacct gatgcagcag ccacgtcgcg aggcccctcc cacgaggccc cttgttgacc     60
agcgctaggg aaggggacca gggagatgct gagaacgggg ccttccgagg gggcaggtgg    120
gactgactgt gacccaacac tccccacccc cctctcccgc tccagagggt gccagcctgg    180
aagctggcaa agtccaatcc acaggtgggc tcagtggggg aggctggtgg cccccacctg    240
gtggggcccc aagctgcctc tgggcggggt gggggctgct cccagcaggg tcccatccag    300
```

```
cttctccctg gggagactca cagttctggg agaagggtcc tgactgcacc gcagcgcccg      360
ccccctcccc agactcaccc aagttctctc tctgcatcgg tgactggtct ccgcatttgc      420
ccaggctggg catctgccca gaggatacgt ccaaaggcag gcaaagccg ggcccgtccc       480 ccggagctcc ccacaggcgc tgagggctgg gctggatctc ggggggtgg agggaggac        540 tcagaaggtg cagcggggtg gagcgaggct gagccaaggt gcacgcgagg ccagagaag      600 gccgaggcgg gcaggaggag agagcgccag cctggagggg ggtgggtgcc ctgggcaggt     660
ctggggctca agaagaagag agtgtgtgtg caggggctg tccaagctgc ccggaggct       720 gcctgcccac ctccagggag caaagcaggg aggctgcagc tggcccggcc ggccgctctc    780
caggaccacg cgtggcccag gcctcaacgc tcctcccaca gcccaggaga cccagggcac    840
cgggtccatt taccgcgggc tccgggtccg tttgcctgcg ccctgggatg gactgtgggg    900
gcggggcgct gtctggggag gagggaggtg tctgaggctg gacaccttga aggcaggtga    960
gagtgacagg tccgtgcgca ggagccttcg gctctggatt ctggccctga gcgagggct     1020 ggctggaaac tgggccgggg ctgccgcagg agagtgtgca gggagaggag acggggtttg   1080
gccccggagg tgccggggtg gtgccctgga gtgcggctga gcgggaagtg ggtgttggcg    1140
tctggagacg gggggtcgtg ggcttgggat ggtgacaaga ccccccaggt ggaggcggcc    1200
gcagaggagg cagagaagcc aggccccagc cccacggcgg gaggcctggg agtcaggagg  1260
gaccagcaga gccctgggct cagtgtcacc ggtcctggca cctcgccgac ggatgtcctg   1320
gccgtgcagt ggttgtcccc tcaccctgag ccctgagaac catgcaggat gctggtgtca  1380
cagcaggaga gggccagggc ctggggagga gtcttactgg aaggccttct ccttccgttt   1440
gcagcaggcg ggaatgactg gggg                                            1464

<210> SEQ ID NO 93
<211> LENGTH: 694
<212> TYPE: DNA
<213> ORGANISM: Pig

<400> SEQUENCE: 93
tggagccagg gcacggcaga gcggtcccga ggccgtgcgt gctgacccgg gggatgggcg    60
gacctggggg tgggctgtga gcccaggcat agggaccccg acttgggcac ggccaggtgg    120
ggccgggcaa gggggaacaa ggacgctggc ctccaagggc cccacgtggg cacagaggaa   180
gagccgaccc aggttgtggg cgcatggaac cccccactct gggggccagg aggccgaacg   240
tcccaagggc tgaggctggg agggaagagt ccctttgggg gtcagtcagt gtcccttgtg   300
ggtgcccccc tgccactggc ggcacctctg accccaactc cttgcgggtg gacggtggat   360
ggatttcctg cagcctttct tctggaatag tctctgccat cctcggggaa gcagtgattg   420
ctctgcccaa gtccaggccc cgccctgcaa ggtgcctccc accccaatga gccccggac    480 agttcgaggg cttctcacgc tactgagggg tatgaacagc tgtcccccctc ggaaagtggg  540 ggacaggccc ctgccactcc atcctcggga cgcccggtct agtcagcact tgtctccctg   600
ccttgtgccc ccctgacctt ttttgaggac catcaaaacc tcagcctctg ccccaggagg   660
tcaagccccc cgtcccccag cccccagacc agca                                 694

<210> SEQ ID NO 94
<211> LENGTH: 900
<212> TYPE: DNA
<213> ORGANISM: Pig
```

<400> SEQUENCE: 94

```
ccagccccat cccccggctg gtcccccacc acacagagcc ccgtttccc aggggacagc      60
acagcctgcc cccaggtctt acataaagtc accttctcag agctcctgtc gcggctcagg    120
ggaatgaatc tgaccagcat ccatgaggac acaggtttga tcccaggccc cgctcagcag    180
gttaaggatc tggcgttgcc gtgagctgtg gtggaggtcg caagacgtgg ctcagatctg    240
gtgtggctgt gactgaggtg gcggccagca gctgcagctc tgattggacc cctagcctgg    300
gaacctccat atgccgcggg tgcagccctg aaggacaaa ataaataaa taaataaaag    360
aagtaaacac accttctcta gccataacca cctgcctagg ggcggagggc caggaagcgg    420
caccccccgc cccaggctgc ccgtgcgccc cgggcaggcg gctcagcctg cttttttgtct   480
gtgatgtgag ccgccccagc cccacatgga ggggctgggc tgcgcagtaa ctgctttaac    540
tgacgggagc ttcgaccagc aattcaccag cgggcatgca gccgggaagg gaagttattc    600
gtgtgtagct attaggcgcc ggagtgaggg tgtgcctcgc cctgggccca ccctggggg    660
gaggcatcac agggggttttg aacacctgcc catgaacacg gggcaaaagc cagccaaggg    720
ggcaggtgcc tgaggctggg aaccaaccccg tgtctctgaa atccggggaa tgcccactgc    780
aggcatgttc aaagggtcaa gaccgggggct ctgcctgaga aggactggcg aaggccaact    840
acaaaagcgc acccctctgt gcaaaccccc aaccaatgga acaaaactcc agaggggcca    900
```

<210> SEQ ID NO 95
<211> LENGTH: 550
<212> TYPE: DNA
<213> ORGANISM: Pig

<400> SEQUENCE: 95

```
agtctgggct gtgtccatgg ggttgccaag gtgccaggca gagaccttgg ggacaaaggt      60
cctgtgagca gaaggacatg gccacgtccc ctgctcagca ggtgcccagg ctggggtctg    120
atgccctcgc tggggtgggg gcgggttgag gggccaggcc cagacaccct tcgtccctgc    180
cggagttgtt tgcccttctg ttcctggaag gccccctgc aggtacagga ggccctggg    240
gctgacgctg caccttctga cacctgtggt cttggggatg ggacaggaca gggagacccc    300
ggggctggac ggagcgggta agacagagag ttgactctgt cctcgagtct gtgcagggct    360
gtccccggct tgggcttcgt ctgcagggcc tttcgggtca gggtggcctc aaggtgacga    420
agacctggtc ctcgggagtc tgcaggcgca aaagttggag cccacccccc cggggagggg    480
gcgccaagga caggagggcc cagggaagtc tggggcctgc aaggccgtcc gggctgggga    540
aggccaaggt                                                          550
```

<210> SEQ ID NO 96
<211> LENGTH: 1200
<212> TYPE: DNA
<213> ORGANISM: Pig
<220> FEATURE:
<221> NAME/KEY: misc_feature
<222> LOCATION: (1074)..(1144)
<223> OTHER INFORMATION: microsatellite PIGQTL2: (GT)8
      GCACGCGTGTGCGTGTGTAC (GT)17

<400> SEQUENCE: 96

```
gtttgctctc agcaggcaag ggcctccgag gccttaatag cccataatga cagcgcccgc      60
tcctggcatg ggccccgcc tggcatgggg cagggcaggg cagagcaagc agcatgcagc    120
ttctaccttc ttccctgacct cgtgccccct tccgaggcct caggggggtcc cccgagtggg    180
```

```
accccagccc tggctctcct ctccagagcc aggcccaagg ctgggagtgg cccagagatg      240
agggtgcccg agcagggcac tgccttggcg tccccatccc tggcgcctca gggccgtact      300
gtccaaaacc aaaagaaagc agtcagcaaa acttctccca gcaagctggg gtcaaaggtc      360
gcttccgagg cgtgatcagg gtggcctttg ctactgtcac cgtgtgccct gggagaggca      420
cagggacaca gacacacacc tccgagaacc tgggcttcc agggcgtcag gctgcctggg       480
ccatcccggg ccctgtggt cccaggatct gccgggaccg tgaggcctgc gtcccaccct       540
ctgcctggga caggccccac agagctcaca gccaggggac cggggacagg gccccgcctg      600
ggccacctgc ctccagcctc acccagcctg gccccaggc ctgtgcctgc gacaccctga      660
gtctcaggac gggcgcggga caaagccgcc cggcccctcc ccggctggg aggagacccg       720 cgtggccctg acgtgtgggc ctgtcagagc tgaaatgtca cagcaattag ccctaacgag      780
gccgagggag ggagcggcgg ggaggccggc ggaggggatc cacgagccga gggcccggag      840
ctggccaccc caccggtcga ttccaggcac tcagggataa ttgggtgttt agaagtcagg      900
cggcagcaga gagcgggcca ggcgggctgt gccccccctc ccaccgcccc ttaacaggtg      960
cccgaacacg caggtctggg gagatgctga ggtcgccaag ggcacccctg gccgtgccgc     1020
gggtgctatg ctggttcggc accatgggag ctgcacctgc agctgtattg gtctgtgtgt     1080
gtgtgtgtgt gcacgcgtgt gcgtgtgtac gtgtgtgtgt gtgtgtgtgt gtgtgtgtgt     1140
gtgtacgtgg ggggggggg caagcccgtg cgtgtggtgc acagtagaca tttagaaggt      1200

<210> SEQ ID NO 97
<211> LENGTH: 600
<212> TYPE: DNA
<213> ORGANISM: Pig

<400> SEQUENCE: 97
ggggaccagg gcccagccct ccagctccca cgcatacctg ctaggagctt gcaacctgcg       60
agagctttgt ggaccccctg ccgggtgacc cctgaagctg gcagctctcc ttggctctgc      120
agcggctctc tacactaccc cctctccagc ggcctcgggc ccagacatca cccacccgca      180
agggaagcag caagcatcca ccagctgggc ccttttcccc cagcctgtga ccggccccgc      240 gcccctcac acctctgcgg tccaagaccc ctctctggct gggccctggt gctgcccttg      300
ccgtgcacat ctggggtcca tacccacca acaggcccca cttttctgtc tcccagtgtc      360 ccctcagct gccctgatgg gcccacacct ggcttctctg ctgccccct tgaccgcaaa       420 aagactgggg tccaggaccc cctgcccat gactgccctg gaagacctca gcctctcct       480 ctcaatcctg acccttaag gctcttgcca cggagaaagc ggctggggtt ggggagggt       540 gtgggtccca aagcagcttg catacttctc ctgactggga gctcattcct ccacagcgtg      600

<210> SEQ ID NO 98
<211> LENGTH: 1350
<212> TYPE: DNA
<213> ORGANISM: Pig

<400> SEQUENCE: 98
cccgccttat ttttaaattt ccgaaaacaa aaccacacc tctcccgtcc ccgaaattat        60
tttggtatag tcttattcaa agaagtcctg ccactgaagc ccacttgtcc tgtcccgggc     120
tgctttggcc aagggccctg acgggcccag ggtggctcat tcccgcatcc ccgcagaggc     180
cgccttcaca tccatgcgg gagcctggct tccggcaccc ggctgtgccc tcgctgtggc      240
catggactgc tttcgcagaa gcatagggc cacaacatgg gacagcctcg ctctgctcgc      300
```

-continued

| | |
|---|---|
| tgtggttccg ctgaacctct cagctggaca tctgggcagc aagcacccca gctttgcttc | 360 |
| aggctctggt tccaggctgg gccctcctcg gccctgcccg ctgggtgcca agcagggctg | 420 |
| gtccggctgt gcccccgggt ctatagaagc ctctgcaggg cttcctacag ccaggctggg | 480 |
| attcggcggc tgcccgggac tgaggccccc tctgagtctg acccccccat ccttccctcc | 540 |
| cacacagccc cccgccccg cttctgcttc agtgaggccc caccctgcct cactcgctga | 600 |
| catttccaga cagggggtt ccaggaagcc ctgagcctgc aggggactca gtgaccagcc | 660 |
| gcatctgaat tttccctcct tctgatctct ggagacacgt ctggctcagc ctggctcgag | 720 |
| tgccctgagc tggggaccag gacagacctg cagatggagg tctgagcctg gcagggcag | 780 |
| ggcccaaggc tcagggagaa attgcaggtg tgagatcaat gaccggagcc tggatggggc | 840 |
| cgccctggcc agggcagctt tctccctgca gctccctgcc actgtccccc ccaactctgg | 900 |
| gctcctgctc tggacccagt tgtgtgttcc cctcctccca gccgagccac cctcccccat | 960 |
| tctgcccccc ccaatccaac ccctatcgt gggaaccagt ggagctgaaa gaaggacccc | 1020 |
| ccaagggccc cccagccgct gtaatccttg gggcctctg cccaggtgcc aggtctcggg | 1080 |
| caggaggggc cgcgggcaca gccgtggcag atgcgccccc caagcctggg ctcggaggag | 1140 |
| ccccgccccc actgacattt ccaggccgcc cgctgcagac ccggctggcc gtgatattta | 1200 |
| gacagggctt atttgccgtg actggttttt gatgactttg gggcccagga tgagctcagc | 1260 |
| cgagcccgcg ttggcccacc ttggtctcag cttgggtttg ataatataac gcgttcaact | 1320 |
| gaaccgctga cgcctgcgtg ggccgaggcc | 1350 |

<210> SEQ ID NO 99
<211> LENGTH: 1354
<212> TYPE: DNA
<213> ORGANISM: Pig

<400> SEQUENCE: 99

| | |
|---|---|
| gcttgcagta gttcatcaga ttggacgact cataaatgtc aagacatcta aagattggtg | 60 |
| catccaatca tttcccacca ggttgttttt ttgtagatgt caagaagctg acccaaaaac | 120 |
| tcacgtggaa atgcacgtca actgggagag ttgaaacaat ttctaaaaag aagaaggacg | 180 |
| tcgtgggagg actcttcgcg ctctttggtt tcgcttcact ttatattatt agttactgat | 240 |
| tttcctaaaa gctgcagtag tccagacagt gggcctctat gaagggaggg gctcagagat | 300 |
| ggttgggaca gaatagaaag cccagaaacg gaccccccgca aatgtggtca attgagtttg | 360 |
| ggcaaggatg tgaaagcggt tcagtggaga agagtctttt caagaaatct ctggtcctgg | 420 |
| atccactgct catccaggcc caagagtgaa cttggcgcac atttctcaca gtgtatacaa | 480 |
| aaactgactc aaaataattc acataccgtc gtgtagcgta tgaagccatg aaacatccag | 540 |
| aagaaaatct cggtaacctc agggcatctg gggcctccac cctcagcacc actgcccttg | 600 |
| ggccagata cttacgtgtt ctcctgtgca ctgtgggacg tgcagccaaa ccccaacaag | 660 |
| gtgaccatca gaaatgtctc cagacgtcgc caaataactg ccagagca caggagcccc | 720 |
| tcactgagaa ccacagggtg gggcagagag atctcagaca tgacacgatt aggggaaaac | 780 |
| aatctgacac actggctttg ttaaatttaa acttttccc ctgtaaaagg caatggtaag | 840 |
| acattaagag gcgaagtggc agactgggag aaaatatttg caaatcatgt atcagatacg | 900 |
| aagaagatgc aggaaatcct caaagttcag tcacaagaaa acccaattca aaaccagca | 960 |
| gagcagacat acgatggcaa ataaccacga gaaagtcagc acccgctgtc cctgggggga | 1020 |

| | |
|---|---|
| cgcgagtcaa agccaggagg acaccaggat atgcccactg ccaaggctac ggataacggg | 1080 |
| aagcaagaga cacagacaga aaggatgctt cggtgctggg gagggtgggg tgggcgggg | 1140 |
| ggtccccccc tggagcagga tgtgaaggca cttgggggg gctctgcact cctgggggcc | 1200 |
| tttggcacag gcggagggcc cgggaaggct ctaggggcac ggagagggt gccaggcttc | 1260 |
| cttacccagc ccaggcagac caggccctgt catgaagcct gacgtgcagc agcaagagca | 1320 |
| acatgctaca gacatgtgtc tgtgtgtgtg tgtg | 1354 |

<210> SEQ ID NO 100
<211> LENGTH: 1000
<212> TYPE: DNA
<213> ORGANISM: Pig

<400> SEQUENCE: 100

| | |
|---|---|
| ggttctcagg cgcacggggc agaggctgag ggtccgaggg ctttgggtg ctggaaagcc | 60 |
| tgagtttgaa tcccagctcg gtttcttaaa gctgtgtctc cacggccaag gaatggggcc | 120 |
| tctctgggaa aggtctgggg tgaggctggc gggacctgcc agccccggag ggcatctgac | 180 |
| cagacagctt ctcaagctca cagggcttca tggcaggatg gggaaggctg tggtggggag | 240 |
| tggggagcac tcgacaccct gtccaggcct cttgagtcac ggtggcctct gaaaaggggt | 300 |
| tctctgtgtc caatgagcaa gtctttgtcc ggggcaggat tactaagtcc aagggtgtct | 360 |
| gccccctccgt ggggcacaga gcaggggccc cagatcacgt ggctgtaact gccaggttgc | 420 |
| aaagcctgcc accatgtccc actgggttct ccagttacct tggaggtgc agggtggggt | 480 |
| gatgggaaa ctgaggcaga gagctggcaa aagagtgccg gcagggactg cgggcgccag | 540 |
| acccagctaa ccgaccctca cacggagctg cttctacttt gcagcctgga cgtgggaaaa | 600 |
| ggttacccca cagcagcgtg tgcaggcacg ctggtatgtc tgtgtactta tgcatatgtt | 660 |
| ctacgtgcat gcacgtgagt gtgctgtgtg cattgtgcct gtgtgtgtgt gcatgtgtgt | 720 |
| gtgcactcat gtgtctatac gtgtgtgtag tgaatgcttg tgcatgtgta tttgcatgtg | 780 |
| tatgtttgta cgtgtgcagt gaatgcatgt gtgtgcagtg gcggcatgtg cgtgtgtgcg | 840 |
| catgtgtctg tttatacctg tgtgtagtga atgcatgtgc atgtgtgtgt ttacatgtgc | 900 |
| acgtgagaat gtgcactcgt gcatgtttgc atgtgagttt catgtacaca tgcttttaac | 960 |
| gtgtgcacgt gtgcacatgt gtttctgtgt cccttgcacg | 1000 |

<210> SEQ ID NO 101
<211> LENGTH: 1500
<212> TYPE: DNA
<213> ORGANISM: Pig

<400> SEQUENCE: 101

| | |
|---|---|
| cgtataaata tattaatata gaataaaata gattgataat atagataaac taaacccatt | 60 |
| atcaataccg ggtggcccca gcaaggata ctagccagtt tatcaaggtg ctaagtcagc | 120 |
| acatagaatg gccacaaacg aaaacctgta ctgcctatgt ccactctaat ggagtatgcc | 180 |
| actgacatca gtggtaggtg agctgagtcc atctgggctc ccagttcggg cccggcttgt | 240 |
| cccccaacgg aggttccttc cagggttccc caaacccaac cgggccccca gtctccctg | 300 |
| tcttgactcg tttctggagt cttctggggc tctgcagtcc tcccttgttg gggcttctgt | 360 |
| cccctgccc ctggccttgc gggctcggcc ctgccctggg tcccgggcct gcgggctcac | 420 |
| cctccttctt tccctggaag agaggagcc aggctgggcc gggccaggag ggaatgcgcc | 480 |
| tgactctgct ccagatggac aggtcgggac atgcagtggc ctcgccttgg gctgctgagc | 540 |

-continued

| | |
|---|---|
| caagagcagg acgggttctt tctggaatgt ggggccagcc aggttcagcg tgtgggtggg | 600 |
| cagccgccag catctgtcag ggccgctgca ggcgcgggga atgacctcga cttctgcttg | 660 |
| gcacccagct ctggaacagc ccctgcgga gcctccgccc agagctgggc cagagggtcc | 720 |
| cctgtgccgg ggaccccagc agggcccctc cctgactctc caacccacct gcctgggagg | 780 |
| agtggccccc tggcctccgt ggatctctgg gtcgggctc agccggcttg acagcctggg | 840 |
| aacagccaat gcacatcccc aggcctggcc acaccttcc accgggagcg ggcggatctg | 900 |
| catttcgcca ggctctgcgg gcagctctga gagccccggg tctcggagcc cagccgtggc | 960 |
| cgttgtacgc cctgggggct gtggacagcg tgtcctcatt gcccctccga ggtccggccc | 1020 |
| aggtcccctc ccacctgctc gcccagagcc ctctccccac caaccacact tcctgctgtt | 1080 |
| ctgcaagcgg gacacacact ccggtttcag gacctttgca cgtgccgctt cctctgcaga | 1140 |
| gaaatgcctg gagcagatgt ttgtccgcac ggctgctccg cgaggcctac cgagagcccc | 1200 |
| tcacctaaac ggccgggcct cagcagcccg gggccctgtc ccaccgccc aggtggtggg | 1260 |
| ttctcctgtg ccagtgtggg catctctgta agatacctgt ttatctgctc atcgtctggt | 1320 |
| ctcccccaga aggtagagca gggcccggca cagccgtcct cggggtggcc actcgccctt | 1380 |
| ggggctcagc ctccatgcag ggagggacgc ctggtgacac gagagcccg tgtgagtgtg | 1440 |
| ccgggccgcc agcctgcctt aggtcacagc caaagccggc attaaccacc aggccctcga | 1500 |

<210> SEQ ID NO 102
<211> LENGTH: 600
<212> TYPE: DNA
<213> ORGANISM: Pig

<400> SEQUENCE: 102

| | |
|---|---|
| tctagaatac ctggccctcc agggacgtgt cctgtagctg cggctttcag ggcaaagtgt | 60 |
| aattaaacat ccccaggctt cccttccagt tggcacaggg cacccacatg aggagcagcc | 120 |
| tctgggtgcc aaagggccca ctggtgccag cgctgggct gagtgcaccc ccgcatgctt | 180 |
| cccgcccact cacctgctgg ccccacccct gaccacagca cctgtgggaa cactaggcct | 240 |
| ggcagccaca cgctgctctc actggaggcc agtgccaggc agcctgcttg gctacgctag | 300 |
| cagatgcccg ctcgcctctg cccctgcccc tagcccatgc aggagcccag ggtggggcac | 360 |
| aggaaggacg attggggccc caggtcaggc acatccaggc cacagccgtg gccacacgaa | 420 |
| ggcggccctg aggggggcgtt ggggggcaga ccctgccccc ccgctgccgc ccagctcca | 480 |
| ggcattaatt cccagggacc tgttgcactg ggtggccgcc agcctgcccc cttgccttcc | 540 |
| aaggcctcta aaatgcccct cttttcgtaa actaggactt accaagctca gcgagccctc | 600 |

<210> SEQ ID NO 103
<211> LENGTH: 1867
<212> TYPE: DNA
<213> ORGANISM: Pig

<400> SEQUENCE: 103

| | |
|---|---|
| agtatatcgg gtgagactgg ggaccggtct gccgggaagc cccaccataa aggccacgtt | 60 |
| gggccacagt ccgggccacg tgagtgtggg cgggtccgcg ggtctgctct tggaacacca | 120 |
| ggatctctaa gaggtaccag ccgaggccaa gttcacgtga gcaagtgagc aaatgactga | 180 |
| atgagagcgt gagcgaatga gtgaggggtg agtccgtcca ccacgcagcc taggctcagc | 240 |
| caaccgctgt ccccgcgtct ccactggtga ccagaacgga aagagtgggg aaagagtggt | 300 |

```
tgtctcccac aacccagtcc ccaaccccc tggacgcccc accccctccag gggtgccggg    360
cctggcctgt gggccccagt ctggaggctc tggcaccttc ctcatccgtt ctcccagcac    420
cccaggttcg tgctgagccc tcctggccca caggcctcgg ggacaaagag ggccacctgg    480
aggctcaggg agcctcacct gcctcgtggt cctggcggag gcgggtctgg acatgtgata    540
gaccggcctg ggctcagcag ctcctgctgg aagatgtcag ggacagcctg ggccactctc    600
ccaccaggag aacttattcc tcggtggggt cccccgggg aagggatggg atcccagcgg    660
ggaccccaga gcgtccagca cacggacctg tccctccagc ccctgcccca cacggatgct    720
cacagctcag cctcgaacac gcacctgttg gactttgcct cctgaggctg tcttctcagc    780
cgacgcgggc ctccgctgca tggtctggaa gcccagtggg actcggtggt gacagggaac    840
aggggctctt ggagtggggt gccgggggag ccccgaggga gctgcttggg cctttgatgg    900
ctgagtgggc tgaagtcagg caggctcccc cagggctccc tgaccccccc cacctcaaaa    960
aatccagagc atcctttgct ttgggtctgg tgaggtctc tgaggtcaga ccctgcgtgg    1020
ctgggccagt ggggctggag caggaagaaa gcaggacagc cccgcccct ggcccagact    1080
ccccaaaccc agcaggagac acctgaaacg ggatggaacc atcctgaaaa gagccacctc    1140
ctcctcctta tgcatcagct gccggggtct gggggcccgc ccaggcccc agatgtccgg    1200
gctgctcccg tctcacatcc aggggtttct gggcccagga ctctgtcccc ccaagcatgc    1260
agagggtcca ggctggggtc ttcatgcctg cccgtgtgca tggtggggaa ggaaggggac    1320
agtctggaga ccccccgccc tccccatgcg tggcgccggg ggacaaagcc ggctggggtc    1380
tcaggtttgg gttcagagca aacgttgatc tgacctggtt ctgagatgct cggcccgatg    1440
ctgcgttgtc cgctcgcatt ttcctgtttt ctctgggagg cgctgcgtgc gctgtggctt    1500
ccggccagcc ccacggaggg acgcagggtg gctggcgggg tctgggggcc cctgcccgca    1560
ccagaacgtc tggctcaggt ttttgtcctc gtgacccatc actaagggcc accctctgac    1620
ccggagccct gtctccgagg tgggaattgg gggctgtccc tggcgtcata ggacctggtt    1680
ggggcatcc aggctgtgt catgcccctc cccagaagac tctgggggct gcggagggt     1740
ttccccagct tcgggccagc ctggggaggg cggaaggcgc tggaggcctt gcctgtccca    1800
gggagcatgg cttcgctgca gactggggcc ccgcacaccc agccaccact ggccgtctgg    1860
aagcact                                                              1867
```

<210> SEQ ID NO 104
<211> LENGTH: 650
<212> TYPE: DNA
<213> ORGANISM: Pig

<400> SEQUENCE: 104

```
gttgaggatt cctcggcaat ttcctcgtca ctggcgctcc aatcgcctcg atgggcttct     60
cctccagata cagctgcaga tcctgggcgg gcacaccgtt gagcgtcacc tcgtagtgca    120
gattgcactc gttgtcaatg gacatccagg ccatgccgac ggcatgtgga ttctgtgcat    180
ccgtgtgctc ctgtcgcttc agcagaatgg gttccgccga gtcccgagca tcggccactg    240
gacggggcac taggcggcca cggatcaggc tcgtctcatg ctcggtggcc acattaacgc    300
ccagttcgcc ggcatacagc gactcgagga ccttgggacc caacttctcc acactaccaa    360
tggcctggtt gaagttgaag ctcggcgtca gatcctccag cttggccttc cgcttgccct    420
gctcctcaat caaactgatg ttgggcctat cccgggtgtt cacgtgctcc gtttcgatgt    480
tgtaggccag agatccatcg gtgttcaagt agacccacgc caaaccgctg ctcttggtcg    540
```

-continued

```
aggattcggc actgtgcggc gccagcaggg tctggaagat ttcgcagctg gctcgggtca    600
cgatgtgtcc ctggatgcgc agatgtgggt acttcttgga ctccacggtc               650
```

<210> SEQ ID NO 105
<211> LENGTH: 1630
<212> TYPE: DNA
<213> ORGANISM: Pig

<400> SEQUENCE: 105

```
ggtgttgtca ctgctgtggc tcagacccct gctgtggcac agggtccatc cttagcccag     60
aaacttgcac atgccacagg tgcagccaaa agaaaattct tactaataag ttgttcattt    120
gcctttacgt agagtggcat caaacagcaa atttaaaaca ccatctatca atacatagac    180
cgcggtcaaa gggaaagaac tttctatttc agcaccttta acatggcttt gcccgaattt    240
gggaccaggg tgctgtgttt tcatctctcc ctgcaggtgg tccccagatg accaggccgg    300
tcctgggcgg gaggagccgg actgtggatc cagttgcttc ccaagacagg ctgacaggag    360
agcagcaagg gccaccccca accgaaacca agccagaac gagcagaaag atgccgtctt     420
ccaagtgggg gctgggagct tcctcccatc ctccggagcc gtgaggctgc cctggagctg    480
gcaggagcca cagaggaccc ggctttgacc gccctctgg gacccacaat caggaccctg     540
actcagatgc tgagggcct ggacaacacc ccaggaccct gctgcttccc cagaaccgct     600
gtgtccatca aggtccagat ggcacccgtg tccccactgg agcacgcact ccgtggggca    660
ggctttccct tgggcaccga tgcaccttga gggcagagac ggggcccaat aaacgtttcc    720
aaaccagtgg gtgagggacc cgaccggccc gacacggcag cccggatgca gggactccgt    780
gcttggccca gcctcccttg gggtggtcct gtgtcctcag gggtggatag gccatcatgt    840
gggtggcctc tggggacatc cgttctctga ttgggtgagt ttcagccaca gagatattcc    900
caggactaca aagctgggtc ccttggggca cctgctgtca caaaagaca aggccctgac     960 ccccagtagc caagttcccc caggggctcc ccagggtctg gtcatccaga ctgtgccagc   1020
cgtgctgccc gccccagtcc tgcctgaccc gagtctctgt aaacatcccc cggccccacc   1080
cagctttacc ccaaggccga agcaccagc ccccctgcac cacagatgag gcccccatgg    1140
ctccccgacc taacttctgt ctgcagttgg ctttcagcct cgggtggggg caaggcctgc   1200
atctcaggct cccggggagaa gttgctgcct ccacagcaga gccaggggcc tgctgaccac   1260
ctgggccggg tcggatctgg tctagaatgc tgctaaggtg tccttgcagg cagccccggg   1320
cggccccgcc ctccaggaag gaagggggaca ttgccaggac tcaggaatga agccatccca   1380
ggttttgaat cccggtccc accaccttcc acctctgacc tcaggcacct cggctttcag    1440
agctgccctt tctgactctg ggacacgggg ctgtgaggcg ctctcggtgt gtgacagctg   1500
ggggggggca ctctctaacg agggtgggcg tgcccaggtg actgaccaca gcccttcct    1560 ctctcaaaaa cgcccgcccg agtgacctca cgggaggcag ggccaggaac ccaaaccaa   1620 accagaatca                                                         1630
```

<210> SEQ ID NO 106
<211> LENGTH: 1820
<212> TYPE: DNA
<213> ORGANISM: Pig
<220> FEATURE:
<221> NAME/KEY: misc_feature
<222> LOCATION: (223)..(260)
<223> OTHER INFORMATION: Microsatellite PIGQTL3: (CA)19

<400> SEQUENCE: 106

```
agtgagccct gcaggacagt ctgctgaggg gtgtctgggc tcctcagagg ctcatggcca      60
cgggcactgg gaggatagca ggtggacccc tgcatccagg tcccaggtcc caggtcccag     120
accccggac aggctttcta tctgcaggag gggggctcct ggggcagcag ggatgtggct      180
gtgaggcctc gtcagtctcc ctgtttctat ctctctctgt atcacacaca cacacacaca     240
cacacacaca cacacacaca cgcacgcacg cacacacaca gaggcgtgac cagggctgca     300
gacagggcca tgggaggact gcccggcagt gcacccagat ggccacacgg tggggccctc     360
gtcccacttt tgctgctgat gcttccgccc aggctgctgg gagcaagcac tagcttccca     420
gggctctgac cagagaggga tgggaggggt catgggtcaa caggcgccag ggaatgggga     480
ataggatctg aggggcgggg gcaaggggcc caggcgaggc tgcagtgccc agagctccct     540
gcacctgcag gaccagccac aggccaacag ctgcaggcag gcagggctg ctcctgtccc      600
cagaagctgg cacagcacat gggtctgac agccccaccc cggcctccc acagaggggc       660
gggtccccca aactcctccc ccgtcccacc tcacagctca gcatctccac tgcctgagga     720
cgagcccaac acacgggcac acacacacat gcacgcacac acatgaatgc acctgcaagc    780
acacactcac acgtaagcag gtacacacat gcatgcacac aatgaacaca catgcacgca     840
cacacgcatg cacacacgca cacacactca aacacgtaca tgcaagcaca tgctggtcct    900
ttgtccccgt ggagggggagg atggaggccc agcccgtggg gagggcatgt ggagtgttgg    960
ggggctggct ccaacgccct cgctcaacag gcaccaacgc tggactgaga taagccgggg    1020
cgctggctcc cttggggccg ctcagcaggt ttgacgccca ccacaggtgg cactgcctct    1080
ttcagaagac ggatgtggcc atgccaccct cacagcctca ccagtccccc ctcagcttta    1140
gtggtgtccc tgtcactgta cccggggcct tccttcttcc agggccaaaa gcgagttcag    1200
gggacagtgg cgcccccata attactcacc caggtgctg tcctctgtgg tggccttgag     1260
gccaaggtgc tcccatgggg gcccacaggg ctggcagggt cacttcctga gagcacccag    1320
ggccagggg gtggcccagg cctggccggt ccccatctgg aatgagggcc ttgcgcagag     1380
gcggtgcacc cctctttaca gcagccccgg gggagagtga ctcctgcgtc atggacctgg    1440
gggctgacct gtcacgtgtc tcgcccagtt gcaccccatc catttccggg tggaagggac    1500
aaagccatcc tggtcgtctc agaggacctc tggagcctct ggccccagc agcccagccc     1560
ctcccgggcc cgcatcctct gcccacccaa aatcacctgt gcccacaggg tcccttctg    1620
ggtgtccagg gcgacccaga actgccctg cagacacacc cagcccagga catgccgcc     1680
ttgccgggcc tgtctgcctg gggcagcctg actgccacag acaggccgct tggaggacca    1740
tctgcctgag cccccaaggc acatcccacg gggcccacac agccagcgcc tgtagacgat    1800
gccacttggg gtgggggag                                                  1820
```

<210> SEQ ID NO 107
<211> LENGTH: 1500
<212> TYPE: DNA
<213> ORGANISM: Pig

<400> SEQUENCE: 107

```
tgccgaatag aggtggaaac caagacccga aaaaatgtcc acattttca attattagaa       60
atttagaaaa atattttaca ggagttaaaa ggtattccat tctgggggcg ggtgggcatg     120
cccacgggcat gcaggcattc cccgaccagc gactgaactc gagccacggc agtcaccatg    180
ctggatcctt aacctgctga gcccctgggc aactccagac actccatatt catgtaaact    240
```

```
atttttaac caaaaaaatg acaaagcttt tcaaaacaaa acacatttca tgggaagagt      300
ggcattgctt cacgcctgga tggtcgctgc ggcttgcggg acgacgaggg ccccgcggg      360 agcgcctccg cacggcgcat caggacgtgg tgtccaggga agcggggtca cttcacggcc      420
tctcgggtgc gcgtgggttt cctttcggc accacacccg gactcagcac ttgggggttc      480
ttaaacgtga gaggcactgc ggggctcgaa gccacatcac tgacctcctc agactctgtt      540
atgtgaaaac ccatccgtcc acgagaccaa agagacagac gaacaaacgc aaggtggcgc      600
ctaggttggg cacagcatga gggcagagcg gaaaccttgg cgaaatcccg gcgaagcctg      660
gacgtcgcca gctcttactt gacgcaaaca taggggggatt caggaactct ctttaccgca     720
tttgcaatta atttgctgca aatctaaaat cgttccaagc acaatgctca ctgcatggaa      780
aaacccaggg gtaggtctcg cccgatcagg atgttttccc gtgccctctg tgcgggtgct      840
gccccctgcg ctggtcagtg agaagtgtcc ctccaccgac gacatgaaac ttcccaggtc      900
cacgctctct gctgtcctgg acgaaaactc atctctgtga atctcccgcc agctccgcgg      960
gagccttcca gggctggaag gacgccgtc ccgttccagg gggcaggtgc acgcttccca      1020
aagctccgcg tcctgctagg acgctcagac ggcatcaccc acaaacccca cgaactgttt     1080
ccctcgaggc gacaggctcg cccttctccg agaaagcagc ccgcacacgt cagcaagggg     1140
ccagctgcgt ttgtaactca aatggccaca tagagtttgt cctggaggca cggggtctgt     1200
ctgggccgca ccactgcaca cgcagaatat gctgggacac gctccggggt ccagcttcat     1260
ggaattaata aagtttactg cttcaccaag tacattctta agtgtagctg gccgccagcc     1320
tgggcgtccg ctccgaggct gcctctctgc ctggaaccct tgtgctgggg gaccctctct     1380
ccagccccac cccagccccg agcccaggca acatccttct tgtaagacac ccgctaccct     1440
gccctcccgc ttctccttct ctggatccaa tctcctccgc ttctaagctc tcttgaggct     1500
```

<210> SEQ ID NO 108
<211> LENGTH: 550
<212> TYPE: DNA
<213> ORGANISM: Pig

<400> SEQUENCE: 108

```
atggcactcg cggttgtgac tgagctaccg gacggcgcga gcaggccac gagggcgaca       60 agcgcgggc tgagaacctg tgcgagggca ggtccctgcg gctgcagaca agcctctatc      120
gcaggcccac agacaggagc ccccgtgtga ccctcaggct gcgagaccaa agtcacggct      180
ctgctgggaa aacctcgaac ctgatgactg ggtgggtgac cccaggacct tgaattccgg      240
cctctgcaga acgctctgag cctacgggag tggccaccct ctcggttagg gcctgtgtcc      300
ttccctggct tccagcctag agcaaaagca ttaaatcaca gtgtggccca gcccggaccg      360
tgcaggacct tagacaaaag aggagggaga gagagatgag gcagagaggc agagagacag      420
aggtggagag acagatagac agagacagag gcagagagag agacagacag acagagacag      480
aggcggagag acagacagag acagaggtgg agagacaggc agacagagac agaggccgag      540
agagagacag                                                             550
```

<210> SEQ ID NO 109
<211> LENGTH: 900
<212> TYPE: DNA
<213> ORGANISM: Pig

<400> SEQUENCE: 109

```
tttctaaact ctcttactag ttctagtttt ctattgtttt ctgggggggt tctatataaa      60
cattcgtgtc gtgattggag atggttttgt tttttcctct ccaaactgta tgccatgtgt     120
ttctttttct tgtcttatca cactggctag gacttccagt aaaacactag atatgaacaa    180
tgagaggaga gccaggcctt cttctcagtc ttggaggaaa cagtcagtct ttcctcattt    240
agaatgagag cttttctttt cttttctttc tttctttctt ttttttttt ttaataggtt     300 aaggaacttc tcttgtattc ttattttttt agagttgtta tttttttttt ctctctttt    360 agggctgcac ccgaggcata tggaggttct aaggctgggg tcgaattgga gctacagtcg    420
atggcctacg ccacagcaat gtgagatctg agccacatct gcgacctata ccacagctca    480
cagcaatgtc agatggttaa cccactgaac aaggccaggg attgagcccg catcctcatg    540
gatgccagtc agtttcgtga ccgctgagcc atgaagggaa cttccaataa tgcaccaatt    600
ttaaatgaaa aagacaaagc atccagccca cagcctgagt aaggagtttg gaggcctgac    660
ccctgcgtgg tcctgggcct gggcctgggc tggtcggggt ggggggggt ggggggggacc    720 ctgtggaccc tccctcctca gccaggcctg cccctccatc cctagctgtc ggggctcgg     780 aggaaggcgg gtggatgacg gtccctggga cccctcctca tatgtatctg ggtccctggt    840
ccctctgagg cccaggtcag gtcatgggag tcaaaggtca gccaaggggg tagcccagag    900
```

<210> SEQ ID NO 110
<211> LENGTH: 950
<212> TYPE: DNA
<213> ORGANISM: Pig

<400> SEQUENCE: 110

```
taacccactg accgaggcca gggatcaaac ctgcaacctc atgcttccta gtcggttcgg    60
taaccactgc gccacaacgg gaactccttt gcttttgttt ttaggatttc acatacacgt    120
gataacgtgc cgtatttatc tttctcatct gaattatttc acttagccta agcccttcag    180
ggtccatcca tggtgctggg agtggcagga tttgcttctt tttttttttt tttttgtggc    240
tgaaaatcag tccaggatta tcttcttttt ctgttcatct gtggaggaca caggctgcgt    300
ccgtgtgacg ctctgccggg aatacggggg ccgatcgctt tctgagccag tgttctcatt    360
ttcttgggag aagtacccgg agtggaacg ctgggtcgtc ctgcagttct gtgctgcatt     420
ttttgaagac gctcggagcg cttttccacag tggctgcacc gactgacatt cccaccgaag   480
tgcacggatt tccccatcct ttttccacgt tttccccgca cttgctattt ttgccctgtg    540
gatgtcggcc tctccgtcag gtgtgagggg agtctccgtg cggcccaggc gaggagcgac    600
cgtgagcgtc gtttcacgtt cctgttgggc cacctgcgtg gcttctccgg aaaaagggct    660
gttcaggctt cttgcccatt tctcagtctg attgtttggg gggtttgctg ttgagttgtg    720
tgagttccgc acgtatgggg ggcatcaacc ctttatcagc tatgcgattg gcaagtccgt    780
tctcccatgt tccgccggcc gccttggcac gtgtgggcgg tctccttggc tcttccttgg    840
tgcagaaggc ttcggtctga tgtgggccca tttgtttatc ttcttttctt tcctcaccgt    900
tgttttgatg tcagatgcaa aaatccattg ccagggtctg tgccgagaac                950
```

<210> SEQ ID NO 111
<211> LENGTH: 306
<212> TYPE: DNA
<213> ORGANISM: Pig

<400> SEQUENCE: 111

```
cgccacctca atcgccggtt tgttctgcaa cacggtccag ataaccagcg cacctaacag     60
```

| | |
|---|---|
| gtcgaacact gccagaactg cgaacagcgg gctgaagccg atggtgtcag ccagtgcacc | 120 |
| gacaaccagc gcaaacagcg tacttgccag ccatgcggac atcccggtta aaccgtttgc | 180 |
| cgttgccact tcgttacgac caaacacatc ggaagagagc gtaatcagcg cgccagacag | 240 |
| tgcctggtgg gcaaaaccac cgatacacag cagcataatt gcgacatacg ggttggtgaa | 300 |
| caggcc | 306 |

<210> SEQ ID NO 112
<211> LENGTH: 800
<212> TYPE: DNA
<213> ORGANISM: Pig

<400> SEQUENCE: 112

| | |
|---|---|
| gttttccatg atgcaccagg ggggccggga ccgcagcagg gaaggctcca tcctggctct | 60 |
| gtaagacctt gaaacacct cattcctctg gtcttggcct gctcttcggt acgccaagtt | 120 |
| gctgagactg atgtggggat cagtggggag caggaatctt tctgattcag ccgtttcaaa | 180 |
| gtgtcccaag cagaagctgt gatggcaatg ccaaggctat ccatggaggt ggctgtgcca | 240 |
| ggggccccat ttcctgggag cccattccag gaaaggaatc ttgtagcccc aggctccagc | 300 |
| agccagtgca cggcccctgg gactatccgg tagatcaga ggaggaaca gagctgtgga | 360 |
| tggtaagcag gtgcccaag tccaatttat gtctgtggtc ccagcagggt gcccaggagg | 420 |
| ccctcgtaa ctcttaagaa tcttggtctg gtcagctaaa ttgtatgacc attgtactga | 480 |
| gcacacatcc cgtttaagta gaattttcaa ggatgactag gagtttgcca cctgaaggca | 540 |
| ggaagggcat tccaggcaga gggtacagag gtgagaggga ggctctgaca ctttgggcgt | 600 |
| gcaggggggtt tgatgtgact gcagctggca cacagtgtat gcccaggcct ggcacggctg | 660 |
| tgttggtgtt tggagaggaa gggagaggtg agttgagccc aaggtcttcc aggccaaaag | 720 |
| actgaaggtg accgcggctg tccggggctg gcccgcagac caggagggag caggtgggag | 780 |
| ctggctcttg ttccggggac | 800 |

<210> SEQ ID NO 113
<211> LENGTH: 3062
<212> TYPE: DNA
<213> ORGANISM: Pig

<400> SEQUENCE: 113

| | |
|---|---|
| cacaccccag gagaggaaag acccacacag tcctgatgac agcttggctc ggggctggag | 60 |
| ccccgagtta taaatgtcca tcacgagctg tgttctgtca gagccatcag tgggaaggcc | 120 |
| aggccagctc agcagcccaa aaatgaagag ctaggtctgg gattgggccc aagcagaggg | 180 |
| cacaggaaag ccacataaac aaggcaccca accccctgt catccaccaa tgtcacattc | 240 |
| aggtcacacc cctggtcttc gggggaggtc ccctaagatc cggtggcagg ggaggaaaa | 300 |
| gtctgactgg attccttgac aggtgtatca gcggaaggcc aggaggagtg ctcgggcact | 360 |
| gccacctccc aggggcatga tggtcatgga ccagatggca gttatgggag gaacctcccc | 420 |
| cgtggtcaga gctctgggtg ctgtacctgg tcatgcattt cgagtggaag gaaagaaaa | 480 |
| catacaactc caccccagc agctttaggc tgttggtcta aggtcctgc ctcctggaag | 540 |
| agacacgcct ctgtcagcgg acactgctaa acctaaagga agaactgcca cctggtcacg | 600 |
| ggacttccta ggccaaccaa cctacaggtg acggcccgga gcatcacgag gaggtagggg | 660 |
| acgggaaggg atgcatttgc tgctcagcgg atccactggg gcgtttctgg agcccccacg | 720 |

-continued

```
cccacacttt actgcaaatg cacaagcccc aggcagcagg acaagtcaca gtagctctgg      780
gttatccaag gagtcaggga cctacctgga agagtctaga acaggtgaca gaggagggag      840
aggatggtac cagcagtata gggagaatca gaaatctgac ccaccctggg ggcctgactg      900
actcccagac caaatgccac actcaggttc cccgtctgcc tgcacttcca gggctgggcc      960 acggagtta tgggcccag gtagcatcag aggctcccag gtacaggcac aagcagcaac       1020
cacaggaggg atccaggcca gggagcatcc aagaagcagc agaagctcca ccttaggtac     1080
agttctggca cctccaagtt gagaacatgt cctagacagt gcctgacccc aacccaatgg     1140
agtgtctggg actagactag gcacgccatt ttggtcccag gttgccccat ctgtacaaag     1200
ggtgtgcggc ccccagggg acacaatgag ctcccatggg aagggtcttg cgaatctcct      1260
tagaagcaga tgtaagaggt gacgtccagc ttgtgcctgg gatgtagaag tggaaaaagc     1320 accctcccc cgacaaggat gaaagcaaga ggcacaaaac aacctgaaat tcccaacgcc      1380
cctggagatc cttggagaac tgggattctc cacctgtagg ggcacctgtg aggagaggct     1440
gtgtgagcac ctgctgacct ggcacagagg atgcccaata ctaagaagca tcagctaaaa     1500
gtctccagga attcctggaa gctgaggaag ggctcaggag agggtacaga agccctgggg    1560
ctatagatat aagggacgtg cacacccact tgcaggtccc catggacccc agggacattc     1620
acagtgatgg gcaagattcc caaaatgcac cccttgtgtg tgggcctggt tcggtgggtc     1680
agcagacacc acaccaaagg cacaaagcac acaccctcag gctactctcc tccctctccc     1740
ttgtggaaca tgagccttga gatgctgggg cacgtgaaaa acactgtcac acttaggtcc     1800
tggtgaaaac tgactgcggc cagcggaaag aatcataaag accctacacc cacacacagc     1860
cttaattaca gctgtgagtg gggctggagc cccaagaatg tctacaccca taagacatag     1920
cgttaatcag aaaaacaaga acagcccaa ccccaccacc aggctgacaa ctaacaggtc      1980
atgttggaat atcactggga atgttctagg agtgtagaaa gacacaccaa ctagggcatg    2040
atgcaaagat aatacttcag cctgggagtg gatgtgacac agggaaaagc ataaagtgat     2100
ggcagaggac tttgatgtca gtgatggaag ccacaaaaac ttctagctta gctccattcc     2160
caacaagatt gactgcaaac cccatgctaa acaacagca aaagaaaga atcctcattt       2220 ccaggcataa aattttcccc ccagtctctg ctgtcctcca taagatgtct gatttcaaca     2280
ggaattacga ggctataaga aaggcaagaa aaaactacac actgtcaaga gaaagccatc     2340
agaataacca gactcgtagc acagacactg gaattgtcag gatattttaa ataaccgtga     2400
caaatacatt aaagattcta atgagaaggg ggtagacatg taagatcaca tagatttcag     2460
caaagagatg aaactcgaag gaaaattaaa tgggagccct agagtgaaaa acactgtagc     2520
agagaagatg ggttcatccg taaacatgac acagcttagg aaagaatcag tgaacttgaa     2580
gacagggcca cagaaaatat ccaaactgaa atgcaaggag gaaaaataat gaaaggggga     2640
gagagaaaaa ataaaagaac aaagcatcca agagctggag ggtgacactg aagaagagag     2700
cataggcata gctggaatct cagaaagaga gaaagaaata acccaagatg taatggatga     2760
gaatttcaca gaagcgttgt caagcaacaa accatacatc caagaagctc agagaacacc     2820
aagcaaggta agtactgtaa aaaaatagcc cgaggtatac ctcattcagg ctgctgaaaa     2880
tccatgacaa aagaagtctt gaaagtagcc agaaacagaa ggcgtgttcc attcagaggg    2940
aaaagacacc attgttgcca gaaaccaaat aaaccagggc tgaaagggta aaactttttt    3000
tttttttttt tttttttttgg ccatgcctgt ggcatgtgga ggtttcccga tcaggatca     3060 ac                                                                   3062
```

<210> SEQ ID NO 114
<211> LENGTH: 1300
<212> TYPE: DNA
<213> ORGANISM: Pig

<400> SEQUENCE: 114

| | | | | | |
|---|---|---|---|---|---|
| aaacggataa | atacaggtga | cccacaggca | gaagctgaag | tacaaacagt | tcacaacggc | 60 |
| acccaaaaaa | taccgaaggc | tcaagggtaa | atctgacccc | agatgaaagg | ccttctcacg | 120 |
| gaaaatggca | aagtggcgct | gagaggcatg | agaggttcga | atagatggag | ggctccgccg | 180 |
| ttttcccggg | tccgaggatt | cagtgacgtc | acgacgccaa | ttcctctgaa | acgcctctct | 240 |
| aggttcagtg | cagcccagac | ccactggcag | ccgccctcgc | tgcagagaca | gcccagctgg | 300 |
| gtcttgaggt | tcctacagcg | aagcaaaggg | tctagaaaaa | gcagacgtct | ctggaaaggg | 360 |
| agaagcagcc | gatggattgg | catacggcga | caggagattc | ctcggacagt | ggcaccagga | 420 |
| gagggtgga | cagagactgg | tgcaaccgag | cgggcccagg | aataagtcca | cacccacacg | 480 |
| taccatctcg | ttgtttattt | atttttttcct | tttcagggcc | actcctgggg | catgtggagg | 540 |
| ctccccagcc | aggagtcgaa | tcggagctgc | agctacaagc | ctaccccaca | gccacagcga | 600 |
| cacaggatct | gagccatgtc | tgcagcctac | accacagctc | ccggcaatat | tggatcctta | 660 |
| acccactgag | caaggccagg | gactgaaccc | acgtgctcat | ggatactagt | tgggtttgtt | 720 |
| accactgagt | cacagtggga | actccttaaa | tttaatttt | tgaaggttca | gaactcttta | 780 |
| attttttagt | gaggtataga | ttatattacg | caccattcct | ttctgacttc | ggtgcacggc | 840 |
| ttttcaacaa | atgggtgctg | gacctgctgg | gtgccttctt | caaatgaacc | acaagccctc | 900 |
| cctcgcgccg | tatgcaaaat | ttaactcgag | gggctcatag | acataaacgt | aaactctaaa | 960 |
| gctataaaat | ttccagaaga | aaacgtaagg | aaaacctttg | gggtcttggg | caaagatttc | 1020 |
| ttacccatga | cagcaaaatt | acaatctaca | gaagaactgg | tggcctttat | cggcatttaa | 1080 |
| aacacctgcc | ctttgaatga | tgctgtcgca | aaaccgaaca | tgcagcaaaa | cggatgcaac | 1140 |
| tagcaggtct | cacactcagt | gacccacgtc | agaaagggaa | agacacgcca | cgtgacatcc | 1200 |
| cttagatgca | gaatgtaaaa | cacggccccc | gtgaaccgac | ctcaagagag | agacagacct | 1260 |
| acagacgcag | caaatttggg | gttgccgagg | gggatgccgg | | | 1300 |

<210> SEQ ID NO 115
<211> LENGTH: 3000
<212> TYPE: DNA
<213> ORGANISM: Pig

<400> SEQUENCE: 115

| | | | | | |
|---|---|---|---|---|---|
| tgtgagaccc | cttggcgggc | caggaccccc | caaggtgacc | gaaggcctca | gcgcccccag | 60 |
| ccgcccatc | cccctctttc | cgacacagg | attttttttcc | caccaagctc | tgttcccttg | 120 |
| gtcacgctct | cacttgagca | gcctcaggtt | ctccggtgc | ctgtatccac | gacagcgtga | 180 |
| ccttcttggt | gtgtcaaccc | aggacccac | gctggccagc | cacgccttcc | cagagcaccc | 240 |
| ccgcccatcc | tcagagtcca | gaggaaaggc | ccccattgac | cccagaaacc | aaaacgcaga | 300 |
| gactctggga | cgccagcaag | aacgtacact | gactcccacc | tgcttcaggc | acggaggcag | 360 |
| gggtgggtta | tgagcgaccc | cgtggaaggg | ccttcttgtc | catcgagggg | cttccagggg | 420 |
| ctcctagacg | gggatgagtg | tggcaacatg | tcgccgcatt | acaaaagacc | ctgcagtgct | 480 |
| gctgggatgg | gtcccccggc | tagaaaagca | aaggattcca | gcccagtcga | gtaggaggcg | 540 |

-continued

```
gcctcggagg ctgcagaggc gcgggggggcg ctgaccacca ctcggcaagc cccgtgttgg    600 agggggacgcc cggcccggct gcagccgtg cgcctccgga taagctccta agaggccgcg    660
tgccccatgc acgcgcgtgc acacactcgc tgcccgaggg tccttcagca cagaccttgt    720
ggggacggag gacctggcag gggtgtggct ctggggaagg ggtctgtccc aggaaccctg    780
ttctggattt gggggtgggc gtggatatcc cgtcccaacc tacagaaggg aggggcttaa    840
aaagagcccc tttggtgtga ggggccagca atcctttggc ttttcttgg cccacttgga    900 gcttgacgtc tggtcagtga ctgggagcca gggccagagg ggggcagccg ggctgaggca    960
ggttcaggcc aaccatctct cggccacact cccgaggtcg ggcagctacg ggccccag    1020 agacacaagc cccaggggtc cttccccccc gccccctgcc ccagatcacc aggagaccca   1080
agcagctctg cctcccgtg cctgagaaat gccccatctg ggtacccaaa tcaccctccc   1140
agaaggtaga gtgggggggcc caggacaggg ggaccccagt tacagagccc caggcaggct   1200
tcccaggggc gaggggactc cgtttggggc acagacggag gcagagcggg ctgatggatt   1260
ctcccccggt tcagggatgc tggctgcctg gcctccagga gccggcggtg ccatctgatc   1320
tgattaaggc ctgcagtccc agctgggcgg gcacagcctg ggggctcggc gggcagggaa   1380
gaaggcgctg tcgcccagc cggtcaggct cgctttctct tcatttcctc tccattaaaa   1440
gtgtcagaac catttattga tttttaaat caggacgtgc tgtccgtgac acagcaaagt   1500
gaacaaaatc agagcaaaga gaggccaggg ctgaagcccc agagggcggc gcctccaatc   1560
cgggttgtgc cccggggctc caagccccctt cttcttctgg ggtcctgggc gtagtggcca   1620
gggcagaatg cacctgccgt catcctggga ggcttggcca tcgctggctt ctgtctcatg   1680
acgcaccgtc gttccatatc tacgaaaaca gcttcgcatt aacaggcagg ggaggcggtt   1740
gtttctcctt tatctgccca ccatcggcgc tggggccacg tggagcccag ccggctgact   1800
tcccgctcgc acgcagggca ctgattgcag gaacgaggac atccagcccc cgcctctcaa   1860
tgccccgggt gctgagagca tttcgcccaa acggcttggg tgggacaagg gatggagctg   1920
tgcgccaggg gcctggctgg ggcagaaggg ggcctgcccg tgtctgcccg tggcctccag   1980
caccctcggc tgccaggctg ctctggagag gtgcccgggg gccgagggcc aggggcaccc   2040
tgttctgccc cacgtctctc tgtcctgctg aaagttccac cagacgcgtg ctatacccct    2100
ggagtcagga ggatggggga tagttgggc ttgacgtctg tttctgaaaa aacaccgttt    2160
tccctgaaat atatatgtat taattttttcg tcaagataaa actgtgtata gtttttcgtg    2220
atgagaaaac gcatccatct tccttagaaa gcctgaagag gtacaggagc ctataaagga    2280
caagatgaca gatgcctcta acgcacacca aatgtgcggt ggcccccagg ggaccgcata    2340
gacggggcgg ctcagatgg ccaccgtgtg cgagggacac ggttcagggt ggcagagtat    2400
tcctgggggg ggggggctca gcggttccca tttccccctc ccttccttcc ttcatttctt    2460
tccttctttc tttcttttg tggttttagg gccgcacccg cggcgtgtgg aggttccag    2520 cctagggggtc taatcagagc tacagctgcc ggcctccacc acagctcacg gcaacgccgg    2580
atccttaacc cacggagcga gaccagggat ggaacctggg acctcatgga tcttagttgg    2640
gtttgttccc gctgagccac aacgggaact ccagccattc ccatttcttg ctccagttcc    2700
aagaattcca attcttattc ctgttcttta aggccagagg cgacagccac gccgagtccc    2760
agaagcaggg ctcaaggatg ctgctgttga ctgtgtccgt gggcggggg agttgataag    2820 aaccccccaac acagggtggt ggccagcaac gggggaggga ggaggggggc tggtggggaa    2880
aagtcccctg aaccccatgg gctgcccccct ccaggctggg gcacgacccc gagccccatg    2940
```

```
gcccgaggag aaacggtccc agccccaggc tgggctcccg caccccctgcc ctgacccccgc    3000

<210> SEQ ID NO 116
<211> LENGTH: 1895
<212> TYPE: DNA
<213> ORGANISM: Pig

<400> SEQUENCE: 116
tcatggaagc ccttatcaca acctcggatc caaaacccac tgcgcgagtc cagggataga      60
actcgcatcc ccacagaccc tatgttgggg tcttaaccag ctgagccaca tggaaactgg     120
gtaatctatt tttagatgtt cctagggttt ttggccttgc ctgtacgtgg ggacgctgct     180
gggccaggga tcaaacccgc gccacagctg tgacccaagc agagcagtga cagcaccgga     240
tccttaagca cgaggccagc agggagcccc tgtgtttaga ttttggtgag gatactgcgt     300
gggattcagg atattcactt tggggctgtt ggaattgccc gtcgctgttt aagcaaagag     360
aaatcccttc actctgtgta actgtgggga atcctttag tctcttgaaa ccattgcgtg      420
tgtttaagag tggtaactct gccaccataa atgcccagac cagcgccttc ctgagatccg     480
cttttgttgc aaatatctgg tttgaatgct tgatcgccc gcaccagacc agggtgggcg      540
gacgccgccg gggacccgac gtgaccatcg tgcttctgta tccgcccttt ctccggcacg     600
cgccccctgg ttgcctctgg ctgcttttag tggaggaact gaagcctcgc cacccagacc     660
ccgagaccgc aggacccaca atgcttcaaa cacctgccct ctgacttttta caggtcaagt     720
tcgccaacgc cgaatttgca ccgattggct acagagagca cggtgcgcc aagcctccac      780
ttggagtttt ataaggtctc cctccagctc gcaatgaaaa tgagctgtga taaggcaaag     840
acaaaattag tatgaaatcc agatgcttca tctacaatac aatgaccgcg ggatttgggt     900
ctgagcgact gaaatcaagg tgggcttccg gagggaggct gttagaggaa aggcattcac     960
ggaggctcag gtccgagagg cttccacacc cctaagaggg ctgagacggc aagtagggac    1020
caagccccgc agtcgggaga gctgggcagg aaggaagtct gaggtcaccc ccacctgggg    1080
aggaactgcc tagagaagcg ggggcgggaa gcagggggatg cccagtccca agacagggac    1140
agggcggaaa gggctctctg caggccctca atgctgccac agtgtcctcg taagagggag    1200
gcagagagaa ttgacaccgg ggagaccacg ggaccacgga ggtggagacc gggctgcccg    1260
cgcgtgccag ttgctcccga agccggcccc tccccagag cctttgggaa gaggcgccaa     1320
cctgcagttc tgctactcgg ggacaggac agggacagcc cctggagcc gcctcttagg      1380
ggcagcatcc cccagaacct tccttaacag accatctgga gagagatggg tctgggctgc    1440
agctcctgga actgttttgc ccaccccgcg agcaccagtg ggtgccagcc tgggctgccc    1500
agcctcaggg ccgggggaggg ctgagggcac tggggcccgg ctctgggact cccctgcctc    1560
ctgcccgtgc aggacagcca cctcccagca tctgcttcct gccacccaca tcccaggac     1620
cgtcagccca ggcatgcccc tggcgtcggc cactcacacc acaggccagg aacccaaggg    1680
ggcaacacag aagggcagtt gccatctgca gatggaatgg acaaactggg gtccgtgatg    1740
atggcaggct ctgggcgccc gggctggcag gggagccagg actgtgcggc catcacagga    1800
agggcatgac ggggtgaaag caagagtgga aacctctgcc acccgcctgg gcgcacatac    1860
cggccacccct gcagccccac ccccatttgt ttgct                              1895

<210> SEQ ID NO 117
<211> LENGTH: 1040
<212> TYPE: DNA
```

<213> ORGANISM: Pig

<400> SEQUENCE: 117

| | | | | | |
|---|---|---|---|---|---|
| gcgcgccgga | tccttaatta | agtctgagag | atctgcggcc | gcggccaggg | tctgcttctg | 60 |
| gccaagtgtg | gggctctgct | ccatcctggc | tcggaggtcc | acccatggca | aagcctgggg | 120 |
| tcctcccact | gaatatttgg | gggtccactc | gtgccaaagg | ctgggtgtcc | agtgtgccaa | 180 |
| cggtacatgg | aagcaatgtc | ttcccaagga | ccgtccaagg | tgtggtcagg | cctggacagc | 240 |
| tgtgagtccc | ttcgggacta | gacttggtgg | ccgaacccta | gggaccgtgc | ccgagggccc | 300 |
| ccacgaggcc | aggtgtttgc | cccagggaca | gaacggccaa | gggtggccga | gggttctttt | 360 |
| tgtttgtttt | ttcttctttc | tcttttctt | tggccgaggg | ttcttaaagc | gctctctctg | 420 |
| ctctttgtcc | cgatcctgag | cgggcagtgt | cctggtcggt | ggggtgctgg | gcagccgcag | 480 |
| cagggctgag | agagcccggc | ttgtcactag | ggcgcgccgg | tgagcccagc | gggcatgccg | 540 |
| tgtccagacg | ttggatgggg | cagcgagggg | actgggtgc | cccagccccc | gtgggaagcc | 600 |
| cgccctgtgg | aagccgctgt | gctcgccaca | acaagcaccg | tcgactagct | ggtgaatcag | 660 |
| cgcccgtcgc | ccgcgtaatc | ccaggcgctt | tctgcccaac | ctgagccctg | accccacacc | 720 |
| ccttgcgacc | gctccgtgga | ccctggggcg | atgaggtgaa | ccgtgggctt | ggccatcgtg | 780 |
| gtggcagacg | tggcacacc | cgtgcgcctg | tcggccccc | tccatccagg | agcagagtgc | 840 |
| gcacccagtg | ggggctgggc | agggagccgc | ctccacctcc | gccctgaggg | gacgggactc | 900 |
| tttcgacccg | gagtgggaag | ggacatatgc | ggacgatgcc | agaccctgtc | tgtgggggga | 960 |
| gggggagaag | gccctctttg | gagaattcca | ggacgggtga | ggaacgtgtg | ctggaccggc | 1020 |
| cgggtcggag | gtgggccttg | | | | | 1040 |

<210> SEQ ID NO 118
<211> LENGTH: 9236
<212> TYPE: DNA
<213> ORGANISM: Pig

<400> SEQUENCE: 118

| | | | | | |
|---|---|---|---|---|---|
| ggcaaccagg | ggaagatggg | gaagcggggt | gcaggggcgt | ttgcgcgggc | caaggaccac | 60 |
| cttggaaatc | tggagcctgg | caggagcggc | gcagggttga | ggggctggct | tgggcagggc | 120 |
| tggctggcac | ctgggagcct | ggcggggttg | aggtccgggc | tcccaggtgc | cctataggca | 180 |
| gggcaacatc | ggcatggggg | gtgacaggcc | cgagctgggg | tgcggaggga | agaggggggga | 240 |
| gccaggcatt | catcccggtc | aattttggtt | tcaggtcgtg | gcggctggtg | gtcaggggga | 300 |
| gttggagaga | ggttcgcccc | ggggcctggg | gcagcggagg | tgtagctggc | agctgtgggc | 360 |
| aggtgaggac | agccgtctgc | cgggccaggt | gagtccccctt | ccctccccag | gccttgtttc | 420 |
| tctggcctcc | tgcatccgga | ggttctgggg | agcgagggcc | ggcgaggcga | agcggctgac | 480 |
| ccccccggcag | agtggcggcg | gacgacaggc | aaggcgggca | gaacaggtga | cacgtctcag | 540 |
| ggggagctgg | gaccgggcgg | ggctgggggg | ccggggccgt | cccaggtgga | aagagcatct | 600 |
| caagcgagtc | tggtgggaga | cgaggcaggg | ctgccagcag | ggaggagacg | caacaggcgg | 660 |
| ggggcattcc | aggcccgggt | cggacaggac | ccgtcggggg | tgtcaggaca | gtggggtccc | 720 |
| cagccgccac | ttcacccact | gcaattcatt | tagtagcagg | tacaggagcg | gctctggccg | 780 |
| ggcctcttga | ggcctgagct | ggagcctcga | gggccggaga | atgggaaaga | aggtgcagtg | 840 |
| tgccagacag | acgtcacctg | gagggagcac | ggccgtgggg | acgggcccca | gagagatttc | 900 |
| ggcagcaggg | aggctgcgcg | ggcccagcct | gcggacgtgc | gttcccacgc | agcactgcgg | 960 |

-continued

```
cccaggggct ggcgcggcag ggcccccggt gtccttggtg gcactgtgcg ccctcgccgc   1020
tcgcccctgg gactggcacg gcagacagga cagcacccag gggagtcaag ggcactgacg   1080
agaccagact aggcgaggcg ggtggggtgg aatggatgtg acctctgggg ggagggaggt   1140
ggggacgcag gcagggcga ggcgccggag cctggcggcg agcgaggcca aggcgggcct   1200
ctgcgggtga caactgagca catatgggta ccttcgcgct cgcaccggag acaggtgagt   1260
gtctggcccc ggcctgccgc cctcccggcc ccgccactgc ctctgccctc ccctcgacc    1320
agggccctct gcttccccac agcctcgtct ccagtgggg tggacacact gccagcacca     1380
caggccggac gccaggatgt gcttggaggg acatgacaca gtccggtgtg acggagaggg   1440
acagacgtga cgccgtccgg ccttcctggt gagcgcaggt ccaggccttg gcccccaggc   1500
cagccgcccc acccccacc cctcatggcc gtcttctgtc ccgcagaaca ctctcggctg     1560
gccccgcggg ggagctgcca cacccagcgt ctgttccttt gccttcctga aggagcacgt   1620
gcatgactgc tgctctctgg accccagaac cctcaaacga caaggtgagg caggtcccgc   1680
ctcgccccac acgtggaagg ggcgtgggcg agagccgggc gctcacggtg cccccctccc   1740
cctgcagaga tggtgctacc cagctcatgc ctgggccttg acccggact tcttcaagtc      1800
ctcctagctc tgactcaaga atatgctgca ttctggagcc actacactac ttgactcagg   1860
aatcagctct ggaaggtggg cgcgcgctcc tcccgctccc ggagcccgc ccgctgcccg     1920
ctccccgctc acgtcctgtc tctgtcctcg tccgcaggtt gagccaaagg aacagacgtc   1980
ccacaccacc ggaccaacgg cacccgcggg gttcccacc cccgcccgg ccactccacc      2040
tcggcggcca ccccctgctg cgccctggag acaccaccag cctccctctc tccccttcct   2100
cctttttttc ctctgtcttt tctcttctct tctttcctct cctttgctca gaagactcgg   2160
ggcatccagg actctgtgtc cccgtccttc ctgaattaat ttgcactaag tcgtttgcac   2220
tggtttggag tcctggaacc agccccgggt ctcggagcgg gtgtgtgagc tgccgagtgg   2280
cctggcctcc tcggcccgcg cccctcagc acctgccatt gtccatctct gtctggggt      2340
gactgggtgg gggcctgagt gtgtggggcc ccgccctccc ctctcctagt ctggaagctc   2400
cgaccaccga gcagacctca aacgctgcac tgagtgtcca tctcgtcatg tgcccctcct   2460
cgccagggcc accccagagc cctggactca tcaataaact cagttaccgg aatctgtctc   2520
agggctttg caattgggct gggggtgcgc cggggaaggg gggatgaga tggggaacat      2580
gcaaggaagg gcctgtgggc tggggacac agaatgggtg gggaggggc tcacaggact      2640
cgggggtaa tgaacgtggg gctgggcgca aggggagtg ggacgtgggg atcagggcgg      2700
ggggcctgga ggatgcaggg tccctgcagg gaaaggggc cgagggcgtg aggcatgtcc     2760
tcagccctga gaggccctac cccacaaagc acagcctgcg cgcgacctcc aggcccccaa   2820
accccgccc cagaccctga agccctggtc cagggcagtg ggtctgactg gcggaaggaa    2880
catgccaccc aggctggcca caccactggg acgcccatgg gcggccactt tcatcaagag   2940
cctggcaggc cctgagtgct gggctggagg gcacagaggg tccccctccc ctcacgcttt   3000
gcggtgctgg ggcaccgcag gagtgcccaa caggagaccc caggaagtct gctgggctgc   3060
agcgaagggc agggtagggg ggcggcccac aggggcccag ctcagtaggc aggtggcagt   3120
gggaggcggc agaaagttgg aaagggtgga ctggcacgt caggatctcg tggcggcagc    3180
cccggagcca cggccttggg tgcactgcag ccccacggt tggtgtcccg gtcccaggca     3240
gcagctgggc tggtgacgcc cctctgcctc tgccacccc ccccaccgcc ccccgccag     3300
```

```
cctcccagcc cctgggcgcc tggcgtgacg ctgggaacgc gagggagcag gcctcggaaa    3360
cagggctggg tccttgaccc cttcctctgc tcagggcagt caggaaatgc ctagcgggcc    3420
gactgaccga gaggagatag cggaggcctg ggagacccg cgctcgtgcc gttcccagcg     3480
tccggccgcg tggcccttgg ctggcctggt ttgggcccca tgagctcacc ccccgccccc    3540
cacagcctcc ccgcgtctgg tctcctctct gggccctgct gtccctcctg acggggaca    3600 gagccctcca gggccccggg gggacggtcc cgggtcagca gggcgggtgg gcagcacagc    3660
tgcgtttggt gaagcccctg cccaaagcac cctcagcgtt tcctctgcgc gtccggccgc    3720
ccccggaggc tttcccaagt ccacgggcaa ctcgcaggcg agcccactcc acctccatca    3780
cgcgggtttg ccagcggca gaagcactcg cccttcaggc gtcaggagtt aagcccctcc     3840
aaggcccggt gctaatcagc tgcctctcct ggagcttcgc aaagcgggct ctcagagccc    3900
agcttcccgg gggctcaccg tggtggcatg ggcaccacag gtggccggag gggcaccgag    3960
cacgacgggg ctgtgggggg tggaggaggg aggttggtga ctccgaacct ctactgaggc    4020
acacagagga cacggccgct tccaggggag tcagcctgcg aagggcagag gggctgtagc    4080
ctcccggtca cgccctcgcc tctgccctgg attcctcctg ggggcccgcg gctcgtcggg    4140
gaggtgagtg cccctggatg ggcgtaggct ggggggggcag ggagtgggg agccccgagg    4200 ccctgggccc acagccctgt cttgccccac acacagggct gtctacactg ggtgcccact    4260
tgctctgctt ctaggctgtt ccctgggcag ctgcctggag ggccgtgggc acagtgcggg    4320
cagccagtgg ggaggccggg gatggggccg gggataggga cccctgcccc tgggtgagcc    4380
ccacctgggc tgggaagaca gcagcagcgc cccttcaggt ccatggacca ggggacccag    4440
ggtggactgt gtttaccttc agcccaggcc agtttcctgc ttgagaaagc ccggagggg     4500 gtgcgggaca ggcccgggcc ccccacgcaa aggcagtttc gcaatgtccc tgcgctgact    4560
gaaatgtcac caggcacacg gcttgaattt ctcccccaga cctggcaggg gcggggtgg     4620 gggcaccggg ctgctgggat cttggcccct gaacctcccc cggccctgcg gccagggagg    4680
gtttaggctg agtgacagcc cacggaaacc tggacccgac atgtctgtgt gtccatgtgt    4740
gtctgtgtgt gcgtccacct atgcgtctgc gtgtgtgtcc atgtgtgtcc acatatctgt    4800
gtccacgtgt ctgtgtccac gtgtctgtgt ccacgtgtgt gtccacgtgt gtccatgtgt    4860
ctatgagtcc ttgtgtgcat ctgtgtgccc gtgtgtctgt gtgtctgtcc cctgcagtcc    4920
ccgtggacct gtctcttata cacatctcaa cctggcagcg cccccttcagg tccatggacc    4980 agggacccca gggtggactg tgtttacctt cagcccaggc cagtttcctg cttgagaaag    5040
cccgggaggg ggtgcgggac aggcccgggc ccccacgca aaggcagttt cgcaatgtcc     5100
ctgcgctgac tgaaatgtca ccaggcacac ggcttgaatt tctcccccag acctggcagg    5160
ggcgggggtg gggcaccgg gctgctggga tcttggcccc tgaacctccc ccggccctgc     5220
ggccagggag ggtttaggct gagtgacagc ccacggaaac ctggacccga catgtctgtg    5280
tgtccatgtg tgtctgtgtg tgcgtccacc tatgcgtctg cgtgtgtgtc catgtgtgtc    5340
cacatatctg tgtccacgtg tctgtgtcca cgtgtctgtg tccacgtgtg tgtccacgtg    5400
tgtccatgtg tctatgagtc cttgtgtgca tctgtgtgcc cgtgtgtctg tgtgtctgtc    5460
ccctgcagtc cccgtggacc tgtgtggtct ctggtgtgca gccctagccg cggcccgtcc    5520
caggctgagt gtccccaggg tgcagcacag ctgtgacgag ggtgtgggtc ccgctggccg    5580
tgtcgctggg ctgtgggccc tatcctcttt gtggctgctc tgcaaggcct gatggctttt    5640
gtgtggcctg gccgttcggg tccatgcccc ctggaagagc aacgtctgag ctagctccac    5700
```

```
gcgtgggtcc atctcggccc aggtttaatg agccactttc aggcagggat tgcacaggag    5760
gcagggtggg aagtggctct gctcagaccc ctgaacaggg tctggagatt ctccaagggc    5820
acaaaagaac ggacgatgcc cctggggtca gcgacaatgc tccctgagaa atcttggcac    5880
acagggctgg gcctgcgagg tggcccctcg ccccacccca gcctcctgga ggacaaccgt    5940
cgccctgctc ccagagctgg ggggcgccac acgtggggca cagggagcat gggcccgatt    6000
ccaggcctgg gctccctctc gtgtccagga tctccccgtg tcttgtctca acaagcccct    6060
gacttggagg ccccagggtg acccctttaaa gggggaacag aaggttctag aaggagcgtg    6120
gccagctttg gcttccctag ggctgtggtg accacactgg gccacggccc aggccacccc    6180
acccgcctcc ttcccctggg cccctcccct tcccgcacc tctccctggc ctgcacctgg    6240
tgacacggct ggctcccagc cagggctgag ggggaccagc ggggcccctt cctggaagcc    6300
cacctgcagg ccggcttgct gggaaggggc ctgctcctcg ccggcccac ccgcccgggg    6360 ccgtttcctg gaagcggtca ctggatattt tgttccttgt cagcgccgag cttgcataaa    6420
gcagacactg agctccttgt cctccgggag cacgcgctcc atcaccgaac acctggccgg    6480
acacaggcgg gcagccgggc ctgggggagc agcgcgggcc tggggccgga ccagcaaacg    6540
atcacggcgc cgagcgcagg gcccgcgccg cttctgcagg ccgcccccac gtgcccaggc    6600
ccagcggtgc ccatcctgca ggctggggag aggctgtggg cgcagagctg agaagggggc    6660
agaggcactg ggggggggaca gccgtgttcc cacactttgc agaaaccttg gccggcctgg    6720
atgtcttgct gggagagctg ggggagggga cagggcagga agccggtccc ccgagcgggg    6780
gtaggaagag gcctcggccc tgggaggagg aggaggggag ggcagtgaga tggaaagagc    6840 accagggggct cgaggcttct ttctggaaca aggactagaa ggaggaggcc gggcagctgc    6900
ttgggatgct tggaacaggc cggccccagt gctgacaggg acgtgacctg ggggccggtc    6960
ccgggcccag gcgggctggg agggcgcctg gtgggtcagc gccactcaga gccctggcag    7020 caggggggcct gggcacggct gcaggacaga gctcaggaca cagatggggg cgaggactga    7080
gtggggcacc acagatgctc ccaggaggtg gccaaggagt ggccttggga tcccaggatg    7140
gccctggtcc cagaagatgc ggcagcccaa gggaccaggc cagggccgca gggggccaca    7200
atctgagcag ggctcaggcc cagggcagag gccccctccc acccagcccct ccctgggccc    7260 gcctctccgt gcaggcagtg ggctcagatg gggcagacat gagaccaggt ccagggagaa    7320
gcggggcccc ttggcttcat tcaggtggct ttcagaccgc gccccgtgcg tggcaaggcc    7380
cacagcgctc aggagcacac agaccccac cacgggctcc cccaggttgg gcggtgacat    7440
cagccctgtg tcaacagcag gagctggcag ctcccaccg gggcttaggg agcggggacc    7500
ctgagccacc ctgccaccgc cccacccac cgtggcccac acgagggccc gctgctctgg    7560
gtctggggcc aaggcccccc aggcgcctgg cactgtctgc ccctcccgct ggctctccgt    7620
ctccagtgtc cccgccagag agcatggggc cacaggcctg aatgccaccc tcttcctccc    7680
tctggagggg gcctgaggtt ttgggggttc acagagtggc ctccggggtg ggtccaggcc    7740
cagcgaggca aagcggaccc cagggagtcc cgcggaatgt gggacagccc cccgtagat    7800 ctcgggggg ccaagctctg gttgacctcc atcctggggc tgtgggcctt tggtcagtgg    7860
ggagggtcat gacacccagc ccaccagctg gtgacagccc tggacgtgcc ggctcaggcc    7920
tggcctgccc ctgcagcctt gaaccccgt tctctgggag tggggcgca ggggcgccg    7980 gggcagggtg agagacgaga gcctctcttc ccagaacttc tgcctgcgat gaggacccag    8040
```

-continued

```
cagggccctc tcctcaccag agggcctctg ccggctgcag ggcccagag aggcccagag     8100 gctggaggcc gggccttggg aagaggccgg acttccagaa accagctgcc cgctccgcag     8160
cacccagcgc ccacttggga gggggcgcg ccccgtgcc ccgcccgggt ccactgctgg       8220
ggccgccaca ataaagtttg tccctgctgg ttactgtccg tgtctgagag gtttctggag     8280
cctggccaca atgggcgtca ggatgcggct gggagggagc ctcgcgagtc agagtgtgct    8340
ggtctcggac aggccccggc gccccagcc cgtgctctgt ggacagatgg gtgggtgggt     8400
gggtgtcgga gggggttgga gagggtgggc gggacgaggg gcttcctgca ctctgtccca    8460
gggaagcggg gaccaaggag gggacagccc ccggtcacca ggagggtcct gtccctctca    8520
ccccccggga caggtgagct ccccggagcc gcccttctgg acaggacccc acggccagg     8580 ccacggcccc cccaccccg tggtccctcc gtcccacggc cggcctgggg ggccacgggc     8640 cagggcccc cgctccccgt tggccctccg agggtgaacg acctcgcctg ggacgtgggg     8700
cagagggcag cgccaagag tgaccccctg ggacacgtgg ctgtttgcag ttctggaggc     8760
agccgagata aagcggctgt tttcccagtg ggctcagggc cagagggggg cgaggggcag    8820
ccccagtcaa ggccgggccg ctgcctcggg ctcccctctg tgcggaggga ggggccggt     8880 tgcacagcag ccctgcccg ccgcccgccc gccggcgcag gcaccgtggg acccggcctg    8940
gtgcccctcc ccgccccctg ctcaggggcc agccctctct ggttcccagg acgccccgc    9000 cccgcaggcg gccagagagt cccagagtgt tagcctccca cgtgtgggat cctgtcatat     9060
gcgacagctt aactcaggcc gaatttcatg ggtcctggat ttgggtgggc acggcccctg    9120
cacagcgggg ctggaagcct aaggcggtgg gcgtgggggt gagaggcccg cagacaacag    9180
gagggaggct gggacacttc aagggttgac atgctatgcc tgtcacggat aaatgc        9236
```

<210> SEQ ID NO 119
<211> LENGTH: 5349
<212> TYPE: DNA
<213> ORGANISM: Pig

<400> SEQUENCE: 119

```
agatgtgtat aagagacagg ggctgggtgg gaaggacaga gggtggggcc ggaggaaatg      60
ggatgcagag cccaccgtgc acgctctgct ggcctttgag cctcgctgag tcgcaagaag     120
ccctcgggcc tggaaacaga ccccggccc ccaccccac cccggccccc ggattacccc      180
ggcatggctg gagggcccga gaagccaccc aggcttcccg tgccgagctg ggtgctgggc   240
ccagccgagc gggcttgacg ccacgcttag ccctccccag ggagcccagg gtcggaagga    300
agaggccggc cggagggccg tggccgctca ggctggaggg ggcccccggg tcaggatggg    360
ccccagacgt ccccgctccc cggccatccg tcacggagct gtcacccagg aacgtgctcc    420
agacgtgctt tcctgccgcc gaggccccga gcaggctcca ggcgccccca ccccgaacg     480 cccacgcaca ccctcggtct gcgaacaccc tgccgtcatc cggtggcccc ggttcccgcc    540
gcccgcgcca tccgggtgcc ccttcctccc tgggtcgggg gccatgccct cagcgggcac   600
gcaggcctgt gcaggtctgt tctgactctt ccccaaagac gcaggccggc tgcgggcgcc    660
ccgacctcgt ctgaggcccg tttgtgctca ctggctgtct cagaaagggg tgcccacggg    720
aagcgcgtgt tccttgggcc gcaaggcaag ggagcccacc ccaaggtggc tgagggcaaa    780
tggcccaggg cctctaagga gtccctgggg gccgggccgg cctgcagctt gaggaggaga    840
gccctggctc tgctcccccg gcaggtgag cccacgcag ggggctcccc agcagccttg     900
gcaggaagca gtgaggaagg ggtgaggatg aaggcaaggg ggcctgcggg gacttgggca    960
```

```
aagcccctga agaactgagt tcctcggaaa ggccggagcc ctcagccgag cctcggcctc    1020
cgagcgatgg aggcggccca cctgcggccc caggtgcag  ctgtgcatcc gtcccctcg     1080 ggcctcccc  tgccccccg  gccaccacac tctccccctt ttgcctttga tcacttgagt    1140
gcgacagctt gtgcggcctg agcccagag accgctgccc cctgccgcc  agcccacgg     1200 gagcgtccac ctgggcctgg cctgggcact catccctccc ggatgaggcc tttctagcct    1260
gggccgcccc gggagcggca gacccagccc ctcgccccc  tccccagtg aaggtgctgc    1320 ctggtggtct ggggaagccc ctggaacagg ggcgcaggt cccacacggg tgctctggcc     1380
tccagctgcc agggagggcc gcgctcaggc cagggtcccc tccaccagaa ccgccagggc    1440 cctgggaaa  acctgtctgt gctaacaggg ccgctccccg ggactccacg gagaggtgcg    1500
agggacccct gagcacccac cgccactaag gggcccagcc agctcgcggg tgcaggcagc    1560
cggctgggcg ctcacatgca tactgctctc tggctttgtg tgtgcgcctg ggttgggggtg   1620 agcggaggtg cccgaaggcg gaagagccca ccctccactc ggggacctat ttcagcaaga    1680
agacggatgg gactgccggg catggacaaa ggaacaggat gaaccttctg gaacgcacaa    1740
ggcttccacg gctgaccggt cataggaagg cgcgtctcta ggccaatcca ccgtccaccg    1800
tccattcccc agccctcgag aggggggcagg atggaccgct gcagcgtgag agagctctgg   1860
ggcgctccca cagggcaaag tcccagggca ctgacctcag agcccaacca ggccaccggg    1920
gctgggccca ccaggagcc  ggggccaggg tcagggtcag ggcccagagt gcgggaaagg    1980
gtggcgtgtt gcttgggcg  gcgggcgcgc agacggcccc tcgcacccc  cgacagcccct    2040 ggagctgagt gaagcccgcg ggtcaccttg ctgggggttg gggtctcctg cgaccggcac    2100
cccagctcag gtcatccttg ctgtaccgca gaggggcagg ggttctgagc agggacaggg    2160
tgggccgcgc aggaagcccc cttctctctg aggctgcccc ggccctggag cctctctggg    2220
gcatgccacc cctctcacag acgcctccca ggagccccca ctttcctgct gcgtggtgag    2280
ggtgtctctc acccgattcc tggcccctgc aggtcgagtg agtccctgct aagcctgggg    2340
ttggagcagg tgcagggcat caccacacag cagcagaggc tgtgggggcc cctgagaggc    2400
gctcccaggt accctcctca ggggctgag  cccggggttg acccgggacc tcgcctgccc    2460
caaagccggc gccctcctcc cgcccgcccg accaggccaa gagaagcagg tgtggggcgg    2520
cacaaaccca agtcagcttc cagatcctgc tggggccgcg ttgaaactcg aagcccccag    2580
gctgggaggt ctagacaccc ctgcccagac cgacagcctg ggcctggctc acagctgcct    2640
ggggccccag gggtgcacct gccctgtggg tgggggtcag agggcaggga accctcggga    2700
aggtccccca gggtcaaggt tgggcctaag ctccggtgac ctctgggaag tctggggctg    2760
ggttttgttc ccagaggaga gagggccagt agcctcagag gggctgtggc acggtgggaa    2820
ggccccaggt gaccccagag cgtgcgaagc aagccccctt gactgcaaag cgcaaagggc    2880
agaggtgggg tgggagcctc gacccccga  gcccaggtac acaggggaa  gggcgaggga    2940 tccggcaggg gccacacccg ccaccccagg cagcccacaa agcctttggg cccggagccc    3000
cagatgggcc cagcccagct ctggaacag  tcttcccaga attccccagc tctgggtacc    3060
aacagggctg cccggccccc agagccctcg ggcgggagac ccttccccag ggggatctcc    3120
taagtggcaa ggcctgttgg gaggggctgg tgagaggcca ctctggcggg aagaccccca    3180
gccacctgga gccccagcc  actgcctgct gcggctccct agggatccag ggccatcaga    3240
gaagctccag cgacactgtt tatttttcaaa tgacactttt taagaaaaac agcctcaccc   3300
```

```
aaatgcttgg ccctgagtct ggaatgtgca gacagacagc tgcccctccc cagagcctgc    3360
acggccctcc gggtggggga ggagcagggg gcacccctgg gaccgggccg caggctgtca    3420
gggcacggaa cgtgtctctg ggccctgtcc tcaattcccg gtgcccagtg gccccaactt    3480
cccagcagac ccagcagggc cccagcttgt cttggcctgg ccgctggtcc tgtcacccca    3540
ggcctggagt tctggaagat tctgctcctg ctcccgtgtg cacataccac tccccggggc    3600
agccctgcac ttctgttcct gctgggctcc ctgcctgcat ccgtgaggcc tgcagcccgc    3660
ctgatcttcc aggtcctcct ccgagccccc gcctccagga agccctccag gagagctcag    3720
gagggtcggc tccctgcgcg cagctgtcag acccctgggc ccaccccgcc ggctgctagg    3780
gtccaggttc cccacaagcc ctcgggcaga ggctgggccg ctgggtccct cggagacaac    3840
tggctccgag gccttgccct agacgggttt ccgggagccc gtcccagcg gcacccactg    3900 agttttgaac acttggcgcc accccacac cccaggcggt ggccaggagg cctcctgggc    3960
agcagacagt ccgtgaggtg gccctggggt ggctcctgac ctgggcgctg gcccagccct    4020
gggcacagct ttccagatct tgcctgccgc ttcctccagg ctgcctcggc ccctcccgcc    4080
tgggggtgcc cagcttttcc tggaggatgc ccacccttgc ccatggtcag ggaggggctg    4140
agaaacccca cctcgtgcct ctgcccggcc tatgccaggg gaaccaggtt ccctcccgca    4200
ggaggggacc gagtccctga cagcccactg cagaggggag gaggtgcctg gctctgcccc    4260
cagccccacc aaccccgtgg cttcctgttt cgcagcccac aaagcactaa aggccgcagg    4320
tcctggaaca tcaaagaccc gggaagtcca ttgtattgaa ttgagtgtaa atgagcctga    4380
ggcctgtggc ttgcgtttcc cacaattacc gctgcccggg aagggctccg gaaccgacac    4440
agcccccagg gccccttgcc catgtgggga gcccaggctg gcctgaagaa gccccataag    4500 gtggaccccca ctttgagccc ccacgagagt gggccaagga ccaggtcagg ggctgcccag    4560
gctctgggcc tcctctgcct gccaggtggg ctccctcggg gcccagcctg gcctgcagga    4620
ccttcccacg ctgagttccc cagcctggta tgagcgtagt ggacggcagc catgcccagc    4680
actcaggggc ctgagggaca gagcgggaac tccagccccc gggtcctcgg ccctaggat    4740 ccttctaggt ggggaagccc aagggagcag agggtgaac gcagctgtgt ggggcccag    4800 gctgccgagc agaccctcc tgctccactc ctcggccgag tgggcgccga gatgccgggg    4860
cagtgccatt tcccaggcgc caccggaggc tcccagaggg agtgaggcac gagctgggag    4920
ggagggcggg ggggctgggg aagcagagag cggaggccgg aggccggtga ggaggcccgg    4980 aggggggcctg gagtcaatga cccagggatt atcgtgctgg gtctttgcaa agttggctga    5040
gcaaacgccg gagccaaggg tcagggagac gggactggcg gggccccgcg gcccccttc    5100 cccttctctgg aaaaagcctg tttcccaggt caaaatccag ctcatgatcc gccccctttg    5160
ggactgatgt tcagaggccc agtggtccca gcacctctgt ccaccgcccc cccacgctc    5220 ccggggccgc caacccctgt gggctgcgag gtgcgggcac ctctcccttc gaagcaaagc    5280
cctgccctgc gtgggcagcg tgatttcctg cttctctggg gctgcacttt gactggggtg    5340
gggggtgg                                                            5349
```

<210> SEQ ID NO 120
<211> LENGTH: 1593
<212> TYPE: DNA
<213> ORGANISM: Pig
<220> FEATURE:
<221> NAME/KEY: misc_feature
<222> LOCATION: (1551)..(1551)
<223> OTHER INFORMATION: Nonspecific nucleotide

<400> SEQUENCE: 120

```
agcccctcag cccctccgag cagctgctgg gctcagcggg ctcgccccc gatgtgcggc      60
cctccataat caatcatgga gggccgggcc cggggggggc gggccgacct gtcagccagc    120
tccaagggca gggacagctg ctgttccgga gggttcccag gggccagccc caccagacag    180
cggcctcggc cccccttccc cgaggggcac ccccacggag ggcccagacc ggagggactc    240
ggggcccaga ggccagggca agagtgaagg cagcgccggt gggagcggcg gtcagcgggg    300
tccaggcttc agttcccaag gagccccatg ccctgagccc gcactgagcc ctgtgcagcc    360
tgtgggtgcc gccgaggccc gccaccccgc ccccaccag cctgggtcg aaggagggag      420
ggggtggcct gacggatggt aacagctgct ccccccacct cgccggcgtg gacagggctc    480
gcttctcctg cccgagcccc cggctgcccc atccgtcacg gccacccag gactgtgcgt     540
ccagcctccc tccctcctaa tcccccgca ttttccgaat tctcgggcca ctgctgcttc     600
ctcctcaaat tcctggcccc cctcgcccca tcccgccat gggaaagggc cgcgatgcca     660
ggacacttgc tcgtctcggc cgggcggggg gaggagcagc tggctgggcc cggcagctgt    720
gaggtgcggg ggtgccaggg agaagggccc agattagggg gcgtcatggg aaagctggga    780
gggaacgcta cccagagccc ctcctgccgc agcctgtgct gctccctctc cgcatttctg    840
gcctctgagt gctccctgga gggaagggac cactgtgtcc tgccggcctc tggctctgcc    900
aggaatgtcc atctgtccgg gccgggttac ctggctcaga gcgtgggtac cagctcatcc    960
agccctgacg cctgctctcg ggaacagtgg atgggccagg cgcccccgtc acaccccgca   1020
gctgggctcc acagacgggc ccgggatggc cacggaggtg ggggcggcc ccagggcgag    1080
gctccctcct ggaagggcta gagtgtgggc tgcgcggaga gggaggccgg acggccaggc   1140
caggtgcagc ccggggcagg tgctggtggg ggctgtgacc cacgtgtgca gctcaagggt   1200
ccaggagccc cagggacaga gcctcaggga cagaccctca gagccacagc aggaagcctg   1260
gtggcagtag ctggcggggc cgtgggggtgc tcggccctgc agacagaggc agaggcaggc   1320
tccctgctga tgacaggggc tttctctgtc ccctgggggg cggaggggc ccgaccatgg    1380
accccgggcc tcctctcgca cgattcccag gccagcctgg tctcaggcag tccaaggttg   1440
cacaatggtc tccatcgtcc agagttcag agccagcact ctcccactgg acggcggccc    1500
ggggtgggct gcaccgccgc tcagggctca gggccgcggc cggccagccc nccgcaggcc   1560
ttgaccctgt ctcttataca catctcaacc ctg                                1593
```

<210> SEQ ID NO 121
<211> LENGTH: 831
<212> TYPE: DNA
<213> ORGANISM: Pig

<400> SEQUENCE: 121

```
tgagatgtgt ataagagaca ggccttgacc ctgggcctgg ctcagctgcg cgccctcctc      60
cttgcagctc cgcctcgacc ccatccatca gccattttcc tacccttcct gtaataaaaa    120
acccgaagcg gcgtggcccc gtgtccgctg gggtgactgc ggcctgcctg ctggtggctc    180
ccacctgggc ccggcccct gaaaacacac acccggcgat ggcttgcccg ggcctggt      240
ggaggggcgg ggggcctcgc ctgcctcttg tctgaaattt tcggtccac atgccccgac    300
tcctctcccg gccacccctg caggcccggc cggtgcccccg gccactttcc cgaaggacgg   360
actcagcatt tcccagggca cctgctgatg gtgcccagac cccgggggcc ttcccgccgg   420
```

```
gcgcggcccc acgtcgcccc tccagtggcc acagcgggcc tgggccaagg ctgggagttc      480
tgcacgggcc tggggagga aggcggggga gagggcacag tctcctggcg gggacgaggg      540
tgggggcagc agtgggag ttcccacagc cggggcagcg ggacgccgct tggctgccct      600
gggtctcagc cggggacagt gcccaccagg agagagacgg cagacagtac agcccacccg      660
ttttatatcc tctcaggcgg tctgtgcttt attggggtaa atatgcagga catagaaact      720
ctgccactgg accccttggc cggggacac agcagcggca ttgcatgctt tctgggtgca      780
gcgcagccag caccaccggc cagagcaccc catcttcccg atcaaccgga c            831

<210> SEQ ID NO 122
<211> LENGTH: 4636
<212> TYPE: DNA
<213> ORGANISM: Pig

<400> SEQUENCE: 122
ctctgggcta gcaccgtggg ggctttgcca gagtggaact gaactgggtc caccccggag       60
cccagagggc ggtgaatggg aggcagagcc catcctggga atggaccaga agaaagggag      120 cggggggtggg ggaaggggca tcagatcctg gtccttcctt gtcgcctgcg gtccctctgc      180
caccactccc cgaagctgat ctggagcaca cgcgtcgtta aagccgccat cgaggcccca      240
cttctgacag acgaagggg gcagagtgcc ttcctcaccg gcctcgccct gggaaggccc      300
ctccctgcag cccaggaagc cagcagcagg tgacagagcc aggggcccag ggccccaggg      360
acgggctcgc gcgcccgagc cggggggtccc ttggcgtccc catcctctcg tcctggagcc      420
ctcctgggtg accacaggaa tgtgcaaggc ggcagccggg tggcggccgg gaggcgggtg      480
ggaggcgggg gggtggcct cttcacgggc gggcctgaga gatgggcgcc cgtccggccc      540 tgcgtcatc gtctccgcgt ctctacccac tgagcaaaga cacacgaaat gaagctcgaa      600
cgagcacagc caaagaacgg ccgtttctgt cctttcttct taatccctt ggcttagggt      660 ttcccggcct ggacagcctg cccaagggca catgggcatc cgtccgggga cattcaggca      720
gtgaccaatc ccaggccacc caggctgtgc cctgcgtcgt gggccatttc ccagccggcc      780
agagatggag cagccactgc gggtccccga gtctcggtga cagtcaag gatggacctt      840 ggatggagac cggcgtgcgg ccatgtccgt gggtgaagga ggcgtgcagg ccgtgctggg      900
ggacatggtt gctgtcccct cggccaaacc atgaaaagca gccctctccc caacccccca      960
gcaccaaccc ggagaccacc ctcggccgga gcccagcacg gccaccgtca cgtctcggtc     1020
gtccagcttg gacaggtca gttcccagat gtccaggctg gagctggtcc ttgaagatcc     1080 tagggggtcca gcccagcaca ggagggccag gtgagagccc cctgtggttc taaggatgca     1140
accagggggc ggcggggtgc ctgccctaga ggggtaact cggcccctg gggaccagtc     1200 accccaggag gtccccagag cccagctcgg agggccacag gtgcccagag tcccacctgg     1260
ggaaggctgc cctcctgcc agcccccgag ccgggcccct ggcgcccgcg tccagccgcg     1320
accccgggga gatattcacc ccctgccccc gtgaatcagg aggccccgag cccatgttt     1380 cagtcctttt cctcccatcc cagcccccca ggagaagagg tgctgaactg gtccccctgg     1440
aggctcctga gccccagaac agtgccctct gagcagacgg gcactctcag accagctcac     1500
gctggacaag tcagctcctg cctgccgcct gatgggcct tggagaagc agacatggtg     1560 aggaaaaggc ccctgtgccc ttcaccctaa ttcccagcc ccaagtccca ctgggttgcc     1620
agcttcaacc taagcaaata attcgtgccc tctaaacaaa cgcgcgggaa tcccacctgc     1680
ccttcccccg cccgcccccc cacccctggc cttgacctcc aaaagcactt gagggggctt     1740
```

```
tctccagaca ccctccaacc ccgaccccat gaagaagggg tgatggggct gttaccccaa    1800
caagcaagag aacgaagccc agagaggagt tggcgtggac agcagggtc aggccccttt     1860 gccccgaggg cagggctggt gccacctggg tcaggcggca ggccctggaa aagcaccgga    1920
aatgagcaca cctgggtctc tagaaggttc ttccagacct ctgggggctg agtcatttca    1980
acactcctgg gccgggcagg gcttcttctt ggccccgagg acaaggtcc ccttcgtccg     2040 gggggtacgg cccctggacc cctgtccccc gcaccccacc ctccgcctgg tgagggccgc    2100
ggccagctct ggacacagat ccctcagagc cccttctccc tccctgctcc ctcgtcttcc    2160
caagatgccc cggcctccag gtggggcagc caggcggcag aatgtggtcc aggcctctcg    2220
gccccaccca cacccccctg ctctgccctg acagcctcca agacgcaggc acgtcgctgc    2280
gttctgcgtc ctgtctcctc atggcacaaa acggtgcccg cctagcttcc cccagagaag    2340
ggagatcgtg ctccccggac ggaccctgct ctgcctgtcc tcccgcccgg ccttcagggc    2400
ctctccccaa gggtggccgc gaggaggccc tcgcctccgg ccacgggggc tccatcctcc    2460
cgagcccgac aggcctccgc ctggtggtcc gacctcttcc ccaaggcccc gcccatcctc    2520
ctcgcgctcc cccaaaccct gcctctttcc ccagcgccct tgtccccacg aagacccctc    2580
cacccgtgcc attacacgct ctcgcccac cctcccagcc accccccctt cccatcctc     2640 ctggaagctc ccacttcctt cccgtctccc acggcagcag agggtcagca gctcaggggt    2700
cctggggccg tggagatggc ctgcccgggg gtctcgctga ccgcctccta cggaagctgt    2760 gccgggggt gggggtgtct ctgcccgaac ggctggagga cgagccacat cccagggcag     2820
ccggaacctg cgtcctggtc tgagacgag aggctgggtg caggtggctg aggggcctgc     2880
acacagcttg gcctggggtc ccctaggtga caacactggc tgaacactca ttgctgctcc    2940
ccttccaggg tgaccctggg gtccccgtgt ggccctcagg gcacacgggg gccccaccag    3000
gcctcacaga accccagtgg gactgcaccc agggcccaca gaagtgcggg ggcactgggg    3060
gtccagaaac aaccccacaa ccaggccaag gtggccaagg ccttactcga gcggggctgc    3120
ccgtcccaag agactctggc cagtcgtccg gatccagctt cccggggccg ggccgcccgc    3180
tgggctccag gcggttctgg ggggccctcc cccgggggtt cgccctccgc tctcagcagc    3240
aggaagagga gcgcggccag cggatgggga gaagagggcg ccctggccat cttgctcccc    3300
ctgggacttg aggagggtct cgggccgggc aggcgggacc gggagccaca gagaccctgg    3360
aggaggcagc atggcgggga ggtgaccggg aagaggggcc gtgtcccagg ctcacagccc    3420
ggcctggccg cccggccctc gggaggcgtg ccgctgaccg cctggccggg aggtttgctg    3480
cgtgtggggt ttgcagaaag tgctgagctg ctgagcccac aggccaggct cagaggggac    3540
aggaaggagg ttgctgccca gcctcgggca ctgctgaccc atctcccgtt tccagggcac    3600
cagagccacc taatctgccg gctctgtgcc cagggacagg cttgcctgat ctctcaaggc    3660
cgggcgctcc gccttccctg ggagagggtt aaacatccag ccccagccag catctcgggc    3720
aggttcctgg ctccccccgc tcgtgcctcc tctgagaccc tggtcggcac acctttccct    3780
tgagaggagg aggaggagga aagcggatgg aaccagtgac cctgcagccc ctgagggcac    3840
cttcccacgt gccccgccc gcccgcgtc ctccgccccc agttctcacg gccccagtcc     3900
tgatggaggg agggcgacct ccgggctccc tggctcccgc cggctccgga agacagggcc    3960
gctcggctgg ggctgcaggg aggggcccga gacgcaggag agcagcccgg aggcaaaccc    4020
cgcgggtctt ccagaaggag gcctggcagg gggaggggg tgccaccact gctgtccctc     4080
```

```
                                    -continued
tcgtgccaca gtggagggtg tgggtgggca gtgccggggt gggaagtgca gaaagaccct      4140
ggaccgtggg gctgggccgc cacgggggag cggggtctgt cagggaccct gggggaggga      4200
ggcgaagggc tggggcagag gccggatcac ttccagattt gctgtgggac caagggccgg      4260
acctcggggt gacttctttt gtgtgctggc cacaggggg ccccggcgag gtcacacgga       4320 aggggcttc ggacctggcc taacaagccc actcccgagg aagatgcaag gggaggcaga       4380
cggaagggcc gaagggggcg atcggggac accgcggcag ggccggggca gagaagggag      4440
gcagagggca gagaagggag gcagagggca gagaaggag gcagagggc cacatgcttg       4500 gagggccagg gaggagcggg aacggcgtcc ggcgtccagc gccgaatcag gcccgtcagg     4560
cggagggtgc gtggacctgc ctggccttca cgagcacagt cagcaggctg tctcttatac     4620
acatctcaac catcat                                                     4636

<210> SEQ ID NO 123
<211> LENGTH: 482
<212> TYPE: DNA
<213> ORGANISM: Pig

<400> SEQUENCE: 123
agcaatgggg ccgtgaccta aggaggcagg cccaggtcag tggggtgacc tctcgtggcc        60
ccgatgtttg gaaatcccca aatcaaaatg acccatccga caagcttgca tgcctgcagg       120
tcgactctag aggatccccg ggtaccgagc tcgaattcgc cctatagtga gtcgtattac       180
aattcactgg ccgtcgtttt acaacgtcgt gactgggaaa accctggcgt tacccaactt       240
aatcgccttg cagcacatcc ccctttcgcc agctggcgta atagcgaaga ggcccgcacc       300
gatcgccctt cccaacagtt gcgcagcctg aatggcgaat ggcgcctgat gcggtatttt       360
ctccttacgc atctgtgcgg tatttcacac cgcatatggt gcactctcag tacaatctgc       420
tctgatgccg catagttaag ccagccccga cacccgccaa cacccgctga cgcgaacccc       480
tt                                                                     482
```

SELECTING ANIMALS FOR PARENTALLY IMPRINTED TRAITS

CROSS-REFERENCE TO RELATED APPLICATIONS

This application is a national stage entry under 35 U.S.C. § 371 of International Application No. PCT/EP99/10209, filed on Dec. 16, 1999, and published as International Publication No. WO 00/36143, in English, on Jun. 22, 2000, which claims the benefit under 35 U.S.C. §§ 119(a) and 365(b) of European Patent Application EP 98204291.3, filed on Dec. 16, 1998.

TECHNICAL FIELD

The invention relates to methods to select breeding animals or animals destined for slaughter for having desired genotypic or potential phenotypic properties, in particular related to muscle mass and/or fat deposition.

BACKGROUND OF THE INVENTION

Breeding schemes for domestic animals have so far focused on farm performance traits and carcass quality. This has resulted in substantial improvements in traits like reproductive success, milk production, lean/fat ratio, prolificacy, growth rate and feed efficiency. Relatively simple performance test data have been the basis for these improvements, and selected traits were assumed to be influenced by a large number of genes, each of small effect (the infinitesimal gene model). There are now some important changes occurring in this area. First, the breeding goal of some breeding organisations has begun to include meat quality attributes in addition to the "traditional" production traits. Second, evidence is accumulating that current and new breeding goal traits may involve relatively large effects (known as major genes), as opposed to the infinitesimal model that has been relied on so far.

Modern DNA-technologies provide the opportunity to exploit these major genes, and this approach is a very promising route for the improvement of meat quality, especially since direct meat quality assessment is not viable for potential breeding animals. Also for other traits such as lean/fat ratio, growth rate and feed efficiency, modern DNA technology can be very effective. Also these traits are not always easy to measure in the living animal.

The evidence for several of the major genes was originally obtained using segregation analysis, i.e., without any DNA marker information. Afterwards, molecular studies were performed to detect the location of these genes on the genetic map. In practice, and except for alleles of very large effect, DNA studies are required to dissect the genetic nature of most traits of economic importance. DNA markers can be used to localise genes or alleles responsible for qualitative traits like coat color, and they can also be used to detect genes or alleles with substantial effects on quantitative traits like growth rate, IMF, etc. In this case, the approach is referred to as QTL (quantitative trait locus) mapping, wherein a QTL comprises at least a part of the nucleic acid genome of an animal where genetic information capable of influencing said quantitative trait (in said animal or in its offspring) is located. Information at the DNA level can not only help to fix a specific major gene in a population, but also assist in the selection of a quantitative trait which is already selected for. Molecular information in addition to phenotypic data can increase the accuracy of selection and therefore the selection response.

Improving meat quality or carcass quality is not just about changing levels of traits like tenderness or marbling, but it is also about increasing uniformity. The existence of major genes provides excellent opportunities for improving meat quality because it allows large steps to be made in the desired direction. It will help to reduce variation, since we can fix relevant genes in our products. Another aspect is that selecting for major genes allows differentiation for specific markets. Studies are underway in several species, particularly, pigs, sheep, deer and beef cattle.

In particular, intense selection for meat production has resulted in animals with extreme muscularity and leanness in several livestock species. In recent years it has become feasible to map and clone several of the genes causing these phenotypes, paving the way towards more efficient marker-assisted selection, targeted drug development (performance-enhancing products) and transgenesis. Mutations in the ryanodine receptor (Fuji et al, 1991; MacLennan and Phillips, 1993) and myostatin (Grobet et al, 1997; Kambadur et al, 1997; McPherron and Lee, 1997) have been shown to cause muscular hypertrophies in pigs and cattle respectively, while genes with major effects on muscularity and/or fat deposition have, for instance, been mapped to pig chromosome 4 (Andersson et al, 1994) and sheep chromosome 18 (Cocket et al, 1996).

DISCLOSURE OF THE INVENTION

However, although there have been successes in identifying QTLs, the information is currently of limited use within commercial breeding programmes. Many workers in this field conclude that it is necessary to identify the particular genes underlying the QTL. This is a substantial task, as the QTL region is usually relatively large and may contain many genes. Identification of the relevant genes from the many that may be involved thus remains a significant hurdle in farm animals.

The invention provides a method for selecting a domestic animal for having desired genotypic or potential phenotypic properties comprising testing the animal for the presence of a parentally imprinted qualitative or quantitative trait locus (QTL). Herein, a domestic animal is defined as an animal being selected or having been derived from an animal having been selected for having desired genotypic or potential phenotypic properties.

Domestic animals provide a rich resource of genetic and phenotypic variation; traditionally, domestication involves selecting an animal or its offspring for having desired genotypic or potential phenotypic properties. This selection process has in the past century been facilitated by growing understanding and utilisation of the laws of Mendelian inheritance. One of the major problems in breeding programmes of domestic animals is the negative genetic correlation between reproductive capacity and production traits. This is, for example, the case in cattle (a high milk production generally results in slim cows and bulls), poultry (broiler lines have a low level of egg production and layers have generally very low muscle growth), pigs (very prolific sows are, in general, fat and have comparatively less meat) or sheep (high prolific breeds have low carcass quality and vice versa). The invention now provides that knowledge of the parental imprinting character of various traits allows to select, for example, sire lines homozygous for a paternally imprinted QTL, for example, linked with muscle production or growth; the selection for such traits can thus be less stringent in dam lines in favour of the reproductive quality. The phenomenon of genetic or parental imprinting has never been utilised in selecting domestic animals; it was never considered feasible to employ this elusive genetic characteristic in practical breeding programmes. The invention provides a breeding programme, wherein knowledge of the parental imprinting character of a desired trait, as demonstrated herein, results in a breeding programme, for example, a BLUP programme, with a modified animal model. This increases the accuracy of the breeding value estimation and speeds up selection compared to conventional breeding programmes. Until now, the effect of a parentally imprinted trait in the estimation of a conventional BLUP programme was neglected; using and understanding the parental character of the desired trait, as provided by the invention, allows selecting on parental imprinting, even without DNA testing. For example, selecting genes characterised by paternal imprinting is provided to help increase uniformity; a (terminal) parent homozygous for the "good or wanted" alleles will pass them to all offspring, regardless of the other parent's alleles, and the offspring will all express the desired parent's alleles. This results in more uniform offspring. Alleles that are interesting or favourable from the maternal side are often the ones that have opposite effects to alleles from the paternal side. For example, in meat animals such as pigs, alleles linked with meat quality traits such as intramuscular fat or muscle mass could be fixed in the dam lines while alleles linked with reduced backfat could be fixed in the sire lines. Other desirable combinations are, for example, fertility and/or milk yield in the female line with growth rates and/or muscle mass in the male lines.

In a preferred embodiment, the invention provides a method for selecting a domestic animal for having desired genotypic or potential phenotypic properties comprising testing a nucleic acid sample from the animal for the presence of a parentally imprinted quantitative trait locus (QTL). A nucleic acid sample can, in general, be obtained from various parts of the animal's body by methods known in the art. Traditional samples for the purpose of nucleic acid testing are blood samples or skin or mucosal surface samples, but samples from other tissues can be used as well; in particular, sperm samples, oocyte or embryo samples can be used. In such a sample, the presence and/or sequence of a specific nucleic acid, be it DNA or RNA, can be determined with methods known in the art, such as hybridisation or nucleic acid amplification or sequencing techniques known in the art. The invention provides testing such a sample for the presence of nucleic acid wherein a QTL or allele associated therewith is associated with the phenomenon of parental imprinting, for example, where it is determined whether a paternal or maternal allele of said QTL is capable of being predominantly expressed in the animal.

The purpose of breeding programmes in livestock is to enhance the performances of animals by improving their genetic composition. In essence, this improvement accrues by increasing the frequency of the most favourable alleles for the genes influencing the performance characteristics of interest. These genes are referred to as QTL. Until the beginning of the nineties, genetic improvement was achieved via the use of biometrical methods, but without molecular knowledge of the underlying QTL.

Since the beginning of the nineties and due to recent developments in genomics, it is conceivable to identify the QTL underlying a trait of interest. The invention now provides identifying and using parentally imprinted QTLs which are useful for selecting animals by mapping quantitative trait loci. Again, the phenomenon of genetic or paternal imprinting has never been utilised in selecting domestic animals; it was never considered feasible to employ this elusive genetic characteristic in practical breeding programmes. For example, Kovacs and Kloting (Biochem. Mol. Biol. Int. 44:399-405, 1998), where parental imprinting is not mentioned, and not suggested, found linkage of a trait in female rats, but not in males, suggesting a possible sex specificity associated with a chromosomal region, which, of course, excludes parental imprinting, a phenomenon wherein the imprinted trait of one parent is preferably but genderaspecifically expressed in his or her offspring.

BRIEF DESCRIPTION OF THE SEVERAL VIEWS OF THE DRAWINGS

Legends to the Figures

FIG. 6: Nucleic acid sequences of contig 1 (SEQ ID NO:10), contig 2 (SEQ ID NO:11), contig 3 (SEQ ID NO:12), contig 4 (SEQ ID NO:13), contig 5 (SEQ ID NO:14), contig 6 (SEQ ID NO:15), contig 7 (SEQ ID NO:16), contig 8 (SEQ ID NO:17), contig 9 (SEQ ID NO:18), contig 10 (SEQ ID NO:19), contig 19 (SEQ ID NO:20), contig 20 (SEQ ID NO:21), contig 21 (SEQ ID NO:22), contig 22 (SEQ ID NO:23), contig 23 (SEQ ID NO:24), contig 24 (SEQ ID NO:25), contig 25 (SEQ ID NO:26), contig 26 (SEQ ID NO:27), contig 27 (SEQ ID NO:28), contig 28 (SEQ ID NO:29), contig 29 (SEQ ID NO:30), contig 30 (SEQ ID NO:31), contig 31 (SEQ ID NO:32), contig 32 (SEQ ID NO:33), contig 33 (SEQ ID NO:34), contig 34 (SEQ ID NO:35), contig 35 (SEQ ID NO:36), contig 36 (SEQ ID NO:37), contig 37 (SEQ ID NO:38), contig 38 (SEQ ID NO:39), contig 39 (SEQ ID NO:40), contig 40 (SEQ ID NO:41), contig 41 (SEQ ID NO:42), contig 42 (SEQ ID NO:43), contig 43 (SEQ ID NO:44), contig 44 (SEQ ID NO:45), contig 45 (SEQ ID NO:46), contig 46 (SEQ ID NO:47), contig 47 (SEQ ID NO:48), contig 48 (SEQ ID NO:49), contig 49 (SEQ ID NO:50), contig 50 (SEQ ID NO:51), contig 51 (SEQ ID NO:52), contig 52 (SEQ ID NO:53), contig 53 (SEQ ID NO:54), contig 54 (SEQ ID NO:55), contig 55 (SEQ ID NO:56), contig 56 (SEQ ID NO:57), contig 57 (SEQ ID NO:58), contig 58 (SEQ ID NO:59), contig 59 (SEQ ID NO:60), contig 60 (SEQ ID NO:61), contig 61 (SEQ ID NO:62), contig 62 (SEQ ID NO:63), contig 63 (SEQ ID NO:64), contig 64 (SEQ ID NO:65), contig 65 (SEQ ID NO:66), contig 66 (SEQ ID NO:67), contig 67 (SEQ ID NO:68), contig 68 (SEQ ID NO:69), contig 69 (SEQ ID NO:70), contig 70 (SEQ ID NO:71), contig 71 (SEQ ID NO:72), contig 72 (SEQ ID NO:73), contig 73 (SEQ ID NO:74), contig 74 (SEQ ID NO:75), contig 75 (SEQ ID NO:76), contig 76 (SEQ ID NO:77), contig 77 (SEQ ID NO:78), contig 78 (SEQ ID NO:79), contig 79 (SEQ ID NO:80), contig 80 (SEQ ID NO:81), contig 81 (SEQ ID NO:82), contig 82 (SEQ ID NO:83), contig 83 (SEQ ID NO:84), contig 84 (SEQ ID NO:85), contig 85 (SEQ ID NO:86), contig 86 (SEQ ID NO:87), contig 87 (SEQ ID NO:88), contig 88 (SEQ ID NO:89), contig 89 (SEQ ID NO:90), contig 90 (SEQ ID NO:91), contig 91 (SEQ ID NO:92), contig 92 (SEQ ID NO:93), contig 93 (SEQ ID NO:94), contig 94 (SEQ ID NO:95), contig 95 (SEQ ID NO:96), contig 96 (SEQ ID NO:97), contig 97, (SEQ ID NO:98), contig 98 (SEQ ID NO:99), contig 99 (SEQ ID NO:100), contig 100 (SEQ ID NO:101), contig 101 (SEQ ID NO:102), contig 102 (SEQ ID NO:103), contig 103 (SEQ ID NO:104), contig 104 (SEQ ID NO:105), contig 105 (SEQ ID NO:106), contig 106 (SEQ ID NO:107), contig 107 (SEQ ID NO:108), contig 108 (SEQ ID NO:109), contig 109 (SEQ ID NO:110), contig 110 (SEQ ID NO:111), contig 111 (SEQ ID NO:112), contig 112 (SEQ ID NO:113), contig 113 (SEQ ID NO:114), contig 114 (SEQ ID NO:115), and contig 115 (SEQ ID NO:116) derived from BAC-PIGF2-1, which was shotgun sequenced using standard procedures and automatic sequencers.

FIG. 8: Nucleic acid sequences of contig 1 (SEQ ID NO:117), contig 2 (SEQ ID NO:118), contig 3 (SEQ ID NO:119), contig 4 (SEQ ID NO:120), contig 5 (SEQ ID NO:121), contig 6 (SEQ ID NO:122), and contig 7 (SEQ ID NO:123) derived from BAC-PIGF2-2, (the 24 Kb NotI fragment not present in BAC-PIGF2-1), which was subcloned and sequenced using the EZ::TN transposon approach and ABI automatic sequencers.

FIG. 10: DNA sequence polymorphisms in the IGF2 and flanking loci from genomic DNA isolated from Piétrain, Large White and Wild Boar individuals. Polymorphisms 1 through 4 occur in contig 3 (SEQ ID NO:12), polymorphisms 5 through 23 occur in contig 4 (SEQ ID NO: 13), polymorphisms 24 through 28 occur in contig 10 (SEQ ID NO:19), polymorphism 29 occurs in contig 57 (SEQ ID NO:58), polymorphism 20 occurs in contig 95 (SEQ ID NO:96), and polymorphism 31 occurs in contig 105 (SEQ ID NO:106).

DETAILED DESCRIPTION OF THE INVENTION

Figure 1:
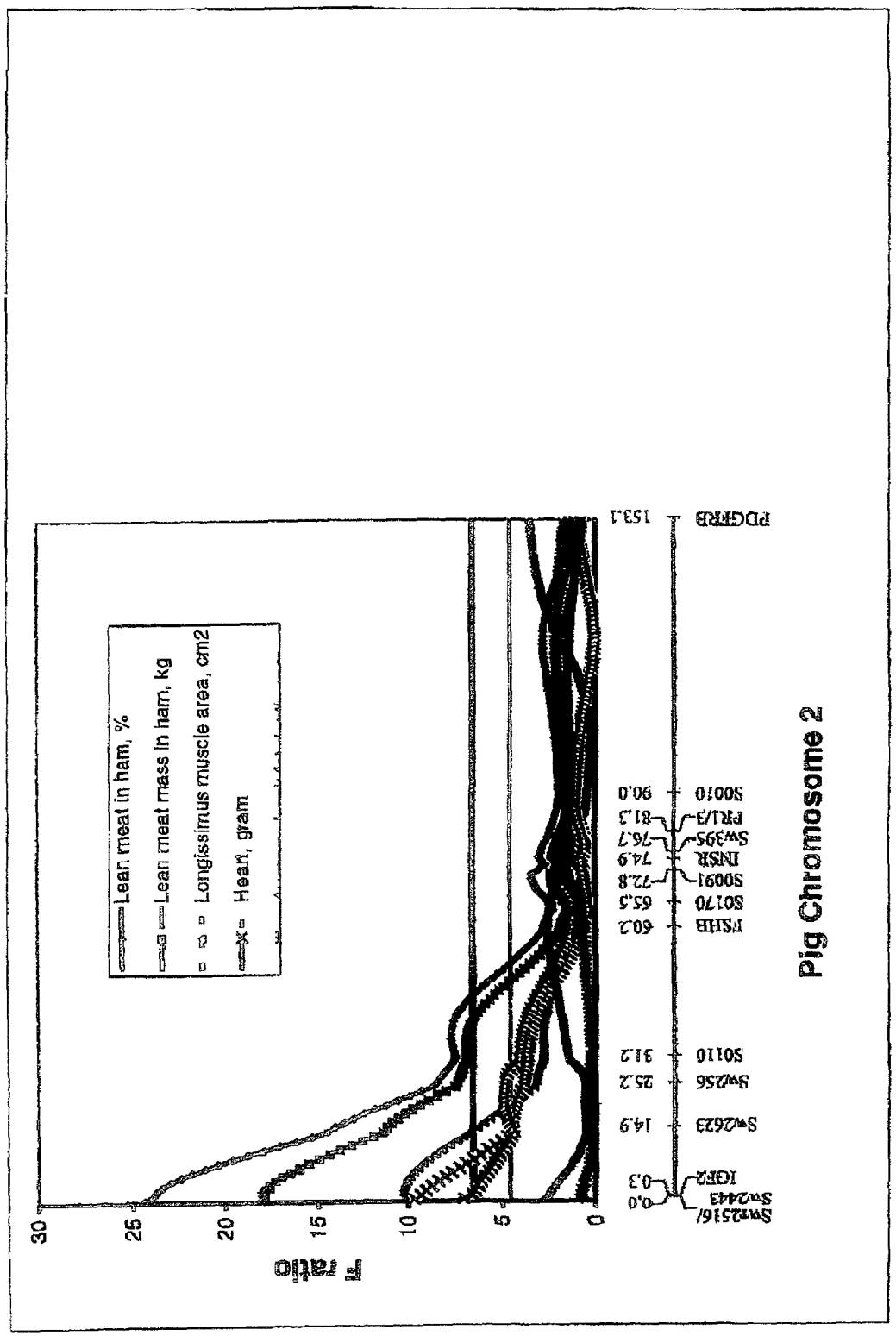
FIG. 1: Test statistic curves obtained in QTL analyses of chromosome 2 in a Wild Boar/Large White intercross. The graph plots the F ratio testing the hypothesis of a single QTL at a given position along the chromosome for the traits indicated. The marker map with the distances between markers in Kosambi centiMorgan is given on the X-axis. The horizontal lines represent genome-wise significant (P<O0.05) and suggestive levels for the trait lean meat in ham; similar significance thresholds were obtained for the other traits.

The invention provides the initial localisation of a parentally imprinted QTL on the genome by linkage analysis with genetic markers, and the actual identification of the parentally imprinted gene(s) and causal mutations therein. Molecular knowledge of such a parentally imprinted QTL allows for more efficient breeding designs herewith provided. Applications of molecular knowledge of parentally imprinted QTLs in breeding programmes include: marker-assisted segregation analysis to identify the segregation of functionally distinct, parentally imprinted QTL alleles in the populations of interest, marker-assisted selection (MAS) performed within lines to enhance genetic response by increasing selection accuracy or selection intensity or by reducing the generation interval using the understanding of the phenomenon of parental imprinting, marker-assisted introgression (MAI) to efficiently transfer favourable parentally imprinted QTL alleles from a donor to a recipient population, genetic engineering of the identified parentally imprinted QTL and genetic modification of the breeding stock using transgenic technology, and development of performance enhancing products using targeted drug development exploiting molecular knowledge of said QTL.

The inventors undertook two independent experiments to determine the practical use of parental imprinting of a QTL.

In a first experiment, performed in a previously described Piétrain×Large White intercross, the likelihood of the data were computed under a model of paternal (paternal allele only expressed) and maternal imprinting (maternal allele only expressed) and compared with the likelihood of the data under a model of a conventional "Mendelian" QTL. The results strikingly demonstrated that the QTL was indeed paternally expressed, the QTL allele (Piétrain or Large White) inherited from the F1 sow having no effect whatsoever on the carcass quality and quantity of the $F_2$ offspring. It was seen that very significant lodscores were obtained when testing for the presence of a paternally expressed QTL, while there was no evidence at all for the segregation of a QTL when studying the chromosomes transmitted by the sows. The same tendency was observed for all traits, showing that the same imprinted gene is responsible for the effects observed on the different traits. Table 1 reports the maximum likelihood (ML) phenotypic means for the $F_2$ offspring sorted by inherited paternal QTL allele.

In a second experiment performed in the Wild Boar X Large White intercross, QTL analyses of body composition, fatness, meat quality, and growth traits were carried out with the chromosome 2 map using a statistical model testing for the presence of an imprinting effect. Clear evidence for a paternally expressed QTL located at the very distal tip of 2p was obtained (FIG. 2; Table 1). The clear paternal expression of a QTL is illustrated by the least squares means which fall into two classes following the population origin of the paternally inherited allele (Table 1). For a given paternally imprinted QTL, implementation of marker-assisted segregation analysis, selection (MAS) and introgression (MAI) can be performed using genetic markers that are linked to the QTL, using genetic markers that are in linkage disequilibrium with the QTL, or using the actual causal mutations within the QTL.

Understanding the parent-of-origin effect characterising a QTL allows for its optimal use in breeding programmes. Indeed, marker-assisted segregation analysis under a model of parental imprinting will yield better estimates of QTL allele effects. Moreover, it allows for the application of specific breeding schemes to optimally exploit a QTL. In one embodiment of the invention, the most favourable QTL alleles would be fixed in breeding animal lines and, for example, used to generate commercial, crossbred males by marker-assisted selection (MAS, within lines) and marker-assisted introgression (MAI, between lines). In another embodiment, the worst QTL alleles would be fixed in the animal lines used to generate commercial crossbred females by MAS (within lines) and MAI (between lines).

In a preferred embodiment of the invention, the animal is a pig. Note, for example, that the invention provides the insight that today half of the offspring from commercially popular Piétrain×Large White crossbred boars inherit an unfavourable Large White muscle mass QTL as provided by the invention, causing considerable loss, and the invention now, for example, provides the possibility to select the better half of the population in that respect. However, it is also possible to select commercial sow lines enriched within the boars unfavourable alleles, allowing the sows to be equipped with other alleles more desirable for, for example, reproductive purposes.

In a preferred embodiment of a method provided by the invention, said QTL is located at a position corresponding to a QTL located at chromosome 2 in the pig. For example, it is known to form comparative mapping data between pig and human, including bidirectional chromosome painting and that SSC2p is homologous to HSAllpter-q13[11,12], HSAllpter-q13 is known to harbour a cluster of imprinted genes: IGF2, INS2, H19, MAH2, $P57^{KIP2}$, $K_vLQTL1$, Tapa1/CD81, Orctl2, Imptl and Ip1. The cluster of imprinted genes located in HSAllpter-q13 is characterised by 8 maternally expressed genes: H19, MASH2, $P57^{KIP2}$, $K_vQTL1$, TAPA1/CD81, ORCTL2, IMPT1 and IP1, and two paternally expressed genes: IGF2 and INS. However, Johanson et al. (Genomics 25:682-690, 1995) and Reik et al. (Trends in Genetics, 13:330-334, 1997) show that the whereabouts of these loci in various animals are not clear. For example, the HSA11 and MMU7 loci do not correspond among each other, the MMU7 and the SSC2 loci do not correspond, whereas the HSA11 and SSC2 loci seem to correspond, and no guidance is given where one or more of, for example, the above-identified parentally expressed individual genes are localised on the three species' chromosomes.

Other domestic animals, such as cattle, sheep, poultry and fish, having similar regions in their genome harbouring such a cluster of imprinted genes or QTLs, the invention herewith provides use of these orthologous regions of other domestic animals in applying the phenomenon of parental imprinting in breeding programmes. In pigs, said cluster is mapped at around position 2p 1.7 of chromosome 2; however, a method as provided by the invention employing (fragments of) said maternally or paternally expressed orthologous or homologous genes or QTLs is advantageously used in other animals as well as for breeding and selecting purposes. For example, a method is provided wherein said QTL is related to the potential muscle mass and/or fat deposition, preferably with limited effects on other traits such as meat quality and daily gain of the animal or wherein said QTL comprises at least a part of an insulin-like growth factor-2 (IGF2) allele. Reik et al. (Trends in Genetics, 13:330-334, 1997) explain that this gene in humans is related to Beckwith-Wiedemann syndrome, an apparently parentally imprinted disease syndrome most commonly seen with human fetuses, where the gene has an important role in prenatal development. No relationship is shown or suggested with postnatal development relating to muscle development or fatness in (domestic) animals.

In a preferred embodiment, the invention provides a method for selecting a pig for having desired genotypic or potential phenotypic properties comprising testing a sample from said pig for the presence of a quantitative trait locus (QTL) located at a Sus scrofa chromosome 2 mapping at position 2p1.7. In particular, the invention relates to the use of genetic markers for the telomeric end of pig chromosome 2p in marker selection (MAS) of a parentally imprinted Quantitative Trait Locus (QTL) affecting carcass yield and quality in pigs. Furthermore, the invention relates to the use of genetic markers associated with the IGF2 locus in MAS in pigs, such as polymorphisms and microsatellites and other characterising nucleic acid sequences shown herein, such as shown in FIGS. 4 to 10. In a preferred embodiment, the invention provides a QTL located at the distal tip of Sus scrofa chromosomes 2 with effects on various measurements of carcass quality and quantity, particularly muscle mass and fat deposition.

In a first experiment, a QTL mapping analysis was performed in a Wild Boar X Large White intercross counting 200 $F_2$ individuals. The $F_2$ animals were sacrificed at a live weight of at least 80 kg or at a maximum age of 190 days. Phenotypic data on birth weight, growth, fat deposition, body composition, weight of internal organs, and meat quality were collected; a detailed description of the phenotypic traits are provided by Andersson et al.[1] and Andersson-Eklund et al.[4]

A QTL (without any significant effect on back-fat thickness) at an unspecified locus on the proximal end of chromosome 2 with moderate effect on muscle mass, and located about 30 cM away from the parentally imprinted QTL reported here, was previously reported by the inventors; whereas the QTL as now provided has a very large effect, explaining at least 20-30% of variance, making the QTL of the present invention commercially very attractive, which is even more so because the present QTL is parentally imprinted. The marker map of chromosome 2p was improved as part of this invention by adding microsatellite markers in order to cover the entire chromosome arm. The following microsatellite markers were used: Swc9, Sw2443, Sw2623, and Swr2516, all from the distal end of 2p[7]. QTL analyses of body composition, fatness, meat quality, and growth traits were carried out with the new chromosome 2 map. Clear evidence for a QTL located at the very distal tip of 2p was obtained (FIG. 1; Table 1). The QTL had very large effects on lean meat content in ham and explained an astonishing 30% of the residual phenotypic variance in the $F_2$ population. Large effects on the area of the longissumus dorsi muscle, on the weight of the heart, and on back-fat thickness (subcutaneous fat) were also noted. A moderate effect on one meat quality trait, reflectance value, was indicated. The QTL had no significant effect on abdominal fat, birth weight, growth, weight of liver, kidney, or spleen (data not shown). The Large White allele at this QTL was associated with larger muscle mass and reduced back-fat thickness consistent with the difference between this breed and the Wild Boar population.

In a second experiment, QTL mapping was performed in a Piétrain×Large White intercross comprising 1125 $F_2$ offspring. The Large White and Piétrain parental breeds differ for a number of economically important phenotypes.

Piétrains are famous for their exceptional muscularity and leanness[10] (FIG. 2), while Large Whites show superior growth performance. Twenty-one distinct phenotypes measuring growth performance (5), muscularity (6), fat deposition (6), and meat quality (4), were recorded on all $F_2$ offspring. In order to map QTL underlying the genetic differences between these breeds, the inventors undertook a whole genome scan using microsatellite markers on an initial sample of 677 $F_2$ individuals. The following microsatellite marker map was used to analyse chromosome 2; SW2443, SWC9 and SW2623, SWR2516-(0,20)-SWR783-(0,29)-SW240-(0,20)-SW776-(0,08)-S0010-(0,04)-SW1695-(0,36)-SWR308. Analysis of pig chromosome 2 using a Maximum Likelihood multipoint algorithm revealed highly significant lodscores (up to 20) for three of the six phenotypes measuring muscularity (% lean cuts, % ham, % loin) and three of the six phenotypes measuring fat deposition (back-fat thickness (BFT), % backfat, % fat cuts) at the distal end of the short arm of chromosome 2 (FIG. 1). Positive lodscores were obtained in the corresponding chromosome region for the remaining six muscularity and fatness phenotypes, however, not reaching the experiment-wise significance threshold ($\alpha$=5%). There was no evidence for an effect of the corresponding QTL on growth performance (including birth weight) or recorded meat quality measurements (data not shown). To confirm this finding, the remaining sample of 355 $F_2$ offspring was genotyped for the four most distal 2p markers and QTL analysis performed for the traits yielding the highest lodscores in the first analysis. Lodscores ranged from 2.1 to 7.7, clearly confirming the presence of a major QTL in this region. Table 2 reports the corresponding ML estimates for the three genotypic means as well as the residual variance. Evidence based on marker-assisted segregation analysis points towards residual segregation at this locus within the Piétrain population.

These experiments, therefore, clearly indicated the existence of a QTL with a major effect on carcass quality and quantity on the telomeric end of pig chromosome arm 2p, the likely existence of an allelic series at this QTL with at least three alleles: Wild-Boar<Large White<Piétrain, and possibly more given the observed segregation within the Piétrain breed.

The effects of the identified QTL on muscle mass and fat deposition are truly major, being of the same magnitude of those reported for the CRC locus though apparently without the associated deleterious effects on meat quality. We estimate that both loci jointly explain close to 50% of the Piétrain versus Large White breed difference for muscularity and leanness. The QTL had very large effects on lean meat content in ham and explained an astonishing 30% of the residual phenotypic variance in the $F_2$ population. Large effects on the area of the longissumus dorsi muscle, on the weight of the heart, and on back-fat thickness (subcutaneous fat) were also noted. A moderate effect an one meat quality trait, reflectance value, was indicated. The QTL had no significant effect on abdominal fat, birth weight, growth, weight of liver, kidney, or spleen (data not shown). The Large White allele at this QTL, when compared to the Wild Boar allele, was associated with larger muscle mass and reduced back-fat thickness consistent with the difference between this breed and the Wild Boar population. The strong imprinting effect observed for all affected traits shows that a single causative locus is involved. The pleiotropic effects on skeletal muscle mass and the size of the heart appear adaptive from a physiological point of view as a larger muscle mass requires a larger cardiac output.

In a further embodiment, the invention provides a method for selecting a pig for having desired genotypic or potential phenotypic properties comprising testing a sample from said pig for the presence of a quantitative trait locus (QTL) located at a Sus scrofa chromosome 2 mapping at position 2p1.7., wherein said QTL comprises at least a part of a Sus scrofa insulin-like growth factor-2 (IGF2) allele or a genomic area closely related thereto, such as polymorphisms and microsatellites and other characterising nucleic acid sequences shown herein, such as shown in FIGS. 4 to 10. The important role of IGF2 for prenatal development is well-documented from knockout mice as well as from its causative role in the human Beckwith-Wiedemann syndrome. This invention demonstrates an important role for the IGF2-region, also for postnatal development.

To show the role of IGF2, the inventors performed the following three experiments:

A genomic IGF2 clone was isolated by screening a porcine BAC library. FISH analysis with this BAC clone gave a strong consistent signal on the terminal part of chromosome 2p.

A polymorphic microsatellite is located in the 3'UTR of IGF2 in mice (GenBank U71085), humans (GenBank S62623), and horse (GenBank AF020598). The possible presence of a corresponding porcine microsatellite was investigated by direct sequencing of the IFG2 3'UTR using the BAC clone. A complex microsatellite was identified about 800 bp downstream of the stop codon; a sequence comparison revealed that this microsatellite was identical to a previously described anonymous microsatellite, Swc9[6]. This marker was used in the initial QTL mapping experiments and its location on the genetic map correspond with the most likely position of the QTL both in the Piétrain×Large White and in the Large White×Wild Boar pedigree.

Analysis of skeletal muscle and liver cDNA from 10-week old fetuses heterozygous for a nt241 (G-A) transversion in the second exon of the porcine IGF2 gene and SWC9 shows that the IGF2 gene is imprinted in these tissues in the pig as well and only expressed from the paternal allele.

Based on a published porcine adult liver cDNA sequence[16], the inventors designed primer pairs allowing amplification of the entire IGF2 coding sequence with 222 bp of leader and 280 bp of trailor sequence from adult skeletal muscle cDNA. Piétrain and Large White RT-PCR products were sequenced, indicating that the coding sequences are identical in both breeds and with the published sequence. However, a G⊗A transition was found in the leader sequence corresponding to exon 2 in man. Following conventional nomenclature, this polymorphism will be referred to as nt241 (G-A). We developed a screening test for this single nucleotide polymorphism 9(SNP) based on the ligation amplification reaction (LAR), allowing us to genotype our pedigree material. Based on these data, IGF2 was shown to colocalize with the SWC9 microsatellite marker ($\theta$=0%), therefore virtually coinciding with the most likely position of the QTL, and well within the 95% support interval for the QTL. Subsequent sequence analysis demonstrated that the microsatellite marker SWC9 is actually located within the 3'UTR of the IGF2 gene.

As previously mentioned, the knowledge of this QTL provides a method for the selection of animals such as pigs with improved carcass merit. Different embodiments of the invention are envisaged, including: marker-assisted segregation analysis to identify the segregation of functionally distinct QTL alleles in the populations of interest; marker-assisted selection (MAS) performed within lines to enhance genetic response by increasing selection accuracy or selection intensity or by reducing the generation interval; and marker-assisted introgression (MAI) to efficiently transfer favourable QTL alleles from a donor to a recipient population, thereby enhancing genetic response in the recipient population. Implementation of embodiments of marker-assisted segregation analysis, selection (MAS) and introgression (MAI) can be performed using genetic markers that are linked to the QTL, genetic markers that are in linkage disequilibrium with the QTL, and the actual causal mutations within the QTL.

In a further embodiment, the invention provides a method for selecting a pig for having desired genotypic or potential phenotypic properties comprising testing a sample from said pig for the presence of a quantitative trait locus (QTL) located at a Sus scrofa chromosome 2 mapping at position 2p1.7., wherein said QTL is paternally expressed, i.e., is expressed from the paternal allele. In man and mouse, IGF2 is known to be imprinted and to be expressed exclusively from the paternal allele in several tissues. Analysis of skeletal muscle cDNA from pigs heterozygous for the SNP and/or SWC9 shows that the same imprinting holds in the pig as well. Understanding the parent-of-origin effect characterising the QTL as provided by the invention now allows for its optimal use in breeding programmes. Indeed, today, half of the offspring from commercially popular Piétrain× Large White crossbred boars inherit the unfavourable Large White allele, causing considerable loss. Using a method as provided by the invention avoids this problem.

The invention furthermore provides an isolated and/or recombinant nucleic acid or functional fragment derived thereof comprising a parentally imprinted quantitative trait locus (QTL) or fragment thereof capable of being predominantly expressed by one parental allele. Having such a nucleic acid as provided by the invention available allows constructing transgenic animals wherein favourable genes are capable of being exclusively or predominantly expressed by one parental allele, thereby equipping the offspring of the animal homozygous for a desired trait with desired properties related to that parental allele that is expressed.

In a preferred embodiment, the invention provides an isolated and/or recombinant nucleic acid or fragment derived thereof comprising a synthetic parentally imprinted quantitative trait locus (QTL) or functional fragment thereof derived from at least one chromosome. Synthetic herein describes a parentally expressed QTL wherein various elements are combined that originate from distinct locations from the genome of one or more animals. The invention provides recombinant nucleic acid wherein sequences related to parental imprinting of one QTL are combined with sequences relating to genes or favourable alleles of a second QTL. Such a gene construct is favourably used to obtain transgenic animals wherein the second QTL has been equipped with paternal imprinting, as opposed to the inheritance pattern in the native animal from which the second QTL is derived. Such a second QTL can, for example, be derived from the same chromosome where the parental imprinting region is located, but can also be derived from a different chromosome from the same or even a different species. In the pig, such a second QTL can, for example, be related to an oestrogen receptor (ESR)-gene (Rothschild et al., PNAS, 93, 201-201, 1996) or a FAT-QTL (Andersson, Science, 263, 1771-1774, 1994) for example, derived from another pig chromosome, such as chromosome 4. A second or further QTL can also be derived from another (domestic) animal or a human.

The invention furthermore provides an isolated and/or recombinant nucleic acid or functional fragment derived thereof at least partly corresponding to a QTL of a pig located at a Sus scrofa chromosome 2 mapping at position 2p1.7 wherein said QTL is related to the potential muscle mass and/or fat deposition of said pig and/or wherein said QTL comprises at least a part of a Sus scrofa insulin-like growth factor-2 (IGF2) allele, preferably at least spanning a region between INS and H19, or preferably derived from a domestic pig, such as a Piétrain, Meishan, Duroc, Landrace or Large White, or from a Wild Boar. For example, a genomic IGF2 clone was isolated by screening a porcine BAC library. FISH analysis with this BAG clone gave a strong, consistent signal on the terminal part of chromosome 2p. A polymorphic microsatellite is located in the 3'UTR of IGF2 in mice (GenBank U71085), humans (GenBank S62623), and horse (GenBank AF020598). The possible presence of a corresponding porcine microsatellite was investigated by direct sequencing of the IGF2 3'UTR using the BAC clone. A complex microsatellite was identified about 800 bp downstream of the stop codon; a sequence comparison revealed that this microsatellite is identical to a previously described anonymous microsatellite, Swc9. PGR primers were designed and the microsatellite (IGF2 ms) was found to be highly polymorphic with three different alleles among the two Wild Boar founders and another two among the eight Large White founders. IGF2 ms was fully informative in the intercross as the breed of origin as well as the parent of origin could be determined with confidence for each allele in each $F_2$ animal.

A linkage analysis using the intercross pedigree was carried out with IGF2 ms and the microsatellites Sw2443, Sw2623, and Swr2516, all from the distal end of $2p^7$. IGF2 was firmly assigned to 2p by highly significant lodscores (e.g. Z=89.0, θ=0.003 against Swr2516). Multipoint analyses, including previously typed chromosome 2 markers, revealed the following order of loci (sex-average map distances in Kosambi cM): Sw2443/Swr2516-0.3-IGF2-14.9-Sw2623-10.3-Sw256. No recombinant was observed between Sw2443 and Swr2516, and the suggested proximal location of IGF2 in relation to these loci is based on a single recombinant giving a lodscore support of 0.8 for the reported order. The most distal marker in our previous QTL study, Sw256, is located about 25 cM from the distal end of the linkage group.

The invention furthermore provides use of a nucleic acid or functional fragment derived thereof according to a method according to the invention. In a preferred embodiment, use of a method according to the invention is provided to select a breeding animal or animal destined for slaughter, or embryos or semen derived from these animals, for having desired genotypic or potential phenotypic properties. In particular, the invention provides such use wherein said properties are related to muscle mass and/or fat deposition. The QTL as provided by the invention may be exploited or used to improve, for example, lean meat content or back-fat thickness by marker-assisted selection within populations or by marker-assisted introgression of favourable alleles from one population to another. Examples of marker-assisted selection using the QTL as provided by the invention are use of marker-assisted segregation analysis with linked markers or with markers in disequilibrium to identify functionally distinct QTL alleles. Furthermore, identification of a causative mutation in the QTL is now possible, again leading to identify functionally distinct QTL alleles. Such functionally distinct QTL alleles located at the distal tip of chromosome 2p with large effects on skeletal muscle mass, the size of the heart, and on back-fat thickness are also provided by the invention. The observation of a similar QTL effect in a Large White×Wild Boar as well as in a Piétrain×Large White intercross provides proof of the existence of a series of at least three distinct functional alleles. Moreover, preliminary evidence based on marker-assisted segregation analysis points towards residual segregation at this locus within the Piétrain population (data not shown). The occurrence of an allelic series as provided by the invention allows identifying causal polymorphisms which—based on the quantitative nature of the observed effect—are unlikely to be gross gene alterations but rather subtle regulatory mutations. The effects on muscle mass of the three alleles rank in the same order as the breeds in which they are found, i.e., Piétrain pigs are more muscular than Large White pigs that in turn have higher lean meat content than Wild Boars. The invention furthermore provides use of the alleles as provided by the invention within line selection or for marker-assisted introgression using linked markers, markers in disequilibrium or alleles comprising causative mutations.

The invention furthermore provides an animal selected by using a method according to the invention. For example, a pig characterised in being homozygous for an allele in a QTL located at a Sus scrofa chromosome 2 mapping at position 2p1.7 can now be selected and is thus provided by the invention. Since said QTL is related to the potential muscle mass and/or fat deposition of said pig and/or said QTL comprises at least a part of a Sus scrofa insulin-like growth factor-2 (IGF2) allele, it is possible to select promising pigs to be used for breeding or to be slaughtered. In particular, an animal according to the invention which is a male is provided. Such a male, or its sperm or an embryo derived thereof, can advantageously be used in breeding animals for creating breeding lines or for finally breeding animals destined for slaughter. In a preferred embodiment of such use as provided by the invention, a male, or its sperm, deliberately selected for being homozygous for an allele causing the extreme muscular hypertrophy and leanness, is used to produce offspring heterozygous for such an allele. Due to said allele's paternal expression, said offspring will also show the favourable traits, for example, related to muscle mass, even if the parent female has a different genetic background. Moreover, it is now possible to positively select the female(s) for having different traits, for example, related to fertility, without having a negative effect on the muscle mass trait that is inherited from the allele from the selected male. For example, earlier such males could occasionally be seen with Piétrain pigs but genetically it was not understood how to most profitably use these traits in breeding programmes.

Furthermore, the invention provides a transgenic animal, sperm and an embryo derived thereof, comprising a synthetic parentally imprinted QTL or functional fragment thereof as provided by the invention, i.e., it is provided by the invention to introduce a favourable recombinant allele; for example, to introduce the oestrogen receptor locus related to increased litter size of an animal homozygously in a parentally imprinted region of a grandparent animal (for example, the father of a hybrid sow if the region was paternally imprinted and the grandparent was a boar); to introduce a favourable fat-related allele or muscle mass-related recombinant allele in a paternally imprinted region, and so on. Recombinant alleles that are interesting or favourable from the maternal side are often the ones that have opposite effects to alleles from the paternal side. For example, in meat animals such as pigs, recombinant alleles linked with meat quality traits such as intramuscular fat or muscle mass could be fixed in the dam lines while recombinant alleles linked with reduced backfat could be fixed in the sire lines. Other desirable combinations are, for example, fertility and/or milk yield in the female line with growth rates and/or muscle mass in the male lines.

The invention is further explained in the detailed description without limiting the invention.

EXAMPLE 1

Wild Boar×Large White Intercrosses

Methods

Isolation of an IGF2 BAC clone and fluorescent in situ hybridisation (FISH). IGF2 primers (F:5'-GGCAAGTTCT-TCCGCTAATGA-3' (SEQ ID NO:1) and R:5'-GCACCG-CAGAATTACGACAA-3' (SEQ ID NO:2)) for PCR amplification of a part of the last exon and 3'UTR were designed on the basis of a porcine IGF2 cDNA sequence (GenBank X56094). The primers were used to screen a porcine BAC library and the clone 253G10 was isolated. Crude BAC DNA was prepared as described[24]. The BAC DNA was linearized with EcoRV and purified with QIAEXII (QIAGEN GmbH, Germany). The clone was labeled with biotin-14-dATP using the GIBCO-BRL Bionick labeling system (BRL18246-015). Porcine metaphase chromosomes were obtained from pokeweed (Seromed) stimulated lymphocytes using standard techniques. The slides were aged for two days at room temperature and then kept at −20° C. until use. FISH analysis was carried out as previously described[25]. The final concentration of the probe in the hybridisation mix was 10 ng/µl. Repetitive sequences were suppressed with standard concentrations of porcine genomic DNA. After post-hybridisation washing, the biotinylated probe was detected with two layers of avidin-FITC (Vector A-2011). The chromosomes were counterstained with 0.3 mg/ml DAPI (4,6-Diamino-2-phenylindole; Sigma D9542), which produced a G-banding like pattern. No posthybridisation banding was needed, since chromosome 2 is easily recognized without banding. A total of 20 metaphase spreads were examined under an Olympus BX-60 fluorescence microscope connected to an IMAC-CCD S30 video camera and equipped with an ISIS 1.65 (Metasystems) software.

About two µg of linearized and purified BAC DNA was used for direct sequencing with 20 pmoles of primers and BigDye Terminator chemistry (Perkin Elmer, USA). DNA sequencing was done from the 3' end of the last exon towards the 3' end of the UTR until a microsatellite was detected. A primer set (F:5'-GTTTCTCCTGTACCCA-CACGCATCCC-3' (SEQ ID NO:3) and R: 5'-Fluorescein-CTACAAGCTGGGCTCAGGG-3' (SEQ ID NO:4)) was designed for the amplification of the IGF2 microsatellite which is about 250 bp long and located approximately 800 bp downstream from the stop codon. The microsatellite was PCR amplified using fluorescently labeled primers and the genotyping was carried out using an ABI377 sequencer and the GeneScan/Genotyper softwares (Perkin Elmer, USA). Two-point and multipoint linkage analyses were done with the Cri-Map software[26].

Animals and Phenotypic Data.

The intercross pedigree comprised two European Wild Boar males and eight Large White females, 4 $F_1$ males and 22 $F_1$ females, and 200 $F_2$ progeny[1]. The $F_2$ animals were sacrificed at a live weight of at least 80 kg or at a maximum age of 190 days. Phenotypic data on birth weight, growth, fat deposition, body composition, weight of internal organs, and meat quality were collected; a detailed description of the phenotypic traits is provided by Andersson et al.[1] and Andersson-Eklund et al.[4]

Statistical Analysis

Interval mapping for the presence of QTL was carried out using a least squares method developed for the analysis of crosses between outbred lines[27]. The method is based on the assumption that the two divergent lines are fixed for alternative QTL alleles. There are four possible genotypes in the $F_2$ generation was regards to the grandparental origin of the alleles at each locus. This makes it possible to fit three effects: additive, dominance, and imprinting[2]. The latter is estimated as the difference between the two types of heterozygotes, the one receiving the Wild Boar allele through an $F_1$ sire and the one receiving it from an $F_1$ dam. An F-ratio was calculated using this model (with 3 d.f) versus a reduced model without a QTL effect for each cM of chromosome 2. The most likely position of a QTL was obtained as the location giving the highest F-ratio. Genome-wise significant thresholds were obtained empirically by a permutation test[28] as described[2]. The QTL model including an imprinting effect was compared with a model without imprinting (with 1 d.f.) to test whether the imprinting effect was significant.

The statistical models also included the fixed effects and covariants that were relevant for the respective traits; see Andersson-Eklund et al.[4] for a more detailed description of the statistical models used. Family was included to account for background genetic effects and maternal effects. Carcass weight was included as a covariant to discern QTL effects on correlated traits, which means that all results concerning body composition were compared at equal weights. Least-squares means for each genotype class at the IGF2 locus were estimated with a single point analysis using Procedure GLM of SAS[29]; the model included the same fixed effects and covariants as used in the interval mapping analyses. The QTL shows a clear parent of origin-specific expression and the map position coincides with that of the insulin-like growth factor II gene (IGF2), indicating IGF2 as the causative gene. A highly significant segregation distortion (excess of Wild Boar-derived alleles) was also observed at this locus. The results demonstrate an important effect of the IGF2 region on postnatal development and it is possible that the presence of a paternally expressed IGF2-linked QTL in humans and in rodent model organisms has so far been overlooked due to experimental design or statistical treatment of data. The study has also important implications for quantitative genetics theory and practical pig breeding.

IGF2 was identified as a positional candidate gene for this QTL due to the observed similarity between pig chromosome 2p and human chromosome 11p. A genomic IGF2 clone was isolated by screening a porcine BAC library. FISH analysis with this BAC clone gave a strong, consistent signal on the terminal part of chromosome 2p (FIG. 1). A polymorphic microsatellite is located in the 3'UTR of IGF2 in mice (GenBank U71085), humans (GenBank S62623), and horse (GenBank AF020598). The possible presence of a corresponding porcine microsatellite was investigated by direct sequencing of the IGF2 3'UTR using the BAC clone. A complex microsatellite was identified about 800 bp downstream of the stop codon; a sequence comparison revealed that this microsatellite is identical to a previously described anonymous microsatellite, Swc9[6]. PCR primers were designed and the microsatellite (IGF2 ms) was found to be highly polymorphic with three different alleles among the two Wild Boar founders and another two among the eight Large White founders. IGF2 ms was fully informative in the intercross as the breed of origin as well as the parent of origin could be determined with confidence for each allele in each $F_2$ animal.

A linkage analysis using the intercross pedigree was carried out with IGF2 ms and the microsatellites Sw2443, Sw2623, and Swr2516, all from the distal end of 2p[7]. IGF2 was firmly assigned to 2p by highly significant lodscores (e.g., Z=89.0, θ=0.003 against Swr2516). Multipoint analyses, including previously typed chromosome 2 markers[8], revealed the following order of loci (sex-average map distances in Kosambi cM): Sw2443/Swr2516-0.3-IGF2-14.9-Sw2623-10.3-Sw256. No recombinant was observed between Sw2443 and Swr2516, and the suggested proximal location of IGF2 in relation to these loci is based on a single recombinant giving a lodscore support of 0.8 for the reported order. The most distal marker in our previous QTL study, Sw256, is located about 25 cM from the distal end of the linkage group.

QTL analyses of body composition, fatness, meat quality, and growth traits were carried out with the new chromosome 2 map using a statistical model testing for the possible presence of an imprinting effect as expected for IGF2. Clear evidence for a paternally expressed QTL located at the very distal tip of 2p was obtained (FIG. 2; Table 1). The QTL had very large effects on lean meat content in ham and explained an astonishing 30% of the residual phenotypic variance in the $F_2$ population. Large effects on the area of the longissumus dorsi muscle, on the weight of the heart, and on back-fat thickness (subcutaneous fat) were also noted. A moderate effect on one meat quality trait, reflectance value, was indicated. The QTL had no significant effect on abdominal fat, birth weight, growth, weight of liver, kidney, or spleen (data not shown). The Large White allele at this QTL was associated with larger muscle mass and reduced back-fat thickness consistent with the difference between this breed and the Wild Boar population. The strong imprinting effect observed for all affected traits strongly suggests a single causative locus. The pleiotropic effects on skeletal muscle mass and the size of the heart appear adaptive from a physiological point of view as a larger muscle mass requires a larger cardiac output. The clear paternal expression of this QTL is illustrated by the least squares means which fall into two classes following the population origin of the paternally inherited allele (Table 1). It is worth noticing though that there was a non-significant trend towards less extreme values for the two heterozygous classes, in particular for the estimated effect on the area of longissimus dorsi. This may be due to chance, but could have a biological explanation, e.g., that there is some expression of the maternally inherited allele or that there is a linked, non-imprinted QTL with minor effects on the traits in question.

Figure 2:
FIG. 2: Piétrain pig with characteristic muscular hypertrophy.

The IGF2-linked QTL and the FAT1 QTL on chromosome 4 1, 9 are by far the two loci with the largest effect on body composition and fatness segregating in this Wild Boar intercross. The IGF2 QTL controls primarily muscle mass whereas FAT1 has major effects on fat deposition including abdominal fat, a trait that was not affected by the IGF2 QTL (FIG. 2). No significant interaction between the two loci was indicated and they control a very large proportion of the residual phenotypic variance in the $F_2$ generation. A model including both QTLs explains 33.1% of the variance for percentage of lean meat in ham, 31.3% for the percentage of lean meat plus bone in back, and 26.2% for average backfat depth (compare with a model including only chromosome 2 effects, Table 1). The two QTLs must have played a major role in the response during selection for lean growth and muscle mass in the Large White domestic pig.

A highly significant segregation distortion was observed in the IGF2 region (excess of Wild Boar-derived alleles) as shown in Table 1 ($\chi 2=11.7$, d.f=2; P=0.003). The frequency of Wild Boar-derived IGF2 alleles was 59% in contrast to the expected 50% and there was twice as many "Wild Boar" as "Large White" homozygotes. This deviation was observed with all three loci at the distal tip and is thus not due to typing errors. The effect was also observed with other loci but the degree of distortion decreased as a function of the distance to the distal tip of the chromosome. Blood samples for DNA preparation were collected at 12 weeks of age and we are convinced that the deviation from expected Mendelian ratios was present at birth as the number of animals lost prior to blood sampling was not sufficient enough to cause a deviation of this magnitude. No other of the more than 250 loci analysed in this pedigree show such a marked segregation distortion (L. Andersson, unpublished). The segregation distortion did not show an imprinting effect, as the frequencies of the two reciprocal types of heterozygotes were identical (Table 1). This does not exclude the possibility that the QTL effects and the segregation distortion are controlled by the same locus. The segregation distortion may be due to meiotic drive favouring the paternally expressed allele during gametogenesis, as the $F_1$ parents were all sired by Wild Boar males. Another possibility is that the segregation distortion may be due to codominant expression of the maternal and paternal allele in some tissues and/or during a critical period of embryo development. Biallelic IGF2 expression has been reported to occur to some extent during human development[10,11] and, interestingly, a strong influence of the parental species background on IGF2 expression was recently found in a cross between *Mus musculus* and *Mus spretus*[12]. It is also interesting that a VNTR polymorphism at the insulin gene, which is very closely linked to IGF2, is associated with size at birth in humans[13]. It is possible that the IGF2-linked QTL in pigs has a minor effect on birth weight, but in our data it was far from significant (FIG. 2) and there was no indication of an imprinting effect.

This study is an advance in the general knowledge concerning the biological importance of the IGF2 locus. The important role of IGF2 for prenatal development is well-documented from knock-out mice[14] as well as from its causative role in the human Beckwith-Wiedemann syndrome[15]. This study demonstrates an important role for the IGF2-region also for postnatal development. It should be stressed that our intercross between outbred populations is particularly powerful to detect QTL with a parent of origin-specific effect on a multifactorial trait. This is because multiple alleles (or haplotypes) are segregating and we could deduce whether a heterozygous $F_2$ animal received the Wild Boar allele from the $F_1$ male or female. It is quite possible that the segregation of a paternally expressed IGF2-linked QTL affecting a trait like obesity has been overlooked in human studies or in intercrosses between inbred rodent populations because of experimental design or statistical treatment of data. An imprinting effect cannot be detected in an intercross between two inbred lines as only two alleles are segregating at each locus. Our result has, therefore, significant bearings on the future analysis of the association between genetic polymorphism in the Insulin-IGF2 region and Type I diabetes[16], obesity[17], and variation in birth weight[13] in humans, as well as for the genetic dissection of complex traits using inbred rodent models. A major impetus for generating an intercross between the domestic pig and its wild ancestor was to explore the possibilities to map and identify major loci that have responded to selection. We have now showed that two single QTLs on chromosome 2 (this study) and 4[1,2] explain as much as one third of the phenotypic variance for lean meat content in the $F_2$ generation. This is a gross deviation from the underlying assumption in the classical infinitesimal model in quantitative genetics theory, namely, that quantitative traits are controlled by an infinite number of loci, each with an infinitesimal effect. If a large proportion of the genetic difference between two divergent populations (e.g., Wild Boar and Large White) is controlled by a few loci, one would assume that selection would quickly fix QTL alleles with large effects leading to a selection plateau. However, this is not the experience in animal breeding programmes or selection experiments where good, persistent, long-term selection responses are generally obtained, provided that the effective population size is reasonably large[18]. A possible explanation for this paradox is that QTL alleles controlling a large proportion of genetic differences between two populations may be due to several consecutive mutations; this may be mutations in the same gene or at several closely linked genes affecting the same trait. It has been argued that new mutations contribute substantially to long-term selection responses[19], but the genomic distribution of such mutations is unknown.

The search for a single causative mutation is the paradigm regarding the analysis of genetic defects in mice and monogenic disorders in humans. We propose that this may not be the case for loci that have been under selection for a large number of generations in domestic animals, crops, or natural populations. This hypothesis predicts the presence of multiple alleles at major QTL. It gains some support from our recent characterisation of porcine coat color variation. We have found that both the alleles for dominant white color and for black-spotting differ from the corresponding wild-type alleles by at least two consecutive mutations with phenotypic effects at the KIT and MC1R loci, respectively[20], 21 In this context, it is highly interesting that in the accompanying example we have identified a third allele at the IGF2-linked QTL. The effects on muscle mass of the three alleles rank in the same order as the breeds in which they are found, i.e., Piétrain pigs are more muscular than Large White pigs, which in turn have a higher lean meat content than Wild Boars.

There are good reasons to decide that IGF2 is the causative gene for the now reported QTL. Firstly, there is a perfect agreement in map localization (FIG. 2). Secondly, it has been shown that IGF2 is paternally expressed in mice, humans, and now in pigs, like the QTL. There are several other imprinted genes in the near vicinity of IGF2 in mice and humans (Mash2, INS2, H19, KVLQT1, TAPA1/CD81, and CDKN1C/p57[KIP2]) but only IGF2 is paternally expressed in adult tissues[22]. We believe that this locus provides a unique opportunity for molecular characterisation of a QTL. The clear paternal expression can be used to exclude genes that do not show this mode of inheritance. Moreover, the presence of an allelic series should facilitate the difficult distinction between causative mutations and linked neutral polymorphism. We have already shown that there is no difference in coding sequence between IGF2 alleles from Piétrain and Large White pigs suggesting that the causative mutations occur in regulatory sequences. An obvious step is to sequence the entire IGF2 gene and its multiple promoters from the three populations. The recent report that a VNTR polymorphism in the promoter region of the insulin (INS) gene affects IGF2 expression[23] suggests that the causative mutations may be at a considerable distance from the IGF2 coding sequence.

The results have several important implications for the pig breeding industry. They show that genetic imprinting is not an esoteric academic question but needs to be considered in practical breeding programmes. The detection of three different alleles in Wild Boar, Large White, and Piétrain populations indicates that further alleles at the IGF2-linked QTL segregate within commercial populations. The paternal expression of the QTL facilitates its detection using large paternal half-sib families as the female contribution can be ignored. The QTL is exploited to improve lean meat content by marker-assisted selection within populations or by marker-assisted introgression of favourable alleles from one population to another.

EXAMPLE 2

PiéTrain×Large White Intercrosses

Methods

Pedigree material: The pedigree material utilised to map QTL was selected from a previously described Piétrain× Large White F2 pedigree comprising >1,800 individuals[6,7]. To assemble this F2 material, 27 Piétrain boars were mated to 20 Large White sows to generate an F1 generation comprising 456 individuals. 31 F1 boars were mated to unrelated 82 F1 sows from 1984 to 1989, yielding a total of 1862 F2 offspring. F1 boars were mated on average to 7 females, and F1 sows to an average of 2, 7 males. Average offspring per boar was 60 and per sow was 23.

Phenotypic information: (i) Data collection: A total of 21 distinct phenotypes were recorded in the F2 generation[6,7]. These included:

five growth traits: birth weight (g), weaning weight (Kg), grower weight (Kg), finisher weight (Kg) and average daily gain (ADG; Kg/day; grower to finisher period);

two body proportion measurements: carcass length (cm); and a conformation score (0 to 10 scale; ref 6);

ten measurements of carcass composition obtained by dissection of the chilled carcasses 24 hours after slaughter. These include measurements of muscularity: % ham (weight hams/carcass weight), % loin (weight loin/carcass weight), % shoulder (weight shoulder/carcass weight), % lean cuts (% ham+% loin+% shoulder); and measurements of fatness: average back-fat thickness (BFT; cm), % backfat (weight backfat/carcass weight), % belly (weight belly/carcass weight), % leaf fat (weight leaffat/carcass weight), % jowl (weight jowl/carcass weight), and "% fat cuts" (% backfat+% belly+% leaf fat+% jowl).

four meat quality measurements: $pH_{LD1}$ (Longissimus dorsi 1 hour after slaughter), $pH_{LD24}$ longissimus dorsi 24 hours after slaughter), $pH_{G1}$ (Gracilis 1 hour after slaughter) and $pH_{G24}$ (Gracilis 24 hours after slaughter). (ii) Data processing: Individual phenotypes were preadjusted for fixed effects (sire, dam, CRC genotype, sex, year-season, parity) and covariants (litter size, birth weight, weaning weight, grower weight, finisher weight) that proved to significantly affect the corresponding trait. Variables included in the model were selected by stepwise regression.

Marker genotyping: Primer pairs utilised for PCR amplification of microsatellite markers are as described[19]. Marker genotyping was performed as previously described[20]. Genotypes at the CRC and MyoD loci were determined using conventional methods as described[1,12]. The LAR test for the IGF2 SNP was developed according to Baron et al.[21] using a primer pair for PCR amplification (5'-CCCCTGACT-TGAGGACGAGCAGCC-3'(SEQ ID NO:5); 5'-ATCGCT-GTGGGCTGGGTGGGCTGCC-3')(SEQ ID NO:6) and a set of three primers for the LAR step (5'-FAM-CGC-CCCAGCTGCCCCCCAG-3'(SEQ ID NO:7); 5'-HEX-CGCCCCAGCTGCCCCCCAA-3'(SEQ ID NO: 8); 5'-CCTGAGCTGCAGCAGGCCAG-3'(SEQ ID NO:9)).

Map construction: Marker maps were constructed using the TWOPOINT, BUILD and CHROMPIC options of the CRIMAP package[22]. To allow utilisation of this package, full-sib families related via the boar or sow were disconnected and treated independently. By doing so, some potentially usable information was neglected, yielding, however, unbiased estimates of recombination rates.

QTL mapping: (i) Mapping Mendelian QTL: Conventional QTL mapping was performed using a multipoint maximum likelihood method. The applied model assumed one segregating QTL per chromosome and fixation of alternate QTL alleles in the respective parental lines, Piétrain (P) and Large White (LW). A specific analysis programme had to be developed to account for the missing genotypes of the parental generation, resulting in the fact that the parental origin of the F1 chromosomes could not be determined. Using a typical "interval mapping" strategy, a hypothetical QTL was moved along the marker map using user-defined steps. At each position, the likelihood (L) of the pedigree data was computed as:

$$L = \sum_{\varphi=1}^{2^l} \prod_{i=0}^{n} \sum_{G=1}^{4} (P(G \mid M_i, \theta, \varphi) P(y_i \mid G))$$

P or right chromosome P), there is a total of $2^r$ combinations for r F1 parents.

$$\prod_{i=0}^{n} n \, F2$$

$$\sum_{G=}^{4}$$

ith F2 offspring, over the four possible QTL genotypes:

P/P, P/L W, LW/P and LW/LW $P(G|M_i,\theta,\phi)M_i$: the marker genotype of the ith F2 offspring and its F1 parents, (ii) the vector of recombination rates between adjacent markers and between the hypothetical QTL and its flanking markers, and (iii) θthe considered marker-QTL phase combination of the F1 parents.

Recombination rates and marker linkage phase of F1 parents are assumed to be known when computing this probability. Both were determined using CRIMAP in the map construction phase (see above).

$P(y_i|G)y_i$) of offspring i, given the QTL genotype under consideration. This probability is computed from the normal density function:

$$P(y_i \mid G) = \frac{1}{\sqrt{2\pi}\sigma} e^{\frac{-(y_i - \mu_G)^2}{2\sigma^2}}$$

$_G$ is the phenotypic mean of the considered QTL genotype (PP, PL, LP or LL) and $\sigma^2$ the residual variance $\sigma^2$ was considered to be the same for the four QTL genotypic classes. The values of $\mu_{PP}$, $\mu_{PL}=\mu_{LP}$, $\mu_{LL}$ and $\sigma^2$ maximizing L were determined using the GEMINI optimisation routine[23]. The likelihood obtained under this alternative $H_1$ hypothesis was compared with the likelihood obtained under the null hypothesis $H_0$ of no QTL, in which the phenotypic means of the four QTL genotypic classes were forced to be identical. The difference between the logarithms of the corresponding likelihoods yields a lodscore measuring the evidence in favour of a QTL at the corresponding map position.

(ii) Significance thresholds: Following Lander & Botstein[24], lodscore thresholds (T) associated with a chosen genome-wise significance level were computed such that:

$$\alpha = (C + 9.21GT)\chi_2^2(4.6T)$$

C corresponds to the number of chromosomes (=19), G corresponds to the length of the genome in Morgans (=29), and $\chi_2^2$ (4.6T) denotes one minus the cumulative distribution function of the chi-squared distribution with 2 d.f Single poignt 21n(LR) were assumed to be distributed as a chi-squared distribution with two degrees of freedom, as we were fitting both an additive and dominance component. To account for the fact that we were analysing multiple traits, significance levels were adjusted by applying a Bonferoni correction corresponding to the effective number of independent traits that were analysed. This effective number was estimated at 16 following the approach described by Spelman et al.[25]. Altogether, this allowed us to set the lodscore threshold associated with an experiment—wise significance level of 5% at 5.8. When attempting to confirm the identified QTL in an independent sample, the same approach was used, however, setting C at 1, G at 25cM and correcting for the analysis of 4.5 independent traits (as only six traits were analysed in this sample). This yielded a lodscore threshold associated with a Type I error of 5% of 2.

(iii) Testing for an imprinted QTL: To test for an imprinted QTL, we assumed that only the QTL alleles transmitted by the parent of a given sex would have an effect on phenotype, the QTL alleles transmitted by the other parent being "neutral". The likelihood of the pedigree data under this hypothesis was computed using equation 1. To compute $P(y_i|G)$, however, the phenotypic means of the four QTL genotypes were set at $\mu_{PP} = \mu_{PL} = \mu_P$ and $\mu_{LP} = \mu_{LL} = \mu_L$ to test for a QTL for which the paternal allele only is expressed, and $\mu_{PP} = \mu_{LP} = \mu_P$ and $\mu_{PL} = \mu_{LL} = \mu_L$ to test for a QTL for which the maternal allele only is expressed. It is assumed in this notation that the first subscript refers to the paternal allele, the second subscript to the maternal allele. $H_0$ was defined as the null-hypothesis of no QTL, $H_1$ testing the presence of a Mendelian QTL, $H_2$ testing the presence of a paternally expressed QTL, and $H_3$ testing the presence of a maternally expressed QTL.

RT-PCR: Total RNA was extracted from skeletal muscle according to Chirgwin et al.[26] RT-PCR was performed using the Gene-Amp RNA PCR Kit (Perkin-Elmer) The PCR products were purified using QiaQuick PCR Purification kit (Qiagen) and sequenced using Dye terminator Cycle Sequencing Ready Reaction (Perkin Elmer) and an ABI373 automatic sequencer. In example 2 we report the identification of a QTL with major effect on muscle mass and fat deposition mapping to porcine 2p1.7. The QTL shows clear evidence for parental imprinting strongly suggesting the involvement of the IGF2 locus.

A Piétrain X Large White intercross comprising 1125 $F_2$ offspring was generated as described[6,7]. The Large White and Piétrain parental breeds differ for a number of economically important phenotypes. Piétrain are famed for their exceptional muscularity and leanness[8] (FIG. 2), while Large Whites show superior growth performance. Twenty-one distinct phenotypes measuring (i) growth performance (5), (ii) muscularity (6), (iii) fat deposition (6), and (iv) meat quality (4) were recorded on all $F_2$ offspring.

Figure 3A:
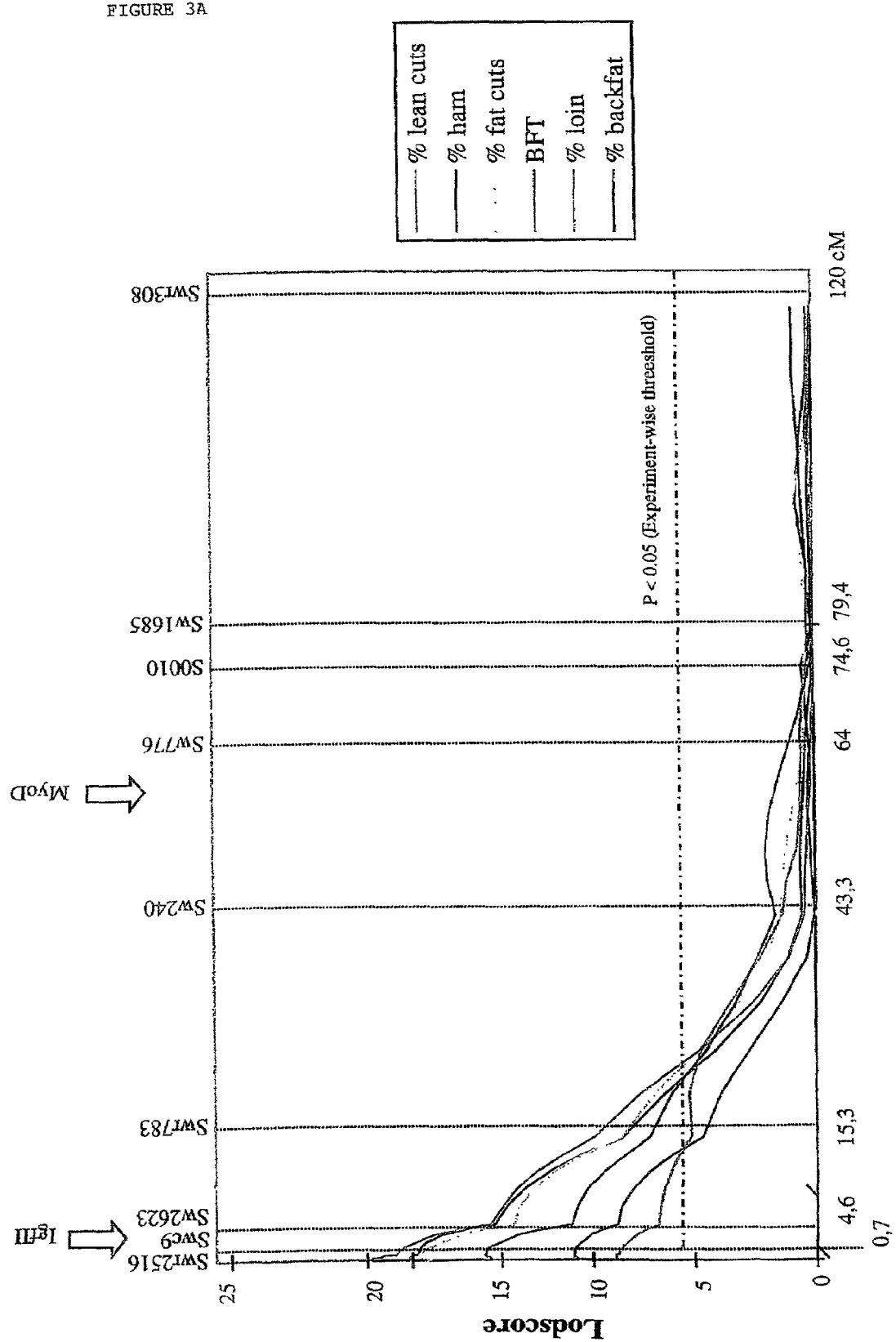
FIGS. 3A-3C: Lodscore curves obtained in a Piétrain× Large White intercross for six phenotypes measuring muscle mass and fat deposition on pig chromosome 2. The most likely positions of the IGF2 and MyoD genes determined by linkage analysis with respect to the microsatellite marker map are shown. $H_0$ was defined as the null-hypothesis of no QTL, $H_1$ as testing for the presence of a Mendelian QTL, $H_2$ as testing for the presence of a paternally expressed QTL, and $H_3$ as testing for the presence of a maternally expressed QTL. 3A: $\log_{10}(H_1/H_0)$, 3B:$\log_{10}(H_2/H_0)$, 3C: $\log_{10}(H_3/H_0)$.

In order to map QTL underlying the genetic differences between these breeds, we undertook a whole genome scan using microsatellite markers on an initial sample of 677 $F_2$ individuals. Analysis of pig chromosome 2 using a ML multipoint algorithm revealed highly significant lodscores (up to 20) for six of the 12 phenotypes measuring muscularity and fat deposition at the distal end of the short arm of chromosome 2 (FIG. 3a). Positive lodscores were obtained for the remaining six phenotypes, however, not reaching the genome-wise significance threshold (=5%). To confirm this finding, the remaining sample of 355 $F_2$ offspring was genotyped for the five most distal 2p markers and QTL analysis performed for the traits yielding the highest lodscores in the first analysis. Lodscores ranged from 2.1 to 7.7, clearly confirming the presence of a major QTL in this region. Table 2 reports the corresponding ML estimates for the three genotypic means as well as the corresponding residual variance.

Figure 4:
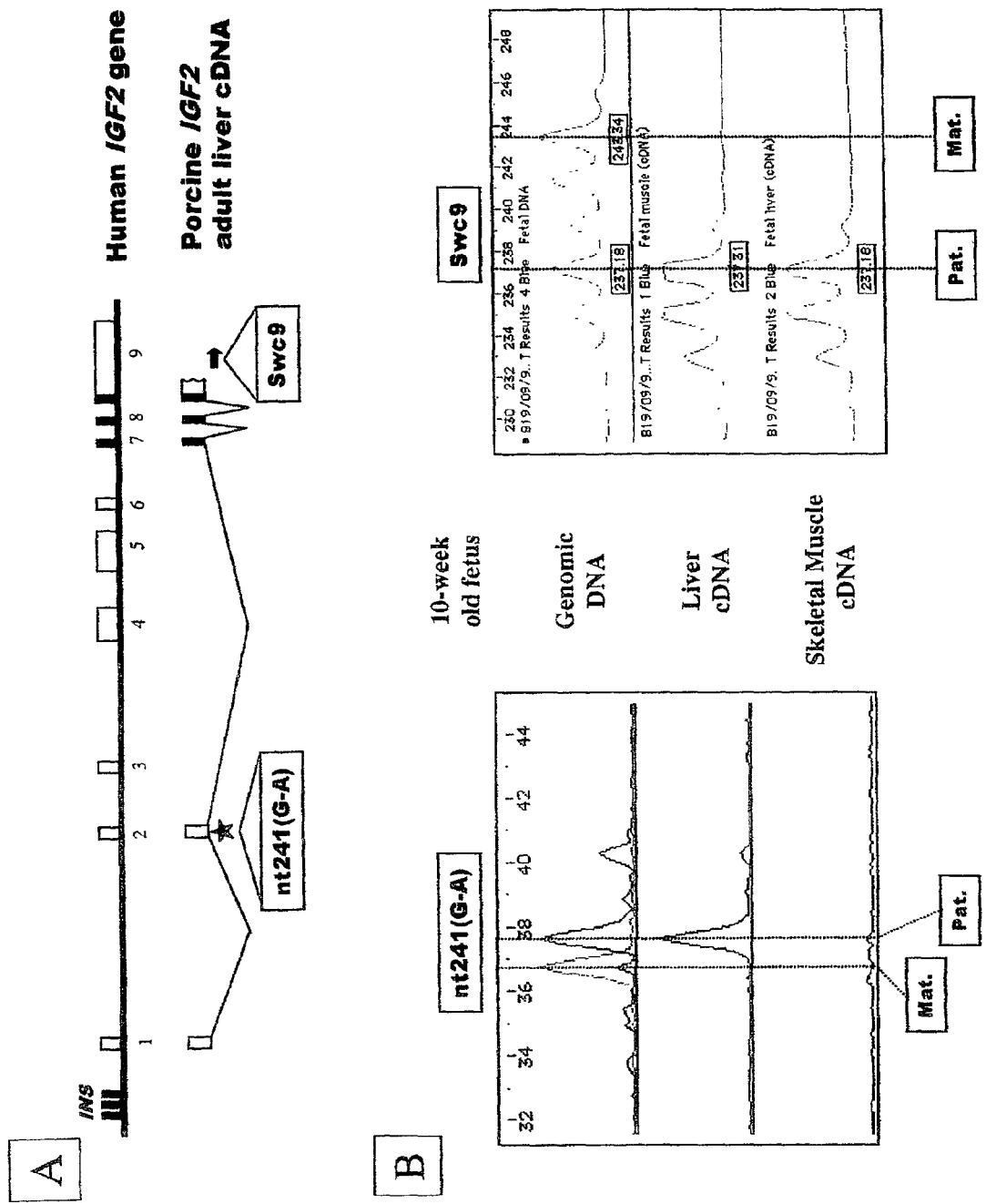
FIG. 4: A. Structure of the human IGF2 gene according to ref. 17, with aligned porcine adult liver cDNA sequence as reported in ref. 16. The position of the nt241(G-A) transition and Swc9 microsatellite are shown. B. The corresponding markers were used to demonstrate the monoallelic (paternal) expression of IGF2 in skeletal muscle and liver of 10-week old fetuses. PCR amplification of the nt421 (G-A) polymorphism and Swc9 microsatellite from genomic DNA clearly shows the heterozygosity of the fetus, while only the paternal allele is detected in liver cDNA (nt421(G-A) and Swc9) and muscle cDNA (Swc9). The absence of RT-PCR product for nt421(G-A) in fetal muscle points towards the absence of mRNA including exon 2 in this tissue. Parental origin of the fetal alleles was determined from the genotypes of the sire and dam (data not shown).

Bidirectional chromosome painting establishes a correspondence between SSC2p and HSA11pter-q13[9,10]. At least two serious candidate genes map to this region in man: the myogenic basic helix-loop-helix factor, MyoD, maps to HSA11p15.4, while IGF2 maps to HSA11p15.5. MyoD is a well-known key regulator of myogenesis and is one of the first myogenic markers to be switched on during development[11]. A previously described amplified sequence polymorphism in the porcine MyoD gene[12] proved to segregate in our $F_2$ material, which was entirely genotyped for this marker. Linkage analysis positioned the MyoD gene in the SW240-SW776 (odds>1000) interval, therefore, well outside the lod-2 drop off support interval for the QTL (FIG. 1). IGF2 is known to enhance both proliferation and differentiation of myoblasts in vitro[13] and to cause a muscular hypertrophy when overexpressed in vivo. Based on a published porcine adult liver cDNA sequence[14], we designed primer pairs allowing us to amplify the entire IGF2 coding sequence with 222 bp of leader and 280 bp of trailor sequence from adult skeletal muscle cDNA. Piétrain and Large White RT-PCR products were sequenced, indicating that the coding sequences were identical in both breeds and with the published sequence. However, a G A transition was found in the leader sequence corresponding to exon 2 in man (FIG. 4). We developed a screening test for this single nucleotide polymorphism (SNP) based on the ligation amplification reaction (LAR), allowing us to genotype our pedigree material. Based on these data, IGF2 was shown to colocalize with the SWC9 microsatellite marker (=0%), therefore, located at approximately 2 centimorgan from the most likely position of the QTL and well within the 95% support interval for the QTL (FIG. 1). Subsequent sequence analysis demonstrated that the microsatellite marker SWC9 is actually located within the 3' UTR of the IGF2 gene. Combined with available comparative mapping data for the PGA and FSH loci, these results suggest the occurrence of an interstitial inversion of a chromosome segment containing MyoD, but not IGF2 which has remained telomeric in both species.

IGF2, therefore, appeared as a strong positional allele having the observed QTL effect. In man and mouse, IGF2 is known to be imprinted and to be expressed exclusively from the paternal allele in several tissues[15]. Analysis of skeletal muscle cDNA from pigs heterozygous for the SNP and/or SWC9 shows that the same imprinting holds in this tissue in the pig as well (FIG. 4). Therefore, if IGF2 were responsible for the observed effect, and knowing that only the paternal IGF2 allele is expressed, one can predict that (i) the paternal allele transmitted by F1 boars (P or LW) would have an effect on the phenotype of F2 offspring, (ii) the maternal allele transmitted by F1 sows (P or LW) would have no effect on phenotype of F2 offspring, and (iii) the likelihood of the data would be superior under a model of a bimodal (1:1) F2 population sorted by inherited paternal allele when compared to a conventional "Mendelian" model of a trimodal (1:2:1) F2 population. The QTL mapping programmes were adapted in order to allow testing of the corresponding hypotheses. $H_0$ was defined as the null-hypothesis of no QTL, $H_1$ as testing for the presence of a Mendelian QTL, $H_2$ as testing for the presence of a paternally expressed QTL, and $H_3$ as testing for the presence of a maternally expressed QTL.

Figure 3B:
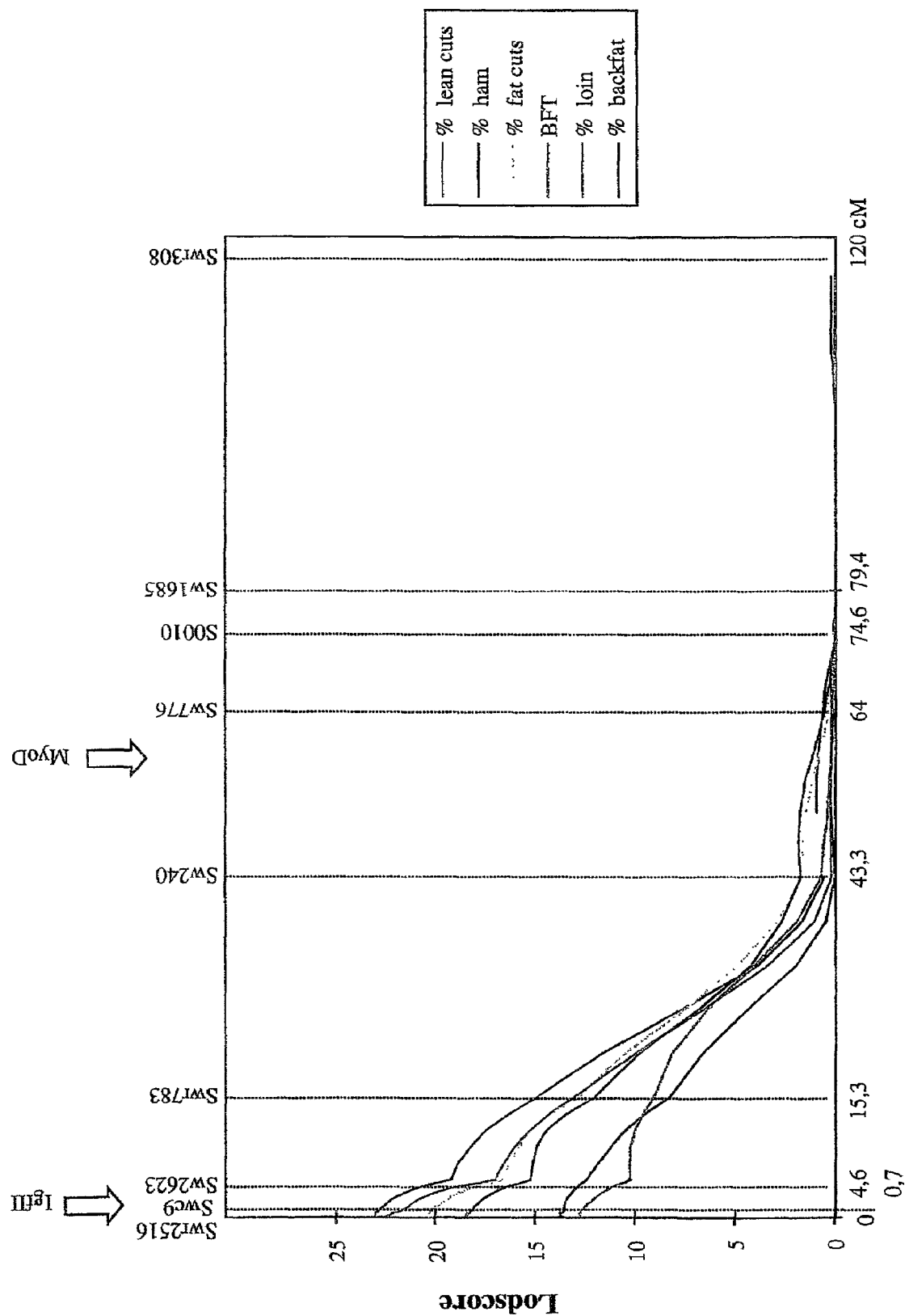
Figure 3C:
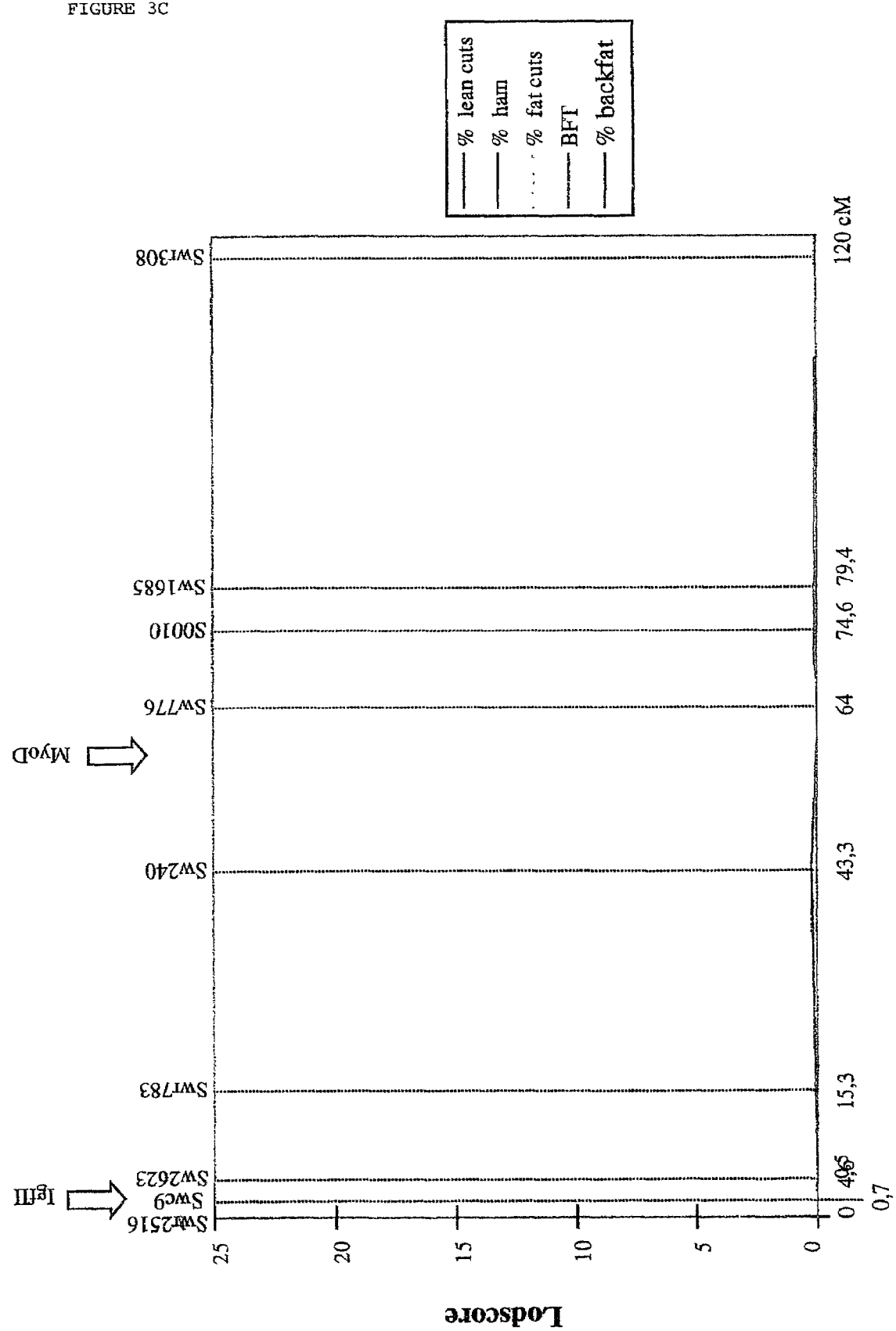

FIG. 3 summarizes the obtained results. FIGS. 3a, 3b and 3c respectively show the lodscore curves corresponding to $\log_{10}(H_2/H_0)$, $\log_{10}(H_3/H_0)$ and $\log_{10}(H2/H1)$. It can be seen that very significant lodscores are obtained when testing for the presence of a paternally expressed QTL, while there is no evidence at all for the segregation of a QTL when studying the chromosomes transmitted by the sows. Also, the hypothesis of a paternally expressed QTL is significantly more likely ($\log_{10}(H_2/H_1) > 3$) than the hypothesis of a "Mendelian" QTL for all examined traits. The fact that the same tendency is observed for all traits indicates that it is likely the same imprinted gene that is responsible for the effects observed on the different traits. Table 2 reports the ML phenotypic means for the F2 offspring sorted by inherited paternal QTL allele. Note that when performing the analysis under a model of a mendelian QTL, the Piétrain and Large White QTL alleles appeared to behave in an additive fashion, the heterozygous genotype exhibiting a phenotypic mean corresponding exactly to the midpoint between the two homozygous genotypes. This is exactly what one would predict when dealing with an imprinted QTL as half of the heterozygous offspring are expected to have inherited the P allele from their sire, the other halve the LW allele.

These data, therefore, confirmed our hypothesis of the involvement of an imprinted gene expressed exclusively from the paternal allele. The fact that the identified chromosomal segment coincides precisely with an imprinted domain documented in man and mice strongly implicates the orthologous region in pigs. At least seven imprinted genes mapping to this domain have been documented (IGF2, Ins2, H19, Mash2, $p57^{KIP2}$, $K_vLQTL1$ and TDAG51) (ref 15 and Andrew Feinberg, personal communication). Amongst these, only IGF2 and Ins2 are paternally expressed. While we cannot exclude that the observed QTL effect is due to an as of yet unidentified imprinted gene in this region, its reported effects on myogenesis in vitro and in vivo[13] strongly implicate IGF2. Particularly the muscular hypertrophy observed in transgenic mice overexpressing IGF2 from a muscle-specific promotor are in support of this hypothesis (Nadia Rosenthal, personal communication). Note that allelic variants of the INS VNTR have recently been shown to be associated with size at birth in man[16], and that the same VNTR has been shown to affect the level of IGF2 expressions[17].

The observation of the same QTL effect in a Large White×Wild Boar intercross indicates the existence of a series of at least three distinct functional alleles. Moreover, preliminary evidence based on marker-assisted segregation analysis points towards residual segregation at this locus within the Piétrain population (data not shown). The occurrence of an allelic series might be invaluable in identifying the causal polymorphisms which—based on the quantitative nature of the observed effect—are unlikely to be gross gene alterations but rather subtle regulatory mutations.

The effects of the identified QTL on muscle mass and fat deposition are truly major, being of the same magnitude of those reported for the CRC locus[6,7] though apparently without the associated deleterious effects on meat quality. We estimate that both loci jointly explain close to 50% of the Piétrain versus Large White breed difference for muscularity and leanness. Understanding the parent-of-origin effect characterising this locus will allow for its optimal use in breeding programmes. Indeed, today, half of the offspring from commercially popular Piétrain×Large White crossbred boars inherit the unfavourable Large White allele causing considerable loss.

The QTL described in this work is the second example of a gene affecting muscle development in livestock species that exhibits a non-mendelian inheritance pattern. Indeed, we have previously shown that the callipyge locus (related to the qualitative trait wherein muscles are doubled) is characterised by polar overdominance in which only the heterozygous individuals that inherit the CLPG mutation from their sire express the double-muscling phenotype[5]. This demonstrates that parent-of-origin effects affecting genes underlying production traits in livestock might be relatively common.

EXAMPLE 3

Generating a Reference Sequence of IGF2 and Flanking Loci in the Pig.

The invention provides an imprinted QTL with a major effect on muscle mass mapping to the IGF2 locus in the pig, and use of the QTL as a tool in marker-assisted selection. To fine tune this tool for marker-assisted selection, as well as to further identify a causal mutation, we have further generated a reference sequence encompassing the entire porcine IGF2 sequence as well as that from flanking genes.

Figure 5:
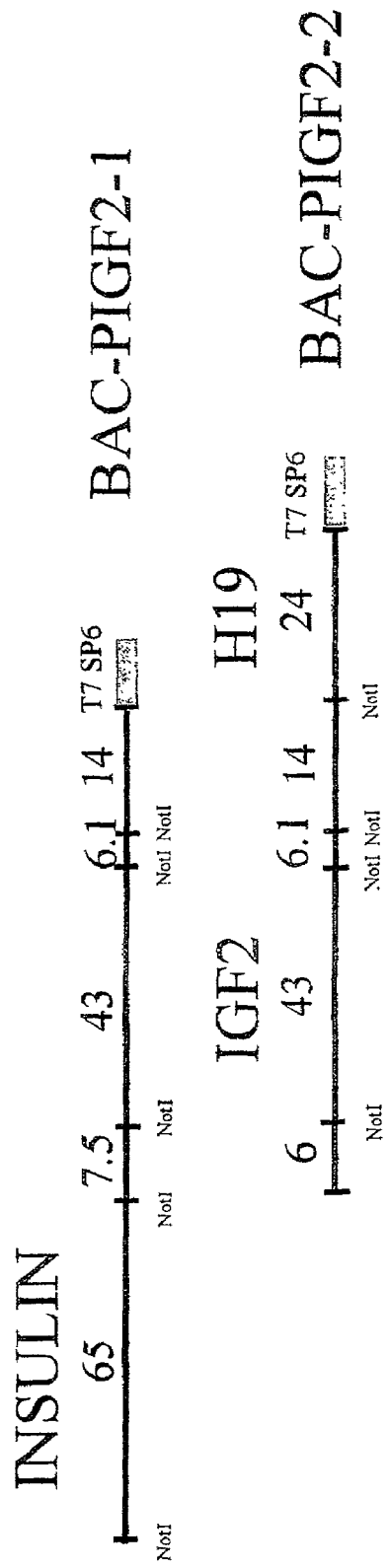
FIG. 5: A NotI restriction map showing the relative position of BAC-PIGF2-1 (comprising INS and IGF2 genes), and BAC-PIGF2-2 (comprising IGF2 and H19 genes).
Figure 7:
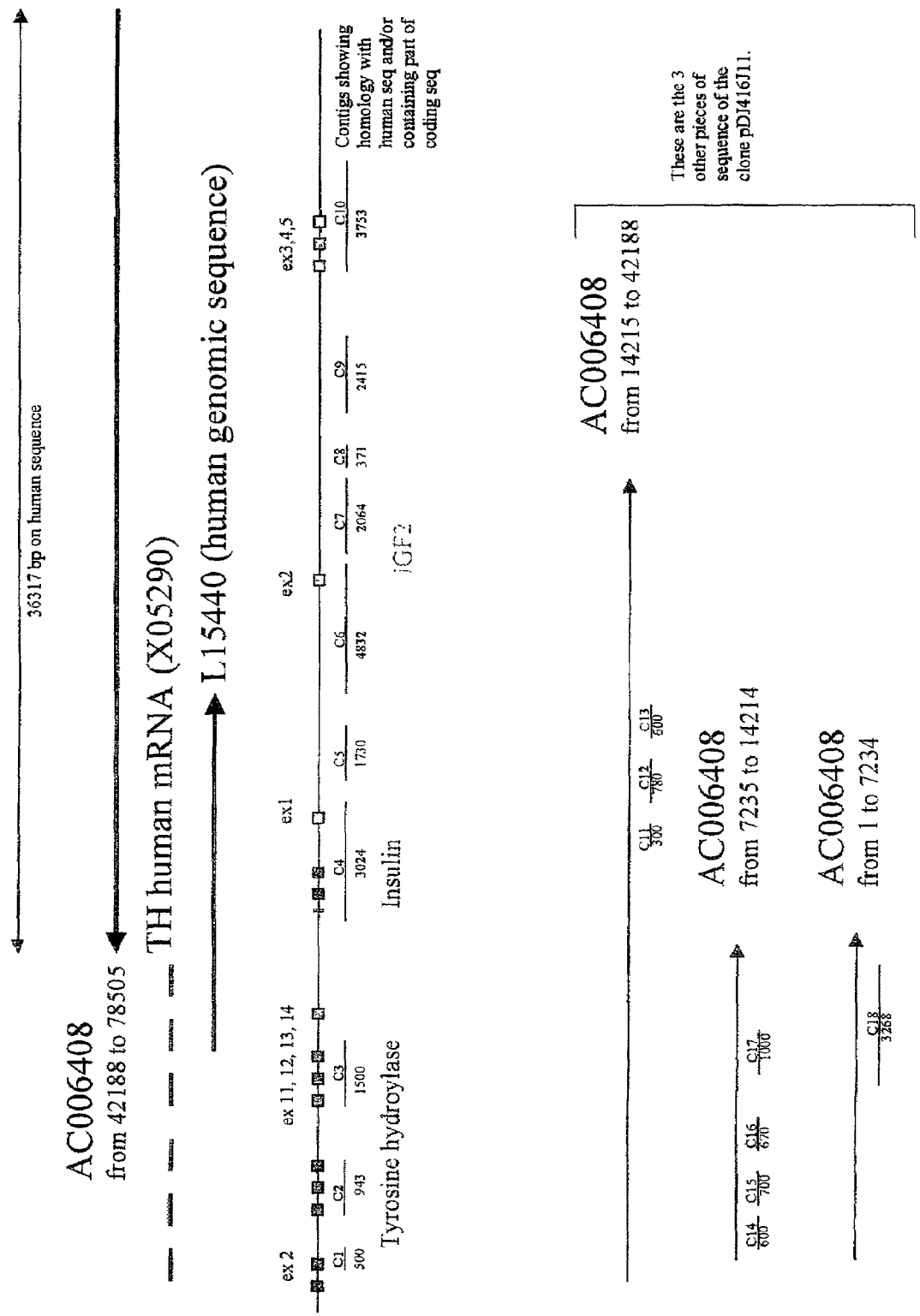
FIG. 7: Similarity between porcine contigs of FIG. 6 and orthologous sequences in human.

To achieve this, we screened a porcine BAC library with IGF2 probes and identified two BACs. BAC-PIGF2-1 proved to contain the INS and IGF2 genes, while BAC-PIGF2-2 proved to contain the IGF2 and H19 genes. The NotI map as well as the relative position of the two BACs is shown in FIG. 5. BAC-PIGF2-1 was shotgun sequenced using standard procedures and automatic sequencers. The resulting sequences were assembled using standard software yielding a total of 115 contigs. The corresponding sequences are reported in FIG. 6. Similarity searches were performed between the porcine contigs and the orthologous sequences in humans. Significant homologies were detected for 18 contigs and are reported in FIG. 7.

Figure 9:
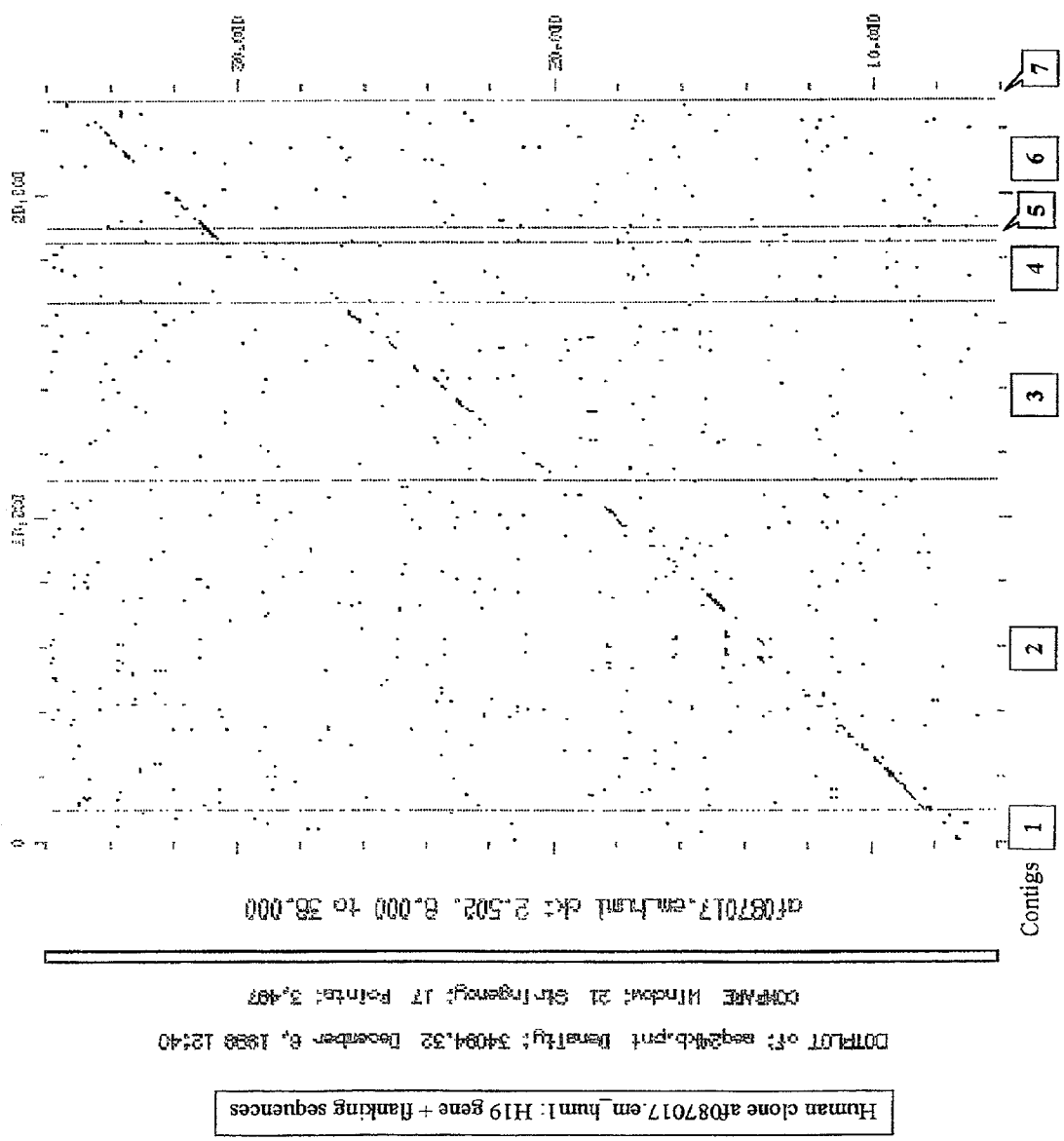
FIG. 9: Similarity between porcine contigs of FIG. 8 and orthologous sequences in human.

For BAC-PIGF2-2, the 24 Kb NotI fragment not present in BACPIGF2-1 was subcloned and sequenced using the EZ::TN transposon approach and ABI automatic sequencers. Resulting sequences were assembled using the Phred-Phrap-Consed programme suit, yielding seven distinct contigs (FIG. 8). The contig sequences were aligned with the corresponding orthologous human sequences using the compare and dotplot programmes of the GCG suite. FIG. 9 summarizes the corresponding results.

EXAMPLE 4

Identification of DNA Sequence Polymorphisms in the IGF2 and Flanking Loci

Based on the reference sequence obtained as described in Example 1, we resequenced part of the IGF2 and flanking loci from genomic DNA isolated from Piétrain, Large White and Wild Boar individuals, allowing identification of DNA sequence polymorphisms such as reported in FIG. 10.

REFERENCES

Literature Cited with Example 1

1. Andersson, L. et al. Genetic mapping of quantitative trait loci for growth and fatness in pigs. Science 263, 1771-1774 (1994).
2. Knott, S. A. et al. Multiple marker mapping of quantitative trait loci in a cross between outbred wild boar and Large White pigs. Genetics 149, 1069-1080 (1998).
3. Edfors-Lilja, I. et al. Mapping quantitative trait loci for immune capacity in the pig. Journal of Immunology 161, 829-835 (1998).
4. Andersson-Eklund, L. et al. Mapping quantitative trait loci for carcass and meat quality traits in a wild boar× Large White intercross. Journal of Animal Science 76, 694-700 (1998).
5. Fronicke, L., Chowdhary, B. P., Scherthan, H. & Gustavsson, I. A comparative map of the porcine and human genomes demonstrates ZOO-FISH and gene mapping-based chromosomal homologies. Mamm Genome 7, 285-90 (1996).
6. Alexander, L. J. et al. Physical assignments of 68 porcine cosmids and lambda clones containing microsatellites. Mammalian Genome 7, 368-372 (1996).
7. Rohrer, G. A. et al. A comprehensive map of the porcine genome. Genome Research 6, 371-391 (1996).
8. Marklund, L. et al. A comprehensive linkage map of the pig based on a wild pig-Large White intercross. Anim Genet 27, 255-69 (1996).
9. Marklund, L., Nyström, P. E., Stern, S., Anderssson-Eklund, L. &Andersson, L. Quantitative trait loci for fatness and growth on pig chromosome 4. Heredity In press (1998).
10. Ohlsson, R., Hedborg, F., Holmgren, L., Walsh, C. & Ekström, T. J. Overlapping patterns of IGF2 and H19 expression during human development: biallelic IGF2 expression correlates with a lack of H19 expression. Development 120, 361-368 (1994).
11. Ekström, T. J., Cui, H., Li, X. & Ohlsson, R. Promoter-specific IGF2 imprinting status and its plasticity during human liver development. Development 121, 309-316 (1995).
12. Hemberger, M. et al. H19 and IGF2 are expressed and differentially imprinted in neuroectoderm-derived cells in the mouse brain. Dev. Genes Evol. 208, 393-402 (1998).
13. Dunger, D. B. et al. Association of the INS VNTR with size at birth. Nature Genetics 19, 98-100 (1998).
14. DeChiara, T. M., Robertson, E. J. & Efstratiadis, A. Parental imprinting of the mouse insulin-like growth factor II gene. Cell 64, 849-859 (1991).
15. Sun, F. L., Dean, W. L., Kelsey, G., Allen, N. D. & Reik, W. Transactivation of IGF2 in a mouse model of Beckwith-Wiedemann syndrome. Nature 389, 809-815 (1997).
16. Davies, J. L. et al. A genome-wide search for human type 1 diabetes susceptibility genes. Nature 371, 130-136 (1994).
17. O'Dell, S. D. et al. ApaI polymorphism in insulin-like growth factor II (IGF2) gene and weight in middle-aged males. International Journal of Obesity 21, 822-825 (1997).
18. Falconer, D. S. & Mackay, T. F. C, Introduction to Quantitative Genetics, (Longman, England, 1996).
19. Hill, W. G. Rates of change in quantitative traits from fixation of new mutations. Proc Natl Acad Sci USA 79, 142-145 (1982).
20. Marklund, S. et al. Molecular basis for the dominant white phenotype in the domestic pig. Genome Research 8, 826-833 (1998).
21. Kijas, J. M. H. et al. Melanocortin receptor 1 (MC1R) mutations and coat color in the pig. Genetics In press (1998).
22. Beechey, C. V. personal communication (1998).
23. Paquette, J., Giannoukakis, N., Polychronakos, C., Vafiadis, P. & Deal, C. The INS 5' variable number of tandem repeats is associated with IGF2 expression in humans. Journal of Biological Chemistry 273, 14158-14164 (1998).
24. Sambrook, J., Fritsch, E. F. & Maniatis, T. Molecular cloning. A laboratory manual, (Cold Spring Harbor Laboratory Press, Cold Spring Harbor, 1989).
25. Chowdhary, B. P., de la Sena, C., Harbitz, I., Eriksson, L. & Gustavsson, I. FISH on metaphase and interphase chromosomes demonstrates the physical order of the genes for GPI, CRC, and LIPE in pigs. Cytogenetics Cell Genetics 71, 175-178 (1995).
26. Green, P., Falls, K. & Crook, S. Documentation for CRI-MAP, version 2.4., (Washington University School of Medicine, St. Louis, Mo., 1990).
27. Haley, C. S., Knott, S. A. & Elsen, J. M. Mapping quantitative trait loci in crosses between outbred lines using least squares. Genetics 136, 1195-1207 (1994).
28. Churchill, G. A. & Doerge, R. W. Empirical threshold values for quantitative trait mapping. Genetics 138, 963-971 (1994).
29. Anonymous. SAS version 6.10, (SAS Institute Inc., Cary, N.C., 1990).

References Used with Example 2:

1. Fuji, J.; Otsu, K.; Zorzato, F.; Deleon, S.; Khanna, V. K., Weiler, J. E. O'Brien, P. J.; MacLennan, D. H. (1991). Identification of a mutation in the porcine ryanodine receptor associated with malignant hyperthermia. Science 253: 448-451.
2. MacLennan, D. H. & Phillips, M. S. (1993). Malignant hyperthermia. Science 256:789-794.
3. Grobet, L.; Royo Martin, L. J.; Poncelet, D.; Pirottin, D.; Brouwers, B.; Riquet, J.; Schoeberlein, A.; Dunner, S.; Menissier, F.; Massabanda, J.; Fries, R.; Hanset, R.; Georges, M. (1997) A deletion in the myostatin gene causes double muscling in cattle. Nature Genetics 17:71-74.
4. Andersson, L.; Haley, C. S.; Ellegren, H.; Knott, S. A.; Johansson, M.; Andersson, K.; Andersson-Eklund, L.; Edfors-Lilja, I.; Fredholm, M.; Hansson, I.; Hakansson, J.; Lundström, K. (1994). Genetic mapping of quantitative trait loci for growth and fatness in pigs. Science 263: 1771-1774.

5. Cockett, N.; Jackson, S.; Shaw, T.; Farnir, F.; Berghmans, S.; Snowder, G.; Nielsen, D.; Georges, M. (1996). Polar overdominance at the ovine callipyge locus. *Science* 273: 236-238.
6. Hanset, R.; Dasnois, C.; Scalais, S.; Michaux, C.; Grobet, L. (1995). Genotypes at the locus for halothane sensitivity and performance in a Piétrain×Large White F2. *Genet. Sel. Evol.* 27: 63-76.
7. Hanset, R.; Dasnois, C.; Scalais, S.; Michaux, C.; Grobet, L. (1995). Introgression into the Piétrain genome of the normal allele at the locus for halothane sensitivity. *Genet. Sel. Evol.* 27: 77-88.
8. Olivier, L.; Lauvergne, J. J. (1967). A study of the inheritance of the muscular hypertrophy of the Piétrain pig: preliminary results. *Annales de Médecine Vétérinaire* 111: 104-109.
9. Rettenberger, G.; Klett, C.; Zechner, U.; Kunz, J.; Vogel, W.; Hameister, H. (1995). Visualisation of the conservation of synteny between humans and pigs by heterologous chromosome painting. *Genomics* 26: 372-378.
10. Goureau, A.; Yerle, M.; Schmitz, A.; Riquet, J.; Milan, D.; Pinton, P.; Frelat, G.; Gellin, J. (1996). Human and porcine correspondence of chromosome segments using bidirectional chromosome painting. *Genomics* 36:252-262.
11. Yun, K.; Wold, B. (1996). Skeletal muscle determination and differentiation: story of a core regulatory network and its context. *Current Opinion in Cell Biology* 8:877-889.
12. Knoll, A.; Nebola, M.; Dvorak, J.; Cepica, S. (1997). Detection of a DdeI PCR RFLP within intron 1 of the porcine MYOD1(MYF3) locus. *Animal Genetics* 28, 308-322.
13. Florini, J. R.; Ewton, D. Z.; McWade, F. J. (1995). IGFs, muscle growth, and myogenesis. *Diabetes Review* 3:73-92.
14. Catchpole, I. R.; Engström, W. (1990). Nucleotide sequence of a porcine insulin-like growth factor II cDNA. *Nucleic Acids Research* 18(21):6430.
15. Feil, R.; Moore, T. F.; Oswald, J.; Walter, J.; Sun, F.; Reik, W. (1997). The imprinted insulin like growth factor 2 gene. Pp70 In Genomic Imprinting. Eds. Reik & Surani. IRL Press at Oxford University Press.
16. Dunger, D. B.; Ong, K. K. L.; Huxtable, S. J.; Sherriff, A.; Woods, K. A.; Ahmed, M. L.; Golding, J.; Pembrey, M. E.; Ring, S.; the AISPAC study team, Bennett, S. T.; Todd, J. A. (1998). Association of the INS VNTR with size at birth. *Nature Genetics* 19: 98-100.
17. Paquette, J.; Giannoukakis, N.; Polychronakos, C.; Vafiadis, P.; Deal, C. (1998). The INS 5' variable number of tandem repeats is associated with IGF2 expression in humans. *J. Biol Chem* 273 (23):14158-14164.
18. Andersson-Eklund, L.; Marklund, L.; Lundström, K.; Haley, C. S.; Andersson, K.; Hansson, I.; Moller, M.; Andersson, L. (1998). Mapping Quantitative Trait Loci for carcass and meat quality traits in a Wild Boar×Large White intercross. *J Anim. Sci.* 76:694-700.
19. Rohrer, G. A.; Alexander, L. J.; Hu, Z.; Keele, J. W.; Smith, T. P.; Beattie, C. W. (1996). A comprehensive map of the porcine genome. *Genome Research*, in the press.
20. Georges, M.; Nielsen, D.; Mackinnon, M.; Mishra, A.; Okimoto, R.; Pasquino, A. T.; Sargeant, L. S.; Sorensen, A.; Steele, M. R.; Zhao, X.; Womack, J. E.; Hoeschele, I. (1995). Mapping quantitative trait loci controlling milk production by exploiting progeny testing. *Genetics* 139: 907-920.
21. Baron, H.; Fung, S.; Aydin, A.; Bahring, S.; Luft, F. C.; Schuster, H. (1996). Oligonucleotide ligation assay (OLA) for the diagnosis of familial hypercholesterolemia. *Nat. Biotechnol.* 14(10): 1279-1282.
22. Lander, E.; Green, P. (1987) Construction of multilocus genetic linkage maps in humans. *Proceedings of National Academy of Science (USA)* 84: 2363-2367.
23. Lalouel, J. M. (1983). Optimization of functions. *Contrib. Epidemiol. Biostat.* 4:235-259.
24. Lander, E. S. & Botstein, D. (1989). Mapping mendelian factors underlying quantitative traits using RFLP linkage maps. *Genetics* 121:185-199.
25. Spelman, R. L.; Coppieters, W.; Karim, L.; van Arendonk, J. A. M.; Bovenhuis, H. (1996). Quantitative trait loci analysis for five milk production traits on chromosome six in the dutch Holstein-Friesian population. *Genetics* 144:1799-1808.
26. Chirgwin, J. M.; Przybyla, A. E.; MacDonald, R. J.; Rutter, W. J. (1979). Isolation of biologically active ribonucleic acid from sources enriched in ribonuclease. *Biochemistry* 18:5294-5299.

TABLE 1

Summary of QTL analysis for pig chromosome 2 in a Wild Boar/Large White intercross[1]

| Trait | F ratio[2] QTL | Imprinting | Map position[3] | Percent of $F_2$ variance[4] | Least Squares means[5] $W^P/W^M$ n = 62 | $W^P/L^M$ n = 43 | $L^P/W^M$ n = 43 | $L^P/L^M$ n = 30 |
|---|---|---|---|---|---|---|---|---|
| Body composition traits | | | | | | | | |
| Lean meat in ham, % | 24.4*** | 19.1*** | 0 | 30.6 | 63.6[a] | 64.2[a] | 66.4[b] | 67.3[b] |
| Lean meat mass in ham, kg | 18.1*** | 16.8*** | 1 | 24.3 | 4.69[a] | 4.72[a] | 4.94[b] | 50.2[b] |
| Lean meat + bone in back, % | 12.2** | 9.6** | 0 | 17.4 | 66.3[a] | 66.7[a] | 69.3[b] | 70.8[b] |
| Longissimus muscle area, cm² | 10.3** | 4.8* | 1 | 15.4 | 31.9[a] | 33.0[a] | 34.5[b] | 35.2[b] |
| Fatness traits | | | | | | | | |
| Average backfat depth, mm | 7.1* | 8.7** | 0 | 10.4 | 27.2[a] | 27.7[a] | 25.5[b] | 24.7[b] |
| Weight of internal organs | | | | | | | | |
| Heart, gram | 9.7** | 11.4*** | 0 | 14.4 | 226[a] | 225[a] | 238[b] | 244[b] |

TABLE 1-continued

Summary of QTL analysis for pig chromosome 2 in a Wild Boar/Large White intercross[1]

| Trait | F ratio[2] QTL | Imprinting | Map position[3] | Percent of $F_2$ variance[4] | Least Squares means[5] | | | |
|---|---|---|---|---|---|---|---|---|
| | | | | | $W^P/W^M$ n = 62 | $W^P/L^M$ n = 43 | $L^P/W^M$ n = 43 | $L^P/L^M$ n = 30 |
| Meat quality traits | | | | | | | | |
| Reflectance value, EEL | 5.7 | 6.1* | 1 | 8.1 | 18.6[a] | 18.4[a] | 21.8[b] | 19.7[a] |

*P < 0.05; P < 0.01; *P < 0.001
[1]Only the traits for which the QTL peak was in the IGF2 region (0-10 cM) and the test statistic reaching the nominal significance threshold of F = 3.9 are included.
[2]"QTL" is the test statistic for the presence of a QTL under a genetic model with additive, dominance, and imprinting effects (3 d.f.) while "Imprinting" is the test statistic for the presence of an imprinting effect (1 d.f.), both obtained at the position of the QTL peak. Genome-wise significance thresholds, estimated by permutation, were used for the QTL test while nominal significance thresholds were used for the Imprinting test.
[3]In cM from the distal end of 2p; IGF2 is located at 0.3 cM.
[4]The reduction in the residual variance of the $F_2$ population effected by inclusion of an imprinted QTL at the given position.
[5]Means and standard errors estimated at the IGF2 locus by classifying the genotypes according to the population and parent of origin of each allele. W and L represent alleles derived from the Wild Boar and Large White founders, respectively; superscripts P and M represent a paternal and maternal origin, respectively. Figures with different letters (superscript a or b) are significantly different at least at the 5% level, and most of them are different at the 1% or 0.1% level.

TABLE 2

Maximum likelihood phenotypic means for the different F2 genotypes estimated under (i) a model of a mendelian QTL, and (ii) a model assuming an imprinted QTL.

| Traits | Mendelian QTL | | | | Imprinted QTL | | |
|---|---|---|---|---|---|---|---|
| | $\mu_{LW/LW}$ | $\mu_{LW/P}$ | $\mu_{P/P}$ | R | $\mu_{PAT/LW}$ | $\mu_{PAT/P}$ | R |
| BFT (cm) | 2.98 | 2.84 | 2.64 | 0.27 | 2.94 | 2.70 | 0.27 |
| % ham | 21.10 | 21.56 | 22.15 | 0.83 | 21.23 | 21.95 | 0.83 |
| % loin | 24.96 | 25.53 | 26.46 | 0.91 | 25.12 | 26.14 | 0.93 |
| % lean cuts | 65.02 | 65.96 | 67.60 | 1.65 | 65.23 | 67.05 | 1.67 |
| % backfat | 6.56 | 6.02 | 5.33 | 0.85 | 6.43 | 5.56 | 0.85 |
| % fat cuts | 28.92 | 27.68 | 26.66 | 1.46 | 28.54 | 26.99 | 1.49 |

The invention claimed is:

1. A method for selecting a pig for breeding by identifying a pig having a paternally imprinted quantitative trait locus (QTL) associated with larger muscle mass and decreased fat deposition such that when the pig is used in a breeding program, the offspring of the pig that inherit said QTL from the male parent have larger muscle mass and decreased fat deposition compared to controls, wherein the method for selecting a pig comprises:

identifying the presence of the paternally imprinted QTL associated with larger muscle mass and decreased fat deposit by detecting one or more genetic markers selected from the group consisting of genetic markers linked to the QTL on chromosome 2 of the pig, genetic markers in linkage disequilibrium with the paternally imprinted QTL on chromosome 2 of the pig, and combinations of any thereof;

wherein the paternally imprinted QTL comprises the insulin-like growth factor-2 gene (IGF-2) as well as the genetic markers Swr2516, Swc9, Sw2623, and Swr783 on chromosome 2 of the pig;

wherein the QTL is present on chromosome 2 of the pig at position 2p1.7; and wherein the identification of the pig having the paternally imprinted QTL associated with larger muscle mass and decreased fat deposit selects the pig for breeding.

* * * * *